US012807675B2

(12) United States Patent
Ayvar et al.

(10) Patent No.: US 12,807,675 B2
(45) Date of Patent: Nov. 24, 2026

(54) SIGNALING DOMAINS FOR CHIMERIC ANTIGEN RECEPTORS

(71) Applicant: Kite Pharma, Inc., Santa Monica, CA (US)

(72) Inventors: Ricardo Ayvar, Santa Monica, CA (US); Jun Feng, San Diego, CA (US); Claudia I. Guevara, South Gate, CA (US); Jodi Murakami, Culver City, CA (US); Heba N. Nowyhed, Los Angeles, CA (US); Sarah K. Wyman, Denver, CO (US)

(73) Assignee: Kite Pharma, Inc., Santa Monica, CA (US)

( * ) Notice: Subject to any disclaimer, the term of this patent is extended or adjusted under 35 U.S.C. 154(b) by 631 days.

(21) Appl. No.: 18/047,480

(22) Filed: Oct. 18, 2022

(65) Prior Publication Data

US 2023/0303655 A1 Sep. 28, 2023

Related U.S. Application Data

(60) Provisional application No. 63/256,956, filed on Oct. 18, 2021.

(51) Int. Cl.
*C07K 14/725* (2006.01)
*A61K 35/17* (2025.01)
(Continued)

(52) U.S. Cl.
CPC .......... *C07K 14/7051* (2013.01); *A61K 35/17* (2013.01); *A61K 40/11* (2025.01);
(Continued)

(58) Field of Classification Search
None
See application file for complete search history.

(56) References Cited

U.S. PATENT DOCUMENTS

| | | | |
|---|---|---|---|
| 2021/0107949 A1 | 4/2021 | Frost et al. | |
| 2021/0269537 A1 | 9/2021 | Dai et al. | |
| 2022/0289814 A1 | 9/2022 | Fan et al. | |

FOREIGN PATENT DOCUMENTS

| | | | |
|---|---|---|---|
| WO | WO-2016054520 A2 * | 4/2016 | ......... C07K 14/7051 |
| WO | WO-2018/102795 A2 | 6/2018 | |
| WO | WO-2019/023396 A1 | 1/2019 | |

(Continued)

OTHER PUBLICATIONS

Kenderian et al. Chimeric antigen receptor T cells and hematopoietic cell transplantation: How not to put the CART before the horse. Biology of Blood and Marrow Transplantation (2017), 23, p. 235-246.*

(Continued)

*Primary Examiner* — Joanne Hama
*Assistant Examiner* — Jami Michelle Gurley

(57) ABSTRACT

Disclosed are chimeric antigen receptors (CARs), comprising an antigen binding domain, a transmembrane domain; a costimulatory domain; and a signaling domain comprising one of a CD3ε signaling domain, a CD3γ signaling domain, a CD3δ signaling domain, or a DAP12 signaling domain. Disclosed is a nucleic acid encoding a CAR and recombinant vector comprising such nucleic acids. Disclosed is a host cell comprising such nucleic acids and recombinant vectors, and a pharmaceutical composition comprising such host cells. Disclosed is method of treating disease in a patient in need of thereof, or inducing an immune response in a subject or immunizing a subject against a cancer.

13 Claims, 3 Drawing Sheets

Specification includes a Sequence Listing.

(51) Int. Cl.
*A61K 40/11* (2025.01)
*A61K 40/31* (2025.01)
*A61K 40/42* (2025.01)
*C07K 14/705* (2006.01)
*C12N 15/85* (2006.01)

(52) U.S. Cl.
CPC .......... *A61K 40/31* (2025.01); *A61K 40/4211* (2025.01); *A61K 40/4221* (2025.01); *C07K 14/70596* (2013.01); *C12N 15/85* (2013.01); *A61K 2239/22* (2023.05); *A61K 2239/38* (2023.05); *A61K 2239/48* (2023.05)

(56) References Cited

FOREIGN PATENT DOCUMENTS

| | | | |
|---|---|---|---|
| WO | WO-2020/068702 | A1 | 4/2020 |
| WO | WO-2020/223327 | A1 | 11/2020 |

OTHER PUBLICATIONS

Mallabiaberrena, et al. An endoplasmic reticulum retention signal in the CD3ε chain of the T-cell receptor. Nature (1992), 357, p. 593-596.*
Mallabiabarrena, et al. A tyrosine-containing motif mediates ER retention of CD3-ε and adopts a helix-turn structure. EMBO Journal (1995), 14:10, p. 2259.*
Mallabiaberrena, et al. A tyrosine-containing motif mediates ER retention of CD3-ε and adopts a helix-turn structure. The EMBO Journal (1995), 14:10, p. 2257-2268.*
UniProt. P07766 CD3E_Human: T-cell surface glycoprotein CD3 epsilon chain. Internet. p. 7.*
Wu, et al. Multiple signaling roles of CD3ε and its application in CAR-T cell therapy. Cell (2020), 182, p. 855-871; KAI2563065.1.*
Xu, et al. Regulation of T cell receptor activation by dynamic membrane binding of the CD3ε cytoplasmic tyrosine-based motif. Cell (2008), 135, 702-713.*
Intl. Search Report—Written Opinion dated Mar. 22, 2023 for PCT/US2022/078283.
Kochenderfer, J.N. et al. (2010) "Eradication of B-lineage cells and regression of lymphoma in a patient treated with autologous T cells genetically engineered to recognize CD19" Blood 116(20):4099-4102.
Office Action dated Nov. 15, 2023 for Taiwanese Appl. No. 111139457.
Office Action dated Apr. 1, 2025 for Japanese Appl. No. 2024-522398.
Office Action received May 28, 2025 for Eurasian Appl. No. 202490664.
Office Action received Aug. 21, 2025 for Egyptian Appl. No. EP/P/2024/00501.
Office Action dated Nov. 14, 2025 for Malaysian Appl. No. PI2024002138.
Office Action dated Nov. 18, 2025 for Japanese Appl. No. 2024-522398.
Office Action received Jan. 28, 2026 for Eurasian Appl. No. 202490664.
2011 "CD3e molecule, epsilon (CD3-TCR complex) [Nomascus concolor]" NCBI GenBank:BAJ16135.1.
Office Action dated Jun. 17, 2026 for United Arab Emirates Appl. No. P2024-00933.

* cited by examiner

SEQUENCE LISTING

```
Sequence total quantity: 95
SEQ ID NO: 1            moltype = AA  length = 120
FEATURE                 Location/Qualifiers
source                  1..120
                        mol_type = protein
                        organism = synthetic construct
SEQUENCE: 1
EVKLQESGPG LVAPSQSLSV TCTVSGVSLP DYGVSWIRQP PRKGLEWLGV IWGSETTYYN  60
SALKSRLTII KDNSKSQVFL KMNSLQTDDT AIYYCAKHYY YGGSYAMDYW GQGTSVTVSS  120

SEQ ID NO: 2            moltype = AA  length = 8
FEATURE                 Location/Qualifiers
source                  1..8
                        mol_type = protein
                        organism = synthetic construct
SEQUENCE: 2
GVSLPDYG                                                           8

SEQ ID NO: 3            moltype = AA  length = 5
FEATURE                 Location/Qualifiers
source                  1..5
                        mol_type = protein
                        organism = synthetic construct
SEQUENCE: 3
DYGVS                                                              5

SEQ ID NO: 4            moltype = AA  length = 7
FEATURE                 Location/Qualifiers
source                  1..7
                        mol_type = protein
                        organism = synthetic construct
SEQUENCE: 4
GVSLPDY                                                            7

SEQ ID NO: 5            moltype = AA  length = 7
FEATURE                 Location/Qualifiers
source                  1..7
                        mol_type = protein
                        organism = synthetic construct
SEQUENCE: 5
IWGSETT                                                            7

SEQ ID NO: 6            moltype = AA  length = 16
FEATURE                 Location/Qualifiers
source                  1..16
                        mol_type = protein
                        organism = synthetic construct
SEQUENCE: 6
VIWGSETTYY NSALKS                                                  16

SEQ ID NO: 7            moltype = AA  length = 5
FEATURE                 Location/Qualifiers
source                  1..5
                        mol_type = protein
                        organism = synthetic construct
SEQUENCE: 7
WGSET                                                              5

SEQ ID NO: 8            moltype = AA  length = 14
FEATURE                 Location/Qualifiers
source                  1..14
                        mol_type = protein
                        organism = synthetic construct
SEQUENCE: 8
AKHYYYGGSY AMDY                                                    14

SEQ ID NO: 9            moltype = AA  length = 12
FEATURE                 Location/Qualifiers
source                  1..12
                        mol_type = protein
                        organism = synthetic construct
```

```
SEQUENCE: 9
HYYYGGSYAM DY                                                    12

SEQ ID NO: 10           moltype = AA  length = 12
FEATURE                 Location/Qualifiers
source                  1..12
                        mol_type = protein
                        organism = synthetic construct
SEQUENCE: 10
HYYYGGSYAM DY                                                    12

SEQ ID NO: 11           moltype = AA  length = 107
FEATURE                 Location/Qualifiers
source                  1..107
                        mol_type = protein
                        organism = synthetic construct
SEQUENCE: 11
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEIT               107

SEQ ID NO: 12           moltype = AA  length = 11
FEATURE                 Location/Qualifiers
source                  1..11
                        mol_type = protein
                        organism = synthetic construct
SEQUENCE: 12
RASQDISKYL N                                                     11

SEQ ID NO: 13           moltype = AA  length = 11
FEATURE                 Location/Qualifiers
source                  1..11
                        mol_type = protein
                        organism = synthetic construct
SEQUENCE: 13
RASQDISKYL N                                                     11

SEQ ID NO: 14           moltype = AA  length = 11
FEATURE                 Location/Qualifiers
source                  1..11
                        mol_type = protein
                        organism = synthetic construct
SEQUENCE: 14
RASQDISKYL N                                                     11

SEQ ID NO: 15           moltype = AA  length = 7
FEATURE                 Location/Qualifiers
source                  1..7
                        mol_type = protein
                        organism = synthetic construct
SEQUENCE: 15
HTSRLHS                                                          7

SEQ ID NO: 16           moltype = AA  length = 7
FEATURE                 Location/Qualifiers
source                  1..7
                        mol_type = protein
                        organism = synthetic construct
SEQUENCE: 16
HTSRLHS                                                          7

SEQ ID NO: 17           moltype = AA  length = 7
FEATURE                 Location/Qualifiers
source                  1..7
                        mol_type = protein
                        organism = synthetic construct
SEQUENCE: 17
HTSRLHS                                                          7

SEQ ID NO: 18           moltype = AA  length = 9
FEATURE                 Location/Qualifiers
source                  1..9
                        mol_type = protein
                        organism = synthetic construct
SEQUENCE: 18
QQGNTLPYT                                                        9

SEQ ID NO: 19           moltype = AA  length = 9
FEATURE                 Location/Qualifiers
```

-continued

```
source                  1..9
                        mol_type = protein
                        organism = synthetic construct
SEQUENCE: 19
QQGNTLPYT                                                        9

SEQ ID NO: 20           moltype = AA  length = 9
FEATURE                 Location/Qualifiers
source                  1..9
                        mol_type = protein
                        organism = synthetic construct
SEQUENCE: 20
QQGNTLPYT                                                        9

SEQ ID NO: 21           moltype = AA  length = 245
FEATURE                 Location/Qualifiers
source                  1..245
                        mol_type = protein
                        organism = synthetic construct
SEQUENCE: 21
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGST SGSGKPGSGE  120
GSTKGEVKLQ ESGPGLVAPS QSLSVTCTVS GVSLPDYGVS WIRQPPRKGL EWLGVIWGSE  180
TTYYNSALKS RLTIIKDNSK SQVFLKMNSL QTDDTAIYYC AKHYYYGGSY AMDYWGQGTS  240
VTVSS                                                            245

SEQ ID NO: 22           moltype = AA  length = 18
FEATURE                 Location/Qualifiers
source                  1..18
                        mol_type = protein
                        organism = synthetic construct
SEQUENCE: 22
GSTSGSGKPG SGEGSTKG                                              18

SEQ ID NO: 23           moltype = AA  length = 119
FEATURE                 Location/Qualifiers
source                  1..119
                        mol_type = protein
                        organism = synthetic construct
SEQUENCE: 23
QVQLVQSGAE VKKPGSSVKV SCKDSGGTFS SYAISWVRQA PGQGLEWMGG IIPIFGTTNY  60
AQQFQGRVTI TADESTSTAY MELSSLRSED TAVYYCAREA VAADWLDPWG QGTLVTVSS   119

SEQ ID NO: 24           moltype = AA  length = 8
FEATURE                 Location/Qualifiers
source                  1..8
                        mol_type = protein
                        organism = synthetic construct
SEQUENCE: 24
GGTFSSYA                                                         8

SEQ ID NO: 25           moltype = AA  length = 5
FEATURE                 Location/Qualifiers
source                  1..5
                        mol_type = protein
                        organism = synthetic construct
SEQUENCE: 25
SYAIS                                                            5

SEQ ID NO: 26           moltype = AA  length = 7
FEATURE                 Location/Qualifiers
source                  1..7
                        mol_type = protein
                        organism = synthetic construct
SEQUENCE: 26
GGTFSSY                                                          7

SEQ ID NO: 27           moltype = AA  length = 8
FEATURE                 Location/Qualifiers
source                  1..8
                        mol_type = protein
                        organism = synthetic construct
SEQUENCE: 27
IIPIFGTT                                                         8

SEQ ID NO: 28           moltype = AA  length = 17
FEATURE                 Location/Qualifiers
```

-continued

```
source                  1..17
                        mol_type = protein
                        organism = synthetic construct
SEQUENCE: 28
GIIPIFGTTN YAQQFQG                                              17

SEQ ID NO: 29           moltype = AA  length = 4
FEATURE                 Location/Qualifiers
source                  1..4
                        mol_type = protein
                        organism = synthetic construct
SEQUENCE: 29
PIFG                                                            4

SEQ ID NO: 30           moltype = AA  length = 12
FEATURE                 Location/Qualifiers
source                  1..12
                        mol_type = protein
                        organism = synthetic construct
SEQUENCE: 30
AREAVAADWL DP                                                   12

SEQ ID NO: 31           moltype = AA  length = 10
FEATURE                 Location/Qualifiers
source                  1..10
                        mol_type = protein
                        organism = synthetic construct
SEQUENCE: 31
EAVAADWLDP                                                      10

SEQ ID NO: 32           moltype = AA  length = 8
FEATURE                 Location/Qualifiers
source                  1..8
                        mol_type = protein
                        organism = synthetic construct
SEQUENCE: 32
AVAADWLD                                                        8

SEQ ID NO: 33           moltype = AA  length = 108
FEATURE                 Location/Qualifiers
source                  1..108
                        mol_type = protein
                        organism = synthetic construct
SEQUENCE: 33
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSRFTFG PGTKVDIK            108

SEQ ID NO: 34           moltype = AA  length = 7
FEATURE                 Location/Qualifiers
source                  1..7
                        mol_type = protein
                        organism = synthetic construct
SEQUENCE: 34
QSVSSSY                                                         7

SEQ ID NO: 35           moltype = AA  length = 12
FEATURE                 Location/Qualifiers
source                  1..12
                        mol_type = protein
                        organism = synthetic construct
SEQUENCE: 35
RASQSVSSSY LA                                                   12

SEQ ID NO: 36           moltype = AA  length = 8
FEATURE                 Location/Qualifiers
source                  1..8
                        mol_type = protein
                        organism = synthetic construct
SEQUENCE: 36
SQSVSSSY                                                        8

SEQ ID NO: 37           moltype =   length =
SEQUENCE: 37
000

SEQ ID NO: 38           moltype = AA  length = 7
FEATURE                 Location/Qualifiers
```

```
source                  1..7
                        mol_type = protein
                        organism = synthetic construct
SEQUENCE: 38
GASSRAT                                                   7

SEQ ID NO: 39           moltype =   length =
SEQUENCE: 39
000

SEQ ID NO: 40           moltype = AA  length = 9
FEATURE                 Location/Qualifiers
source                  1..9
                        mol_type = protein
                        organism = synthetic construct
SEQUENCE: 40
QQYGSSRFT                                                 9

SEQ ID NO: 41           moltype = AA  length = 9
FEATURE                 Location/Qualifiers
source                  1..9
                        mol_type = protein
                        organism = synthetic construct
SEQUENCE: 41
QQYGSSRFT                                                 9

SEQ ID NO: 42           moltype = AA  length = 6
FEATURE                 Location/Qualifiers
source                  1..6
                        mol_type = protein
                        organism = synthetic construct
SEQUENCE: 42
YGSSRF                                                    6

SEQ ID NO: 43           moltype = AA  length = 245
FEATURE                 Location/Qualifiers
source                  1..245
                        mol_type = protein
                        organism = synthetic construct
SEQUENCE: 43
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSRFTFG PGTKVDIKGS TSGSGKPGSG  120
EGSTKGQVQL VQSGAEVKKP GSSVKVSCKD SGGTFSSYAI SWVRQAPGQG LEWMGGIIPI  180
FGTTNYAQQF QGRVTITADE STSTAYMELS SLRSEDTAVY YCAREAVAAD WLDPWGQGTL  240
VTVSS                                                     245

SEQ ID NO: 44           moltype = AA  length = 21
FEATURE                 Location/Qualifiers
source                  1..21
                        mol_type = protein
                        organism = synthetic construct
SEQUENCE: 44
MALPVTALLL PLALLLHAAR P                                   21

SEQ ID NO: 45           moltype =   length =
SEQUENCE: 45
000

SEQ ID NO: 46           moltype = AA  length = 8
FEATURE                 Location/Qualifiers
source                  1..8
                        mol_type = protein
                        organism = synthetic construct
SEQUENCE: 46
GGGSGGGS                                                  8

SEQ ID NO: 47           moltype = AA  length = 39
FEATURE                 Location/Qualifiers
source                  1..39
                        mol_type = protein
                        organism = synthetic construct
SEQUENCE: 47
IEVMYPPPYL DNEKSNGTII HVKGKHLCPS PLFPGPSKP                39

SEQ ID NO: 48           moltype = AA  length = 30
FEATURE                 Location/Qualifiers
source                  1..30
                        mol_type = protein
                        organism = synthetic construct
```

```
SEQUENCE: 48
LDNEKSNGTI IHVKGKHLCP SPLFPGPSKP                                30

SEQ ID NO: 49          moltype = AA  length = 55
FEATURE                Location/Qualifiers
source                 1..55
                       mol_type = protein
                       organism = synthetic construct
SEQUENCE: 49
FVPVFLPAKP TTTPAPRPPT PAPTIASQPL SLRPEACRPA AGGAVHTRGL DFACD     55

SEQ ID NO: 50          moltype = AA  length = 27
FEATURE                Location/Qualifiers
source                 1..27
                       mol_type = protein
                       organism = synthetic construct
SEQUENCE: 50
FWVLVVVGGV LACYSLLVTV AFIIFWV                                   27

SEQ ID NO: 51          moltype = AA  length = 28
FEATURE                Location/Qualifiers
source                 1..28
                       mol_type = protein
                       organism = synthetic construct
SEQUENCE: 51
IYIWAPLAGT CGVLLLSLVI TLYCNHRN                                  28

SEQ ID NO: 52          moltype = AA  length = 55
FEATURE                Location/Qualifiers
source                 1..55
                       mol_type = protein
                       organism = synthetic construct
SEQUENCE: 52
KNRKAKAKPV TRGAGAGGRQ RGQNKERPPP VPNPDYEPIR KGQRDLYSGL NQRRI     55

SEQ ID NO: 53          moltype = DNA  length = 165
FEATURE                Location/Qualifiers
source                 1..165
                       mol_type = other DNA
                       organism = synthetic construct
SEQUENCE: 53
aagaaccgga aggccaaggc caagcctgtg acaagaggtg ctggtgctgg cggcagacag  60
agaggccaga acaaagaaag acctcctcct gtgcctaatc ctgactacga gcccatccgg  120
aagggccaga gagatctgta cagcggcctg aaccagcggc ggatt               165

SEQ ID NO: 54          moltype = DNA  length = 165
FEATURE                Location/Qualifiers
source                 1..165
                       mol_type = other DNA
                       organism = synthetic construct
SEQUENCE: 54
aagaaccgca aagcaaaggc aaaacccgtc acacgaggag cgggcgcagg gggacgacaa  60
cgcggtcaga ataaggaacg cccgcctcca gtaccaaatc cagattatga accaattcgg  120
aagggacaac gcgatctcta ctccggtctc aatcagaggc gaatt               165

SEQ ID NO: 55          moltype = AA  length = 45
FEATURE                Location/Qualifiers
source                 1..45
                       mol_type = protein
                       organism = synthetic construct
SEQUENCE: 55
GHETGRLSGA ADTQALLRND QVYQPLRDRD DAQYSHLGGN WARNK                45

SEQ ID NO: 56          moltype = DNA  length = 135
FEATURE                Location/Qualifiers
source                 1..135
                       mol_type = other DNA
                       organism = synthetic construct
SEQUENCE: 56
ggacacgaaa caggcagact ttctggcgcc gctgatacac aggccctgct gagaaacgac  60
caggtgtacc agcctctgag agacagagat gacgcccagt actctcacct cggcggcaat  120
tgggccagaa acaag                                                 135

SEQ ID NO: 57          moltype = AA  length = 45
FEATURE                Location/Qualifiers
source                 1..45
                       mol_type = protein
                       organism = synthetic construct
```

```
SEQUENCE: 57
GQDGVRQSRA SDKQTLLPND QLYQPLKDRE DDQYSHLQGN QLRRN                  45

SEQ ID NO: 58           moltype = DNA  length = 135
FEATURE                 Location/Qualifiers
source                  1..135
                        mol_type = other DNA
                        organism = synthetic construct
SEQUENCE: 58
ggacaggatg gcgtcagaca gagcagagcc agcgacaagc aaaccctgct gcctaacgac  60
cagctgtacc agcctctgaa ggacagagag gacgaccagt acagccatct gcagggcaac  120
cagctgcgga gaaac                                                   135

SEQ ID NO: 59           moltype = AA  length = 52
FEATURE                 Location/Qualifiers
source                  1..52
                        mol_type = protein
                        organism = synthetic construct
SEQUENCE: 59
YFLGRLVPRG RGAAEAATRK QRITETESPY QELQGQRSDV YSDLNTQRPY YK          52

SEQ ID NO: 60           moltype = DNA  length = 156
FEATURE                 Location/Qualifiers
source                  1..156
                        mol_type = other DNA
                        organism = synthetic construct
SEQUENCE: 60
tacttcctgg gcagactggt gcctagagga agaggagctg ctgaggctgc taccagaaag  60
cagagaatca ccgagaccga gagcccttac caggagctgc agggacagag aagcgacgtg  120
tacagcgacc tgaacaccca gagaccttac tacaag                            156

SEQ ID NO: 61           moltype = AA  length = 41
FEATURE                 Location/Qualifiers
source                  1..41
                        mol_type = protein
                        organism = synthetic construct
SEQUENCE: 61
RSKRSRLLHS DYMNMTPRRP GPTRKHYQPY APPRDFAAYR S                      41

SEQ ID NO: 62           moltype = AA  length = 401
FEATURE                 Location/Qualifiers
source                  1..401
                        mol_type = protein
                        organism = synthetic construct
SEQUENCE: 62
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGST SGSGKPGSGE  120
GSTKGEVKLQ ESGPGLVAPS QSLSVTCTVS GVSLPDYGVS WIRQPPRKGL EWLGVIWGSE  180
TTYYNSALKS RLTIIKDNSK SQVFLKMNSL QTDDTAIYYC AKHYYYGGSY AMDYWGQGTS  240
VTVSSAAALD NEKSNGTIIH VKGKHLCPSP LFPGPSKPFW VLVVVGGVLA CYSLLVTVAF  300
IIFWVRSKRS RLLHSDYMNM TPRRPGPTRK HYQPYAPPRD FAAYRSKNRK AKAKPVTRGA  360
GAGGRQRGQN KERPPPVPNP DYEPIRKGQR DLYSGLNQRR I                      401

SEQ ID NO: 63           moltype = DNA  length = 1203
FEATURE                 Location/Qualifiers
source                  1..1203
                        mol_type = other DNA
                        organism = synthetic construct
SEQUENCE: 63
gatatacaga tgacccaaac gacgtctagc ctcagtgcgt cactcgggga tcgggtgaca  60
attagctgca gggctagcca ggatatttca aaatatctta actggtatca acaaaagcca  120
gatggaaccg taaaactgct catataccac accagtcgcc tgcattcagg ggttccgagc  180
cgcttttctg ggagcggtag cggaactgat tatagcttga caataagcaa cctcgagcag  240
gaagacattg cgacgtactt ctgtcagcaa gggaacacgc tgccgtatac cttcggtggc  300
ggcactaaac tggaaatcac gggatctacg tctggatccg gaaaacctgg atctggtgaa  360
ggatccacta aaggcgaagt caagttgcaa gagtctggac ctggtctcgt ggcaccttca  420
cagtcactct ccgttacctg taccgtatct ggagtttcac ttcccgacta tggcgtgtca  480
tggatacgcc aaccaccgcg aaaaggtctt gaatggctgg gcgttatctg gggatccgaa  540
accacatact acaactctgc gctcaagtca cggctgacta ttataaagga caattcaaag  600
agccaagtgt tcctgaaaat gaacagcctg cagactgatg acactgcaat atattactgc  660
gccaagcatt actattacgg cggatcttac gcgatggatt attggggcca gggcacctct  720
gtaacagtca gctccgcggc cgcattggac aatgaaaaat ccaatggcac aataattcat  780
gtaaagggca aacacttgtg tcctagccca ctctttcctg gtccgtctaa accgttttgg  840
gtgctcgttg tggttggagg cgtcctggct tgttactctc tgttggtgac tgtagccttt  900
ataatattct gggttagaag caaacgaagt aggcttttac attcagacta tatgaacatg  960
acaccaagac gccccggccc cacaagaaaa cactatcagc cctatgctcc gcctcgggac  1020
ttcgctgctt accgaagcaa gaaccgcaaa gcaaaggcaa aacccgtcac acgaggagcg  1080
```

```
ggcgcagggg gacgacaacg cggtcagaat aaggaacgcc cgcctccagt accaaatcca  1140
gattatgaac caattcggaa gggacaacgc gatctctact ccggtctcaa tcagaggcga  1200
att                                                                1203

SEQ ID NO: 64          moltype = DNA  length = 1203
FEATURE                Location/Qualifiers
source                 1..1203
                       mol_type = other DNA
                       organism = synthetic construct
SEQUENCE: 64
gacatccaaa tgacccaaac cacctcctcc ctgagcgcct cccttggaga ccgagttacc  60
atctcctgcc gagcttctca agacatctcc aagtacttga attggtatca acaaaagccc  120
gacggaaccg tgaagctgct gatctaccac acatcccggc tgcactctgg cgttccctca  180
agattctccg gctctggaag cggaaccgac tactccctga ccatctccaa cctggagcaa  240
gaggacatcg ctacctactt ctgccaacaa ggcaacaccc tgccttacac cttcggagga  300
ggaaccaagc tggagatcac cggaagcaca agcggatctg gcaagcctgg aagcggagag  360
ggaagcacca agggagaggt gaagctgcaa gagagcggac ctggattggt ggccccctca  420
caatccctga gcgttacatg cactgtgagc ggcgtgtccc ttcctgacta cggcgtttcc  480
tggatccgcc aacctccaag aaagggactg gagtggctgg gagtgatctg gggaagcgag  540
accacctact acaactccgc cctgaagagc cgactgacca tcatcaagga caactccaag  600
agccaagtgt tcctgaagat gaactctctc caaaccgacg acaccgctat ctactactgc  660
gctaagcact actactacgg aggaagctac gctatggact actggggaca aggcacctct  720
gtgaccgtct cctctgccgc cgctctggac aacgagaaga gcaacggaac catcatccac  780
gtgaagggaa agcacctgtg cccctctcct ctgttccctg gaccctccaa gcctttctgg  840
gtgctcgtgg tggtgggagg agtgctggct tgctactccc tgcttgtgac cgtggctttc  900
atcatcttct gggttagaag caagagaagc agactgctgc acagcgacta catgaacatg  960
acccctagaa ggcccggacc taccagaaag cactaccagc cttacgctcc tcctagagac  1020
ttcgctgctt acagaagcaa gaaccggaag gccaaggcca agcctgtgac aagaggtgct  1080
ggtgctggcg gcagacagag aggccagaac aaagaaagac ctcctcctgt gcctaatcct  1140
gactacgagc ccatccggaa gggccagaga gatctgtaca gcggcctgaa ccagcggcgg  1200
att                                                                1203

SEQ ID NO: 65          moltype = AA  length = 391
FEATURE                Location/Qualifiers
source                 1..391
                       mol_type = protein
                       organism = synthetic construct
SEQUENCE: 65
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGST SGSGKPGSGE  120
GSTKGEVKLQ ESGPGLVAPS QSLSVTCTVS GVSLPDYGVS WIRQPPRKGL EWLGVIWGSE  180
TTYYNSALKS RLTIIKDNSK SQVFLKMNSL QTDDTAIYYC AKHYYYGGSY AMDYWGQGTS  240
VTVSSAAALD NEKSNGTIIH VKGKHLCPSP LFPGPSKPFW VLVVVGGVLA CYSLLVTVAF  300
IIFWVRSKRS RLLHSDYMNM TPRRPGPTRK HYQPYAPPRD FAAYRSGHET GRLSGAADTQ  360
ALLRNDQVYQ PLRDRDDAQY SHLGGNWARN K                                 391

SEQ ID NO: 66          moltype = DNA  length = 1173
FEATURE                Location/Qualifiers
source                 1..1173
                       mol_type = other DNA
                       organism = synthetic construct
SEQUENCE: 66
gacatccaaa tgacccaaac cacctcctcc ctgagcgcct cccttggaga ccgagttacc  60
atctcctgcc gagcttctca agacatctcc aagtacttga attggtatca acaaaagccc  120
gacggaaccg tgaagctgct gatctaccac acatcccggc tgcactctgg cgttccctca  180
agattctccg gctctggaag cggaaccgac tactccctga ccatctccaa cctggagcaa  240
gaggacatcg ctacctactt ctgccaacaa ggcaacaccc tgccttacac cttcggagga  300
ggaaccaagc tggagatcac cggaagcaca agcggatctg gcaagcctgg aagcggagag  360
ggaagcacca agggagaggt gaagctgcaa gagagcggac ctggattggt ggccccctca  420
caatccctga gcgttacatg cactgtgagc ggcgtgtccc ttcctgacta cggcgtttcc  480
tggatccgcc aacctccaag aaagggactg gagtggctgg gagtgatctg gggaagcgag  540
accacctact acaactccgc cctgaagagc cgactgacca tcatcaagga caactccaag  600
agccaagtgt tcctgaagat gaactctctc caaaccgacg acaccgctat ctactactgc  660
gctaagcact actactacgg aggaagctac gctatggact actggggaca aggcacctct  720
gtgaccgtct cctctgccgc cgctctggac aacgagaaga gcaacggaac catcatccac  780
gtgaagggaa agcacctgtg cccctctcct ctgttccctg gaccctccaa gcctttctgg  840
gtgctcgtgg tggtgggagg agtgctggct tgctactccc tgcttgtgac cgtggctttc  900
atcatcttct gggttagaag caagagaagc agactgctgc acagcgacta catgaacatg  960
acccctagaa ggcccggacc taccagaaag cactaccagc cttacgctcc tcctagagac  1020
ttcgctgctt acagaagcgg acacgaaaca ggcagacttt ctggcgccgc tgatacacag  1080
gccctgctga gaaacgacca ggtgtaccag cctctgagag acagagatga cgcccagtac  1140
tctcacctcg gcggcaattg ggccagaaac aag                               1173

SEQ ID NO: 67          moltype = AA  length = 391
FEATURE                Location/Qualifiers
source                 1..391
                       mol_type = protein
                       organism = synthetic construct
```

SEQUENCE: 67
DIQMTQTTSS LSASLGDRVT ISCRASQDIS KYLNWYQQKP DGTVKLLIYH TSRLHSGVPS 60
RFSGSGSGTD YSLTISNLEQ EDIATYFCQQ GNTLPYTFGG GTKLEITGST SGSGKPGSGE 120
GSTKGEVKLQ ESGPGLVAPS QSLSVTCTVS GVSLPDYGVS WIRQPPRKGL EWLGVIWGSE 180
TTYYNSALKS RLTIIKDNSK SQVFLKMNSL QTDDTAIYYC AKHYYYGGSY AMDYWGQGTS 240
VTVSSAAALD NEKSNGTIIH VKGKHLCPSP LFPGPSKPFW VLVVVGGVLA CYSLLVTVAF 300
IIFWVRSKRS RLLHSDYMNM TPRRPGPTRK HYQPYAPPRD FAAYRSGQDG VRQSRASDKQ 360
TLLPNDQLYQ PLKDREDDQY SHLQGNQLRR N 391

SEQ ID NO: 68 moltype = DNA length = 1173
FEATURE Location/Qualifiers
source 1..1173
mol_type = other DNA
organism = synthetic construct
SEQUENCE: 68
gacatccaaa tgacccaaac cacctcctcc ctgagcgcct cccttggaga ccgagttacc 60
atctcctgcc gagcttctca agacatctcc aagtacttga attggtatca acaaaagccc 120
gacggaaccg tgaagctgct gatctaccac acatcccggc tgcactctgg cgttccctca 180
agattctccg gctctggaag cggaaccgac tactccctga ccatctccaa cctggagcaa 240
gaggacatcg ctacctactt ctgccaacaa ggcaacaccc tgccttacac cttcggagga 300
ggaaccaagc tggagatcac cggaagcaca agcggatctg gcaagcctgg aagcggagag 360
ggaagcacca agggagaggt gaagctgcaa gagagcggac ctggattggt ggccccctca 420
caatccctga gcgttacatg cactgtgagc ggcgtgtccc ttcctgacta cggcgtttcc 480
tggatccgcc aacctccaag aaagggactg gagtggctgg gagtgatctg ggaagcgag 540
accacctact acaactccgc cctgaagagc cgactgacca tcatcaagga caactccaag 600
agccaagtgt tcctgaagat gaactctctc caaaccgacg acaccgctat ctactactgc 660
gctaagcact actactacgg aggaagctac gctatggact actggggaca aggcacctct 720
gtgaccgtct cctctgccgc cgctctggac aacgagaaga gcaacggaac catcatccac 780
gtgaagggaa agcacctgtg cccctctcct ctgttccctg gaccctccaa gcctttctgg 840
gtgctcgtgg tggtgggagg agtgctggct tgctactccc tgcttgtgac cgtggctttc 900
atcatcttct gggttagaag caagagaagc agactgctgc acagcgacta catgaacatg 960
acccctagaa ggcccggacc taccagaaag cactaccagc cttacgctcc tcctagagac 1020
ttcgctgctt acagaagcgg acaggatggc gtcagacaga gcagagccag cgacaagcaa 1080
accctgctgc ctaacgacca gctgtaccag cctctgaagg acagagagga cgaccagtac 1140
agccatctgc agggcaacca gctgcggaga aac 1173

SEQ ID NO: 69 moltype = AA length = 398
FEATURE Location/Qualifiers
source 1..398
mol_type = protein
organism = synthetic construct
SEQUENCE: 69
DIQMTQTTSS LSASLGDRVT ISCRASQDIS KYLNWYQQKP DGTVKLLIYH TSRLHSGVPS 60
RFSGSGSGTD YSLTISNLEQ EDIATYFCQQ GNTLPYTFGG GTKLEITGST SGSGKPGSGE 120
GSTKGEVKLQ ESGPGLVAPS QSLSVTCTVS GVSLPDYGVS WIRQPPRKGL EWLGVIWGSE 180
TTYYNSALKS RLTIIKDNSK SQVFLKMNSL QTDDTAIYYC AKHYYYGGSY AMDYWGQGTS 240
VTVSSAAALD NEKSNGTIIH VKGKHLCPSP LFPGPSKPFW VLVVVGGVLA CYSLLVTVAF 300
IIFWVRSKRS RLLHSDYMNM TPRRPGPTRK HYQPYAPPRD FAAYRSYFLG RLVPRGRGAA 360
EAATRKQRIT ETESPYQELQ GQRSDVYSDL NTQRPYYK 398

SEQ ID NO: 70 moltype = DNA length = 1194
FEATURE Location/Qualifiers
source 1..1194
mol_type = other DNA
organism = synthetic construct
SEQUENCE: 70
gacatccaaa tgacccaaac cacctcctcc ctgagcgcct cccttggaga ccgagttacc 60
atctcctgcc gagcttctca agacatctcc aagtacttga attggtatca acaaaagccc 120
gacggaaccg tgaagctgct gatctaccac acatcccggc tgcactctgg cgttccctca 180
agattctccg gctctggaag cggaaccgac tactccctga ccatctccaa cctggagcaa 240
gaggacatcg ctacctactt ctgccaacaa ggcaacaccc tgccttacac cttcggagga 300
ggaaccaagc tggagatcac cggaagcaca agcggatctg gcaagcctgg aagcggagag 360
ggaagcacca agggagaggt gaagctgcaa gagagcggac ctggattggt ggccccctca 420
caatccctga gcgttacatg cactgtgagc ggcgtgtccc ttcctgacta cggcgtttcc 480
tggatccgcc aacctccaag aaagggactg gagtggctgg gagtgatctg ggaagcgag 540
accacctact acaactccgc cctgaagagc cgactgacca tcatcaagga caactccaag 600
agccaagtgt tcctgaagat gaactctctc caaaccgacg acaccgctat ctactactgc 660
gctaagcact actactacgg aggaagctac gctatggact actggggaca aggcacctct 720
gtgaccgtct cctctgccgc cgctctggac aacgagaaga gcaacggaac catcatccac 780
gtgaagggaa agcacctgtg cccctctcct ctgttccctg gaccctccaa gcctttctgg 840
gtgctcgtgg tggtgggagg agtgctggct tgctactccc tgcttgtgac cgtggctttc 900
atcatcttct gggttagaag caagagaagc agactgctgc acagcgacta catgaacatg 960
acccctagaa ggcccggacc taccagaaag cactaccagc cttacgctcc tcctagagac 1020
ttcgctgctt acagaagcta cttcctgggc agactggtgc ctagaggaag aggagctgct 1080
gaggctgcta ccagaaagca gagaatcacc gagaccgaga gcccttacca ggagctgcag 1140
ggacagagaa gcgacgtgta cagcgacctg aacacccaga gaccttacta caag 1194

SEQ ID NO: 71 moltype = AA length = 458
FEATURE Location/Qualifiers

```
source                  1..458
                        mol_type = protein
                        organism = synthetic construct
SEQUENCE: 71
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGST SGSGKPGSGE  120
GSTKGEVKLQ ESGPGLVAPS QSLSVTCTVS GVSLPDYGVS WIRQPPRKGL EWLGVIWGSE  180
TTYYNSALKS RLTIIKDNSK SQVFLKMNSL QTDDTAIYYC AKHYYYGGSY AMDYWGQGTS  240
VTVSSAAALD NEKSNGTIIH VKGKHLCPSP LFPGPSKPFW VLVVVGGVLA CYSLLVTVAF  300
IIFWVRSKRS RLLHSDYMNM TPRRPGPTRK HYQPYAPPRD FAAYRSRVKF SRSADAPAYQ  360
QGQNQLYNEL NLGRREEYDV LDKRRGRDPE MGGKPRRKNP QEGLYNELQK DKMAEAYSEI  420
GMKGERRRGK GHDGLYQGLS TATKDTYDAL HMQALPPR                         458

SEQ ID NO: 72           moltype = DNA  length = 1374
FEATURE                 Location/Qualifiers
source                  1..1374
                        mol_type = other DNA
                        organism = synthetic construct
SEQUENCE: 72
gacatccaaa tgacccaaac cacctcctcc ctgagcgcct cccttggaga ccgagttacc  60
atctcctgcc gagcttctca agacatctcc aagtacttga attggtatca acaaaagccc  120
gacggaaccg tgaagctgct gatctaccac acatcccggc tgcactctgg cgttccctca  180
agattctccg gctctggaag cggaaccgac tactccctga ccatctccaa cctggagcaa  240
gaggacatcg ctacctactt ctgccaacaa ggcaacaccc tgccttacac cttcggagga  300
ggaaccaagc tggagatcac cggaagcaca agcggatctg gcaagcctgg aagcggagag  360
ggaagcacca agggagaggt gaagctgcaa gagagcggac ctggattggt ggccccctca  420
caatccctga gcgttacatg cactgtgagc ggcgtgtccc ttcctgacta cggcgtttcc  480
tggatccgcc aacctccaag aaagggactg gagtggctgg gagtgatctg ggaagcgag  540
accacctact acaactccgc cctgaagagc cgactgacca tcatcaagga caactccaag  600
agccaagtgt tcctgaagat gaactctctc caaaccgacg acaccgctat ctactactgc  660
gctaagcact actactacgg aggaagctac gctatggact actggggaca aggcacctct  720
gtgaccgtct cctctgccgc cgctctggac aacgagaaga gcaacggaac catcatccac  780
gtgaagggaa agcacctgtg cccctctcct ctgttccctg gaccctccaa gcctttctgg  840
gtgctcgtgg tggtgggagg agtgctggct tgctactccc tgcttgtgac cgtggctttc  900
atcatcttct gggttagaag caagagaagc agactgctgc acagcgacta catgaacatg  960
acccctagaa ggcccggacc taccagaaag cactaccagc cttacgctcc tcctagagac  1020
ttcgctgctt acagaagcag ggtgaagttc tcaagaagcg ctgacgctcc tgcttaccaa  1080
caaggccaaa accaactgta caacgagctg aacctgggaa gaagagagga atacgacgtc  1140
ctggacaaga gaagaggaag agaccctgag atgggaggaa agccaagaag aaagaaccct  1200
caagagggcc tgtacaacga gctgcaaaag gacaagatgg ctgaggctta ctccgagatc  1260
ggaatgaagg gagagagaag aagaggaaag ggacacgacg gactgtacca aggcctgagc  1320
accgctacca aggacaccta cgacgctctg cacatgcaag ccctgcctcc tagg        1374

SEQ ID NO: 73           moltype = AA  length = 458
FEATURE                 Location/Qualifiers
source                  1..458
                        mol_type = protein
                        organism = synthetic construct
SEQUENCE: 73
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGST SGSGKPGSGE  120
GSTKGEVKLQ ESGPGLVAPS QSLSVTCTVS GVSLPDYGVS WIRQPPRKGL EWLGVIWGSE  180
TTYYNSALKS RLTIIKDNSK SQVFLKMNSL QTDDTAIYYC AKHYYYGGSY AMDYWGQGTS  240
VTVSSAAALD NEKSNGTIIH VKGKHLCPSP LFPGPSKPFW VLVVVGGVLA CYSLLVTVAF  300
IIFWVRSKRS RLLHSDYMNM TPRRPGPTRK HYQPYAPPRD FAAYRSRVKF SRSADAPAYQ  360
QGQNQLYNEL NLGRREEYDV LDKRRGRDPE MGGKPRRKNP QEGLFNELQK DKMAEAFSEI  420
GMKGERRRGK GHDGLFQGLS TATKDTFDAL HMQALPPR                         458

SEQ ID NO: 74           moltype = DNA  length = 1374
FEATURE                 Location/Qualifiers
source                  1..1374
                        mol_type = other DNA
                        organism = synthetic construct
SEQUENCE: 74
gacatccaaa tgacccaaac cacctcctcc ctgagcgcct cccttggaga ccgagttacc  60
atctcctgcc gagcttctca agacatctcc aagtacttga attggtatca acaaaagccc  120
gacggaaccg tgaagctgct gatctaccac acatcccggc tgcactctgg cgttccctca  180
agattctccg gctctggaag cggaaccgac tactccctga ccatctccaa cctggagcaa  240
gaggacatcg ctacctactt ctgccaacaa ggcaacaccc tgccttacac cttcggagga  300
ggaaccaagc tggagatcac cggaagcaca agcggatctg gcaagcctgg aagcggagag  360
ggaagcacca agggagaggt gaagctgcaa gagagcggac ctggattggt ggccccctca  420
caatccctga gcgttacatg cactgtgagc ggcgtgtccc ttcctgacta cggcgtttcc  480
tggatccgcc aacctccaag aaagggactg gagtggctgg gagtgatctg ggaagcgag  540
accacctact acaactccgc cctgaagagc cgactgacca tcatcaagga caactccaag  600
agccaagtgt tcctgaagat gaactctctc caaaccgacg acaccgctat ctactactgc  660
gctaagcact actactacgg aggaagctac gctatggact actggggaca aggcacctct  720
gtgaccgtct cctctgccgc cgctctggac aacgagaaga gcaacggaac catcatccac  780
gtgaagggaa agcacctgtg cccctctcct ctgttccctg gaccctccaa gcctttctgg  840
gtgctcgtgg tggtgggagg agtgctggct tgctactccc tgcttgtgac cgtggctttc  900
```

```
atcatcttct gggttagaag caagagaagc agactgctgc acagcgacta catgaacatg  960
acccctagaa ggcccggacc taccagaaag cactaccagc cttacgctcc tcctagagac  1020
ttcgctgctt acagaagccg ggtgaagttc tcaagaagcg ctgacgctcc tgcttaccaa  1080
caaggccaaa accaactgta caacgagctg aacctgggaa gaagagagga atacgacgtc  1140
ctggacaaga gaagaggaag agaccctgag atgggaggaa agccaagaag aaagaaccct  1200
caagagggcc tgtttaacga gctgcaaaag gacaagatgg ctgaggcttt ctccgagatc  1260
ggaatgaagg gagagagaag aagaggaaag ggacacgacg gactgttcca aggcctgagc  1320
accgctacca aggacacctt cgacgctctg cacatgcaag ccctgcctcc tagg        1374

SEQ ID NO: 75          moltype = AA  length = 458
FEATURE                Location/Qualifiers
source                 1..458
                       mol_type = protein
                       organism = synthetic construct
SEQUENCE: 75
DIQMTQTTSS LSASLGDRVT ISCRASQDIS KYLNWYQQKP DGTVKLLIYH TSRLHSGVPS  60
RFSGSGSGTD YSLTISNLEQ EDIATYFCQQ GNTLPYTFGG GTKLEITGST SGSGKPGSGE  120
GSTKGEVKLQ ESGPGLVAPS QSLSVTCTVS GVSLPDYGVS WIRQPPRKGL EWLGVIWGSE  180
TTYYNSALKS RLTIIKDNSK SQVFLKMNSL QTDDTAIYYC AKHYYYGGSY AMDYWGQGTS  240
VTVSSAAALD NEKSNGTIIH VKGKHLCPSP LFPGPSKPFW VLVVVGGVLA CYSLLVTVAF  300
IIFWVRSKRS RLLHSDYMNM TPRRPGPTRK HYQPYAPPRD FAAYRSRVKF SRSADAPAYQ  360
QGQNQLYNEL NLGRREEYDV LDKRRGRDPE MGGKPRRKNP QEGLYNELQK DKMAEAYSEI  420
GMKGERRRGK GHDGLYQGLS TATKDTYDAL HMQALPPR                          458

SEQ ID NO: 76          moltype = DNA  length = 1374
FEATURE                Location/Qualifiers
source                 1..1374
                       mol_type = other DNA
                       organism = synthetic construct
SEQUENCE: 76
gatatacaga tgacccaaac gacgtctagc ctcagtgcgt cactcgggga tcgggtgaca  60
attagctgca gggctagcca ggatatttca aaatatctta actggtatca acaaaagcca  120
gatggaaccg taaaactgct catataccac accagtcgcc tgcattcagg ggttccgagc  180
cgcttttctg ggagcggtag cggaactgat tatagcttga caataagcaa cctcgagcag  240
gaagacattg cgacgtactt ctgtcagcaa gggaacacgc tgccgtatac cttcggtggc  300
ggcactaaac tggaaatcac gggatctacg tctggatccg gaaaacctgg atctggtgaa  360
ggatccacta aaggcgaagt caagttgcaa gagtctggac ctggtctcgt ggcaccttca  420
cagtcactct ccgttacctg taccgtatct ggagtttcac ttcccgacta tggcgtgtca  480
tggatacgcc aaccaccgcg aaaaggtctt gaatggctgg gcgttatctg gggatccgaa  540
accacatact acaactctgc gctcaagtca cggctgacta ttataaagga caattcaaag  600
agccaagtgt tcctgaaaat gaacagcctg cagactgatg acactgcaat atattactgc  660
gccaagcatt actattacgg cggatcttac gcgatggatt attggggcca gggcacctct  720
gtaacagtca gctccgcggc cgcattggac aatgaaaaat ccaatggcac aataattcat  780
gtaaagggca aacacttgtg tcctagccca ctctttcctg gtccgtctaa accgttttgg  840
gtgctcgttg tggttggagg cgtcctggct tgttactctc tgttggtgac tgtagccttt  900
ataatattct gggttagaag caaacgaagt aggcttttac attcagacta tatgaacatg  960
acaccaagac gccccggccc cacaagaaaa cactatcagc cctatgctcc gcctcgggac  1020
ttcgctgctt accgaagcag agttaagttc agcaggagcg ccgacgcacc tgcctaccaa  1080
caagggcaga atcaactgta caacgagctg aacctgggca gacgggagga atacgatgtg  1140
ctggacaaga ggagaggcag agaccccgag atgggcggca aacctagaag aaagaacccc  1200
caggagggcc tgtataatga gctccagaag gataagatgg ccgaggccta cagcgagatc  1260
ggcatgaagg gcgaaagaag aagaggcaag ggccacgacg gcctctacca gggcttaagc  1320
acagctacta aggacaccta cgacgccctg cacatgcaag ctctgccccc taga        1374

SEQ ID NO: 77          moltype = AA  length = 45
FEATURE                Location/Qualifiers
source                 1..45
                       mol_type = protein
                       organism = synthetic construct
SEQUENCE: 77
TTTPAPRPPT PAPTIASQPL SLRPEACRPA AGGAVHTRGL DFACD                  45

SEQ ID NO: 78          moltype = AA  length = 24
FEATURE                Location/Qualifiers
source                 1..24
                       mol_type = protein
                       organism = synthetic construct
SEQUENCE: 78
IYIWAPLAGT CGVLLLSLVI TLYC                                         24

SEQ ID NO: 79          moltype = DNA  length = 150
FEATURE                Location/Qualifiers
source                 1..150
                       mol_type = other DNA
                       organism = synthetic construct
SEQUENCE: 79
aagaaccgca aagcaaaggc aaaacccgtc acacgaggag cgggcgcagg gggacgacaa  60
cgcggtcaga ataaggaacg cccgcctcca gtaccaaatc cagattatga accaattcgg  120
aagggacaac gcgatctcta ctccggtctc                                   150
```

```
SEQ ID NO: 80          moltype = DNA  length = 165
FEATURE                Location/Qualifiers
source                 1..165
                       mol_type = other DNA
                       organism = synthetic construct
SEQUENCE: 80
aagaaccgca aagcaaaggc aaaacccgtc acacgaggag cgggcgcagg gggacgacaa  60
cgcggtcaga ataaggaacg cccgcctcca gtaccaaatc cagattatga accaattcgg  120
aagggacaac gcgatctcta ctccggtctc aatcagaagc gaatt                  165

SEQ ID NO: 81          moltype = DNA  length = 165
FEATURE                Location/Qualifiers
source                 1..165
                       mol_type = other DNA
                       organism = synthetic construct
SEQUENCE: 81
aagaaccgca aagcaaaggc aaaacccgtc acacgaggag cgggcgcagg gggacgacaa  60
cgcggtcaga ataaggaacg cccgcctcca gtaccaaatc cagattatga accaattcgg  120
aagggacaac gcgatctcta caacggtctc aatcagaagc gaatt                  165

SEQ ID NO: 82          moltype = DNA  length = 336
FEATURE                Location/Qualifiers
source                 1..336
                       mol_type = other DNA
                       organism = synthetic construct
SEQUENCE: 82
cgggtgaagt tctcaagaag cgctgacgct cctgcttacc aacaaggcca aaaccaactg  60
tacaacgagc tgaacctggg aagaagagag gaatacgacg tcctggacaa gagaagagga  120
agagaccctg agatgggagg aaagccaaga agaaagaacc ctcaagaggg cctgtttaac  180
gagctgcaaa aggacaagat ggctgaggct ttctccgaga tcggaatgaa gggagagaga  240
agaagaggaa agggacacga cggactgttc caaggcctga gcaccgctac caaggacacc  300
ttcgacgctc tgcacatgca agccctgcct cctagg                            336

SEQ ID NO: 83          moltype = DNA  length = 135
FEATURE                Location/Qualifiers
source                 1..135
                       mol_type = other DNA
                       organism = synthetic construct
SEQUENCE: 83
ggacacgaaa caggcagact ttctggcgcc gctgatacac aggccctgct gagaaacgac  60
caggtgtacc agcctctgag agacagagat gacgcccagt actctcacct cggcggcaat  120
tgggccagaa acaag                                                   135

SEQ ID NO: 84          moltype = DNA  length = 135
FEATURE                Location/Qualifiers
source                 1..135
                       mol_type = other DNA
                       organism = synthetic construct
SEQUENCE: 84
ggacaggatg gcgtcagaca gagcagagcc agcgacaagc aaaccctgct gcctaacgac  60
cagctgtacc agcctctgaa ggacagagag gacgaccagt acagccatct gcagggcaac  120
cagctgcgga gaaac                                                   135

SEQ ID NO: 85          moltype = DNA  length = 156
FEATURE                Location/Qualifiers
source                 1..156
                       mol_type = other DNA
                       organism = synthetic construct
SEQUENCE: 85
tacttcctgg gcagactggt gcctagagga agaggagctg ctgaggctgc taccagaaag  60
cagagaatca ccgagaccga gagcccttac caggagctgc agggacagag aagcgacgtg  120
tacagcgacc tgaacaccca gagaccttac tacaag                            156

SEQ ID NO: 86          moltype = DNA  length = 336
FEATURE                Location/Qualifiers
source                 1..336
                       mol_type = other DNA
                       organism = synthetic construct
SEQUENCE: 86
agagttaagt tcagcaggag cgccgacgca cctgcctacc aacaagggca gaatcaactg  60
tacaacgagc tgaacctggg cagacgggag gaatacgatg tgctggacaa gaggagaggc  120
agagaccccg agatgggcgg caaacctaga agaaagaacc cccaggaggg cctgtataat  180
gagctccaga aggataagat ggccgaggcc tacagcgaga tcggcatgaa gggcgaaaga  240
agaagaggca agggccacga cggcctctac cagggcttaa gcacagctac taaggacacc  300
tacgacgccc tgcacatgca agctctgccc cctaga                            336

SEQ ID NO: 87          moltype = AA  length = 50
FEATURE                Location/Qualifiers
```

```
source                  1..50
                        mol_type = protein
                        organism = synthetic construct
SEQUENCE: 87
KNRKAKAKPV TRGAGAGGRQ RGQNKERPPP VPNPDYEPIR KGQRDLYSGL            50

SEQ ID NO: 88           moltype = AA  length = 55
FEATURE                 Location/Qualifiers
source                  1..55
                        mol_type = protein
                        organism = synthetic construct
SEQUENCE: 88
KNRKAKAKPV TRGAGAGGRQ RGQNKERPPP VPNPDYEPIR KGQRDLYSGL NQKRI      55

SEQ ID NO: 89           moltype = AA  length = 55
FEATURE                 Location/Qualifiers
source                  1..55
                        mol_type = protein
                        organism = synthetic construct
SEQUENCE: 89
KNRKAKAKPV TRGAGAGGRQ RGQNKERPPP VPNPDYEPIR KGQRDLYNGL NQKRI      55

SEQ ID NO: 90           moltype = DNA  length = 1266
FEATURE                 Location/Qualifiers
source                  1..1266
                        mol_type = other DNA
                        organism = synthetic construct
SEQUENCE: 90
atggcacttc cagtcaccgc actcttgctt ccactggcct tgttgctgca tgctgcgcgg  60
ccagatatac agatgaccca aacgacgtct agcctcagtg cgtcactcgg ggatcgggtg  120
acaattagct gcagggctag ccaggatatt tcaaaatatc ttaactggta tcaacaaaag  180
ccagatggaa ccgtaaaact gctcatatac cacaccagtc gcctgcattc aggggttccg  240
agccgctttt ctgggagcgg tagcggaact gattatagct tgacaataag caacctcgag  300
caggaagaca ttgcgacgta cttctgtcag caagggaaca cgctgccgta taccttcggt  360
ggcggcacta aactggaaat cacgggatct acgtctggat ccggaaaacc tggatctggt  420
gaaggatcca ctaaaggcga agtcaagttg caagagtctg gacctggtct cgtggcacct  480
tcacagtcac tctccgttac ctgtaccgta tctggagttt cacttcccga ctatggcgtg  540
tcatggatac gccaaccacc gcgaaaaggt cttgaatggc tgggcgttat ctggggatcc  600
gaaaccacat actacaactc tgcgctcaag tcacggctga ctattataaa ggacaattca  660
aagagccaag tgttcctgaa aatgaacagc ctgcagactg atgacactgc aatatattac  720
tgcgccaagc attactatta cggcggatct tacgcgatgg attattgggg ccagggcacc  780
tctgtaacag tcagctccgc ggccgcattg gacaatgaaa aatccaatgg cacaataatt  840
catgtaaagg gcaaacactt gtgtcctagc ccactctttc ctggtccgtc taaaccgttt  900
tgggtgctcg ttgtggttgg aggcgtcctg gcttgttact ctctgttggt gactgtagcc  960
tttataatat tctgggttag aagcaaacga agtaggcttt tacattcaga ctatatgaac  1020
atgacaccaa gacgccccgg ccccacaaga aaacactatc agccctatgc tccgcctcgg  1080
gacttcgctg cttaccgaag caagaaccgc aaagcaaagg caaaacccgt cacacgagga  1140
gcgggcgcag ggggacgaca acgcggtcag aataaggaac gcccgcctcc agtaccaaat  1200
ccagattatg aaccaattcg gaagggacaa cgcgatctct actccggtct caatcagagg  1260
cgaatt                                                             1266

SEQ ID NO: 91           moltype = DNA  length = 1437
FEATURE                 Location/Qualifiers
source                  1..1437
                        mol_type = other DNA
                        organism = synthetic construct
SEQUENCE: 91
atggctctgc ctgtgaccgc tctgctgttg ccccttgctt tactcctgca cgccgcaaga  60
cccgacatcc aaatgaccca aaccacctcc tccctgagcg cctcccttgg agaccgagtt  120
accatctcct gccgagcttc tcaagacatc tccaagtact tgaattggta tcaacaaaag  180
cccgacggaa ccgtgaagct gctgatctac cacacatccc ggctgcactc tggcgttccc  240
tcaagattct ccggctctgg aagcggaacc gactactccc tgaccatctc caacctggag  300
caagaggaca tcgctaccta cttctgccaa caaggcaaca ccctgcctta caccttcgga  360
ggaggaacca agctggagat caccggaagc acaagcggat ctggcaagcc tggaagcgga  420
gagggaagca ccaagggaga ggtgaagctg caagagagcg gacctggatt ggtggccccc  480
tcacaatccc tgagcgttac atgcactgtg agcggcgtgt cccttcctga ctacggcgtt  540
tcctggatcc gccaacctcc aagaaaggga ctggagtggc tgggagtgat ctggggaagc  600
gagaccacct actacaactc cgccctgaag agccgactga ccatcatcaa ggacaactcc  660
aagagccaag tgttcctgaa gatgaactct ctccaaaccg acgacaccgc tatctactac  720
tgcgctaagc actactacta cggaggaagc tacgctatgg actactgggg acaaggcacc  780
tctgtgaccg tctcctctgc cgccgctctg gacaacgaga agagcaacgg aaccatcatc  840
cacgtgaagg gaaagcacct gtgcccctct cctctgttcc ctggaccctc caagcctttc  900
tgggtgctcg tggtggtggg aggagtgctg gcttgctact ccctgcttgt gaccgtggct  960
ttcatcatct tctgggttag aagcaagaga agcagactgc tgcacagcga ctacatgaac  1020
atgaccccta gaaggcccgg acctaccaga aagcactacc agccttacgc tcctcctaga  1080
gacttcgctg cttacagaag cagggtgaag ttctcaagaa gcgctgacgc tcctgcttac  1140
caacaaggcc aaaaccaact gtacaacgag ctgaacctgg gaagaagaga ggaatacgac  1200
gtcctggaca agagaagagg aagagaccct gagatgggag gaaagccaag aagaaagaac  1260
cctcaagagg gcctgtacaa cgagctgcaa aaggacaaga tggctgaggc ttactccgag  1320
```

-continued

```
atcggaatga agggagagag aagaagagga aagggacacg acggactgta ccaaggcctg  1380
agcaccgcta ccaaggacac ctacgacgct ctgcacatgc aagccctgcc tcctagg     1437

SEQ ID NO: 92            moltype = AA  length = 50
FEATURE                  Location/Qualifiers
source                   1..50
                         mol_type = protein
                         organism = synthetic construct
VARIANT                  1..5
                         note = This region may encompass 1-5 repeating residues
VARIANT                  6..10
                         note = This region may encompass 1-5 repeating residues
VARIANT                  11..15
                         note = This region may encompass 1-5 repeating residues
VARIANT                  16..20
                         note = This region may encompass 1-5 repeating residues
VARIANT                  21..25
                         note = This region may encompass 1-5 repeating residues
VARIANT                  26..30
                         note = This region may encompass 1-5 repeating residues
VARIANT                  31..35
                         note = This region may encompass 1-5 repeating residues
VARIANT                  36..40
                         note = This region may encompass 1-5 repeating residues
VARIANT                  41..45
                         note = This region may encompass 1-5 repeating residues
VARIANT                  46..50
                         note = This region may encompass 1-5 repeating residues
SEQUENCE: 92
GGGGGSSSSS GGGGGSSSSS GGGGGSSSSS GGGGGSSSSS GGGGGSSSSS             50

SEQ ID NO: 93            moltype = AA  length = 41
FEATURE                  Location/Qualifiers
source                   1..41
                         mol_type = protein
                         organism = synthetic construct
SEQUENCE: 93
KRGRKKLLYI FKQPFMRPVQ TTQEEDGCSC RFPEEEEGGC E                      41

SEQ ID NO: 94            moltype = AA  length = 112
FEATURE                  Location/Qualifiers
source                   1..112
                         mol_type = protein
                         organism = synthetic construct
SEQUENCE: 94
RVKFSRSADA PAYQQGQNQL YNELNLGRRE EYDVLDKRRG RDPEMGGKPR RKNPQEGLFN  60
ELQKDKMAEA FSEIGMKGER RRGKGHDGLF QGLSTATKDT FDALHMQALP PR          112

SEQ ID NO: 95            moltype = AA  length = 112
FEATURE                  Location/Qualifiers
source                   1..112
                         mol_type = protein
                         organism = synthetic construct
SEQUENCE: 95
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112
```

SIGNALING DOMAINS FOR CHIMERIC ANTIGEN RECEPTORS

CROSS-REFERENCES TO RELATED APPLICATIONS

This application claims the benefit of priority to U.S. Provisional Patent Application No. 63/256,956, filed 18 Oct. 2021 and titled "Chimeric Antigen Receptor (CAR) T Cell Therapy," the entirety of which is incorporated by reference herein.

SEQUENCE LISTING

The instant application contains a Sequence Listing which has been submitted electronically in XML format and is hereby incorporated by reference in its entirety. Said XML copy, created on Dec. 12, 2022, is named K-1133-US-NP_SL.xml and is 104,891 bytes in size.

TECHNICAL FIELD

The present disclosure relates to the field of cell therapy, and more specifically, to chimeric antigen receptor (CAR) cell therapy.

BACKGROUND

Human cancers are by their nature comprised of normal cells that have undergone a genetic or epigenetic conversion to become abnormal cancer cells. In doing so, cancer cells begin to express proteins and other antigens that are distinct from those expressed by normal cells. These aberrant tumor antigens can be used by the body's innate immune system to specifically target and kill cancer cells. However, cancer cells employ various mechanisms to prevent immune cells, such as T and B lymphocytes, from successfully targeting cancer cells.

Current T cell therapies rely on enriched or modified human T cells to target and kill cancer cells in a patient. To increase the ability of T cells to target and kill a particular cancer cell, methods have been developed to engineer T cells to express constructs, which direct T cells to a particular target cancer cell. Chimeric antigen receptors (CARs), which comprise binding domains capable of interacting with a particular tumor antigen, allow T cells to target and kill cancer cells that express the particular tumor antigen.

A need exists for improved methods of generating antigen receptor modified T cells for specifically targeting and killing cancer cells in an autologous or allogeneic setting.

SUMMARY

Disclosed are chimeric antigen receptors (CAR), comprising at least one antigen binding domain, a transmembrane domain; a costimulatory domain; and a signaling domain comprising one of a CD3ε signaling domain, a CD3γ signaling domain, a CD3δ signaling domain, or a DAP-12 signaling domain.

In certain embodiments the CAR comprises an anti-CD19 binding domain having an HCDR1, an HCDR2, and an HCDR3; and an LCDR1, an LCDR2, and an LCDR3, wherein the HCDR 1 comprises an amino acid sequence according to any one of SEQ ID NOs: 2-4; the HCDR2 comprises an amino acid sequence according to any one of SEQ ID NOs: 5-7; the HCDR3 comprises an amino acid sequence according to any one of SEQ ID NOs: 8-10; the LCDR1 comprises an amino acid sequence according to any one of SEQ ID NOs: 12-14; the LCDR2 comprises an amino acid sequence according to any one of SEQ ID NOs: 15-17; and the LCDR3 comprises an amino acid sequence according to any one of SEQ ID NOs: 18-20.

In certain embodiments the CAR comprises an anti-CD19 binding domain having an HCDR1, an HCDR2, and an HCDR3; and an LCDR1, an LCDR2, and an LCDR3, wherein the HCDR1 comprises an amino acid sequence according to any one of SEQ ID NOs: 24-26; the HCDR2 comprises an amino acid sequence according to any one of SEQ ID NOs: 27-29; the HCDR3 comprises an amino acid sequence according to any one of SEQ ID NOs: 30-32; the LCDR1 comprises an amino acid sequence according to any one of SEQ ID NOs: 34-36; the LCDR2 comprises an amino acid sequence according to any one of SEQ ID NOs: 37-39; and the LCDR3 comprises an amino acid sequence according to any one of SEQ ID NOs: 40-42.

In embodiments the CAR comprises a heavy chain variable domain comprising the HCDR1, the HCDR2, and the HCDR3; and a first light chain variable domain comprising the LCDR1, the LCDR2, and the LCDR3 wherein: the heavy chain variable domain is at least 80% identical to SEQ ID NO: 1; and the light chain variable domain is at least 80% identical to SEQ ID NO: 11, or the heavy chain variable domain is at least 80% identical to SEQ ID NO: 24; and the light chain variable domain is at least 80% identical to SEQ ID NO: 33.

In embodiments the HCDR1, the HCDR2, the HCDR3; the LCDR1, the LCDR2, and the LCDR3 are comprised by a single polypeptide.

In embodiments the anti-CD19 binding domain comprises an scFv. In embodiments the scFv comprises an amino acid sequence according to one of SEQ ID NOs: 21 or 43.

In embodiments the signaling domain comprises a CD3ε signaling domain with the amino acid sequence according to any one of SEQ ID NO: 52, SEQ ID NO: 87, SEQ ID NO: 88, and SEQ ID NO: 89. In embodiments the signaling domain comprises a CD3γ signaling domain with the amino acid sequence according to SEQ ID NO: 57. In embodiments the signaling domain comprises a CD3δ signaling domain with the amino acid sequence according to SEQ ID NO: 55. In embodiments the signaling domain comprises a DAP-12 signaling domain with the amino acid sequence according to SEQ ID NO: 59.

In embodiments the transmembrane domain is a CD28 transmembrane domain. In embodiments the costimulatory domain comprises a CD28 costimulatory domain.

In embodiments the anti-CD19 CAR comprises an amino acid sequence according to any one of SEQ ID NOs: 62, 65, 67, and 69.

Disclosed is a nucleic acid encoding a CAR disclosed herein. Disclosed is a recombinant vector comprising such nucleic acids. Disclosed is a host cell transduced with such nucleic acids and recombinant vectors. In embodiments the host cell comprises a T cell, iNKT cell, or a NK cell.

Disclosed is a pharmaceutical composition comprising such T cells, iNKT cells and/or NK cells. Disclosed is method of treating disease in a patient in need of thereof, comprising administering the T cell, iNKT cell and/or the NK cell or the pharmaceutical composition to the patient. Disclosed is a method of inducing an immune response in a subject or immunizing a subject against a cancer, the method comprising administering to the subject the T cell, INKT cell and/or the NK cell or the pharmaceutical composition the patient. In embodiments, the cancer is acute lymphoblastic leukemia (ALL) (including non T cell ALL), acute myeloid leukemia, B cell prolymphocytic leukemia, B cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia, chronic or acute leukemia, diffuse large B cell lymphoma (DLBCL), follicular lymphoma (FL), hairy cell leukemia, Hodgkin's Disease, malignant lymphoproliferative conditions, MALT lymphoma, mantle cell lymphoma, Marginal zone lymphoma, monoclonal gammapathy of undetermined significance (MGUS), multiple myeloma, myelodysplasia and myelodysplastic syndrome, non-Hodgkin's lymphoma (NHL), plasma cell proliferative disorder (including asymptomatic myeloma (smoldering multiple myeloma or indolent myeloma), plasmablastic lymphoma, plasmacytoid dendritic cell neoplasm, plasmacytomas (including plasma cell dyscrasia; solitary myeloma; solitary plasmacytoma; extramedullary plasmacytoma; and multiple plasmacytoma), POEMS syndrome (also known as Crow-Fukase syndrome; Takatsuki disease; and PEP syndrome), primary mediastinal large B cell lymphoma (PMBC), small cell- or a large cell-follicular lymphoma, splenic marginal zone lymphoma (SMZL), systemic amyloid light chain amyloidosis, T cell acute lymphoid leukemia ("TALL"), T cell lymphoma, transformed follicular lymphoma, or Waldenstrom macroglobulinemia, Mantle cell lymphoma (MCL), Transformed follicular lymphoma (TFL), Primary mediastinal B cell lymphoma (PMBCL), Multiple myeloma, Hairy cell lymphoma/leukemia, or a combination thereof.

DETAILED DESCRIPTION

Terms

Figure 1:
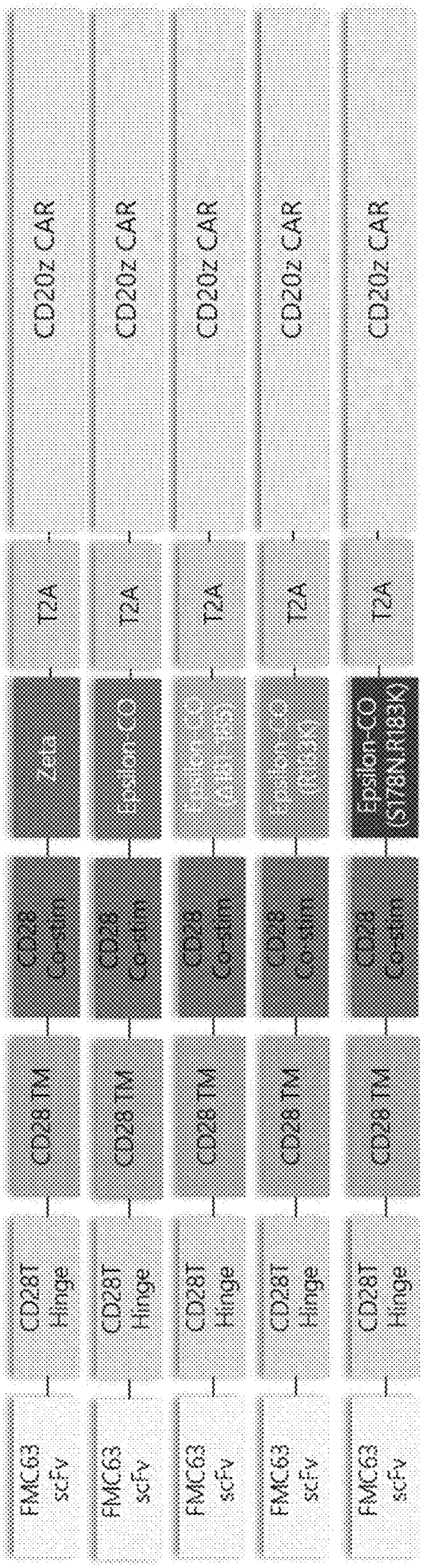
FIG. 1 illustrates embodiments of an anti-CD19 CAR with a signaling domain selected from the group consisting of a CD3 Zeta, codon optimized CD3 Epsilon, codon optimized Epsilon (Δ181-185), codon optimized Epsilon (R183K), and codon optimized Epsilon (S178N.R183K) in a bicistronic format with a second generation CD20 CD3 Zeta (CD20z) CAR.

In order for the present disclosure to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The term "and/or" where used herein is to be taken as specific disclosure of each of the two specified features or components with or without the other. Thus, the term "and/or" as used in a phrase such as "A and/or B" herein is intended to include A and B; A or B; A (alone); and B (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "e.g.," as used herein, is used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided.

Unless specifically stated or evident from context the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within one or more than one standard deviation per the practice in the art. "About" or "comprising essentially of" can mean a range of up to 10% (i.e., ±10%). Thus, "about" can be understood to be within 10%, 9%, 8%, 7%, 6%, 5%, 4%, 3%, 2%, 1%, 0.5%, 0.1%, 0.05%, 0.01%, or 0.001% greater or less than the stated value. For example, about 5 mg can include any amount between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "comprising essentially of" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Système International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, "The Concise Dictionary of Biomedicine and Molecular Biology", $2^{nd}$ ed., (2001), CRC Press; "The Dictionary of Cell & Molecular Biology", $5^{th}$ ed., (2013), Academic Press; and "The Oxford Dictionary Of Biochemistry And Molecular Biology", Cammack et al. eds., $2^{nd}$ ed, (2006), Oxford University Press, provide those of skill in the art with a general dictionary for many of the terms used in this disclosure.

"Administering" refers to the physical introduction of an agent to a subject, such as an engineered T cell disclosed herein, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The terms, "activated" and "activation" refer to the state of a T cell that has been sufficiently stimulated to induce detectable cellular proliferation. In one embodiment, activation may also be associated with induced cytokine production, and detectable effector functions. The term "activated T cells" refers to, among other things, T cells that are proliferating. Signals generated through the TCR alone may be insufficient for full activation of the T cell and one or more secondary or costimulatory signals may also be required. Thus, T cell activation comprises a primary stimulation signal through the TCR/CD3 complex and one or more secondary costimulatory signals. Costimulation may be evidenced by proliferation and/or cytokine production by T cells that have received a primary activation signal, such as stimulation through the TCR/CD3 complex.

The term "agent" may refer to a molecule or entity of any class comprising, or a plurality of molecules or entities, any of which may be, for example, a polypeptide, nucleic acid, saccharide, lipid, small molecule, metal, cell (such as a T cell or progenitor of such cells), or organism (for example, a fraction or extract thereof) or component thereof. In some embodiments, an agent may be utilized in isolated or pure form. In some embodiments, an agent may be utilized in a crude or impure form. In some embodiments, an agent may be provided as a population, collection, or library, for example that may be screened to identify or characterize members present therein.

The term "allogeneic" refers to any material derived from one individual which is then introduced to another individual of the same species, e.g., allogeneic T cell transplantation.

The term "autologous" refers to any material derived from the same individual to which it is later to be re-introduced. For example, the engineered autologous cell therapy method described herein involves collection of lymphocytes from a patient, which are then engineered to express, e.g., a CAR construct, and then administered back to the same patient.

The term "antibody" (Ab) includes, without limitation, a glycoprotein immunoglobulin which binds specifically to an antigen. In general, and antibody can comprise at least two heavy (H) chains and two light (L) chains interconnected by disulfide bonds, or an antigen-binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region comprises one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system. In general, human antibodies are approximately 150 kD tetrameric agents composed of two identical heavy (H) chain polypeptides (about 50 kD each) and two identical light (L) chain polypeptides (about 25 kD each) that associate with each other into what is commonly referred to as a "Y-shaped" structure. The heavy and light chains are linked or connected to one another by a single disulfide bond; two other disulfide bonds connect the heavy chain hinge regions to one another, so that the dimers are connected to one another and the tetramer is formed. Naturally-produced antibodies are also glycosylated, e.g., on the CH2 domain.

The term "human antibody" is intended to comprise antibodies having variable and constant domain sequences generated, assembled, or derived from human immunoglobulin sequences, or sequences indistinguishable therefrom. In some embodiments, antibodies (or antibody components) may be considered to be "human" even though their amino acid sequences comprise residues or elements not encoded by human germline immunoglobulin sequences (e.g., variations introduced by in vitro random or site-specific mutagenesis or introduced by in vivo somatic mutation). The term "humanized" is intended to comprise antibodies having a variable domain with a sequence derived from a variable domain of a non-human species (e.g., a mouse), modified to be more similar to a human germline encoded sequence. In some embodiments, a "humanized" antibody comprises one or more framework domains having substantially the amino acid sequence of a human framework domain, and one or more complementary determining regions having substantially the amino acid sequence as that of a non-human antibody. In some embodiments, a humanized antibody comprises at least a portion of an immunoglobulin constant region (Fc), generally that of a human immunoglobulin constant domain. In some embodiments, a humanized antibodies may comprise a $C_H1$, hinge, $C_H2$, $C_H3$, and, optionally, a $C_H4$ region of a human heavy chain constant domain.

Antibodies can include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, $F(ab')_2$ fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen binding fragments of any of the above. In certain embodiments, antibodies described herein refer to polyclonal antibody populations. Antibodies may also comprise, for example, Fab' fragments, Fd' fragments, Fd fragments, isolated CDRs, single chain Fvs, polypeptide-Fc fusions, single domain antibodies (e.g., shark single domain antibodies such as IgNAR or fragments thereof), camelid antibodies, single chain or Tandem diabodies (TandAb®), Anticalins®, Nanobodies® minibodies, BiTE®s, ankyrin repeat proteins or DARPINs®, Avimers®, DARTs, TCR-like antibodies, Adnectins®, Affilins®, Transbodies®, Affibodies®, TrimerX®, MicroProteins, Fynomers®, Centyrins®, and KALBITOR®s.

An immunoglobulin may derive from any of the commonly known isotypes, including but not limited to IgA, secretory IgA, IgG, IgE and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or non-human Abs; wholly synthetic Abs; and single chain Abs. A nonhuman Ab may be humanized by recombinant methods to reduce its immunogenicity in man. Where not expressly stated, and unless the context indicates otherwise, the term "antibody" also includes an antigen binding fragment or an antigen-binding portion of any of the aforementioned immunoglobulins, and includes a monovalent and a divalent fragment or portion, and a single chain Ab.

An "antigen binding molecule," "antigen binding portion," "antigen binding fragment," or "antibody fragment" or "antigen binding domain" refers to any molecule that comprises the antigen binding parts (e.g., CDRs) of the antibody from which the molecule is derived. An antigen binding molecule can include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In certain embodiments an antigen binding molecule is a chimeric antigen receptor (CAR). In certain embodiments, the antigen binding molecule or domain binds CD19. In certain embodiments, the antigen binding molecule or domain is an antibody fragment that specifically binds to the antigen, including one or more of the complementarity determining regions (CDRs) thereof. In further embodiments, the antigen binding molecule is a single chain variable fragment (scFv).

In some instances, a CDR is substantially identical to one found in a reference antibody (e.g., an antibody of the present disclosure) and/or the sequence of a CDR provided in the present disclosure. In some embodiments, a CDR is substantially identical to a reference CDR (e.g., a CDR provided in the present disclosure, for example in Table 4) in that it is either identical in sequence or contains between 1, 2, 3, 4, or 5 (e.g., 1-5) amino acid substitutions as compared with the reference CDR. In some embodiments a CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR (e.g., 85-90%, 85-95%, 85-100%, 90-95%, 90-100%, or 95-100%). In some embodiments a CDR is substantially identical to a reference CDR in that it shows at least 96%, 96%, 97%, 98%, 99%, or 100% sequence identity with the reference CDR. In some embodiments a CDR is substantially identical to a reference CDR in that one amino acid within the CDR is deleted, added, or substituted as compared with the reference CDR while the CDR has an amino acid sequence that is otherwise identical with that of the reference CDR. In some embodiments a CDR is substantially identical to a reference CDR in that 2, 3, 4, or 5 (e.g., 2-5) amino acids within the CDR are deleted, added, or substituted as compared with the reference CDR while the CDR has an amino acid sequence that is otherwise identical to the reference CDR. In various embodiments, an antigen binding fragment binds a same antigen as a reference antibody. In various embodiments, an antigen binding fragment cross-competes with the reference antibody, for example, binding to substantially the same or identical epitope as the reference antibody.

An antigen binding fragment may be produced by any means. For example, in some embodiments, an antigen binding fragment may be enzymatically or chemically produced by fragmentation of an intact antibody. In some embodiments, an antigen binding fragment may be recombinantly produced (such as by expression of an engineered nucleic acid sequence). In some embodiments, an antigen binding fragment may be wholly or partially synthetically produced. In some embodiments, an antigen binding fragment may have a length of at least about 50, 60, 70, 80, 90, 100, 110, 120, 130, 140, 150, 160, 170, 180, 190 amino acids or more; in some embodiments at least about 200 amino acids (e.g., 50-100, 50-150, 50-200, or 100-200 amino acids).

The term "variable region" or "variable domain" is used interchangeably. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody or an antigen-binding molecule thereof.

The terms "VH" and "VH domain" are used interchangeably to refer to the heavy chain variable region of an antibody or an antigen-binding molecule thereof.

A number of definitions of the CDRs are commonly in use: Kabat numbering, Chothia numbering, AbM numbering, or contact numbering. The AbM definition is a compromise between the two used by Oxford Molecular's AbM antibody modelling software. The contact definition is based on an analysis of the available complex crystal structures.

TABLE 1

| CDR Numbering | | | | |
|---|---|---|---|---|
| Loop | Kabat | AbM | Chothia | Contact |
| L1 | L24--L34 | L24--L34 | L24--L34 | L30--L36 |
| L2 | L50--L56 | L50--L56 | L50--L56 | L46--L55 |
| L3 | L89--L97 | L89--L97 | L89--L97 | L89--L96 |
| H1 | H31--H35B (Kabat Numbering) | H26--H35B | H26--H32..34 | H30--H35B |
| H1 | H31--H35 (Chothia Numbering) | H26--H35 | H26--H32 | H30--H35 |
| H2 | H50--H65 | H50--H58 | H52--H56 | H47--H58 |
| H3 | H95--H102 | H95--H102 | H95--H102 | H93--H101 |

The term "Kabat numbering" and like terms are recognized in the art and refer to a system of numbering amino acid residues in the heavy and light chain variable regions of an antibody, or an antigen-binding molecule thereof. In certain aspects, the CDRs of an antibody can be determined according to the Kabat numbering system (see, e.g., Kabat E A & Wu T T (1971) Ann NY Acad Sci 190:382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

In certain aspects, the CDRs of an antibody can be determined according to the Chothia numbering scheme, which refers to the location of immunoglobulin structural loops (see, e.g., Chothia C & Lesk A M, (1987), J Mol Biol 196:901-917; Al-Lazikani B et al., (1997) J Mol Biol 273:927-948; Chothia C et al., (1992) J Mol Biol 227:799-817; Tramontano A et al., (1990) J Mol Biol 215 (1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). In a specific embodiment, the CDRs of the antibodies described herein have been determined according to the Chothia numbering scheme.

The terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

The term "heavy chain" when used in reference to an antibody can refer to any distinct type, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., $IgG_1$, $IgG_2$, $IgG_3$ and $IgG_4$.

The term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

An "antigen" refers to a compound, composition, or substance that may stimulate the production of antibodies or a T cell response in a human or animal, including compositions (such as one that includes a tumor-specific protein) that are injected or absorbed into a human or animal. An antigen reacts with the products of specific humoral or cellular immunity, including those induced by heterologous antigens, such as the disclosed antigens. A "target antigen" or "target antigen of interest" is an antigen that is not substantially found on the surface of other normal (desired) cells and to which a binding domain of a CAR contemplated herein, is designed to bind. A person of skill in the art would readily understand that any macromolecule, including virtually all proteins or peptides, can serve as an antigen. An antigen can be endogenously expressed, i.e. expressed by genomic DNA, or can be recombinantly expressed. An antigen can be specific to a certain tissue, such as a cancer cell, or it can be broadly expressed. In addition, fragments of larger molecules can act as antigens. In one embodiment, antigens are tumor antigens. In one particular embodiment, the antigen is all or a fragment of CD19. In certain embodiments, the antigen may include, but is not limited to, 707-AP (707 alanine proline), AFP (alpha (α)-fetoprotein), ART-4 (adenocarcinoma antigen recognized by T4 cells), BAGE (B antigen; b-catenin/m, b-catenin/mutated), BCMA (B cell maturation antigen), Bcr-abl (breakpoint cluster region-Abelson), CAIX (carbonic anhydrase IX), CD19 (cluster of differentiation 19), CD20 (cluster of differentiation 20), CD22 (cluster of differentiation 22), CD30 (cluster of differentiation 30), CD33 (cluster of differentiation 33), CD44v7/8 (cluster of differentiation 44, exons 7/8), CAMEL (CTL-recognized antigen on melanoma), CAP-1 (carcinoembryonic antigen peptide-1), CASP-8 (caspase-8), CDC27m (cell-division cycle 27 mutated), CDK4/m (cycline-dependent kinase 4 mutated), CEA (carcinoembryonic antigen), C-type lectin-like-1 (CLL-1), CT (cancer/testis (antigen)), Cyp-B (cyclophilin B), DAM (differentiation antigen melanoma), EGFR (epidermal growth factor receptor), EGFRvlll (epidermal growth factor receptor, variant III), EGP-2 (epithelial glycoprotein 2), EGP-40 (epithelial glycoprotein 40), Erbb2, 3, 4 (erythroblastic leukemia viral oncogene homolog-2, -3, 4), ELF2M (elongation factor 2 mutated), ETV6-AML1 (Ets variant gene 6/acute myeloid leukemia 1 gene ETS), FBP (folate binding protein), fAchR (Fetal acetylcholine receptor), G250 (glycoprotein 250), GAGE (G antigen), GD2 (disialoganglioside 2), GD3 (disialoganglioside 3), glypican 3 (GPC3), GnT-V (N-acetylglucosaminyltransferase V), Gp100 (glycoprotein 100 kD), HAGE (helicose antigen), HER-2/neu (human epidermal receptor-2/neurological; also known as EGFR2), HLA-A (human leukocyte antigen-A) HPV (human papilloma virus), HSP70-2M (heat shock protein 70-2 mutated), HST-2 (human signet ring tumor-2), hTERT or hTRT (human telomerase reverse transcriptase), iCE (intestinal carboxyl esterase), IL-13R-a2 (Interleukin-13 receptor subunit alpha-2), KIAA0205, KDR (kinase insert domain receptor), K-light chain, LAGE (L antigen), LDLR/FUT (low density lipid receptor/GDP-L-fucose: b-D-galactosidase 2-a-Lfucosyltransferase), LeY (Lewis-Y antibody), L1 CAM (L1 cell adhesion molecule), MAGE (melanoma antigen), MAGE-A1 (Melanoma-associated antigen 1), mesothelin, Murine CMV infected cells, MART-1/Melan-A (melanoma antigen recognized by T cells-I/Melanoma antigen A), MC1 R (melanocortin 1 receptor), Myosin/m (myosin mutated), MUC1 (mucin 1), MUM-1, -2, -3 (melanoma ubiquitous mutated 1, 2, 3), NA88-A (NA cDNA clone of patient M88), NKG2D (Natural killer group 2, member D) ligands, NY-BR-1 (New York breast differentiation antigen 1), NY-ESO-1 (New York esophageal squamous cell carcinoma-1), oncofetal antigen (h5T4), P15 (protein 15), p190 minor bcr-abl (protein of 190KD bcr-abl), Pml/RARa (promyelocytic leukaemia/retinoic acid receptor a), PRAME (preferentially expressed antigen of melanoma), PSA (prostate-specific antigen), PSCA (Prostate stem cell antigen), PSMA (prostate-specific membrane antigen), RAGE (renal antigen), RU1 or RU2 (renal ubiquitous 1 or 2), SAGE (sarcoma antigen), SART-1 or SART-3 (squamous antigen rejecting tumor 1 or 3), SSX1, -2, -3, 4 (synovial sarcoma X1, -2, -3, -4), TAA (tumor-associated antigen), TAG-72 (Tumor-associated glycoprotein 72), TEL/AML1 (translocation Ets-family leukemia/acute myeloid leukemia 1), TPI/m (triosephosphate isomerase mutated), TRP-1 (tyrosinase related protein 1, or gp75), TRP-2 (tyrosinase related protein 2), TRP-2/INT2 (TRP-2/intron 2), VEGF-R2 (vascular endothelial growth factor receptor 2), or WT1 (Wilms' tumor gene).

A "target" is any molecule bound by a binding domain, antigen binding system, CAR or antigen binding agent, e.g., an antibody.

"Antigen-specific targeting region" (ASTR) refers to the region of the CAR which targets specific antigens. The targeting regions on the CAR are extracellular. In some embodiments, the antigen-specific targeting regions comprise an antibody or a functional equivalent thereof or a fragment thereof or a derivative thereof and each of the targeting regions target a different antigen. The targeting regions may comprise full length heavy chain, Fab fragments, single chain Fv (scFv) fragments, divalent single chain antibodies or diabodies, each of which are specific to the target antigen. There are, however, numerous alternatives, such as linked cytokines (which leads to recognition of cells bearing the cytokine receptor), affibodies, ligand binding domains from naturally occurring receptors, soluble protein/peptide ligand for a receptor (for example on a tumor cell), peptides, and vaccines to prompt an immune response, which may each be used in various embodiments of this disclosure. In fact, almost any molecule that binds a given antigen with high affinity can be used as an antigen-specific targeting region, as will be appreciated by those of skill in the art.

"Antigen presenting cell" or "APC" refers to cells that process and present antigens to T cells. Exemplary APCs comprise dendritic cells, macrophages, B cells, certain activated epithelial cells, and other cell types capable of TCR stimulation and appropriate T cell costimulation.

An "anti-tumor effect" refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor.

Two events or entities are "associated" with one another if the presence, level, and/or form of one is correlated with that of the other. For example, an entity (e.g., polypeptide, genetic signature, metabolite, microbe, etc.) is considered to be associated with a disease, disorder, or condition, if its presence, level, and/or form correlates with incidence of and/or susceptibility to the disease, disorder, or condition (e.g., across a relevant population). For example, two or more entities are physically "associated" with one another if they interact, directly or indirectly, so that they are and/or remain in physical proximity with one another (e.g., bind). In additional examples, two or more entities that are physically associated with one another are covalently linked or connected to one another, or non-covalently associated, for example by means of hydrogen bonds, van der Waals interaction, hydrophobic interactions, magnetism, and combinations thereof.

"Binding affinity" generally refers to the strength of the sum total of non-covalent interactions between a single binding site of a molecule (e.g., an antibody) and its binding partner (e.g., an antigen). Unless indicated otherwise "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as BIACORE® or KinExA.

The term "KD" (M) refers to the dissociation equilibrium constant of a particular antibody-antigen interaction, or the dissociation equilibrium constant of an antibody or antibody-binding fragment binding to an antigen. There is an inverse relationship between $K_D$ and binding affinity, therefore the smaller the $K_D$ value, the higher, i.e. stronger, the affinity. Thus, the terms "higher affinity" or "stronger affinity" relate to a higher ability to form an interaction and therefore a smaller $K_D$ value, and conversely the terms "lower affinity" or "weaker affinity" relate to a lower ability to form an interaction and therefore a larger $K_D$ value. In some circumstances, a higher binding affinity (or $K_D$) of a particular molecule (e.g. antibody) to its interactive partner molecule (e.g. antigen X) compared to the binding affinity of the molecule (e.g. antibody) to another interactive partner molecule (e.g. antigen Y) may be expressed as a binding ratio determined by dividing the larger $K_D$ value (lower, or weaker, affinity) by the smaller $K_D$ (higher, or stronger, affinity), for example expressed as 5-fold or 10-fold greater binding affinity, as the case may be.

The term "$k_d$" (sec−1 or 1/s) refers to the dissociation rate constant of a particular antibody-antigen interaction, or the dissociation rate constant of an antibody or antibody-binding fragment. Said value is also referred to as the $k_{oi}r$ value.

The term "$k_a$" (M-1×sec−1 or 1/M) refers to the association rate constant of a particular antibody-antigen interaction, or the association rate constant of an antibody or antibody-binding fragment.

The term "$K_A$" (M-1 or 1/M) refers to the association equilibrium constant of a particular antibody-antigen interaction, or the association equilibrium constant of an antibody or antibody binding fragment. The association equilibrium constant is obtained by dividing the $k_a$ by the $k_d$.

The term "binding" generally refers to a non-covalent association between or among two or more entities. Direct binding involves physical contact between entities or moieties. "Indirect" binding involves physical interaction by way of physical contact with one or more intermediate entities. Binding between two or more entities may be assessed in any of a variety of contexts, e.g., where interacting entities or moieties are studied in isolation or in the context of more complex systems (e.g., while covalently or otherwise associated with a carrier entity and/or in a biological system such as a cell).

The terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, BIACORE®, KinExA 3000 instrument (Sapidyne Instruments, Boise, ID), or other assays known in the art. In a specific embodiment, molecules that specifically bind to an antigen bind to the antigen with a $K_A$ that is at least 2 logs, 2.5 logs, 3 logs, 4 logs or greater than the $K_A$ when the molecules bind to another antigen. Binding may comprise preferential association of a binding domain, antibody, or a CAR with a target of the binding domain, antibody, or CAR as compared to association of the binding domain, antibody, or CAR with an entity that is not the target (i.e. non-target). In some embodiments, a binding domain, antibody, or CAR selectively binds a target if binding between the binding domain, antibody, or CAR and the target is greater than 2-fold, greater than 5-fold, greater than 10-fold, 20-fold, 30-fold, 40-fold, 50-fold, 60-fold, 70-fold, 80-fold, 90-fold, or greater than 100-fold as compared with binding of the binding domain, antibody, or CAR and a non-target. In some embodiments, a binding domain, antibody, or CAR selectively binds a target if the binding affinity is less than about $10^{-5}$ M, less than about $10^{-6}$ M, less than about $10^{-7}$ M, less than about $10^{-8}$ M, or less than about $10^{-9}$ M.

In another embodiment, molecules that specifically bind to an antigen bind with a dissociation constant ($K_d$) of about $1\times10^{-7}$ M. In some embodiments, the antigen binding molecule specifically binds an antigen with "high affinity" when the $K_d$ is about $1\times10^{-9}$ M to about $5\times10^{-9}$ M. In some embodiments, the antigen binding molecule specifically binds an antigen with "very high affinity" when the $K_d$ is $1\times10^{-10}$ M to about $5\times10^{-10}$ M. In one embodiment, the antigen binding molecule has a $K_d$ of $10^{-9}$ M. In one embodiment, the off-rate is less than about $1\times10^{5}$. In embodiments, the antigen binding molecule binds CD19 with a $K_d$ of about $1\times10^{-10}$ M to about $5\times10^{-10}$ M.

In certain embodiments, provided herein is an antibody or an antigen binding molecule thereof that binds to the target human antigen, e.g., In certain embodiments, the antigen binding molecule binds to CD19 with a 5%, 10%, 15%, 20%, 25%, 30%, 35%, 40%, 45%, 50%, 55%, 60%, 65%, 70% or higher affinity than to another species of the target antigen as measured by, e.g., a radioimmunoassay, surface plasmon resonance, or kinetic exclusion assay. In a specific embodiment, an antibody or an antigen binding molecule thereof described herein, which binds to a target human antigen, will bind to another species of the target antigen with less than 10%, 15%, or 20% of the binding of the antibody or an antigen binding molecule thereof to the human antigen as measured by, e.g., a radioimmunoassay, surface plasmon resonance, or kinetic exclusion assay.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor. Examples of cancers that can be treated by the methods of the present disclosure include, but are not limited to, cancers of the immune system including lymphoma, leukemia, myeloma, and other leukocyte malignancies. In some embodiments, the methods of the present disclosure can be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. In one particular embodiment, the cancer is multiple myeloma. The particular cancer can be responsive to chemo- or radiation therapy or the cancer can be refractory. A refractory cancer refers to a cancer that is not amendable to surgical intervention and the cancer is either initially unresponsive to chemo- or radiation therapy or the cancer becomes unresponsive over time. Cancer further includes relapsed or refractory after two or more lines of systemic therapy, including diffuse large B-cell lymphoma (DLBCL) not otherwise specified, primary mediastinal large B-cell lymphoma after two or more lines of systemic therapy, high grade B-cell lymphoma, and DLBCL arising from follicular lymphoma, and follicular lymphoma.

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1$\alpha$ (MIP-1$\alpha$, MIP-1a), MIP-1$\beta$ (MIP-1b), gamma-induced protein 10 (IP-10), and thymus and activation regulated chemokine (TARC or CCL17).

"Chimeric antigen receptor" or "CAR" refers to a molecule engineered to comprise a binding domain and a means of activating immune cells (for example T cells such as naive T cells, central memory T cells, effector memory T cells, iNKT cells, NK cells or combination thereof) upon antigen binding. CARs are also known as artificial T cell receptors, chimeric T cell receptors or chimeric immunoreceptors. In some embodiments, a CAR comprises a binding domain, an extracellular domain, a transmembrane domain, one or more co-stimulatory domains, and an intracellular signaling domain. A T cell that has been genetically engineered to express a chimeric antigen receptor may be referred to as a CAR T cell.

"Extracellular domain" (or "ECD") refers to a portion of a polypeptide that, when the polypeptide is present in a cell membrane, is understood to reside outside of the cell membrane, in the extracellular space.

The term "extracellular ligand-binding domain," as used herein, refers to an oligo-or polypeptide that is capable of binding a ligand, e.g., a cell surface molecule. For example, the extracellular ligand-binding domain may be chosen to recognize a ligand that acts as a cell surface marker on target cells associated with a particular disease state (e.g., cancer). Examples of cell surface markers that may act as ligands include those associated with viral, bacterial and parasitic infections, autoimmune disease and cancer cells.

The binding domain of the CAR may be followed by a "spacer," or, "hinge," which refers to the region that moves the antigen binding domain away from the effector cell surface to enable proper cell/cell contact, antigen binding and activation (Patel et al., Gene Therapy, 1999; 6:412-419). The hinge region in a CAR is generally between the transmembrane (TM) and the binding domain. In certain embodiments, a hinge region is an immunoglobulin hinge region and may be a wild type immunoglobulin hinge region or an altered wild type immunoglobulin hinge region. Other exemplary hinge regions used in the CARs described herein include the hinge region derived from the extracellular regions of type 1 membrane proteins such as CD8alpha, CD4, CD28 and CD7, which may be wild-type hinge regions from these molecules or may be altered.

The "transmembrane" region or domain is the portion of the CAR that anchors the extracellular binding portion to the plasma membrane of the immune effector cell, and facilitates binding of the binding domain to the target antigen. The transmembrane domain may be a CD3zeta transmembrane domain, however other transmembrane domains that may be employed include those obtained from CD8alpha, CD4, CD28, CD45, CD9, CD16, CD22, CD33, CD64, CD80, CD86, CD134, CD137, and CD154. In one embodiment, the transmembrane domain is the transmembrane domain of CD137. In certain embodiments, the transmembrane domain is synthetic in which case it would comprise predominantly hydrophobic residues such as leucine and valine.

The "intracellular signaling domain" or "signaling domain" refers to the part of the chimeric antigen receptor protein that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. The term "effector function" refers to a specialized function of the cell. Effector function of the T cell, for example, may be cytolytic activity or help or activity including the secretion of a cytokine. Thus, the terms "intracellular signaling domain" or "signaling domain," used interchangeably herein, refer to the portion of a protein which transduces the effector function signal and that directs the cell to perform a specialized function. While usually the entire intracellular signaling domain can be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal. The intracellular signaling domain is also known as the, "signal transduction domain," and is typically derived from portions of the human CD3 or FcRy chains.

It is known that signals generated through the T cell receptor alone are insufficient for full activation of the T cell and that a secondary, or costimulatory signal is also required. Thus, T cell activation can be said to be mediated by two distinct classes of cytoplasmic signaling sequences: those that initiate antigen dependent primary activation through the T cell receptor (primary cytoplasmic signaling sequences) and those that act in an antigen independent manner to provide a secondary or costimulatory signal (secondary cytoplasmic signaling sequences). Cytoplasmic signaling sequences that act in a primary activation manner may contain signaling motifs which are known as immunoreceptor tyrosine-based activation motif or ITAMs. Examples of ITAM containing primary cytoplasmic signaling sequences that are of particular use in the disclosure include those derived from DAP-12, CD3gamma, CD3delta, and CD3epsilon.

As used herein, the term, "costimulatory signaling domain," or "costimulatory domain", refers to the portion of the CAR comprising the intracellular domain of a costimulatory molecule. Costimulatory molecules are cell surface molecules other than antigen receptors or Fc receptors that provide a second signal required for efficient activation and function of T lymphocytes upon binding to antigen. Examples of such co-stimulatory molecules include CD27, CD28, 4-1BB (CD137), OX40 (CD134), CD30, CD40, PD-1, ICOS (CD278), LFA-1, CD2, CD7, LIGHT, NKD2C, B7-H2 and a ligand that specifically binds CD83. Accordingly, while the present disclosure provides exemplary costimulatory domains derived from CD28 and 4-1BB, other costimulatory domains are contemplated for use with the CARs described herein. The inclusion of one or more costimulatory signaling domains may enhance the efficacy and expansion of T cells expressing CAR receptors. The intracellular signaling and costimulatory signaling domains may be linked in any order in tandem to the carboxyl terminus of the transmembrane domain.

Although scFv-based CARs engineered to contain a signaling domain from CD3 or FcRgamma have been shown to deliver a potent signal for T cell activation and effector function, they are not sufficient to elicit signals that promote T cell survival and expansion in the absence of a concomitant costimulatory signal. Other CARs containing a binding domain, a hinge, a transmembrane and the signaling domain together with one or more costimulatory signaling domains (e.g., intracellular costimulatory domains derived from 4-1BB, CD28, CD137, CD134 and CD278) may more effectively direct antitumor activity as well as increased cytokine secretion, lytic activity, survival and proliferation in CAR expressing T cells in vitro, and in animal models and cancer patients (Milone et al., Molecular Therapy, 2009; 17:1453-1464; Zhong et al., Molecular Therapy, 2010; 18:413-420; Carpenito et al., PNAS, 2009; 106:3360-3365).

A "costimulatory signal" refers to a signal, which in combination with a primary signal, such as TCR/CD3 ligation, leads to a T cell response, such as, but not limited to, proliferation and/or upregulation or down regulation of key molecules.

A "costimulatory ligand" includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand can include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), OX40 ligand, PD-L2, or programmed death (PD)-L1. A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CD1-1a, CD1-1b, CD1-1c, CD1-1d, CDS, CEACAM1, CRT AM, DAP-10, DNAMI (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, LIGHT, LIGHT (tumor necrosis factor superfamily member 14; TNFSF14), LTBR, Ly9 (CD229), lymphocyte function-associated antigen-1 (LFA-1 (CD1 1a/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Ly108), SLAMF7, SLP-76, TNF, TNFr, TNFR2, Toll ligand receptor, TRANCE/RANKL, VLA1, or VLA-6, or fragments, truncations, or combinations thereof.

A "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody or antigen-binding molecule thereof can be replaced with an amino acid residue with a similar side chain. In general, two sequences are generally considered to be "substantially similar" if they contain a conservative amino acid substitution in corresponding positions. For example, certain amino acids are generally classified as "hydrophobic" or "hydrophilic" amino acids, and/or as having "polar" or "non-polar" side chains. Substitution of one amino acid for another of the same type may be considered a conservative substitution. Exemplary amino acid categorizations are summarized in Tables 2 and 3 below:

TABLE 2

| Amino Acid | 3-Letter | 1-Letter | Property | Property | Hydropathy Index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | 0.7 |
| Tryptophan | Trp | W | nonpolar | neutral | −0.9 |
| Tyrosine | Tyr | Y | polar | neutral | 1.3 |
| Valine | Val | V | nonpolar | neutral | 4.2 |

TABLE 3

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

"Combination therapy" refers to those situations in which a subject is simultaneously exposed to two or more therapeutic regimens (e.g., two or more therapeutic moieties). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

"Corresponding to" may be used to designate the position/identity of a structural element in a molecule or composition through comparison with an appropriate reference molecule or composition. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, for purposes of simplicity, residues in a polypeptide may be designated using a canonical numbering system based on a reference related polypeptide, so that an amino acid "corresponding to" a residue at position 100, for example, need not actually be the 100th amino acid in an amino acid chain provided it corresponds to the residue found at position 100 in the reference polypeptide. Various sequence alignment strategies are available, comprising software programs such as, for example, BLAST, CS-BLAST, CUDASW++, DIAMOND, FASTA, GGSEARCH/GLSEARCH, Genoogle, HMMER, HHpred/HHsearch, IDF, Infernal, KLAST, USEARCH, parasail, PSI-BLAST, PSI-Search, ScalaBLAST, Sequilab, SAM, SSEARCH, SWAPHI, SWAPHI-LS, SWIMM, or SWIPE that may be utilized, for example, to identify "corresponding" residues in polypeptides and/or nucleic acids in accordance with the present disclosure.

An antigen binding molecule, such as an antibody, an antigen binding fragment thereof, CAR or TCR, "cross-competes" with a reference binding molecule, such as an antibody or an antigen binding fragment thereof, if the interaction between an antigen and the first antigen binding molecule blocks, limits, inhibits, or otherwise reduces the ability of the reference binding molecule to interact with the antigen. Cross competition can be complete, e.g., binding of the antigen binding molecule to the antigen completely blocks the ability of the reference binding molecule to bind the antigen, or it can be partial, e.g., binding of the antigen binding molecule to the antigen reduces the ability of the reference antigen binding molecule to bind the antigen. In certain embodiments, an antigen binding molecule that cross-competes with a reference antigen binding molecule binds the same or an overlapping epitope as the reference antigen binding molecule. In other embodiments, the antigen binding molecule that cross-competes with a reference antigen binding molecule binds a different epitope than the reference antigen binding molecule. Numerous types of competitive binding assays can be used to determine if one antigen binding molecule competes with another, for example: solid phase direct or indirect radioimmunoassay (RIA); solid phase direct or indirect enzyme immunoassay (EIA); sandwich competition assay (Stahli et al., 1983, Methods in Enzymology 9:242-253); solid phase direct biotin-avidin EIA (Kirkland et al., 1986, J. Immunol. 137:3614-3619); solid phase direct labeled assay, solid phase direct labeled sandwich assay (Harlow and Lane, 1988, *Antibodies, A Laboratory Manual*, Cold Spring Harbor Press); solid phase direct label RIA using 1-125 label (Morel et al., 1988, Molec. Immunol. 25:7-15); solid phase direct biotin-avidin EIA (Cheung, et al., 1990, Virology 176:546-552); and direct labeled RIA (Moldenhauer et al., 1990, Scand. J. Immunol. 32:77-82).

A "cytokine," refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

By "decrease" or "lower," or "lessen," or "reduce," or "abate" refers generally to the ability of a composition contemplated herein to produce, elicit, or cause a lesser physiological response (i.e., a downstream effect) compared to the response caused by either the vehicle alone (i.e., an active moiety) or a control molecule/composition. A "decrease" or "reduced" amount is typically a "statistically significant" amount, and may include an decrease that is 1.1, 1.2, 1.5, 2, 2.5, 3, 3.5, 4, 4.5, 5, 5.5, 6, 6.5, 7, 7.5, 8, 8.5, 9, 9.5, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition.

The term "domain" refers to a portion of an entity. In some embodiments, a "domain" is associated with a structural and/or functional feature of the entity, e.g., so that, when the domain is physically separated from the rest of its parent entity, it substantially or entirely retains the structural and/or functional feature. In some embodiments, a domain may comprise a portion of an entity that, when separated from that (parent) entity and linked or connected with a different (recipient) entity, substantially retains and/or imparts on the recipient entity one or more structural and/or functional features, e.g., that characterized it in the parent entity. In some embodiments, a domain is a portion of a molecule (e.g., a small molecule, carbohydrate, lipid, nucleic acid, or polypeptide). In some embodiments, a domain is a section of a polypeptide; in some such embodiments, a domain is characterized by a structural element (e.g., an amino acid sequence or sequence motif, α-helix character, β-sheet character, coiled-coil character, random coil character, etc.), and/or by a functional feature (e.g., binding activity, enzymatic activity, folding activity, signaling activity, etc.).

The term "dosage form" may be used to refer to a physically discrete unit of an active agent (e.g., an antigen binding system or antibody) for administration to a subject. Generally, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population. The total amount of a therapeutic composition or agent administered to a subject is determined by one or more medical practitioners and may involve administration of more than one dosage forms.

The term "dosing regimen" may be used to refer to a set of one or more unit doses that are administered individually to a subject. In some embodiments, a given therapeutic agent has a recommended dosing regimen, which may involve one or more doses. In some embodiments, a dosing regimen comprises a plurality of doses each of which is separated in time from other doses. In some embodiments, a dosing regimen comprises a plurality of doses and consecutive doses are separated from one another by time periods of equal length; in some embodiments, a dosing regimen comprises a plurality of doses and consecutive doses are separated from one another by time periods of at least two different lengths. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen is periodically adjusted to achieve a desired or beneficial outcome.

"Effector cell" refers to a cell of the immune system that expresses one or more Fc receptors and mediates one or more effector functions. In some embodiments, effector cells may comprise, without limitation, one or more of monocytes, macrophages, neutrophils, dendritic cells, eosinophils, mast cells, platelets, large granular lymphocytes, Langerhans' cells, natural killer (NK) cells, T-lymphocytes, and B-lymphocytes. Effector cells may be of any organism comprising, without limitation, humans, mice, rats, rabbits, and monkeys.

"Effector function" refers to a biological result of interaction of an antibody Fc region with an Fc receptor or ligand. Effector functions comprise, without limitation, antibody-dependent cell-mediated cytotoxicity (ADCC), antibody-dependent cell-mediated phagocytosis (ADCP), and complement-mediated cytotoxicity (CMC). An effector function may be antigen binding dependent, antigen binding independent, or both. ADCC refers to lysis of antibody-bound target cells by immune effector cells. Without wishing to be bound by any theory, ADCC is generally understood to involve Fc receptor (FcR)-bearing effector cells recognizing and subsequently killing antibody-coated target cells (e.g., cells that express on their surface antigens to which an antibody is bound). Effector cells that mediate ADCC may comprise immune cells, comprising yet not limited to, one or more of natural killer (NK) cells, macrophages, neutrophils, eosinophils.

An "epitope" refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50 (Pt 4): 339-350; McPherson A (1990) Eur J Biochem 189:1-23; Chayen NE (1997) Structure 5:1269-1274; McPherson A (1976) J Biol Chem 251:6300-6303). Antibody: antigen crystals may be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. 2004/0014194), and BUSTER (Bricogne G (1993) Acta Crystallogr D Biol Crystallogr 49 (Pt 1): 37-60; Bricogne G (1997) Meth Enzymol 276A: 361-423, ed Carter C W; Roversi P et al., (2000) Acta Crystallogr D Biol Crystallogr 56 (Pt 10): 1316-1323). Mutagenesis mapping studies may be accomplished using any method known to one of skill in the art. See, e.g., Champe M et al., (1995) J Biol Chem 270:1388-1394 and Cunningham B C & Wells J A (1989) Science 244:1081-1085 for a description of mutagenesis techniques, including alanine scanning mutagenesis techniques.

"Endogenous" with reference to a gene, protein, and/or nucleic acid refers to the natural presence of that gene, protein, and/or nucleic acid in a cell, such as an immune cell.

"Exogenous" refers to an introduced agent, such as a nucleic acid, gene, or protein, into a cell, for example from an outside source. A nucleic acid introduced into a cell is exogenous even if it encodes a protein which is naturally found in the cell. Such exogenous introduction of a nucleic acid encoding a protein can be used to increase the expression of the protein over the level that would naturally be found in the cell under similar conditions, e.g., without introduction of the exogenous nucleic acid.

The term "excipient" refers to an agent that may be comprised in a composition, for example to provide or contribute to a desired consistency or stabilizing effect. In some embodiments, a suitable excipient may comprise, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, or the like.

A "fragment" or "portion" of a material or entity as described herein has a structure that comprises a discrete portion of the whole, e.g., of a physical entity or abstract entity. In some embodiments, a fragment lacks one or more moieties found in the whole. In some embodiments, a fragment consists of or comprises a characteristic structural element, domain or moiety found in the whole. In some embodiments, a polymer fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer (e.g., 85-90%, 85-95%, 85-100%, 90-95%, 90-100%, or 95-100%). The whole material or entity may in some embodiments be referred to as the "parent" of the fragment.

The term "fusion polypeptide" or "fusion protein" generally refers to a polypeptide comprising at least two segments. Generally, a polypeptide containing at least two such segments is considered to be a fusion polypeptide if the two segments are moieties that (1) are not comprised in nature in the same peptide, and/or (2) have not previously been linked or connected to one another in a single polypeptide, and/or (3) have been linked or connected to one another through action of the hand of woman/man. In embodiments, a CAR is a fusion protein.

The term "gene product" or "expression product" generally refers to an RNA transcribed from the gene (pre- and/or post-processing) or a polypeptide (pre- and/or post-modification) encoded by an RNA transcribed from the gene.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which can either be obtained from a patient or a donor. The cell can be modified to express an exogenous construct, such as, e.g., a chimeric antigen receptor (CAR), which is incorporated into the cell's genome. Engineering generally comprises manipulation by the hand of man. For example, a polynucleotide is considered to be "engineered" when two or more sequences, that are not linked or connected together in that order in nature, are manipulated by the hand of man to be directly linked or connected to one another in the engineered polynucleotide. In the context of manipulation of cells by techniques of molecular biology, a cell or organism is considered to be "engineered" if it has been manipulated so that its genetic information is altered (e.g., new genetic material not previously present has been introduced, for example by transformation, somatic hybridization, transfection, transduction, electroporation or other mechanism, or previously present genetic material is altered or removed, for example by substitution or deletion mutation, or by other protocols). In some embodiments, a binding agent is a modified lymphocyte, e.g., a T cell, may be obtained from a patient or a donor. An engineered cell may be modified to express an exogenous construct, such as, e.g., a chimeric antigen receptor (CAR), which is incorporated into the cell's genome. Progeny of an engineered polynucleotide or binding agent are generally referred to as "engineered" even though the actual manipulation was performed on a prior entity. In some embodiments, "engineered" refers to an entity that has been designed and produced. The term "designed" refers to an agent (i) whose structure is or was selected by the hand of man; (ii) that is produced by a process requiring the hand of man; and/or (iii) that is distinct from natural substances and other known agents.

A "T cell receptor" or "TCR" refers to antigen-recognition molecules present on the surface of T cells. During normal T cell development, each of the four TCR genes, α, β, γ, and δ, may rearrange leading to highly diverse TCR proteins. In embodiments, a T cell disclosed herein has been engineered to reduce, eliminate and/or inhibit the surface expression of the α chain of the TCR receptor.

The term "heterologous" means from any source other than naturally occurring sequences. For example, a heterologous sequence included as a part of a costimulatory protein is amino acids that do not naturally occur as, i.e., do not align with, the wild type human costimulatory protein. For example, a heterologous nucleotide sequence refers to a nucleotide sequence other than that of the wild-type human costimulatory protein-encoding sequence.

Term "identity" refers to the overall relatedness between polymeric molecules, e.g., between nucleic acid molecules (e.g., DNA molecules and/or RNA molecules) and/or between polypeptide molecules. Methods for the calculation of a percent identity as between two provided polypeptide sequences are known. Calculation of the percent identity of two nucleic acid or polypeptide sequences, for example, may be performed by aligning the two sequences for optimal comparison purposes (e.g., gaps may be introduced in one or both of a first and a second sequences for optimal alignment and non-identical sequences may be disregarded for comparison purposes). The nucleotides or amino acids at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, optionally taking into account the number of gaps, and the length of each gap, which may need to be introduced for optimal alignment of the two sequences. Comparison or alignment of sequences and determination of percent identity between two sequences may be accomplished using a mathematical algorithm, such as BLAST (basic local alignment search tool). In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical (e.g., 85-90%, 85-95%, 85-100%, 90-95%, 90-100%, or 95-100%).

To calculate percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span," as determined by the algorithm). In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm. Other algorithms are also available for comparison of amino acid or nucleic acid sequences, comprising those available in commercial computer programs such as BLASTN for nucleotide sequences and BLASTP, gapped BLAST, and PSI-BLAST for amino acid sequences. Exemplary such programs are described in Altschul, et al., Basic local alignment search tool, J. Mol. Biol., 215 (3): 403-410, 1990; Altschul, et al., Methods in Enzymology; Altschul, et al., "Gapped BLAST and PSI-BLAST: a new generation of protein database search programs," Nucleic Acids Res. 25:3389-3402, 1997; Baxevanis, et al., Bioinformatics: A Practical Guide to the Analysis of Genes and Proteins, Wiley, 1998; and Misener, et al., (eds.), Bioinformatics Methods and Protocols (Methods in Molecular Biology, Vol. 132), Humana Press, 1999. In addition to identifying similar sequences, the programs mentioned above generally provide an indication of the degree of similarity. In some embodiments, two sequences are considered to be substantially similar if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are similar and/or identical over a relevant stretch of residues (e.g., 85-90%, 85-95%, 85-100%, 90-95%, 90-100%, or 95-100%). In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues. Sequences with substantial sequence similarity may be homologs of one another.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions.

The terms "improve," "increase," "inhibit," and "reduce" indicate values that are relative to a baseline or other reference measurement. In some embodiments, an appropriate reference measurement may comprise a measurement in certain system (e.g., in a single individual) under otherwise comparable conditions absent presence of (e.g., prior to and/or after) an agent or treatment, or in presence of an appropriate comparable reference agent. In some embodiments, an appropriate reference measurement may comprise a measurement in comparable system known or expected to respond in a comparable way, in presence of the relevant agent or treatment.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, NK cells, iNKT cells, and T cell therapies. T cell therapy can include adoptive T cell therapy, tumor-infiltrating lymphocyte (TIL) immunotherapy, autologous cell therapy, engineered autologous cell therapy (eACT™), and allogeneic T cell transplantation. Examples of T cell therapies are described in U.S. Patent Publication Nos. 2014/0154228 and 2002/0006409, U.S. Pat. No. 5,728,388, and International Publication No. WO 2008/081035.

The T cells of the immunotherapy can come from any source known in the art. For example, T cells can be differentiated in vitro from a hematopoietic stem cell population or can be obtained from a subject, for example for transplantation into a second subject after engineering. T cells can be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "in vitro" refers to events occurring in an artificial environment, e.g., in a test tube, reaction vessel, cell culture, etc., rather than within a multi-cellular organism. The term "in vitro cell" refers to any cell which is cultured ex vivo. In particular, an in vitro cell can include a T cell. The term "in vivo" refers to events that occur within a multi-cellular organism, such as a human or a non-human animal.

The term "isolated" refers to a substance that (1) has been separated from at least some components with which it was associated at an earlier time or with which the substance would otherwise be associated, and/or (2) is present in a composition that comprises a limited or defined amount or concentration of one or more known or unknown contaminants. An isolated substance, in some embodiments, may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% (e.g., 85-90%, 85-95%, 85-100%, 90-95%, 90-100%, or 95-100%) of other non-substance components with which the substance was associated at an earlier time, e.g., other components or contaminants with which the substance was previously or otherwise would be associated. In certain instances, a substance is isolated if it is present in a composition that comprises a limited or reduced amount or concentration of molecules of a same or similar type. For instance, in certain instances, a nucleic acid, DNA, or RNA substance is isolated if it is present in a composition that comprises a limited or reduced amount or concentration of non-substance nucleic acid, DNA, or RNA molecules. For instance, in certain instances, a polypeptide substance is isolated if it is present in a composition that comprises a limited or reduced amount or concentration of non-substance polypeptide molecules. In certain embodiments, an amount may be, e.g., an amount measured relative to the amount of a desired substance present in a composition. In certain embodiments, a limited amount may be an amount that is no more than 100% of the amount of substance in a composition, e.g., no more than 1%, 5%, 10%, 20%, 30%, 40%, 50%, 60%, 70%, 80%, 90%, or 95% of the amount of substance in a composition (e.g., 85-90%, 85-95%, 85-100%, 90-95%, 90-100%, or 95-100%). In certain instances, a composition is pure or substantially pure with respect to a selected substance. In some embodiments, an isolated substance is about 80%, about 85%, about 90%, about 91%, about 92%, about 93%, about 94%, about 95%, about 96%, about 97%, about 98%, about 99%, or more than about 99% pure (e.g., 85-90%, 85-95%, 85-100%, 90-95%, 90-100%, or 95-100%). A substance is "pure" if it is substantially free of other components or of contaminants. In some embodiments, a substance may still be considered "isolated" or even "pure," after having been combined with certain other components such as, for example, one or more carriers or excipients (e.g., buffer, solvent, water, etc.); in such embodiments, percent isolation or purity of the substance is calculated without comprising such carriers or excipients.

"Linker" (L) or "linker domain" or "linker region" refers to an oligo- or polypeptide region from about 1 to 100 amino acids in length, for example linking together any of the domains/regions of a CAR, and/or scFv, or ever one of more of those polypeptides together. Linkers may be composed of flexible residues like glycine and serine so that the adjacent protein domains are free to move relative to one another. Longer linkers may be used when it is desirable to ensure that two adjacent domains do not sterically interfere with one another. Linkers may be cleavable or non-cleavable. Examples of cleavable linkers include 2A linkers (for example T2A), 2A-like linkers or functional equivalents thereof and combinations thereof. Other linkers will be apparent to those of skill in the art and may be used in connection with this disclosure. A linker may be a portion of a multi-element agent that connects different elements to one another. For example, a polypeptide comprises two or more functional or structural domains may comprise a stretch of amino acids between such domains that links them to one another. In some embodiments, a polypeptide comprising a linker element has an overall structure of the general form S1-L-S2, wherein S1 and S2 may be the same or different and represent two domains associated with one another by the linker. In some embodiments, a polypeptide linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length (e.g., 1 to 10, 1 to 20, 1 to 30, 1 to 40, 1 to 50, 1 to 60, 1 to 70, 1 to 80, 1 to 90, 1 to 100, 10 to 20, 10 to 30, 10 to 40, 10 to 50, 10 to 60, 10 to 70, 10 to 80, 10 to 90, or 10 to 100 amino acids in length). In some embodiments, a linker is characterized in that it tends not to adopt a rigid three-dimensional structure, and instead provides flexibility to the polypeptide. In another example it may be used to connect to or more polypeptides to be expressed. Other linkers include non-cleavable linkers. A number of linkers are employed to realize the subject invention including "flexible linkers." The latter are rich in glycine. Klein et al., Protein Engineering, Design & Selection Vol. 27, No. 10, pp. 325-330, 2014; Priyanka et al., Protein Sci., 2013 February; 22 (2): 153-167.

In some embodiments, the linker is a synthetic linker. A synthetic linker can have a length of from about 10 amino acids to about 200 amino acids, e.g., from 10 to 25 amino acids, from 25 to 50 amino acids, from 50 to 75 amino acids, from 75 to 100 amino acids, from 100 to 125 amino acids, from 125 to 150 amino acids, from 150 to 175 amino acids, or from 175 to 200 amino acids. A synthetic linker can have a length of from 10 to 30 amino acids, e.g., 10, 11, 12, 13, 14, 15, 16, 17, 18, 19, 20, 21, 22, 23, 24, 25, 26, 27, 28, 29, or 30 amino acids. A synthetic linker can have a length of from 30 to 50 amino acids, e.g., from 30 to 35 amino acids, from 35 to 40 amino acids, from 40 to 45 amino acids, or from 45 to 50 amino acids.

In some embodiments, the linker is a flexible linker. In some embodiments, the linker is rich in glycine (Gly or G)

residues. In some embodiments, the linker is rich in serine (Ser or S) residues. In some embodiments, the linker is rich in glycine and serine residues. In some embodiments, the linker has one or more glycine-serine residue pairs (GS), e.g., 1, 2, 3, 4, 5, 6, 7, 8, 9, or 10 or more GS pairs.

The term "lymphocyte" includes natural killer (NK) cells, T cells, iNKT cell, or B cells. NK cells are a type of cytotoxic (cell toxic) lymphocyte that represent a component of the inherent immune system. NK cells reject tumors and cells infected by viruses. It works through the process of apoptosis or programmed cell death. They were termed "natural killers" because they do not require activation in order to kill cells. T cells play a role in cell-mediated-immunity (no antibody involvement). Its T cell receptors (TCR) differentiate themselves from other lymphocyte types. The thymus, a specialized organ of the immune system, is primarily responsible for the T cell's maturation. There are six types of T cells, namely: Helper T cells (e.g., CD4+ cells), Cytotoxic T cells (also known as TC, cytotoxic T lymphocyte, CTL, T-killer cell, cytolytic T cell, CD8+ T cells or killer T cell), Memory T cells ((i) stem memory $T_{SCM}$ cells, like naive cells, are CD45RO−, CCR7+, CD45RA+, CD62L+ (L-selectin), CD27+, CD28+ and IL-7Rα+, but they also express large amounts of CD95, IL-2Rβ, CXCR3, and LFA-1, and show numerous functional attributes distinctive of memory cells); (ii) central memory $T_{CM}$ cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T cells (Tregs, suppressor T cells, or CD4+CD25+ regulatory T cells), Natural Killer T cells (NKT) and Gamma Delta T cells. B-cells, on the other hand, play a role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

The term "neutralizing" refers to an antigen binding molecule, scFv, antibody, or a fragment thereof, that binds to a ligand and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

"Nucleic acid" refers to any polymeric chain of nucleotides. A nucleic acid may be DNA, RNA, or a combination thereof. In some embodiments, a nucleic acid comprises one or more natural nucleic acid residues. In some embodiments, a nucleic acid comprises of one or more nucleic acid analogs. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 1 10, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long (e.g., 20 to 100, 20 to 500, 20 to 1000, 20 to 2000, or 20 to 5000 or more residues). In some embodiments, a nucleic acid is partly or wholly single stranded; in some embodiments, a nucleic acid is partly or wholly double stranded. In some embodiments a nucleic acid has a nucleotide sequence comprising at least one element that encodes, or is the complement of a sequence that encodes, a polypeptide.

"Operably linked" refers to a juxtaposition where the components described are in a relationship permitting them to function in their intended manner. For example, a control element "operably linked" to a functional element is associated in such a way that expression and/or activity of the functional element is achieved under conditions compatible with the control element.

A "patient" includes any human who is afflicted with a cancer (e.g., prostate cancer). The terms "subject" and "patient" are used interchangeably herein.

The terms "peptide," "polypeptide," and "protein" are used interchangeably, and refer to a compound comprised of amino acid residues covalently linked by peptide bonds. A protein or peptide contains at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "pharmaceutically acceptable" refers to a molecule or composition that, when administered to a recipient, is not deleterious to the recipient thereof, or that any deleterious effect is outweighed by a benefit to the recipient thereof. With respect to a carrier, diluent, or excipient used to formulate a composition as disclosed herein, a pharmaceutically acceptable carrier, diluent, or excipient must be compatible with the other ingredients of the composition and not deleterious to the recipient thereof, or any deleterious effect must be outweighed by a benefit to the recipient. The term "pharmaceutically acceptable carrier" means a pharmaceutically-acceptable material, composition or vehicle, such as a liquid or solid filler, diluent, excipient, or solvent encapsulating material, involved in carrying or transporting an agent from one portion of the body to another (e.g., from one organ to another). Each carrier present in a pharmaceutical composition must be "acceptable" in the sense of being compatible with the other ingredients of the formulation and not deleterious to the patient, or any deleterious effect must be outweighed by a benefit to the recipient. Some examples of materials which may serve as pharmaceutically acceptable carriers comprise: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline;

Ringer's solution; ethyl alcohol; pH buffered solutions; polyesters, polycarbonates and/or polyanhydrides; and other non-toxic compatible substances employed in pharmaceutical formulations.

The term "pharmaceutical composition" refers to a composition in which an active agent is formulated together with one or more pharmaceutically acceptable carriers. In some embodiments, the active agent is present in a unit dose amount appropriate for administration in a therapeutic regimen that shows a statistically significant probability of achieving a predetermined therapeutic effect when administered to a relevant subject or population. In some embodiments, a pharmaceutical composition may be formulated for administration in solid or liquid form, comprising, without limitation, a form adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

The term "proliferation" refers to an increase in cell division, either symmetric or asymmetric division of cells. In some embodiments, "proliferation" refers to the symmetric or asymmetric division of T cells. "Increased proliferation" occurs when there is an increase in the number of cells in a treated sample compared to cells in a non-treated sample.

The term "reference" describes a standard or control relative to which a comparison is performed. For example, in some embodiments, an agent, animal, individual, population, sample, sequence, or value of interest is compared with a reference or control that is an agent, animal, individual, population, sample, sequence, or value. In some embodiments, a reference or control is tested, measured, and/or determined substantially simultaneously with the testing, measuring, or determination of interest. In some embodiments, a reference or control is a historical reference or control, optionally embodied in a tangible medium. Generally, a reference or control is determined or characterized under comparable conditions or circumstances to those under assessment. When sufficient similarities are present to justify reliance on and/or comparison to a selected reference or control.

"Regulatory T cells" ("Treg", "Treg cells", or "Tregs") refer to a lineage of CD4+ T lymphocytes that participate in controlling certain immune activities, e.g., autoimmunity, allergy, and response to infection. Regulatory T cells may regulate the activities of T cell populations and may also influence certain innate immune system cell types. Tregs may be identified by the expression of the biomarkers CD4, CD25 and Foxp3, and low expression of CD127. Naturally occurring Treg cells normally constitute about 5-10% of the peripheral CD4+ T lymphocytes. However, Treg cells within a tumor microenvironment (i.e., tumor-infiltrating Treg cells), Treg cells may make up as much as 20-30% of the total CD4+ T lymphocyte population.

The term "sample" generally refers to an aliquot of material obtained or derived from a source of interest. In some embodiments, a source of interest is a biological or environmental source. In some embodiments, a source of interest may comprise a cell or an organism, such as a cell population, tissue, or animal (e.g., a human). In some embodiments, a source of interest comprises biological tissue or fluid. In some embodiments, a biological tissue or fluid may comprise amniotic fluid, aqueous humor, ascites, bile, bone marrow, blood, breast milk, cerebrospinal fluid, cerumen, chyle, chime, ejaculate, endolymph, exudate, feces, gastric acid, gastric juice, lymph, mucus, pericardial fluid, perilymph, peritoneal fluid, pleural fluid, pus, rheum, saliva, sebum, semen, serum, smegma, sputum, synovial fluid, sweat, tears, urine, vaginal secretions, vitreous humour, vomit, and/or combinations or component(s) thereof. In some embodiments, a biological fluid may comprise an intracellular fluid, an extracellular fluid, an intravascular fluid (blood plasma), an interstitial fluid, a lymphatic fluid, and/or a transcellular fluid. In some embodiments, a biological fluid may comprise a plant exudate. In some embodiments, a biological tissue or sample may be obtained, for example, by aspirate, biopsy (e.g., fine needle or tissue biopsy), swab (e.g., oral, nasal, skin, or vaginal swab), scraping, surgery, washing or lavage (e.g., brocheoalvealar, ductal, nasal, ocular, oral, uterine, vaginal, or other washing or lavage). In some embodiments, a biological sample comprises cells obtained from an individual. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. Such a "processed sample" may comprise, for example nucleic acids or proteins extracted from a sample or obtained by subjecting a primary sample to one or more techniques such as amplification or reverse transcription of nucleic acid, isolation and/or purification of certain components, etc.

"Single chain variable fragment", "single-chain antibody variable fragments" or "scFv" antibodies refer to forms of antibodies comprising the variable regions of only the heavy and light chains, connected by a linker peptide.

The term "stage of cancer" refers to a qualitative or quantitative assessment of the level of advancement of a cancer. In some embodiments, criteria used to determine the stage of a cancer may comprise, without limitation, one or more of where the cancer is located in a body, tumor size, whether the cancer has spread to lymph nodes, whether the cancer has spread to one or more different parts of the body, etc. In some embodiments, cancer may be staged using the so-called TNM System, according to which T refers to the size and extent of the main tumor, usually called the primary tumor; N refers to the number of nearby lymph nodes that have cancer; and M refers to whether the cancer has metastasized. In some embodiments, a cancer may be referred to as Stage 0 (abnormal cells are present without having spread to nearby tissue, also called carcinoma in situ, or CIS; CIS is not cancer, though could become cancer), Stage I-III (cancer is present; the higher the number, the larger the tumor and the more it has spread into nearby tissues), or Stage IV (the cancer has spread to distant parts of the body). In some embodiments, a cancer may be assigned to a stage selected from the group consisting of: in situ; localized (cancer is limited to the place where it started, with no sign that it has spread); regional (cancer has spread to nearby lymph nodes, tissues, or organs): distant (cancer has spread to distant parts of the body); and unknown (there is not enough information to determine the stage).

"Stimulation," refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex, that specifically binds with a cognate stimulatory ligand present on an antigen present cell. A "stimulatory ligand" is a ligand that when present on an antigen presenting cell (e.g., an APC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an anti-CD3 antibody (such as OKT3), an MHC Class I molecule loaded with a peptide, a superagonist anti-CD2 antibody, and a superagonist anti-CD28 antibody.

The phrase "therapeutic agent" may refer to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms or human subjects. In some embodiments, an appropriate population may be defined by various criteria, such as a certain age group, gender, genetic background, preexisting clinical conditions, in accordance with presence or absence of a biomarker, etc. In some embodiments, a therapeutic agent is a substance that may be used to alleviate, ameliorate, relieve, inhibit, prevent, delay onset of, reduce severity of, and/or reduce incidence of one or more symptoms or features of a disease, disorder, and/or condition. In some embodiments, a therapeutic agent is an agent that has been or is required to be approved by a government agency before it may be marketed for administration to humans. In some embodiments, a therapeutic agent is an agent for which a medical prescription is required for administration to humans.

A "therapeutically effective amount," "effective dose," "effective amount," or "therapeutically effective dosage" of a therapeutic agent, e.g., engineered CAR T cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

"Transformation" refers to any process by which exogenous DNA is introduced into a host cell. Transformation may occur under natural or artificial conditions using various methods. Transformation may be achieved using any known method for the insertion of foreign nucleic acid sequences into a prokaryotic or eukaryotic host cell. In some embodiments, some transformation methodology is selected based on the host cell being transformed and/or the nucleic acid to be inserted. Methods of transformation may comprise, yet are not limited to, viral infection, electroporation, and lipofection. In some embodiments, a "transformed" cell is stably transformed in that the inserted DNA is capable of replication either as an autonomously replicating plasmid or as part of the host chromosome. In some embodiments, a transformed cell may express introduced nucleic acid.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission. In some embodiments, treatment may be of a subject who does not exhibit signs of the relevant disease, disorder and/or condition and/or of a subject who exhibits only early signs of the disease, disorder, and/or condition. In some embodiments, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

The term "vector" refers to a recipient nucleic acid molecule modified to comprise or incorporate a provided nucleic acid sequence. One type of vector is a "plasmid," which refers to a circular double stranded DNA molecule into which additional DNA may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) may be integrated into the genome of a host cell upon introduction into the host cell, and thereby are replicated along with the host genome. Moreover, certain vectors comprise sequences that direct expression of inserted genes to which they are operatively linked. Such vectors may be referred to herein as "expression vectors." Standard techniques may be used for engineering of vectors, e.g., as found in Sambrook et al., *Molecular Cloning: A Laboratory Manual* (2d ed., Cold Spring Harbor Laboratory Press, Cold Spring Harbor, N.Y. (1989)), which is incorporated herein by reference.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

The disclosure may employ, unless indicated specifically to the contrary, methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); Harlow and Lane, *Antibodies*, (Cold Spring Harbor Laboratory Press, Cold Spring Harbor, N.Y., 1998) *Current Protocols in Immunology* Q. E. Coligan, A. M. Kruisbeek, D. H. Margulies, E. M. Shevach and W. Strober, eds., 1991); *Annual Review of Immunology*; as well as monographs in journals such as *Advances in Immunology*.

Disclosed herein is a next generation CAR T-cell therapy targeted against one or more cell-surface antigens, for the treatment of B-cell malignancies, such as relapsed or refractory (r/r) B-cell malignancies. The allogeneic chimeric antigen receptor (CAR) T-cell may be engineered from T cells derived from healthy human donors. The autologous chimeric antigen receptor (CAR) T-cell may be engineered from appropriate human cancer patients. These engineered T cells undergo insertion of an engineered retroviral vector encoding a gene for a CAR construct, in certain aspects an anti-CD19 CAR. The next-generation CAR constructs utilize one of five signaling domains, including CD3γ, CD3δ, CD3ε, novel, modified CD3ε or DAP-12, as replacements for CD3 Zeta, standard in a CAR.

CD19 (also known as Cluster of Differentiation 19, B-lymphocyte antigen CD19, B-lymphocyte surface antigen B4, B4, CVID3, Differentiation antigen CD19) is a protein that is encoded by the CD19 gene in humans. Unless otherwise indicated, it is to be appreciated the references to CD19 in the present disclosure relate to human CD19. It is found on the surface of B cells. Since CD19 expression is a hallmark of B cells, it may be useful as an antigen, e.g., in recognizing B cells and cancer cells that arise from B cells, e.g., B-cell lymphomas. Anti-CD19 antibodies may bind CD19 expressed on, e.g., B lymphocytes in peripheral blood and spleen, B cell chronic lymphocytic leukemia (B-CLL) cells, pro lymphocytic leukemia (PLL) cells, hairy cell leukemia (HCL) cells, common acute lymphoblastic leukemia (CALL) cells, pre-B acute lymphoblastic leukemia (pre-B-ALL) cells, and NULL-acute lymphoblastic leukemia (NULL-ALL) cells, to provide a few non limiting examples. An exemplary pharmaceutical product that comprises an antigen binding system that comprises an anti-CD19 binding domain is the pharmaceutical product YESCARTA®. YESCARTA® is a CD19-directed genetically modified autologous T cell immunotherapy (See YESCARTA® FDA-approved package insert, the entirety of which is incorporated herein by reference with respect to methods and compositions relating to immunotherapy). Another exemplary pharmaceutical product that comprises an antigen binding system that comprises an anti-CD19 binding domain is the pharmaceutical product KYMRIAH®.

Both YESCARTA® and KYMRIAH® comprise antibody binding domains derived from an anti-human CD19 antibody. Many anti-CD19 antibodies are thought to bind an epitope of CD19 encoded in exon 4 of the CD19 gene. Other anti-CD19 binding domains may recognize different epitopes of CD19, or the same epitope with differential affinities.

An anti-CD19 binding domain of the present disclosure may comprise antigen-binding sequences as found in an antibody described herein. In some embodiments, an anti-CD19 binding domain of the present disclosure comprises an antigen binding fragment provided herein.

In various embodiments, an anti-CD19 binding domain of the present disclosure comprises at least one HCDR provided herein, e.g., at least one HCDR disclosed in Table 4 or Table 5. In various embodiments, an anti-CD19 binding domain of the present disclosure comprises two HCDRs provided herein, e.g., at least two HCDRs disclosed in Table 4 or Table 5. In various embodiments, an anti-CD19 binding domain of the present disclosure comprises three HCDRs provided herein, e.g., three HCDRs disclosed in Table 4 or Table 5.

In various embodiments, an anti-CD19 binding domain of the present disclosure comprises at least one LCDR provided herein, e.g., at least one LCDR disclosed in Table 4 or Table 5. In various embodiments, an anti-CD19 binding domain of the present disclosure comprises two LCDRs provided herein, e.g., at least two LCDRs disclosed in Table 4 or Table 5. In various embodiments, an anti-CD19 binding domain of the present disclosure comprises three LCDRs provided herein, e.g., three LCDRs disclosed in Table 4 or Table 5.

In various embodiments, an anti-CD19 binding domain of the present disclosure comprises at least one HCDR provided herein, e.g., at least one HCDR disclosed in Table 4 or Table 5 and at least one LCDR provided herein, e.g., at least one LCDR disclosed in Table 4 or Table 5. In various embodiments, an anti-CD19 binding domain of the present disclosure comprises two HCDRs provided herein, e.g., at least two HCDRs disclosed in Table 4 or Table 5, and two LCDRs provided herein, e.g., at least two LCDRs disclosed in Table 4 or Table 5. In various embodiments, an anti-CD19 binding domain of the present disclosure comprises three HCDRs provided herein, e.g., three HCDRs disclosed in Table 4 or Table 5, and three LCDRs provided herein, e.g., three LCDRs disclosed in Table 4 or Table 5.

In various embodiments, an anti-CD19 binding domain of the present disclosure comprises at least one heavy chain framework region (heavy chain FR) of a heavy chain variable domain disclosed herein, e.g., at least one heavy chain FR of a heavy chain variable domain disclosed in Table 4 or Table 5. In various embodiments, an anti-CD19 binding domain of the present disclosure comprises two heavy chain FRs of a heavy chain variable domain disclosed herein, e.g., at least two heavy chain FRs of a heavy chain variable domain disclosed in Table 4 or Table 5. In various embodiments, an anti-CD19 binding domain of the present disclosure comprises three heavy chain FRs of a heavy chain variable domain disclosed herein, e.g., three heavy chain FRs of a heavy chain variable domain disclosed in Table 4 or Table 5.

In various embodiments, an anti-CD19 binding domain of the present disclosure comprises at least one light chain FR of a light chain variable domain disclosed herein, e.g., at least one light chain FR of a light chain variable domain disclosed in Table 4 or Table 5. In various embodiments, an anti-CD19 binding domain of the present disclosure comprises two light chain FRs of a light chain variable domain disclosed herein, e.g., at least two light chain FRs of a light chain variable domain disclosed in Table 4 or Table 5. In various embodiments, an anti-CD19 binding domain of the present disclosure comprises three light chain FRs of a light chain variable domain disclosed herein, e.g., three light chain FRs of a light chain variable domain disclosed in Table 4 or Table 5.

In various embodiments, an anti-CD19 binding domain of the present disclosure comprises at least one heavy chain FR of a heavy chain variable domain disclosed herein, e.g., at least one heavy chain FR of a heavy chain variable domain disclosed in Table 4 or Table 5, and at least one light chain FR of a light chain variable domain disclosed herein, e.g., at least one light chain FR of a light chain variable domain disclosed in Table 4 or Table 5. In various embodiments, an anti-CD19 binding domain of the present disclosure comprises two heavy chain FRs of a heavy chain variable domain disclosed herein, e.g., at least two heavy chain FRs of a heavy chain variable domain disclosed in Table 4 or Table 5, and two light chain FRs of a light chain variable domain disclosed herein, e.g., at least two light chain FRs of a light chain variable domain disclosed in Table 4 or Table 5. In various embodiments, an anti-CD19 binding domain of the present disclosure comprises three heavy chain FRs of a heavy chain variable domain disclosed herein, e.g., three heavy chain FRs of a heavy chain variable domain disclosed in Table 4 or Table 5, and three light chain FRs of a light chain variable domain disclosed herein, e.g., three light chain FRs of a light chain variable domain disclosed in Table 4 or Table 5.

In various embodiments, an anti-CD19 binding domain of the present disclosure comprises one, two, or three FRs that together or each individually have at least 75% identity (e.g., at least 75%, at least 80%, at least 90%, at least 95%, or 100% identity; e.g., 85-90%, 85-95%, 85-100%, 90-95%, 90-100%, or 95-100%) to corresponding FR(s) of a heavy chain variable domain of a heavy chain variable domain disclosed in in Table 4 or Table 5. In various embodiments, an anti-CD19 binding domain of the present disclosure comprises one, two, or three FRs that together or each individually have at least 75% identity (e.g., at least 75%, at least 80%, at least 90%, at least 95%, or 100% identity; e.g., 85-90%, 85-95%, 85-100%, 90-95%, 90-100%, or 95-100%) to corresponding FR(s) of a light chain variable domain of a light chain variable domain disclosed in Table 4 or Table 5.

In various embodiments, an anti-CD19 binding domain of the present disclosure comprises at least one heavy chain variable domain having at least 75% sequence identity to a heavy chain variable domain disclosed in Table 4 or Table 5 (e.g., at least 75%, at least 80%, at least 90%, at least 95%, or 100% identity; e.g., 85-90%, 85-95%, 85-100%, 90-95%, 90-100%, or 95-100%). In various embodiments, an anti-CD19 binding domain of the present disclosure comprises two heavy chain variable domains each having at least 75% sequence identity to a heavy chain variable domain disclosed in Table 4 or Table 5 (e.g., at least 75%, at least 80%, at least 90%, at least 95%, or 100% identity; e.g., 85-90%, 85-95%, 85-100%, 90-95%, 90-100%, or 95-100%), which heavy chain variable domains may be same or different.

In various embodiments, an anti-CD19 binding domain of the present disclosure comprises at least one light chain variable domain having at least 75% sequence identity to a light chain variable domain disclosed in Table 4 or Table 5 (e.g., at least 75%, at least 80%, at least 90%, at least 95%, or 100% identity; e.g., 85-90%, 85-95%, 85-100%, 90-95%, 90-100%, or 95-100%). In various embodiments, an anti-CD19 binding domain of the present disclosure comprises two light chain variable domains each having at least 75% sequence identity to a light chain variable domain disclosed in Table 4 or Table 5 (e.g., at least 75%, at least 80%, at least 90%, at least 95%, or 100% identity; e.g., 85-90%, 85-95%, 85-100%, 90-95%, 90-100%, or 95-100%), which light chain variable domains may be same or different.

In various embodiments, an anti-CD19 binding domain of the present disclosure comprises at least one heavy chain variable domain having at least 75% sequence identity to a heavy chain variable domain disclosed in Table 4 or Table 5 (e.g., at least 75%, at least 80%, at least 90%, at least 95%, or 100% identity; e.g., 85-90%, 85-95%, 85-100%, 90-95%, 90-100%, or 95-100%) and at least one light chain variable domain having at least 75% sequence identity to a light chain variable domain disclosed in Table 4 or Table 5 (e.g., at least 75%, at least 80%, at least 90%, at least 95%, or 100% identity; e.g., 85-90%, 85-95%, 85-100%, 90-95%, 90-100%, or 95-100%).

In various embodiments, an anti-CD19 binding domain of the present disclosure comprises two heavy chain variable domains each having at least 75% sequence identity to a heavy chain variable domain disclosed in Table 4 or Table 5 (e.g., at least 75%, at least 80%, at least 90%, at least 95%, or 100% identity; e.g., 85-90%, 85-95%, 85-100%, 90-95%, 90-100%, or 95-100%) and two light chain variable domains each having at least 75% sequence identity to a light chain variable domain disclosed in Table 4 or Table 5 (e.g., at least 75%, at least 80%, at least 90%, at least 95%, or 100% identity; e.g., 85-90%, 85-95%, 85-100%, 90-95%, 90-100%, or 95-100%), where, in various embodiments, (i) each of the heavy chain variable domains may be same or different; or (ii) each of the light chain variable domains may be same or different.

TABLE 4

Exemplary anti-CD19 Antibody Sequences (Ab1)

| SEQ ID NO: | Description | Sequence |
|---|---|---|
| 1 | Heavy Chain Variable Domain | EVKLQESGPGLVAPSQSLSVTCTVSGVSLPDYGVSWIRQPPRKGLEWLGVIWGSETTYYNSALKSRLTIIKDNSKSQVFLKMNSLQTDDTAIYYCAKHYYYGGSYAMDYWGQGTSVTVSS |
| 2 | CDRH1 IMGT (Prot) | GVSLPDYG |
| 3 | CDRH1 Kabat (Prot) | DYGVS |

TABLE 4-continued

| Exemplary anti-CD19 Antibody Sequences (Ab1) | | |
|---|---|---|
| SEQ ID NO: | Description | Sequence |
| 4 | CDRH1 Chothia (Prot) | GVSLPDY |
| 5 | CDRH2 IMGT (Prot) | IWGSETT |
| 6 | CDRH2 Kabat (Prot) | VIWGSETTYYNSALKS |
| 7 | CDRH2 Chothia (Prot) | WGSET |
| 8 | CDRH3 IMGT (Prot) | AKHYYYGGSYAMDY |
| 9 | CDRH3 Kabat (Prot) | HYYYGGSYAMDY |
| 10 | CDRH3 Chothia (Prot) | HYYYGGSYAMDY |
| 11 | Light Chain Variable Domain | DIQMTQTTSSLSASLGDRVTISCRASQDISKYLNWYQ QKPDGTVKLLIYHTSRLHSGVPSRFSGSGSGTDYSLTI SNLEQEDIATYFCQQGNTLPYTFGGGTKLEIT |
| 12 | CDRL1 IMGT (Prot) | RASQDISKYLN |
| 13 | CDRL1 Kabat (Prot) | RASQDISKYLN |
| 14 | CDRL1 Chothia (Prot) | RASQDISKYLN |
| 15 | CDRL2 IMGT (Prot) | HTSRLHS |
| 16 | CDRL2 Kabat (Prot) | HTSRLHS |
| 17 | CDRL2 Chothia (Prot) | HTSRLHS |
| 18 | CDRL3 IMGT (Prot) | QQGNTLPYT |
| 19 | CDRL3 Kabat (Prot) | QQGNTLPYT |
| 20 | CDRL3 Chothia (Prot) | QQGNTLPYT |
| 21 | scFv (Prot) | DIQMTQTTSSLSASLGDRVTISCRASQDISKYLNWYQ QKPDGTVKLLIYHTSRLHSGVPSRFSGSGSGTDYSLTI SNLEQEDIATYFCQQGNTLPYTFGGGTKLEITGSTSGS GKPGSGEGSTKGEVKLQESGPGLVAPSQSLSVTCTVS GVSLPDYGVSWIRQPPRKGLEWLGVIWGSETTYYNS ALKSRLTIIKDNSKSQVFLKMNSLQTDDTAIYYCAKH YYYGGSYAMDYWGQGTSVTVSS |
| 22 | Linker (Prot) | GSTSGSGKPGSGEGSTKG |

TABLE 5

| Exemplary anti-CD19 Antibody Sequences (Ab2) | | |
|---|---|---|
| SEQ ID NO: | Description | Sequence |
| 23 | Heavy Chain Variable Domain | QVQLVQSGAEVKKPGSSVKVSCKDSGGTFSSYAISW VRQAPGQGLEWMGGIIPIFGTTNYAQQFQGRVTITAD |

TABLE 5-continued

Exemplary anti-CD19 Antibody Sequences (Ab2)

| SEQ ID NO: | Description | Sequence |
|---|---|---|
| | | ESTSTAYMELSSLRSEDTAVYYCAREAVAADWLDP WGQGTLVTVSS |
| 24 | CDRH1 IMGT (Prot) | GGTFSSYA |
| 25 | CDRH1 Kabat (Prot) | SYAIS |
| 26 | CDRH1 Chothia (Prot) | GGTFSSY |
| 27 | CDRH2 IMGT (Prot) | IIPIFGTT |
| 28 | CDRH2 Kabat (Prot) | GIIPIFGTTNYAQQFQG |
| 29 | CDRH2 Chothia (Prot) | PIFG |
| 30 | CDRH3 IMGT (Prot) | AREAVAADWLDP |
| 31 | CDRH3 Kabat (Prot) | EAVAADWLDP |
| 32 | CDRH3 Chothia (Prot) | AVAADWLD |
| 33 | Light Chain Variable Domain | EIVLTQSPGTLSLSPGERATLSCRASQSVSSSYLAWY QQKPGQAPRLLIYGASSRATGIPDRFSGSGSGTDFTLT ISRLEPEDFAVYYCQQYGSSRFTFGPGTKVDIK |
| 34 | CDRL1 IMGT (Prot) | QSVSSSY |
| 35 | CDRL1 Kabat (Prot) | RASQSVSSSYLA |
| 36 | CDRL1 Chothia (Prot) | SQSVSSSY |
| | CDRL2 IMGT (Prot) | GAS |
| 38 | CDRL2 Kabat (Prot) | GASSRAT |
| | CDRL2 Chothia (Prot) | GAS |
| 40 | CDRL3 IMGT (Prot) | QQYGSSRFT |
| 41 | CDRL3 Kabat (Prot) | QQYGSSRFT |
| 42 | CDRL3 Chothia (Prot) | YGSSRF |
| 43 | scFv (Prot) | EIVLTQSPGTLSLSPGERATLSCRASQSVSSSYLAWY QQKPGQAPRLLIYGASSRATGIPDRFSGSGSGTDFTLT ISRLEPEDFAVYYCQQYGSSRFTFGPGTKVDIKGSTS GSGKPGSGEGSTKGQVQLVQSGAEVKKPGSSVKVSC KDSGGTFSSYAISWVRQAPGQGLEWMGGIIPIFGTTN YAQQFQGRVTITADESTSTAYMELSSLRSEDTAVYY CAREAVAADWLDPWGQGTLVTVSS |
| 22 | Linker (Prot) | GSTSGSGKPGSGEGSTKG |

Chimeric antigen receptors (CARs) are engineered receptors that may direct or redirect T cells (e.g., donor T cells) to target a selected antigen. A CAR may be engineered to recognize an antigen and, when bound to that antigen (such as CD19), activate the immune cell to attack and destroy the cell bearing that antigen. When these antigens exist on tumor cells, an immune cell that expresses the CAR may target and kill the tumor cell. CARs generally comprise an extracellular binding domain that mediates antigen binding (e.g., an anti-CD19 binding domain), a transmembrane domain that spans, or is understood to span, the cell membrane when the CAR is present at a cell surface or cell membrane, and an intracellular (or cytoplasmic) signaling domain.

One or more antigen binding domains determine the target(s) of an antigen binding system. A binding domain may comprise a binding domain to any antigen of interest, e.g., an antibody provided by the present disclosure, e.g., a binding motif of the present disclosure. Binding domains are used in chimeric antigen receptors at least in part because they may be engineered to be expressed as part of a single chain along with the other CAR components. See, for example, U.S. Pat. Nos. 7,741,465, and 6,319,494 as well as Eshhar et al., Cancer Immunol Immunotherapy (1997) 45:131-136, Krause et al., J. Exp. Med., Volume 188, No. 4, 1998 (619-626); Finney et al., Journal of Immunology, 1998, 161:2791-2797, each of which is incorporated herein by reference with respect to binding domains in CARs. A binding domain or scFv, is a single chain antigen binding fragment comprising a heavy chain variable domain and a light chain variable domain, which heavy chain variable domain and light chain variable domain are linked or connected together. See, for example, U.S. Pat. Nos. 7,741,465, and 6,319,494 as well as Eshhar et al., Cancer Immunol Immunotherapy (1997) 45:131-136, each of which is incorporated herein by reference with respect to binding domains. When derived from a parent antibody, a binding domain may retain some of, retain all of, or essentially retain the parent antibody's binding of a target antigen. In some embodiments, a CAR contemplated herein comprises antigen-specific binding domain that may be a scFv (a murine, human or humanized scFv) that binds an antigen expressed on a cancer cell. In a certain embodiment, the scFv binds CD19.

In certain embodiments, the CARs contemplated herein may comprise linker residues between the various domains, e.g., between VH and VL domains, added for appropriate spacing conformation of the molecule. CARs contemplated herein, may comprise one, two, three, four, or five or more linkers. In some embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

Illustrative examples of linkers include glycine polymers (G) n; glycine-serine polymers $(G_{1-5}S_{1-5})n$, where n is an integer of at least one, two, three, four, or five (SEQ ID NO: 92); glycine-alanine polymers; alanine-serine polymers; and other flexible linkers known in the art. Glycine and glycine-serine polymers are relatively unstructured, and therefore may be able to serve as a neutral tether between domains of fusion proteins such as the CARs described herein. Glycine accesses more phi-psi space than even alanine and is much less restricted than residues with longer side chains (see Scheraga, *Rev. Computational Chem.* 11173-142 (1992)). Other linkers contemplated herein include Whitlow linkers (see Whitlow, *Protein Eng.* 6(8): 989-95 (1993)). The ordinarily skilled artisan will recognize that design of a CAR in some embodiments may include linkers that are all or partially flexible, such that the linker may include a flexible linker as well as one or more portions that confer less flexible structure to provide for a desired CAR structure. In one embodiment, any of the constructs described herein may comprise a "GS" linker. In another embodiment, any of the constructs described herein comprise a "GSG" linker. In an example a glycine-serine linker comprises or consists of the amino acid sequence GS. In an example a glycine-serine linker comprises or consists of the amino acid sequence GGGSGGGS (SEQ ID NO: 46). In another embodiment, the CARs described herein comprise the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 22).

In certain embodiments, an anti-CD19 binding domain of the present disclosure comprises a binding domain that comprises a heavy chain variable domain of the present disclosure, a light chain variable domain of the present disclosure, and a linker having at least 75% sequence identity to SEQ ID NO: 22 (e.g., at least 75%, at least 80%, at least 90%, at least 95%, or 100% identity; e.g., 85-90%, 85-95%, 85-100%, 90-95%, 90-100%, or 95-100%). In certain embodiments, an anti-CD19 binding domain of the present disclosure comprises a binding domain that comprises a linker according to SEQ ID NO: 22.

The engineered CARs described herein may also comprise an N-terminal signal peptide or tag at the N-terminus of the scFv or antigen binding domain. In one embodiment, a heterologous signal peptide may be used. The antigen binding domain or scFV may be fused to a leader or a signal peptide that directs the nascent protein into the endoplasmic reticulum and subsequent translocation to the cell surface. It is understood that, once a polypeptide containing a signal peptide is expressed at the cell surface, the signal peptide is generally proteolytically removed during processing of the polypeptide in the endoplasmic reticulum and translocation to the cell surface. Thus, a polypeptide such as the CAR constructs described herein, are generally expressed at the cell surface as a mature protein lacking the signal peptide, whereas the precursor form of the polypeptide includes the signal peptide. Any suitable signal sequence known in the art may be used. Similarly, any known tag sequence known in the art may also be used. In certain embodiments, a binding domain of the present disclosure comprises an anti-CD19 binding domain that comprises a heavy chain variable domain of the present disclosure, a light chain variable domain of the present disclosure, and a signal sequence having at least 75% sequence identity to SEQ ID NO: 44 (e.g., at least 75%, at least 80%, at least 90%, at least 95%, or 100% identity; e.g., 85-90%, 85-95%, 85-100%, 90-95%, 90-100%, or 95-100%), MALPVTALLLPLALLLHAARP (SEQ ID NO: 44).

In embodiments, a CAR comprises a scFv that further comprises a variable region linking sequence. A "variable region linking sequence," is an amino acid sequence that connects a heavy chain variable region to a light chain variable region and provides a spacer function compatible with interaction of the two sub-binding domains so that the resulting polypeptide retains a specific binding affinity to the same target molecule as an antibody that comprises the same light and heavy chain variable regions. In one embodiment, the variable region linking sequence is 1, 2, 3, 4, 5, 6, 7, 8, 9, 10, 11, 12, 13, 14, 15, 16, 17, 18, 19, 20, 21, 22, 23, 24, 25, or more amino acids long.

In embodiments, the binding domain of the CAR is followed by one or more "spacer domains," which refers to the region that moves the antigen binding domain away from the effector cell surface to enable proper cell/cell contact, antigen binding and activation (Patel et al., *Gene Therapy,*

1999; 6:412-419). The spacer domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain may include the amino acid sequence of a naturally occurring immunoglobulin hinge region or an altered immunoglobulin hinge region.

The binding domain of the CAR may generally be followed by one or more "hinge domains," which plays a role in positioning the antigen binding domain away from the effector cell surface to enable proper cell/cell contact, antigen binding and activation. A CAR generally comprises one or more hinge domains between the binding domain and the transmembrane domain. The hinge domain may be derived either from a natural, synthetic, semi-synthetic, or recombinant source. The hinge domain may include the amino acid sequence of a naturally occurring immunoglobulin hinge region or an altered immunoglobulin hinge region.

In some embodiments, an antigen binding system of the present disclosure may comprise a hinge that is, is from, or is derived from (e.g., comprises all or a fragment of) an immunoglobulin-like hinge domain. In some embodiments, a hinge domain is from or derived from an immunoglobulin. In some embodiments, a hinge domain is selected from the hinge of IgG1, IgG2, IgG3, IgG4, IgA, IgD, IgE, or IgM, or a fragment thereof.

A hinge may be derived from a natural source or from a synthetic source. Hinge domains suitable for use in the CARs described herein include the hinge region derived from the extracellular regions of type 1 membrane proteins such as CD8α, CD4, CD28 and CD7, which may be wild-type hinge regions from these molecules or may be altered, for example a truncated CD28 hinge domain. A hinge may be derived from a natural source or from a synthetic source. In some embodiments, an Antigen binding system of the present disclosure may comprise a hinge that is, is from, or is derived from (e.g., comprises all or a fragment of) CD2, CD3 delta, CD3 epsilon, CD3 gamma, CD4, CD7, CD8α, CD8β, CD11a (ITGAL), CD11b (ITGAM), CD11c (ITGAX), CD11d (ITGAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (BY55), CD162 (SELPLG), CD226 (DNAMI), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA1-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, or Toll ligand receptor, or which is a fragment or combination thereof. In embodiments, the hinge domain comprises a CD28 hinge region. In embodiments the CARs described herein comprise a hinge domain from CD28 having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 47 (IEVMYPPPYLD-NEKSNGTIIHVKGKHLCPSPLFPGPSKP (SEQ ID NO: 47)). In embodiments, the hinge domain comprises a CD28T hinge region. In embodiments the CARs described herein comprise a hinge domain from CD28 having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 48 (LD-NEKSNGTIIHVKGKHLCPSPLFPGPSKP (SEQ ID NO: 48)). In embodiments, the hinge domain comprises a CD8a hinge region. In embodiments the CARs described herein comprise a hinge domain from CD8a having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 49 or 77

```
                                        (SEQ ID NO: 49))
FVPVFLPAKPTTTPAPRPPTPAPTIASQPLSLRPEACRPAAGGAVH

TRGLDFACD

                                        (SEQ ID NO: 77))
TTTPAPRPPTPAPTIASQPLSLRPEACRPAAGGAVHTRGLDFACD.
```

Polynucleotide and polypeptide sequences of these hinge domains are known. In some embodiments, the polynucleotide encoding a hinge domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a nucleotide sequence known. In some embodiments, the polypeptide sequence of a hinge domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a known polypeptide sequence.

In general, a "transmembrane domain" (e.g., of an antigen binding system) refers to a domain having an attribute of being present in the membrane when present in a molecule at a cell surface or cell membrane (e.g., spanning a portion or all of a cellular membrane). A costimulatory domain for an antigen binding system of the present disclosure may further comprise a transmembrane domain and/or an intracellular signaling domain. It is not required that every amino acid in a transmembrane domain be present in the membrane. For example, in some embodiments, a transmembrane domain is characterized in that a designated stretch or portion of a protein is substantially located in the membrane. Amino acid or nucleic acid sequences may be analyzed using a variety of algorithms to predict protein subcellular localization (e.g., transmembrane localization). The programs psort (PSORT.org) and Prosite (prosite.expasy.org) are exemplary of such programs.

The type of transmembrane domain comprised in an antigen binding system described herein is not limited to any type. In some embodiments, a transmembrane domain is selected that is naturally associated with a binding domain and/or intracellular domain. In some instances, a transmembrane domain comprises a modification of one or more amino acids (e.g., deletion, insertion, and/or substitution), e.g., to avoid binding of such domains to a transmembrane domain of the same or different surface membrane proteins to minimize interactions with other members of the receptor complex. A transmembrane domain may be derived either from a natural or from a synthetic source. Where the source is natural, a domain may be derived from any membrane-bound or transmembrane protein. Exemplary transmembrane domains may be derived from (e.g., may comprise at least a transmembrane domain of) an alpha, beta or zeta chain of a T-cell receptor, CD28, CD3 epsilon, CD3 delta, CD3 gamma, CD45, CD4, CD5, CD7, CD8, CD8 alpha, CD8beta, CD9, CD11a, CD11b, CD11c, CD11d, CD16, CD22, CD27, CD33, CD37, CD64, CD80, CD86, CD134, CD137, TNFSFR25, CD154, 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD276 (B7-H3), CD29, CD30, CD40, CD49a, CD49D, CD49f, CD69, CD84, CD96 (Tactile), CDS, CEACAM1, CRT AM, cytokine receptor, DAP-10, DNAMI (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that binds with CD83, LIGHT, LIGHT, LTBR, Ly9 (CD229), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof. In some embodiments, a transmembrane domain may be synthetic (and can, e.g., comprise predominantly hydrophobic residues such as leucine and valine). In some embodiments, a triplet of phenylalanine, tryptophan and valine are comprised at each end of a synthetic transmembrane domain. In some embodiments, a transmembrane domain is directly linked or connected to a cytoplasmic domain. In some embodiments, a short oligo- or polypeptide linker (e.g., between 2 and 10 amino acids in length) may form a linkage between a transmembrane domain and an intracellular domain. In some embodiments, a linker is a glycine-serine doublet. In embodiments the CARs described herein comprise a TM domain from CD28 having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 50 (FWVLVVVGGVLACYSLLVTVAFIIFWV (SEQ ID NO: 50)). In embodiments the CARs described herein comprise a TM domain from CD8a having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) of SEQ ID NO: 51 or SEQ ID NO: 78

```
(IYIWAPLAGTCGVLLLSLVITLYCNHRN (SEQ ID NO: 51)).

(IYIWAPLAGTCGVLLLSLVITLYC (SEQ ID NO: 78)).
```

Polynucleotide and polypeptide sequences of transmembrane domains provided herein are known. In some embodiments, the polynucleotide encoding a transmembrane domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a nucleotide sequence known. In some embodiments, the polypeptide sequence of a transmembrane domain comprises a polypeptide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% (e.g., 85-90%, 85-95%, 85-100%, 90-95%, 90-100%, or 95-100%) identical to a polypeptide sequence known. Optionally, short spacers may form linkages between any or some of the extracellular, transmembrane, and intracellular domains of the CAR.

Intracellular signaling domains that may transduce a signal upon binding of an antigen to an immune cell are known, any of which may be comprised in an antigen binding system of the present disclosure. For example, cytoplasmic sequences of a T cell receptor (TCR) are known to initiate signal transduction following TCR binding to an antigen (see, e.g., Brownlie et al., Nature Rev. Immunol. 13:257-269 (2013)).

In embodiments, CARs contemplated herein comprise an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. In some embodiments, a signaling domain and/or activation domain comprises a cytoplasmic signaling domain derived from CD3γ, CD3δ, CD3ε, or DAP-12, or a fragment, truncation, or a combination thereof.

The term "effector function" refers to a specialized function of the cell. Effector function of the T cell, for example, may be cytolytic activity or help or activity including the secretion of a cytokine. Thus, the term "intracellular signaling domain" refers to the portion of a protein which transduces the effector function signal and that directs the cell to perform a specialized function. While usually the entire intracellular signaling domain may be employed, in many cases it is not necessary to use the entire domain. To the extent that a truncated portion of an intracellular signaling domain is used, such truncated portion may be used in place of the entire domain as long as it transduces the effector function signal. The term intracellular signaling domain is meant to include any truncated portion of the intracellular signaling domain sufficient to transducing effector function signal.

In one embodiment, the CARs have a CD3ε domain having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence according to:

KNRKAKAKPVTRGAGAGGRQRGQNKER-PPPVPNPDYEPIRKGQRDLYSGLNQRRI (SEQ ID NO: 52). In embodiments, CD3ε domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

(SEQ ID NO: 53)
AAGAACCGGAAGGCCAAGGCCAAGCCTGTGACAAGAGGTGCTGGTGCTGG

CGGCAGACAGAGAGGCCAGAACAAAGAAAGACCTCCTCCTGTGCCTAATC

CTGACTACGAGCCCATCCGGAAGGGCCAGAGAGATCTGTACAGCGGCCTG

AACCAGCGGCGGATT.

In embodiments, CD3ε domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

(SEQ ID NO: 54)
AAGAACCGCAAAGCAAAGGCAAAACCCGTCACACGAGGAGCGGGCGCAGG

GGGACGACAACGCGGTCAGAATAAGGAACGCCCGCCTCCAGTACCAAATC

CAGATTATGAACCAATTCGGAAGGGACAACGCGATCTCTACTCCGGTCTC

AATCAGAGGCGAATT.

In one embodiment, the CARs have a novel CD3ε domain, referred to as Epsilon-CO (Δ181-185), having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence according to:

KNRKAKAKPVTRGAGAGGRQRGQNKER-PPPVPNPDYEPIRKGQRDLYSGL (SEQ ID NO: 87). In embodiments, the CD3ε domain, referred to as Epsilon-CO (Δ181-185) is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

(SEQ ID NO: 79)
AAGAACCGCAAAGCAAAGGCAAAACCCGTCACACGAGGAGCGGGCGCAGG

GGGACGACAACGCGGTCAGAATAAGGAACGCCCGCCTCCAGTACCAAATC

CAGATTATGAACCAATTCGGAAGGGACAACGCGATCTCTACTCCGGTCTC.

In one embodiment, the CARs have a novel CD3ε domain, referred to as Epsilon-CO (R183K), having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence according to:

KNRKAKAKPVTRGAGAGGRQRGQNKER-PPPVPNPDYEPIRKGQRDLYSGLNQKRI (SEQ ID NO: 88). In embodiments, CD3ε domain, referred to as Epsilon-CO (R183K), is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

(SEQ ID NO: 80)
AAGAACCGCAAAGCAAAGGCAAAACCCGTCACACGAGGAGCGGGCGCAGG

GGGACGACAACGCGGTCAGAATAAGGAACGCCCGCCTCCAGTACCAAATC

CAGATTATGAACCAATTCGGAAGGGACAACGCGATCTCTACTCCGGTCTC

AATCAGAAGCGAATT.

In one embodiment, the CARs have a novel CD3ε domain, referred to as Epsilon-CO (S178N.R183K), having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence according to:

KNRKAKAKPVTRGAGAGGRQRGQNKER-PPPVPNPDYEPIRKGQRDLYNGLNQKRI (SEQ ID NO: 89). In embodiments, CD3ε domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

(SEQ ID NO: 81)
AAGAACCGCAAAGCAAAGGCAAAACCCGTCACACGAGGAGCGGGCGCAGG

GGGACGACAACGCGGTCAGAATAAGGAACGCCCGCCTCCAGTACCAAATC

CAGATTATGAACCAATTCGGAAGGGACAACGCGATCTCTACAACGGTCTC

AATCAGAAGCGAATT.

In certain aspects, the novel CD3ε domains, Epsilon-CO (Δ181-185), Epsilon-CO (R183K), and Epsilon-CO (S178N.R183K) improve trafficking of a CAR to a cell membrane.

In one embodiment, the CARs have a CD3δ domain having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence according to:

(SEQ ID NO: 55)
GHETGRLSGAADTQALLRNDQVYQPLRDRDDAQYSHLGGNWARNK.

In embodiments, CD3δ domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

(SEQ ID NO: 56)
GGACACGAAACAGGCAGACTTTCTGGCGCCGCTGATACACAGGCCCTGCT
GAGAAACGACCAGGTGTACCAGCCTCTGAGAGACAGAGATGACGCCCAGT
ACTCTCACCTCGGCGGCAATTGGGCCAGAAACAAG.

In one embodiment, the CARs have a CD3γ domain having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence according to:

(SEQ ID NO: 57)
GQDGVRQSRASDKQTLLPNDQLYQPLKDREDDQYSHLQGNQLRRN.

In embodiments, CD3γ domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

(SEQ ID NO: 58)
GGACAGGATGGCGTCAGACAGAGCAGAGCCAGCGACAAGCAAACCCTGCT
GCCTAACGACCAGCTGTACCAGCCTCTGAAGGACAGAGAGGACGACCAGT
ACAGCCATCTGCAGGGCAACCAGCTGCGGAGAAAC.

In one embodiment, the CARs have a DAP-12 domain having the amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence according to:

YFLGRLVPRGRGAAEAATRKQRITETESPYQELQG-QRSDVYSDLNTQRPYYK (SEQ ID NO: 59). In embodiments, DAP-12 domain is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

(SEQ ID NO: 60)
TACTTCCTGGGCAGACTGGTGCCTAGAGGAAGAGGAGCTGCTGAGGCTGC
TACCAGAAAGCAGAGAATCACCGAGACCGAGAGCCCTTACCAGGAGCTGC
AGGGACAGAGAAGCGACGTGTACAGCGACCTGAACACCCAGAGACCTTAC
TACAAG.

It is known that signals generated through the TCR alone are insufficient for full activation of the T cell and that a secondary or costimulatory signal may also be required. Thus, T cell activation may be said to be mediated by two distinct classes of intracellular signaling domains: primary signaling domains that initiate antigen-dependent primary activation through the TCR (e.g., a TCR/CD3 complex) and costimulatory signaling domains that act in an antigen independent manner to provide a secondary or costimulatory signal. In some embodiments, a CAR contemplated herein comprises an intracellular signaling domain that comprises one or more "costimulatory signaling domain" and a "primary signaling domain."

CARs contemplated herein comprise one or more costimulatory signaling domains to enhance the efficacy and expansion of T cells expressing CAR receptors. As used herein, the term, "costimulatory signaling domain," or "costimulatory domain", refers to an intracellular signaling domain of a costimulatory molecule. In some embodiments, costimulatory molecules may include CD27, CD28, CD137 (4-IBB), OX40 (CD134), CD30, CD40, PD-I, ICOS (CD278), CTLA4, LFA-1, CD2, CD7, LIGHT, TRIM, LCK3, SLAM, DAPIO, LAG3, HVEM, and NKD2C, and CD83. In embodiments, the CARs described herein comprise a CD28 costimulatory domain having the amino acid sequence of having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 61.

(SEQ ID NO: 61)
RSKRSRLLHSDYMNMTPRRPGPTRKHYQPYAPPRDFAAYRS.

In embodiments, the CARs described herein comprise a 4-1BB costimulatory domain having the amino acid sequence of having at least 75% sequence identity to (such as, at least 75%, at least 80%, at least 90%, at least 95%, or 100% identity; e.g., 85-90%, 85-95%, 85-100%, 90-95%, 90-100%, or 95-100%) SEQ ID NO: 93.

(SEQ ID NO: 93)
KRGRKKLLYIFKQPFMRPVQTTQEEDGCSCRFPEEEEGGCE.

Components of a CAR may be exchanged or "swapped" using routine techniques of biotechnology for equivalent components. To provide just a few non-limiting and partial examples, a CAR of the present disclosure may comprise a binding domain as provided herein in combination with a hinge provided herein and a costimulatory domain provided herein. In certain examples, a CAR of the present disclosure may comprise a leader sequence as provided herein together with a binding domain as provided herein in combination with a hinge provided herein and s costimulatory domain provided herein.

In certain aspects, the present disclosure comprises nucleic acids encoding anti-CD19 binding domains provided herein. In certain further aspects, the present disclosure comprises nucleic acids encoding antibodies provided herein, comprising, without limitation, nucleic acids encoding anti-CD19 binding domains. In certain further aspects, the present disclosure comprises nucleic acids encoding antigen binding systems provided herein, comprising without limitation nucleic acids encoding anti-CD19 chimeric antigen receptors.

In embodiments, an anti-CD19 CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence according to:

(SEQ ID NO: 62)
DIQMTQTTSSLSASLGDRVTISCRASQDISKYLNWYQQKPDGTVKLLIYH
TSRLHSGVPSRFSGSGSGTDYSLTISNLEQEDIATYFCQQGNTLPYTFGG
GTKLEITGSTSGSGKPGSGEGSTKGEVKLQESGPGLVAPSQSLSVTCTVS
GVSLPDYGVSWIRQPPRKGLEWLGVIWGSETTYYNSALKSRLTIIKDNSK

-continued

```
SQVFLKMNSLQTDDTAIYYCAKHYYYGGSYAMDYWGQGTSVTVSSAAALD
NEKSNGTIIHVKGKHLCPSPLFPGPSKPFWVLVVVGGVLACYSLLVTVAF
IIFWVRSKRSRLLHSDYMNMTPRRPGPTRKHYQPYAPPRDFAAYRSKNRK
AKAKPVTRGAGAGGRQRGQNKERPPPVPNPDYEPIRKGQRDLYSGLNQRR
I.
```

In embodiments an anti-CD19 CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

GATATACAGATGACC-CAAACGACGTCTAGCCTCAGTGCGT-CACTCGGGGATCGGGT GACAATT-AGCTGCAGGGCTAGCCAGGATATTTCAAAATATCT TAACTGGTATCAAC AAAAGCCAGATGGAACCGTAAAACTGCT-CATATACCACACCAGTCGCCTGCATTCA GGGGTTCCGAGCCGCTTTTCTGG-GAGCGGTAGCGGAACtGAt-TATAGCTTGACAATA AGCAACCTCGAGCAG-GAAGACATTGCGACGTACTTCTGTCAGCAAGG-GAACACGCT GCCGTATACCTTCGGTGGCGGCACTAAACTG-GAAATCACGGGATCTACGTCTGGAT CCG-GAAAACCTGGATCTGGTGAAGGATC-CACTAAAGGCGAAGTCAAGTTGCAAGA GTCTGGACCTGGTCTCGTGGCACCTTCACAGT-CACTCTCCGTTACCTGTACCGTATCT GGAGTTT-CACTTCCCGACTATGGCGTGTCATGGATACGC-CAACCACCGCGAAAAGG TCTTGAATGGCTGGGCGTTATCTGGG-GATCCGAAACCACATACTACAACTCTGCGCT CAAGTCACGGCTGACTATTATAAAGGACAATT-CAAAGAGCCAAGTGTTCCTGAAAA TGAACAGCCTGCAGACT-GATGACACTGCAATATATTACTGCGCCAAGCAT-TACTATT ACGGCGGATCTTACGCGATGGATTAT-TGGGGCCAGGGCACCTCTGTAACAGTCAGC TCCGCGGCCGCATTGGACAATGAAAAATC-CAATGGCACAATAATTCATGTAAAGGG CAAACACTTGTGTCCTAGCC-CACTCTTTCCTGGTCCGTCTAAACCGTTTTGG-GTGCTC GTTGTGGTTG-GAGGCGTCCTGGCTTGT-TACTCTCTGTTGGTGACTGTAGCCTTTATAA TATTCTGGGT-TAGAAGCAAACGAAGTAGGCTTTTACATTCA-GACTATATGAACATG ACACCAA-GACGCCCCGGCCCCACAAGAAAACACTATC-AGCCCTATGCTCCGCCTCG GGACTTCGCTGCT-TACCGAAGCAAGAACCGCAAAGCAAAGGCA-AAACCCGTCACAC GAGGAGCGGGCGCAGG-GGGACGACAACGCGGTCAGAATAAGGAACG-CCCGCCTCC AGTACCAAATCCAGATTATGAAC-CAATTCGGAAGGGACAACGCGATCTC-TACTCCG GTCTCAATCAGAGGCGAATT (SEQ ID NO: 63). In embodiments an anti-CD19 CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

```
                                           (SEQ ID NO: 64)
GACATCCAAATGACCCAAACCACCTCCTCCCTGAGCGCCTCCCTTGGAG
ACCGAGTTACCATCTCCTGCCGAGCTTCTCAAGACATCTCCAAGTACTTG
AATTGGTATCAACAAAAGCCCGACGGAACCGTGAAGCTGCTGATCTACCA
CACATCCCGGCTGCACTCTGGCGTTCCCTCAAGATTCTCCGGCTCTGGAA
GCGGAACCGACTACTCCCTGACCATCTCCAACCTGGAGCAAGAGGACATC
GCTACCTACTTCTGCCAACAAGGCAACACCCTGCCTTACACCTTCGGAGG
AGGAACCAAGCTGGAGATCACCGGAAGCACAAGCGGATCTGGCAAGCCTG
GAAGCGGAGAGGGAAGCACCAAGGGAGAGGTGAAGCTGCAAGAGAGCGGA
CCTGGATTGGTGGCCCCCTCACAATCCCTGAGCGTTACATGCACTGTGAG
CGGCGTGTCCCTTCCTGACTACGGCGTTTCCTGGATCCGCCAACCTCCAA
GAAAGGGACTGGAGTGGCTGGGAGTGATCTGGGGAAGCGAGACCACCTAC
TACAACTCCGCCCTGAAGAGCCGACTGACCATCATCAAGGACAACTCCAA
GAGCCAAGTGTTCCTGAAGATGAACTCTCTCCAAACCGACGACACCGCTA
TCTACTACTGCGCTAAGCACTACTACTACGGAGGAAGCTACGCTATGGAC
TACTGGGGACAAGGCACCTCTGTGACCGTCTCCTCTGCCGCCGCTCTGGA
CAACGAGAAGAGCAACGGAACCATCATCCACGTGAAGGGAAAGCACCTGT
GCCCCTCTCCTCTGTTCCCTGGACCCTCCAAGCCTTTCTGGGTGCTCGTG
GTGGTGGGAGGAGTGCTGGCTTGCTACTCCCTGCTTGTGACCGTGGCTTT
CATCATCTTCTGGGTTAGAAGCAAGAGAAGCAGACTGCTGCACAGCGACT
ACATGAACATGACCCCTAGAAGGCCCGGACCTACCAGAAAGCACTACCAG
CCTTACGCTCCTCCTAGAGACTTCGCTGCTTACAGAAGCAAGAACCGGAA
GGCCAAGGCCAAGCCTGTGACAAGAGGTGCTGGTGCTGGCGGCAGACAGA
GAGGCCAGAACAAAGAAAGACCTCCTCCTGTGCCTAATCCTGACTACGAG
CCCATCCGGAAGGGCCAGAGAGATCTGTACAGCGGCCTGAACCAGCGGCG
GATT.
```

In embodiments, an anti-CD19 CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence according to:

DIQMTQTTSSLSASLGDRVTISCRASQDISKY-LNWYQQKPDGTVKLLIYHTSRLHSGVPS RFSGSGSGTDYSLTISNLEQEDI-ATYFCQQGNTLPYTFGGGTKLEITGST-SGSGKPGSGEG STKGEVKLQESGPGLVAP-SQSLSVTCTVSGVSLPDYGVSWIRQPPRKGLE-WLGVIWGSE TTYYN-SALKSRLTIIKDNSKSQVFLKMNSLQTDDTAIYY-CAKHYYYGGSYAMDYWGQ GTSVTVS-SAAALDNEKSNGTIIHVKGKHLCPSPLFPGPSK-PFWVLVVVGGVLACYSLLV TVAFIIFWVR-SKRSRLLHSDYMNMTPRRPGPTRKHYQPYAP-PRDFAAYRSGHETGRLSG AADTQALLRNDQVYQPLRDRDDAQYSHLGGN-WARNK (SEQ ID NO: 65). In embodiments an anti-CD19 CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

(SEQ ID NO: 66)

GACATCCAAATGACCCAAACCACCTCCTCCCTGAGCGCCTCCCTTGGAG
ACCGAGTTACCATCTCCTGCCGAGCTTCTCAAGACATCTCCAAGTACTT
GAATTGGTATCAACAAAAGCCCGACGGAACCGTGAAGCTGCTGATCTAC
CACACATCCCGGCTGCACTCTGGCGTTCCCTCAAGATTCTCCGGCTCTG
GAAGCGGAACCGACTACTCCCTGACCATCTCCAACCTGGAGCAAGAGGA
CATCGCTACCTACTTCTGCCAACAAGGCAACACCCTGCCTTACACCTTC
GGAGGAGGAACCAAGCTGGAGATCACCGGAAGCACAAGCGGATCTGGCA
AGCCTGGAAGCGGAGAGGGAAGCACCAAGGGAGAGGTGAAGCTGCAAGA
GAGCGGACCTGGATTGGTGGCCCCCTCACAATCCCTGAGCGTTACATGC
ACTGTGAGCGGCGTGTCCCTTCCTGACTACGGCGTTTCCTGGATCCGCC
AACCTCCAAGAAAGGGACTGGAGTGGCTGGGAGTGATCTGGGGAAGCGA
GACCACCTACTACAACTCCGCCCTGAAGAGCCGACTGACCATCATCAAG
GACAACTCCAAGAGCCAAGTGTTCCTGAAGATGAACTCTCTCCAAACCG
ACGACACCGCTATCTACTACTGCGCTAAGCACTACTACTACGGAGGAAG
CTACGCTATGGACTACTGGGGACAAGGCACCTCTGTGACCGTCTCCTCT
GCCGCCGCTCTGGACAACGAGAAGAGCAACGGAACCATCATCCACGTGA
AGGGAAAGCACCTGTGCCCCTCTCCTCTGTTCCCTGGACCCTCCAAGCC
TTTCTGGGTGCTCGTGGTGGTGGGAGGAGTGCTGGCTTGCTACTCCCTG
CTTGTGACCGTGGCTTTCATCATCTTCTGGGTTAGAAGCAAGAGAAGCA
GACTGCTGCACAGCGACTACATGAACATGACCCCTAGAAGGCCCGGACC
TACCAGAAAGCACTACCAGCCTTACGCTCCTCCTAGAGACTTCGCTGCT
TACAGAAGCGGACACGAAACAGGCAGACTTTCTGGCGCCGCTGATACAC
AGGCCCTGCTGAGAAACGACCAGGTGTACCAGCCTCTGAGAGACAGAGA
TGACGCCCAGTACTCTCACCTCGGCGGCAATTGGGCCAGAAACAAG.

In an embodiment, an anti-CD19 CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence according to:

(SEQ ID NO: 67)

DIQMTQTTSSLSASLGDRVTISCRASQDISKYLNWYQQKPDGTVKLLIY
HTSRLHSGVPSRFSGSGSGTDYSLTISNLEQEDIATYFCQQGNTLPYTF
GGGTKLEITGSTSGSGKPGSGEGSTKGEVKLQESGPGLVAPSQSLSVTC
TVSGVSLPDYGVSWIRQPPRKGLEWLGVIWGSETTYYNSALKSRLTIIK
DNSKSQVFLKMNSLQTDDTAIYYCAKHYYYGGSYAMDYWGQGTSVTVSS
AAALDNEKSNGTIIHVKGKHLCPSPLFPGPSKPFWVLVVVGGVLACYSL

-continued

LVTVAFIIFWVRSKRSRLLHSDYMNMTPRRPGPTRKHYQPYAPPRDFAA
YRSGQDGVRQSRASDKQTLLPNDQLYQPLKDREDDQYSHLQGNQLRRN.

In embodiments an anti-CD19 CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

(SEQ ID NO: 68)

GACATCCAAATGACCCAAACCACCTCCTCCCTGAGCGCCTCCCTTGGAG
ACCGAGTTACCATCTCCTGCCGAGCTTCTCAAGACATCTCCAAGTACTT
GAATTGGTATCAACAAAAGCCCGACGGAACCGTGAAGCTGCTGATCTAC
CACACATCCCGGCTGCACTCTGGCGTTCCCTCAAGATTCTCCGGCTCTG
GAAGCGGAACCGACTACTCCCTGACCATCTCCAACCTGGAGCAAGAGGA
CATCGCTACCTACTTCTGCCAACAAGGCAACACCCTGCCTTACACCTTC
GGAGGAGGAACCAAGCTGGAGATCACCGGAAGCACAAGCGGATCTGGCA
AGCCTGGAAGCGGAGAGGGAAGCACCAAGGGAGAGGTGAAGCTGCAAGA
GAGCGGACCTGGATTGGTGGCCCCCTCACAATCCCTGAGCGTTACATGC
ACTGTGAGCGGCGTGTCCCTTCCTGACTACGGCGTTTCCTGGATCCGCC
AACCTCCAAGAAAGGGACTGGAGTGGCTGGGAGTGATCTGGGGAAGCGA
GACCACCTACTACAACTCCGCCCTGAAGAGCCGACTGACCATCATCAAG
GACAACTCCAAGAGCCAAGTGTTCCTGAAGATGAACTCTCTCCAAACCG
ACGACACCGCTATCTACTACTGCGCTAAGCACTACTACTACGGAGGAAG
CTACGCTATGGACTACTGGGGACAAGGCACCTCTGTGACCGTCTCCTCT
GCCGCCGCTCTGGACAACGAGAAGAGCAACGGAACCATCATCCACGTGA
AGGGAAAGCACCTGTGCCCCTCTCCTCTGTTCCCTGGACCCTCCAAGCC
TTTCTGGGTGCTCGTGGTGGTGGGAGGAGTGCTGGCTTGCTACTCCCTG
CTTGTGACCGTGGCTTTCATCATCTTCTGGGTTAGAAGCAAGAGAAGCA
GACTGCTGCACAGCGACTACATGAACATGACCCCTAGAAGGCCCGGACC
TACCAGAAAGCACTACCAGCCTTACGCTCCTCCTAGAGACTTCGCTGCT
TACAGAAGCGGACAGGATGGCGTCAGACAGAGCAGAGCCAGCGACAAGC
AAACCCTGCTGCCTAACGACCAGCTGTACCAGCCTCTGAAGGACAGAGA
GGACGACCAGTACAGCCATCTGCAGGGCAACCAGCTGCGGAGAAAC.

In an embodiment, an anti-CD19 CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence according to:

(SEQ ID NO: 69)

DIQMTQTTSSLSASLGDRVTISCRASQDISKYLNWYQQKPDGTVKLLIY
HTSRLHSGVPSRFSGSGSGTDYSLTISNLEQEDIATYFCQQGNTLPYTF
GGGTKLEITGSTSGSGKPGSGEGSTKGEVKLQESGPGLVAPSQSLSVTC

-continued

TVSGVSLPDYGVSWIRQPPRKGLEWLGVIWGSETTYYNSALKSRLTIIK

DNSKSQVFLKMNSLQTDDTAIYYCAKHYYYGGSYAMDYWGQGTSVTVSS

AAALDNEKSNGTIIHVKGKHLCPSPLFPGPSKPFWVLVVVGGVLACYSL

LVTVAFIIFWVRSKRSRLLHSDYMNMTPRRPGPTRKHYQPYAPPRDFAA

YRSYFLGRLVPRGRGAAEAATRKQRITETESPYQELQGQRSDVYSDLNT

QRPYYK.

In embodiments an anti-CD19 CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

(SEQ ID NO: 70)

GACATCCAAATGACCCAAACCACCTCCTCCCTGAGCGCCTCCCTTGGAG

ACCGAGTTACCATCTCCTGCCGAGCTTCTCAAGACATCTCCAAGTACTT

GAATTGGTATCAACAAAAGCCCGACGGAACCGTGAAGCTGCTGATCTAC

CACACATCCCGGCTGCACTCTGGCGTTCCCTCAAGATTCTCCGGCTCTG

GAAGCGGAACCGACTACTCCCTGACCATCTCCAACCTGGAGCAAGAGGA

CATCGCTACCTACTTCTGCCAACAAGGCAACACCCTGCCTTACACCTTC

GGAGGAGGAACCAAGCTGGAGATCACCGGAAGCACAAGCGGATCTGGCA

AGCCTGGAAGCGGAGAGGGAAGCACCAAGGGAGAGGTGAAGCTGCAAGA

GAGCGGACCTGGATTGGTGGCCCCCTCACAATCCCTGAGCGTTACATGC

ACTGTGAGCGGCGTGTCCCTTCCTGACTACGGCGTTTCCTGGATCCGCC

AACCTCCAAGAAAGGGACTGGAGTGGCTGGGAGTGATCTGGGGAAGCGA

GACCACCTACTACAACTCCGCCCTGAAGAGCCGACTGACCATCATCAAG

GACAACTCCAAGAGCCAAGTGTTCCTGAAGATGAACTCTCTCCAAACCG

ACGACACCGCTATCTACTACTGCGCTAAGCACTACTACTACGGAGGAAG

CTACGCTATGGACTACTGGGGACAAGGCACCTCTGTGACCGTCTCCTCT

GCCGCCGCTCTGGACAACGAGAAGAGCAACGGAACCATCATCCACGTGA

AGGGAAAGCACCTGTGCCCCTCTCCTCTGTTCCCTGGACCCTCCAAGCC

TTTCTGGGTGCTCGTGGTGGTGGGAGGAGTGCTGGCTTGCTACTCCCTG

CTTGTGACCGTGGCTTTCATCATCTTCTGGGTTAGAAGCAAGAGAAGCA

GACTGCTGCACAGCGACTACATGAACATGACCCCTAGAAGGCCCGGACC

TACCAGAAAGCACTACCAGCCTTACGCTCCTCCTAGAGACTTCGCTGCT

TACAGAAGCTACTTCCTGGGCAGACTGGTGCCTAGAGGAAGAGGAGCTG

CTGAGGCTGCTACCAGAAAGCAGAGAATCACCGAGACCGAGAGCCCTTA

CCAGGAGCTGCAGGGACAGAGAAGCGACGTGTACAGCGACCTGAACACC

CAGAGACCTTACTACAAG.

In embodiments, an anti-CD19 CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence according to:

(SEQ ID NO: 71)

DIQMTQTTSSLSASLGDRVTISCRASQDISKYLNWYQQKPDGTVKLLIY

HTSRLHSGVPSRFSGSGSGTDYSLTISNLEQEDIATYFCQQGNTLPYTF

GGGTKLEITGSTSGSGKPGSGEGSTKGEVKLQESGPGLVAPSQSLSVTC

TVSGVSLPDYGVSWIRQPPRKGLEWLGVIWGSETTYYNSALKSRLTIIK

DNSKSQVFLKMNSLQTDDTAIYYCAKHYYYGGSYAMDYWGQGTSVTVSS

AAALDNEKSNGTIIHVKGKHLCPSPLFPGPSKPFWVLVVVGGVLACYSL

LVTVAFIIFWVRSKRSRLLHSDYMNMTPRRPGPTRKHYQPYAPPRDFAA

YRSRVKFSRSADAPAYQQGQNQLYNELNLGRREEYDVLDKRRGRDPEMG

GKPRRKNPQEGLYNELQKDKMAEAYSEIGMKGERRRGKGHDGLYQGLST

ATKDTYDALHMQALPPR.

In embodiments, an anti-CD19 CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

(SEQ ID NO: 72)

GACATCCAAATGACCCAAACCACCTCCTCCCTGAGCGCCTCCCTTGGAG

ACCGAGTTACCATCTCCTGCCGAGCTTCTCAAGACATCTCCAAGTACTT

GAATTGGTATCAACAAAAGCCCGACGGAACCGTGAAGCTGCTGATCTAC

CACACATCCCGGCTGCACTCTGGCGTTCCCTCAAGATTCTCCGGCTCTG

GAAGCGGAACCGACTACTCCCTGACCATCTCCAACCTGGAGCAAGAGGA

CATCGCTACCTACTTCTGCCAACAAGGCAACACCCTGCCTTACACCTTC

GGAGGAGGAACCAAGCTGGAGATCACCGGAAGCACAAGCGGATCTGGCA

AGCCTGGAAGCGGAGAGGGAAGCACCAAGGGAGAGGTGAAGCTGCAAGA

GAGCGGACCTGGATTGGTGGCCCCCTCACAATCCCTGAGCGTTACATGC

ACTGTGAGCGGCGTGTCCCTTCCTGACTACGGCGTTTCCTGGATCCGCC

AACCTCCAAGAAAGGGACTGGAGTGGCTGGGAGTGATCTGGGGAAGCGA

GACCACCTACTACAACTCCGCCCTGAAGAGCCGACTGACCATCATCAAG

GACAACTCCAAGAGCCAAGTGTTCCTGAAGATGAACTCTCTCCAAACCG

ACGACACCGCTATCTACTACTGCGCTAAGCACTACTACTACGGAGGAAG

CTACGCTATGGACTACTGGGGACAAGGCACCTCTGTGACCGTCTCCTCT

GCCGCCGCTCTGGACAACGAGAAGAGCAACGGAACCATCATCCACGTGA

AGGGAAAGCACCTGTGCCCCTCTCCTCTGTTCCCTGGACCCTCCAAGCC

TTTCTGGGTGCTCGTGGTGGTGGGAGGAGTGCTGGCTTGCTACTCCCTG

CTTGTGACCGTGGCTTTCATCATCTTCTGGGTTAGAAGCAAGAGAAGCA

GACTGCTGCACAGCGACTACATGAACATGACCCCTAGAAGGCCCGGACC

TACCAGAAAGCACTACCAGCCTTACGCTCCTCCTAGAGACTTCGCTGCT

TACAGAAGCAGGGTGAAGTTCTCAAGAAGCGCTGACGCTCCTGCTTACC

AACAAGGCCAAAACCAACTGTACAACGAGCTGAACCTGGGAAGAAGAGA

GGAATACGACGTCCTGGACAAGAGAAGAGGAAGAGACCCTGAGATGGGA

GGAAAGCCAAGAAGAAAGAACCCTCAAGAGGGCCTGTACAACGAGCTGC

-continued

AAAAGGACAAGATGGCTGAGGCTTACTCCGAGATCGGAATGAAGGGAGA

GAGAAGAAGAGGAAAGGGACACGACGGACTGTACCAAGGCCTGAGCACC

GCTACCAAGGACACCTACGACGCTCTGCACATGCAAGCCCTGCCTCCTA

GG.

In embodiments, an anti-CD19 CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence according to:

(SEQ ID NO: 73)

DIQMTQTTSSLSASLGDRVTISCRASQDISKYLNWYQQKPDGTVKLLIY

HTSRLHSGVPSRFSGSGSGTDYSLTISNLEQEDIATYFCQQGNTLPYTF

GGGTKLEITGSTSGSGKPGSGEGSTKGEVKLQESGPGLVAPSQSLSVTC

TVSGVSLPDYGVSWIRQPPRKGLEWLGVIWGSETTYYNSALKSRLTIIK

DNSKSQVFLKMNSLQTDDTAIYYCAKHYYYGGSYAMDYWGQGTSVTVSS

AAALDNEKSNGTIIHVKGKHLCPSPLFPGPSKPFWVLVVVGGVLACYSL

LVTVAFIIFWVRSKRSRLLHSDYMNMTPRRPGPTRKHYQPYAPPRDFAA

YRSRVKFSRSADAPAYQQGQNQLYNELNLGRREEYDVLDKRRGRDPEMG

GKPRRKNPQEGLFNELQKDKMAEAFSEIGMKGERRRGKGHDGLFQGLST

ATKDTFDALHMQALPPR.

In embodiments, an anti-CD19 CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

(SEQ ID NO: 74)

GACATCCAAATGACCCAAACCACCTCCTCCCTGAGCGCCTCCCTTGGAG

ACCGAGTTACCATCTCCTGCCGAGCTTCTCAAGACATCTCCAAGTACTT

GAATTGGTATCAACAAAAGCCCGACGGAACCGTGAAGCTGCTGATCTAC

CACACATCCCGGCTGCACTCTGGCGTTCCCTCAAGATTCTCCGGCTCTG

GAAGCGGAACCGACTACTCCCTGACCATCTCCAACCTGGAGCAAGAGGA

CATCGCTACCTACTTCTGCCAACAAGGCAACACCCTGCCTTACACCTTC

GGAGGAGGAACCAAGCTGGAGATCACCGGAAGCACAAGCGGATCTGGCA

AGCCTGGAAGCGGAGAGGGAAGCACCAAGGGAGAGGTGAAGCTGCAAGA

GAGCGGACCTGGATTGGTGGCCCCCTCACAATCCCTGAGCGTTACATGC

ACTGTGAGCGGCGTGTCCCTTCCTGACTACGGCGTTTCCTGGATCCGCC

AACCTCCAAGAAAGGGACTGGAGTGGCTGGGAGTGATCTGGGGAAGCGA

GACCACCTACTACAACTCCGCCCTGAAGAGCCGACTGACCATCATCAAG

GACAACTCCAAGAGCCAAGTGTTCCTGAAGATGAACTCTCTCCAAACCG

ACGACACCGCTATCTACTACTGCGCTAAGCACTACTACTACGGAGGAAG

CTACGCTATGGACTACTGGGGACAAGGCACCTCTGTGACCGTCTCCTCT

-continued

GCCGCCGCTCTGGACAACGAGAAGAGCAACGGAACCATCATCCACGTGA

AGGGAAAGCACCTGTGCCCCTCTCCTCTGTTCCCTGGACCCTCCAAGCC

TTTCTGGGTGCTCGTGGTGGTGGGAGGAGTGCTGGCTTGCTACTCCCTG

CTTGTGACCGTGGCTTTCATCATCTTCTGGGTTAGAAGCAAGAGAAGCA

GACTGCTGCACAGCGACTACATGAACATGACCCCTAGAAGGCCCGGACC

TACCAGAAAGCACTACCAGCCTTACGCTCCTCCTAGAGACTTCGCTGCT

TACAGAAGCCGGGTGAAGTTCTCAAGAAGCGCTGACGCTCCTGCTTACC

AACAAGGCCAAAACCAACTGTACAACGAGCTGAACCTGGGAAGAAGAGA

GGAATACGACGTCCTGGACAAGAGAAGAGGAAGAGACCCTGAGATGGGA

GGAAAGCCAAGAAGAAAGAACCCTCAAGAGGGCCTGTTTAACGAGCTGC

AAAAGGACAAGATGGCTGAGGCTTTCTCCGAGATCGGAATGAAGGGAGA

GAGAAGAAGAGGAAAGGGACACGACGGACTGTTCCAAGGCCTGAGCACC

GCTACCAAGGACACCTTCGACGCTCTGCACATGCAAGCCCTGCCTCCTA

GG.

In embodiments, an anti-CD19 CAR construct has an amino acid sequence having at least 75% sequence identity to (such as, at least 75%, at least 80%, at least 90%, at least 95%, or 100% identity; e.g., 85-90%, 85-95%, 85-100%, 90-95%, 90-100%, or 95-100%) the amino acid sequence according to:

(SEQ ID NO: 75)

DIQMTQTTSSLSASLGDRVTISCRASQDISKYLNWYQQKPDGTVKLLIY

HTSRLHSGVPSRFSGSGSGTDYSLTISNLEQEDIATYFCQQGNTLPYTF

GGGTKLEITGSTSGSGKPGSGEGSTKGEVKLQESGPGLVAPSQSLSVTC

TVSGVSLPDYGVSWIRQPPRKGLEWLGVIWGSETTYYNSALKSRLTIIK

DNSKSQVFLKMNSLQTDDTAIYYCAKHYYYGGSYAMDYWGQGTSVTVSS

AAALDNEKSNGTIIHVKGKHLCPSPLFPGPSKPFWVLVVVGGVLACYSL

LVTVAFIIFWVRSKRSRLLHSDYMNMTPRRPGPTRKHYQPYAPPRDFAA

YRSRVKFSRSADAPAYQQGQNQLYNELNLGRREEYDVLDKRRGRDPEMG

GKPRRKNPQEGLYNELQKDKMAEAYSEIGMKGERRRGKGHDGLYQGLST

ATKDTYDALHMQALPPR.

In embodiments, an anti-CD19 CAR is encoded by a nucleic acid having at least 75% sequence identity to (such as, at least 75%, at least 80%, at least 90%, at least 95%, or 100% identity; e.g., 85-90%, 85-95%, 85-100%, 90-95%, 90-100%, or 95-100%) the nucleic acid having the sequence according to:

(SEQ ID NO: 76)

GATATACAGATGACCCAAACGACGTCTAGCCTCAGTGCGTCACTCGGGG

ATCGGGTGACAATTAGCTGCAGGGCTAGCCAGGATATTTCAAAATATCT

TAACTGGTATCAACAAAAGCCAGATGGAACCGTAAAACTGCTCATATAC

CACACCAGTCGCCTGCATTCAGGGGTTCCGAGCCGCTTTTCTGGGAGCG

GTAGCGGAACtGAtTATAGCTTGACAATAAGCAACCTCGAGCAGGAAGA

CATTGCGACGTACTTCTGTCAGCAAGGGAACACGCTGCCGTATACCTTC

-continued

```
GGTGGCGGCACTAAACTGGAAATCACGGGATCTACGTCTGGATCCGGAA
AACCTGGATCTGGTGAAGGATCCACTAAAGGCGAAGTCAAGTTGCAAGA
GTCTGGACCTGGTCTCGTGGCACCTTCACAGTCACTCTCCGTTACCTGT
ACCGTATCTGGAGTTTCACTTCCCGACTATGGCGTGTCATGGATACGCC
AACCACCGCGAAAAGGTCTTGAATGGCTGGGCGTTATCTGGGGATCCGA
AACCACATACTACAACTCTGCGCTCAAGTCACGGCTGACTATTATAAAG
GACAATTCAAAGAGCCAAGTGTTCCTGAAAATGAACAGCCTGCAGACTG
ATGACACTGCAATATATTACTGCGCCAAGCATTACTATTACGGCGGATC
TTACGCGATGGATTATTGGGGCCAGGGCACCTCTGTAACAGTCAGCTCC
GCGGCCGCATTGGACAATGAAAAATCCAATGGCACAATAATTCATGTAA
AGGGCAAACACTTGTGTCCTAGCCCACTCTTTCCTGGTCCGTCTAAACC
GTTTTGGGTGCTCGTTGTGGTTGGAGGCGTCCTGGCTTGTTACTCTCTG
TTGGTGACTGTAGCCTTTATAATATTCTGGGTTAGAAGCAAACGAAGTA
GGCTTTTACATTCAGACTATATGAACATGACACCAAGACGCCCCGGCCC
CACAAGAAAACACTATCAGCCCTATGCTCCGCCTCGGGACTTCGCTGCT
TACCGAAGCAGAGTTAAGTTCAGCAGGAGCGCCGACGCACCTGCCTACC
AaCAAGGGCAGAATCAACTGTACAACGAGCTGAACCTGGGCAGACGGGA
GGAATACGATGTGCTGGACAAGAGGAGAGGCAGAGACCCCGAGATGGGC
GGCAAACCTAGAAGAAAGAACCCCCAGGAGGGCCTGTATAATGAGCTCC
AGAAGGATAAGATGGCCGAGGCCTACAGCGAGATCGGCATGAAGGGCGA
AAGAAGAAGAGGCAAGGGCCACGACGGCCTCTACCAGGGCTTAAGCACA
GCTACTAAGGACACCTACGACGCCCTGCACATGCAAGCTCTGCCCCCTA
GA.
```

Generally, it is understood that any appropriate viral vector or vectors may be used for transduction of the engineered constructs described herein. In one embodiment described herein, a cell (e.g., T cell) is transduced with a retroviral vector, e.g., a γ-retroviral vector, encoding an engineered anti-CD19 CAR as described herein.

As used herein, the term "retrovirus" refers to an RNA virus that reverse transcribes its genomic RNA into a linear double-stranded DNA copy and subsequently covalently integrates its genomic DNA into a host genome. Illustrative retroviruses suitable for use in some embodiments, include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis encephalitis virus (CAEV); equine infectious anemia virus (EIAV); feline immunodeficiency virus (FIV); bovine immune deficiency virus (BIV); and simian immunodeficiency virus (SIV).

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell or may include sequences sufficient to allow integration into host cell DNA. Useful vectors include, for example, plasmids (e.g., DNA plasmids or RNA plasmids), transposons, cosmids, bacterial artificial chromosomes, and viral vectors. Useful viral vectors include, e.g., replication defective retroviruses and lentiviruses.

As will be evident to one of skill in the art, the term "viral vector" is widely used to refer either to a nucleic acid molecule (e.g., a transfer plasmid) that includes virus-derived nucleic acid elements that typically facilitate transfer of the nucleic acid molecule or integration into the genome of a cell or to a viral particle that mediates nucleic acid transfer. Viral particles will typically include various viral components and sometimes also host cell components in addition to nucleic acid(s).

The term viral vector may refer either to a virus or viral particle capable of transferring a nucleic acid into a cell or to the transferred nucleic acid itself. Viral vectors and transfer plasmids contain structural and/or functional genetic elements that are primarily derived from a virus. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, including LTRs that are primarily derived from a lentivirus. The term "hybrid vector" refers to a vector, LTR or other nucleic acid containing both retroviral, e.g., lentiviral, sequences and non-retroviral viral sequences. In one embodiment, a hybrid vector refers to a vector or transfer plasmid comprising retroviral e.g., lentiviral, sequences for reverse transcription, replication, integration and/or packaging.

In some embodiments, the terms "lentiviral vector," "lentiviral expression vector" may be used to refer to lentiviral transfer plasmids and/or infectious lentiviral particles. Where reference is made herein to elements such as cloning sites, promoters, regulatory elements, heterologous nucleic acids, etc., it is to be understood that the sequences of these elements are present in RNA form in the lentiviral particles of the disclosure and are present in DNA form in the DNA plasmids of the disclosure. In one embodiment described herein, the expression vector is a lentivirus expression vector.

At each end of the provirus are structures called "long terminal repeats" or "LTRs." The term "long terminal repeat (LTR)" refers to domains of base pairs located at the ends of retroviral DNAs which, in their natural sequence context, are direct repeats and contain U3, Rand U5 regions. LTRs generally provide functions fundamental to the expression of retroviral genes (e.g., promotion, initiation and polyadenylation of gene transcripts) and to viral replication. The LTR contains numerous regulatory signals including transcriptional control elements, polyadenylation signals and sequences needed for replication and integration of the viral genome. The viral LTR is divided into three regions called U3, R, and U5. The U3 region contains the enhancer and promoter elements. The U5 region is the sequence between the primer binding site and the R region and contains the polyadenylation sequence. The R (repeat) region is flanked by the U3 and U5 regions. The LTR is composed of U3, R and U5 regions and appears at both the 5' and 3' ends of the viral genome. Adjacent to the 5' LTR are sequences necessary for reverse transcription of the genome (the tRNA primer binding site) and for efficient packaging of viral RNA into particles (the Psi site).

As used herein, the term "packaging signal" or "packaging sequence" refers to sequences located within the retroviral genome which are required for insertion of the viral RNA into the viral capsid or particle, see e.g., Clever et al., 1995. J of Virology, Vol. 69, No. 4; pp. 2101-2109. Several retroviral vectors use the minimal packaging signal (also referred to as the psi ['P] sequence) needed for encapsidation of the viral genome. Thus, as used herein, the terms "packaging sequence," "packaging signal," "psi" and the symbol "P," are used in reference to the non-coding sequence required for encapsidation of retroviral RNA strands during viral particle formation.

In various embodiments, vectors comprise modified 5' LTR and/or 3' LTRs. Either or both of the LTR may comprise one or more modifications including, but not limited to, one or more deletions, insertions, or substitutions. Modifications of the 3' LTR are often made to improve the safety of lentiviral or retroviral systems by rendering viruses replication-defective. As used herein, the term "replication-defective" refers to virus that is not capable of complete, effective replication such that infective virions are not produced (e.g., replication-defective lentiviral progeny). The term "replication-competent" refers to wild-type virus or mutant virus that is capable of replication, such that viral replication of the virus is capable of producing infective virions (e.g., replication-competent lentiviral progeny).

"Self-inactivating" (SIN) vectors refers to replication-defective vectors, e.g., retroviral or lentiviral vectors, in which the right (3') LTR enhancer-promoter region, known as the U3 region, has been modified (e.g., by deletion or substitution) to prevent viral transcription beyond the first round of viral replication. This is because the right (3 ') LTR U3 region is used as a template for the left (5') LTR U3 region during viral replication and, thus, the viral transcript cannot be made without the U3 enhancer-promoter. In a further embodiment of the disclosure, the 3'LTR is modified such that the U5 region is replaced, for example, with an ideal poly (A) sequence. It should be noted that modifications to the LTRs such as modifications to the 3'LTR, the 5'LTR, or both 3' and 5'LTRs, are also contemplated herein.

An additional safety enhancement is provided by replacing the U3 region of the 5'LTR with a heterologous promoter to drive transcription of the viral genome during production of viral particles. Examples of heterologous promoters which may be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus because there is no complete U3 sequence in the virus production system. In certain embodiments, the heterologous promoter has additional advantages in controlling the manner in which the viral genome is transcribed. For example, the heterologous promoter may be inducible, such that transcription of all or part of the viral genome will occur only when the induction factors are present. Induction factors include, but are not limited to, one or more chemical compounds or the physiological conditions such as temperature or pH, in which the host cells are cultured.

In some embodiments, viral vectors comprise a TAR element. The term "TAR" refers to the "trans-activation response" genetic element located in the R region of lentiviral (e.g., HIV) LTRs. This element interacts with the lentiviral trans-activator (tat) genetic element to enhance viral replication.

The "R region" refers to the region within retroviral LTRs beginning at the start of the capping group (i.e., the start of transcription) and ending immediately prior to the start of the poly A tract. The R region is also defined as being flanked by the U3 and U5 regions. The R region plays a role during reverse transcription in permitting the transfer of nascent DNA from one end of the genome to the other.

As used herein, the term "FLAP element" refers to a nucleic acid whose sequence includes the central polypurine tract and central termination sequences (cPPT and CTS) of a includes the central polypurine tract and central termination sequences (cPPT and CTS) of a retrovirus, e.g., HIV-I or HIV-2. Suitable FLAP elements are described in U.S. Pat. No. 6,682,907 and in Zennou, et al., 2000, Cell, 101:173. During HIV-I reverse transcription, central initiation of the plus-strand DNA at the central polypurine tract (cPPT) and central termination at the central termination sequence (CTS) lead to the formation of a three-stranded DNA structure: the HIV-I central DNA flap. While not wishing to be bound by any theory, the DNA flap may act as a cis-active determinant of lentiviral genome nuclear import and/or may increase the titer of the virus.

In one embodiment, retroviral or lentiviral transfer vectors comprise one or more export elements. The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. J Virol. 65:1053; and Cullen et al., 1991. Cell 58:423), and the hepatitis B virus post-transcriptional regulatory element (HPRE). Generally, the RNA export element is placed within the 3' UTR of a gene and may be inserted as one or multiple copies.

In other embodiments, expression of heterologous sequences in viral vectors is increased by incorporating post-transcriptional regulatory elements, efficient polyadenylation sites, and optionally, transcription termination signals into the vectors. A variety of posttranscriptional regulatory elements may increase expression of a heterologous nucleic acid at the protein, e.g., woodchuck hepatitis virus post-transcriptional regulatory element (WPRE; Zufferey et al., 1999, J Virol., 73:2886); the post-transcriptional regulatory element present in hepatitis B virus (HPRE) (Huang et al., Mol. Cell. Biol., 5:3864); and the like (Liu et al., 1995, Genes Dev., 9:1766).

In some embodiments, vectors may include regulatory oligonucleotides having transcriptional or translational regulatory activity. Such an oligonucleotide can be used in a variety of gene expression configurations for regulating control of expression. A transcriptional regulatory oligonucleotide can increase (enhance) or decrease (silence) the level of expression of a recombinant expression construct. Regulatory oligonucleotides may selectively regulate expression in a context specific manner, including, for example, for conferring tissue specific, developmental stage specific, or the like expression of the polynucleotide, including constitutive or inducible expression. A regulatory oligonucleotide of the disclosure also can be a component of an expression vector or of a recombinant nucleic acid molecule comprising the regulatory oligonucleotide operatively linked to an expressible polynucleotide. A regulatory element can be of various lengths from a few nucleotides to several hundred nucleotides.

Elements directing the efficient termination and polyadenylation of the heterologous nucleic acid transcripts increases heterologous gene expression. Transcription termination signals are generally found downstream of the polyadenylation signal. In some embodiments, vectors comprise a polyadenylation sequence 3' of a polynucleotide encoding a polypeptide to be expressed. The term "poly A site" or "poly A sequence" as used herein denotes a DNA sequence which directs both the termination and polyadenylation of the nascent RNA transcript by RNA polymerase II. Polyadenylation sequences may promote mRNA stability by addition of a poly A tail to the 3' end of the coding sequence and thus, contribute to increased translational efficiency. Efficient polyadenylation of the recombinant transcript is desirable as transcripts lacking a poly A tail are unstable and are rapidly degraded. Illustrative examples of poly A signals that may be used in a vector of the disclosure, includes an ideal poly A sequence (e.g., AATAAA, ATTAAA, AGTAAA), a bovine growth hormone poly A sequence (BGHpA), a rabbit β-globin poly A sequence (rβgpA), or another suitable heterologous or endogenous poly A sequence known in the art.

Also described herein are "codon-optimized" nucleic acids. A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells or in a particular mammalian species (such as human cells) by replacing at least one, more than one, or a significant number, of codons of the native sequence with codons that are more frequently or most frequently used in the genes of that species. Codon optimization does not alter the amino acid sequence of the encoded protein.

The codon-optimized nucleotide sequences presented in the instant disclosure can present improved properties related to expression efficacy. In some embodiments, the DNA sequence to be transcribed may be optimized to facilitate more efficient transcription and/or translation. In some embodiments, the DNA sequence may be optimized regarding cis-regulatory elements (e.g., TATA box, termination signals, and protein binding sites), artificial recombination sites, chi sites, CpG dinucleotide content, negative CpG islands, GC content, polymerase slippage sites, and/or other elements relevant to transcription; the DNA sequence may be optimized regarding cryptic splice sites, mRNA secondary structure, stable free energy of mRNA, repetitive sequences, RNA instability motif, and/or other elements relevant to mRNA processing and stability; the DNA sequence may be optimized regarding codon usage bias, codon adaptability, internal chi sites, ribosomal binding sites (e.g., IRES), premature polyA sites, Shine-Dalgarno (SD) sequences, and/or other elements relevant to translation; and/or the DNA sequence may be optimized regarding codon context, codon-anticodon interaction, translational pause sites, and/or other elements relevant to protein folding.

The vectors may have one or more LTRs, wherein any LTR comprises one or more modifications, such as one or more nucleotide substitutions, additions, or deletions. The vectors may further comprise one of more accessory elements to increase transduction efficiency (e.g., a cPPT/FLAP), viral packaging (e.g., a Psi (') packaging signal, RRE), and/or other elements that increase therapeutic gene expression (e.g., poly (A) sequences), and may optionally comprise a WPRE or HPRE. The skilled artisan would appreciate that many other different embodiments may be fashioned from the existing embodiments of the disclosure.

A "host cell" includes cells transfected, infected, or transduced in vivo, ex vivo, or in vitro with a recombinant vector or a polynucleotide of the disclosure. Host cells may include packaging cells, producer cells, and cells infected with viral vectors. In some embodiments, host cells infected with viral vector of the disclosure are administered to a subject in need of therapy. In certain embodiments, the term "target cell" is used interchangeably with host cell and refers to transfected, infected, or transduced cells of a desired cell type. In some embodiments, the target cell is a T cell.

Large scale viral particle production is often necessary to achieve a reasonable viral titer. Viral particles are produced by transfecting a transfer vector into a packaging cell line that comprises viral structural and/or accessory genes, e.g., gag, pol, env, tat, rev, vif, vpr, vpu, vpx, or nef genes or other retroviral genes.

As used herein, the term "packaging vector" refers to an expression vector or viral vector that lacks a packaging signal and comprises a polynucleotide encoding one, two, three, four or more viral structural and/or accessory genes. Typically, the packaging vectors are included in a packaging cell, and are introduced into the cell via transfection, transduction or infection. Methods for transfection, transduction or infection are well known by those of skill in the art. A retroviral/lentiviral transfer vector of the present disclosure may be introduced into a packaging cell line, via transfection, transduction or infection, to generate a producer cell or cell line. The packaging vectors of the present disclosure may be introduced into human cells or cell lines by common methods including, e.g., calcium phosphate transfection, lipofection or electroporation. In some embodiments, the packaging vectors are introduced into the cells together with a dominant selectable marker, such as neomycin, hygromycin, puromycin, blasticidin, zeocin, thymidine kinase, DHFR, Gln synthetase or ADA, followed by selection in the presence of the appropriate drug and isolation of clones. A selectable marker gene may be linked physically to genes encoding by the packaging vector, e.g., by IRES or self-cleaving viral peptides.

Viral envelope proteins (env) determine the range of host cells which may ultimately be infected and transformed by recombinant retroviruses generated from the cell lines. In the case of lentiviruses, such as HIV-1, HIV-2, SIV, FIV and EIV, the env proteins include gp41 and gp120. In some embodiments, the viral env proteins expressed by packaging cells of the disclosure are encoded on a separate vector from the viral gag and pol genes, as has been previously described.

Illustrative examples of retroviral-derived env genes which may be employed in the embodiments described herein include, but are not limited to: MLV envelopes, IOAI envelope, BAEV, FeLV-B, RDI 14, SSAV, Ebola, Sendai, FPV (Fowl plague virus), and influenza virus envelopes. Similarly, genes encoding envelopes from RNA viruses (e.g., RNA virus families of Picomaviridae, Calciviridae, Astroviridae, Togaviridae, Flaviviridae, Coronaviridae, Paramyxoviridae, Rhabdoviridae, Filoviridae, Orthomyxoviridae, Bunyaviridae, Arenaviridae, Reoviridae, Bimaviridae, Retroviridae) as well as from the DNA viruses (families of Hepadnaviridae, Circoviridae, Parvoviridae, Papovaviridae, Adenoviridae, Herpesviridae, Poxyiridae, and Iridoviridae) may be utilized. Representative examples include, FeLV, VEE, HFVW, WDSV, SFV, Rabies, ALV, BIV, BL V, EBV, CAEV, SNV, ChTL V, STLV, MPMV SMRV, RAV, FuSV, MH2, AEV, AMV, CTIO, and EIAV.

In other embodiments, envelope proteins for pseudotyping a virus of present disclosure include, but are not limited to any of the following virus: Influenza A such as H1N1, H1N2, H3N2 and H5N1 (bird flu), Influenza B, Influenza C virus, Hepatitis A virus, Hepatitis B virus, Hepatitis C virus, Hepatitis D virus, Hepatitis E virus, Rotavirus, any virus of the Norwalk virus group, enteric adenoviruses, parvovirus, Dengue fever virus, Monkey pox, Mononegavirales, Lyssavirus such as rabies virus, Lagos bat virus, Mokola virus, Duvenhage virus, European bat virus 1 & 2 and Australian bat virus, Ephemerovirus, Vesiculovirus, Vesicular Stomatitis Virus (VSV), Herpes viruses such as Herpes simplex virus types 1 and 2, varicella zoster, cytomegalovirus, Epstein-Barr virus (EBV), human herpesviruses (HHV), human herpesvirus type 6 and 8, Human immunodeficiency virus (HIV), papilloma virus, murine gamma herpes virus, Arenaviruses such as Argentine hemorrhagic fever virus, Bolivian hemorrhagic fever virus, Sabia-associated hemorrhagic fever virus, Venezuelan hemorrhagic fever virus, Lassa fever virus, Machupo virus, Lymphocytic choriomeningitis virus (LCMV), Bunyaviridiae such as Crimean-Congo hemorrhagic fever virus, Hantavirus, hemorrhagic fever with renal syndrome causing virus, Rift Valley fever virus, Filoviridae (filovirus) including Ebola hemorrhagic fever and Marburg hemorrhagic fever, Flaviviridae including Kaysanur Forest disease virus, Omsk hemorrhagic fever virus, Tick-borne encephalitis causing virus and Paramyxoviridae such as Hendra virus and Nipah virus, variola major and variola minor (smallpox), alphaviruses such as Venezuelan equine encephalitis virus, eastern equine encephalitis virus, western equine encephalitis virus, SARS-associated coronavirus (SARS-Co V), West Nile virus, or any encephaliltis causing virus.

The terms "pseudotype" or "pseudotyping" as used herein, refer to a virus whose viral envelope proteins have been substituted with those of another virus possessing other characteristics. For example, HIV may be pseudotyped with vesicular stomatitis virus G-protein (VSV-G) envelope proteins, which allows HIV to infect a wider range of cells because HIV envelope proteins (encoded by the env gene) normally target the virus to CD4+ presenting cells.

As used herein, the term "packaging cell lines" is used in reference to cell lines that do not contain a packaging signal, but do stably or transiently express viral structural proteins and replication enzymes (e.g., gag, pol and env) which are necessary for the correct packaging of viral particles. Any suitable cell line may be employed to prepare packaging cells of the disclosure. Generally, the cells are mammalian cells. In another embodiment, the cells used to produce the packaging cell line are human cells. Suitable cell lines which may be used to produce the packaging cell line include, for example, CHO cells, BHK cells, MDCK cells, C3H 10T1/2 cells, FLY cells, Psi-2 cells, BOSC 23 cells, P A317 cells, WEHI cells, COS cells, BSC 1 cells, BSC 40 cells, BMT 10 cells, VERO cells, W138 cells, MRC5 cells, A549 cells, HTI080 cells, 293 cells, 293T cells, B-50 cells, 3T3 cells, NIH3T3 cells, HepG2 cells, Saos-2 cells, Huh7 cells, HeLa cells, W163 cells, 211 cells, and 211A cells.

As used herein, the term "producer cell line" refers to a cell line which is capable of producing recombinant retroviral particles, comprising a packaging cell line and a transfer vector construct comprising a packaging signal. The production of infectious viral particles and viral stock solutions may be carried out using conventional techniques. Methods of preparing viral stock solutions are known in the art and are illustrated by, e.g., Y. Soneoka et al. (1995) Nucl. Acids Res. 23:628-633, and N. R. Landau et al. (1992) J Virol. 66:5110-5113. Infectious virus particles may be collected from the packaging cells using conventional techniques. For example, the infectious particles may be collected by cell lysis, or collection of the supernatant of the cell culture, as is known in the art. Optionally, the collected virus particles may be purified if desired. Suitable purification techniques are well known to those skilled in the art.

The delivery of a gene(s) or other polynucleotide sequence using a retroviral or lentiviral vector by means of viral infection rather than by transfection is referred to as "transduction." In one embodiment, retroviral vectors are transduced into a cell through infection and provirus integration. In certain embodiments, a target cell, e.g., a T cell, is "transduced" if it comprises a gene or other polynucleotide sequence delivered to the cell by infection using a viral or retroviral vector. In some embodiments, a transduced cell comprises one or more genes or other polynucleotide sequences delivered by a retroviral or lentiviral vector in its cellular genome.

In some embodiments, host cells expressing one or more of the constructs of the disclosure (e.g., anti-CD19 CAR). The host cells may be administered to a subject to treat and/or prevent T cell malignancies. Other methods relating to the use of viral vectors in gene therapy, which may be utilized according to certain embodiments of the present disclosure, may be found in, e.g., Kay, M. A. (1997) Chest 111(6 Supp.): 138S-142S; Ferry, N. and Heard, J. M. (1998) Hum. Gene Ther. 9:1975-81; Shiratory, Y. et al., (1999) Liver 19:265-74; Oka, K. et al., (2000) Curr. Opin. Lipidol. 11:179-86; Thule, P. M. and Liu, J. M. (2000) Gene Ther. 7:1744-52; Yang, N. S. (1992) Crit. Rev. Biotechnol. 12:335-56; Alt, M. (1995) J Hepatol. 23:746-58; Brody, S. L. and Crystal, R. G. (1994) Ann. NY Acad. Sci. 716:90-101; Strayer, D. S. (1999) Expert Opin. Investig. Drugs 8:2159-2172; Smith-Arica, J. R. and Bartlett, J. S. (2001) Curr. Cardiol. Rep. 3:43-49; and Lee, H. C. et al., (2000) Nature 408:483-8.

In addition to the introduction of a CAR the engineered T cells of this disclosure can be further engineered to reduce, and/or eliminate expression of TCRα and B2M, for example using one or more ZFNs or CRISPR/sgRNA that target the TRAC and B2M genes. It is understood that the descendants of cells targeted by the ZFNs may not themselves comprise the molecule, polynucleotides and/or vectors described herein, but, in these cells, a TCR and/or B2M gene is inactivated.

The compositions described herein may comprise T cell compositions, as contemplated herein. One embodiment described herein is a composition comprising a modified T cell that expresses an anti-CD19 CAR where the expression, such as detectable surface expression of TCR and B2M has been reduced and/or eliminated. Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions of the present disclosure may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the ability of the composition to deliver the intended therapy.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier which has been approved by the United States Food and Drug Administration as being acceptable for use in humans or domestic animals. Exemplary pharmaceutically acceptable carriers include, but are not limited to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations.

In one embodiment described herein, compositions of the present disclosure comprise an amount of modified T cells contemplated herein. It may generally be stated that a pharmaceutical composition comprising the T cells contemplated herein may be administered at a dosage of $10^2$ to $10^{10}$ cells/kg body weight, $10^5$ to $10^9$ cells/kg body weight, $10^5$ to $10^8$ cells/kg body weight, 105 to $10^7$ cells/kg body weight, $10^7$ to $10^9$ cells/kg body weight, or $10^7$ to $10^8$ cells/kg body weight, including all integer values within those ranges. The number of cells will depend upon the ultimate use for which the composition is intended as will the type of cells included therein. T cells modified to express an engineered TCR or CAR may be administered multiple times at dosages within these ranges. The cells may be allogeneic, syngeneic, xenogeneic, or autologous to the patient undergoing therapy. If desired, the treatment may also include administration of mitogens (e.g., PHA) or lymphokines, cytokines, and/or chemokines (e.g., IFN-γ, IL-2, IL-7, IL-15, IL-12, TNF-alpha, IL-18, and TNF-beta, GM-CSF, IL-4, IL-13, Flt3-L, RANTES, MIP1α, etc.) as described herein to enhance engraftment and function of infused T cells.

Generally, compositions comprising the cells activated and expanded as described herein may be utilized in the treatment and prevention of diseases that arise in individuals who are immunocompromised or immunosuppressed. In some, compositions comprising the modified T cells contemplated herein are used in the treatment of cancers. The modified T cells described herein may be administered either alone, or as a pharmaceutical composition in combination with carriers, diluents, excipients, and/or with other components such as IL-2, IL-7, and/or IL-15 or other cytokines or cell populations. In some embodiments, pharmaceutical compositions contemplated herein comprise an amount of genetically modified T cells, in combination with one or more pharmaceutically or physiologically acceptable carriers, diluents or excipients.

Pharmaceutical compositions comprising modified T cells contemplated herein may further comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure may be formulated for parenteral administration, e.g., intravascular (intravenous or intra-arterial), intraperitoneal or intramuscular administration.

The liquid pharmaceutical compositions, whether they be solutions, suspensions or other like form, may include one or more of the following: sterile diluents such as water for injection, saline solution, such as physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation may be enclosed in ampoules, disposable syringes or multiple dose vials made of glass or plastic. Sterile injectable pharmaceutical composition are also included.

In some embodiments, compositions contemplated herein comprise an effective amount of an expanded modified T cell composition, alone or in combination with one or more therapeutic agents. Thus, the T cell compositions may be administered alone or in combination with other known cancer treatments, such as radiation therapy, chemotherapy, transplantation, immunotherapy, hormone therapy, photodynamic therapy, etc. The compositions may also be administered in combination with antibiotics and anti-viral agents. Such therapeutic agents may be accepted in the art as a treatment for a disease state as described herein, such as a cancer. In one embodiment the compositions contemplated herein may also be administered with inhibitors of TGF-β, for example the small molecule inhibitor LY55299. Exemplary therapeutic agents contemplated include cytokines, growth factors, steroids, NSAIDs, DMARDs, anti-inflammatories, chemotherapeutics, radiotherapeutics, therapeutic antibodies, or other active and ancillary agents.

In certain embodiments, compositions comprising T cells contemplated herein may be administered in conjunction with any number of chemotherapeutic agents. Illustrative examples of chemotherapeutic agents include but are not limited to alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RPS 2000; difluoromethylomithine (DMFO); retinoic acid derivatives such as Targretin™ (bexarotene), Panretin™ (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4 (5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

A variety of other therapeutic agents may be used in conjunction with the compositions described herein. In one embodiment, the composition comprising T cells is administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

In some embodiments, NSAIDs are chosen from the group consisting of ibuprofen, naproxen, naproxen sodium, Cox-2 inhibitors such as VIOXX® (rofecoxib) and CELEBREX® (celecoxib), and sialylates. Exemplary analgesics are chosen from the group consisting of acetaminophen, oxycodone, tramadol or proporxyphene hydrochloride. Exemplary glucocorticoids are chosen from the group consisting of cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary disease-modifying anti-rheumatic drugs (DMARDs) include azathioprine, cyclophosphamide, cyclosporine, methotrexate, penicillamine, leflunomide, sulfasalazine, hydroxychloroquine, Gold (oral (auranofin) and intramuscular) and minocycline.

In other embodiments, the therapeutic antibodies suitable for combination with the CAR modified T cells contemplated herein, include but are not limited to, abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farietuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, namatumab, naptumomab, necitumumab, nimotuzumab, nofetumomab, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49 and 3F8.

In some embodiments, the compositions described herein are administered in conjunction with a cytokine. By "cytokine" as used herein is meant a generic term for proteins released by one cell population that act on another cell as intercellular mediators. Examples of such cytokines are lymphokines, monokines, chemokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-10, IL-11, IL-12; IL-15, a tumor necrosis factor such as TNF-$\alpha$ or TNF-$\beta$; and other polypeptide factors including LIF and kit ligand (KL). As used herein, the term cytokine includes proteins from natural sources or from recombinant cell culture, and biologically active equivalents of the native sequence cytokines.

Any cell may be used as a host cell for the polynucleotides, the vectors, or the polypeptides of the present disclosure. In some embodiments, the cell can be a prokaryotic cell, fungal cell, yeast cell, or higher eukaryotic cells such as a mammalian cell. Suitable prokaryotic cells include, without limitation, eubacteria, such as Gram-negative or Gram-positive organisms, for example, Enterobactehaceae such as *Escherichia*, e.g., *E. coli; Enterobacter; Erwinia; Klebsiella; Proteus; Salmonella*, e.g., *Salmonella typhimurium; Serratia*, e.g., *Serratia marcescans*, and *Shigella*; Bacilli such as *B. subtilis* and *B. licheniformis; Pseudomonas* such as *P. aeruginosa*; and *Streptomyces*. In some embodiments, the cell is a human cell. In some embodiments, the cell is an immune cell.

In some embodiments, the immune cell is selected from the group consisting of a T cell, a B cell, a tumor infiltrating lymphocyte (TIL), a TCR expressing cell, a natural killer (NK) cell, a dendritic cell, a granulocyte, an innate lymphoid cell, a megakaryocyte, a monocyte, a macrophage, a platelet, a thymocyte, and a myeloid cell. In one embodiment, the immune cell is an engineered allogeneic T cell. Unlike antibody therapies or standalone CAR modified T cells, T cells (or any cells as described above) modified to express the anti-CD19 CAR are able to replicate in vivo, and thus contribute to long-term persistence that may lead to sustained cancer therapy.

In another embodiment, T cells expressing the anti-CD19 CAR may undergo T cell expansion such that a population of therapeutic T cells may remain or persist for an extended period. Thus, another embodiment described herein is a method of expanding a population of T cells comprising administering to a subject in need thereof a therapeutically effective amount of the T cells described herein.

In one embodiment described herein, the population of T cells remains between at between about 50% to about 100% after 7 days, at between about 60% to about 90% after 7 days, or at between about 70% to about 80% after 7 days. In another embodiment described herein, the population of T cells remains at about 50% after 7 days, at about 60% after 7 days, at about 70% after 7 days, at about 80% after 7 days, at about 90% after 7 days or at about 100% after 7 days.

Another embodiment described herein is a method of treating a cancer in a subject in need thereof comprising administering an effective amount, e.g., therapeutically effective amount of a composition comprising T cells expressing a CAR as described herein. The quantity and frequency of administration will be determined by such factors as the condition of the patient, and the type and severity of the patient's disease, although appropriate dosages may be determined by clinical trials.

Another embodiment described herein is a method of treating a hepatic cancer in a subject in need thereof comprising administering an effective amount, e.g., therapeutically effective amount of a composition comprising T cells expressing a CAR construct described herein. The quantity and frequency of administration will be determined by such factors as the condition of the patient, and the type and severity of the patient's disease, although appropriate dosages may be determined by clinical trials.

In some embodiments, compositions comprising T cells genetically modified with a vector comprising a promoter operably linked to a polynucleotide encoding a expressing a CAR are used in the treatment of various cancers.

In other embodiments, methods comprising administering a therapeutically effective amount of modified T cells contemplated herein or a composition comprising the same, to a patient in need thereof, alone or in combination with one or more therapeutic agents, are provided. In certain embodiments, the cells of the disclosure are used in the treatment of patients at risk for developing a cancer. Thus, the present disclosure provides methods for the treatment or prevention of a cancer comprising administering to a subject in need thereof, a therapeutically effective amount of the modified T cells of the disclosure.

One of ordinary skill in the art would recognize that multiple administrations of the compositions of the disclosure may be required to affect the desired therapy. For example, a composition may be administered 1, 2, 3, 4, 5, 6, 7, 8, 9, or 10 or more times over a span of 1 week, 2 weeks, 3 weeks, 1 month, 2 months, 3 months, 4 months, 5 months, 6 months, 1 year, 2 years, 5, years, 10 years, or more.

In certain embodiments, it may be desirable to administer activated T cells to a subject and then subsequently redraw blood (or have an apheresis performed), activate T cells therefrom according to the present disclosure, and reinfuse the patient with these activated and expanded T cells. This process may be carried out multiple times every few weeks. In certain embodiments, T cells may be activated from blood draws of from 10cc to 400cc. Not to be bound by theory, using this multiple blood draw/multiple reinfusion protocol may serve to select out certain populations of T cells.

The administration of the compositions contemplated herein may be carried out in any convenient manner, including by aerosol inhalation, injection, ingestion, transfusion, implantation or transplantation. In some embodiments, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

In one embodiment, a subject in need thereof is administered an effective amount of a composition to increase a cellular immune response to a cancer in the subject. The immune response may include cellular immune responses mediated by cytotoxic T cells capable of killing infected cells, regulatory T cells, and helper T cell responses. Humoral immune responses, mediated primarily by helper T cells capable of activating B cells thus leading to antibody production, may also be induced. A variety of techniques may be used for analyzing the type of immune responses induced by the compositions of the present disclosure, which are well described in the art; e.g., Current Protocols in Immunology, Edited by: John E. Coligan, Ada M. Kruisbeek, David H. Margulies, Ethan M. Shevach, Warren Strober (2001) John Wiley & Sons, NY, N.Y.

In the case of T cell-mediated killing, CAR-ligand binding initiates CAR signaling to the T cell, resulting in activation of a variety of T cell signaling pathways that induce the T cell to produce or release proteins capable of inducing target cell apoptosis by various mechanisms. These T cell-mediated mechanisms include (but are not limited to) the transfer of intracellular cytotoxic granules from the T cell into the target cell, T cell secretion of proinflammatory cytokines that may induce target cell killing directly (or indirectly via recruitment of other killer effector cells), and up regulation of death receptor ligands (e.g. FasL) on the T cell surface that induce target cell apoptosis following binding to their cognate death receptor (e.g. Fas) on the target cell.

In embodiments described herein is a method of treating a subject diagnosed with a cancer, comprising removing T cells from a donor, genetically modifying said T cells with a vector comprising a nucleic acid encoding an engineered expressing the CAR constructs described herein and, thereby producing a population of modified T cells, and administering the population of modified T cells to the a patient who is not the same as the donor.

The methods for administering the cell compositions described herein includes any method which is effective to result in reintroduction of ex vivo genetically modified immune effector cells that either directly express an engineered CAR in the subject or on reintroduction of the genetically modified progenitors of immune effector cells that on introduction into a subject differentiate into mature immune effector cells that express the engineered expressing the anti-CD19 CAR constructs described herein.

Although the foregoing disclosure has been described in some detail by way of illustration and example for purposes of clarity of understanding, it will be readily apparent to one of ordinary skill in the art in light of the teachings of this disclosure that certain changes and modifications may be made thereto without departing from the spirit or scope of the appended claims. The following examples are provided by way of illustration only and not by way of limitation. Those skilled in the art will readily recognize a variety of noncritical parameters that could be changed or modified to yield essentially similar results.

EXAMPLES

Example 1

ITAM-containing domains were selected for the signaling domain in place of CD3 Zeta as a next generation anti-CD19 chimeric antigen receptor (CAR) to enhance the therapeutic potential. An anti-CD19 second generation chimeric antigen receptor (CAR), having the architecture anti-CD19 scFv, CD28 Hinge, CD28 transmembrane, CD28 costim domain and CD3zeta signaling domain was used as the parental template to engineer and synthesize seven daughter constructs. These constructs are henceforth referred to as CD19-Zeta-1xx, CD19-Epsilon, CD19-Delta, CD19-Gamma, CD19-Dap12, CD19-Zeta-CO (codon optimized), and CD19-Epsilon-CO (codon optimized). To generate the daughter constructs, the CD3 Zeta signaling domain at nucleic acids 3316 to 3651 of the parental template was replaced with the following sequences:

```
Zeta 1xx:
                                                   (SEQ ID NO 94)
RVKFSRSADAPAYQQGQNQLYNELNLGRREEYDVLDKRRGRDPEMGGKP
RRKNPQEGLFNELQKDKMAEAFSEIGMKGERRRGKGHDGLFQGLSTATK
DTFDALHMQALPPR.

Epsilon:
                                                   (SEQ ID NO 52)
KNRKAKAKPVTRGAGAGGRQRGQNKERPPPVPNPDYEPIRKGQRDLYSG
LNQRRI,

Delta:
                                                   (SEQ ID NO 55)
GHETGRLSGAADTQALLRNDQVYQPLRDRDDAQYSHLGGNWARNK.

Gamma:
                                                   (SEQ ID NO 57)
GQDGVRQSRASDKQTLLPNDQLYQPLKDREDDQYSHLQGNQLRRN.

Dap 12:
                                                   (SEQ ID NO 59)
YFLGRLVPRGRGAAEAATRKQRITETESPYQELQGQRSDVYSDLNTQRP
YYK,.

Zeta-CO:
                                                   (SEQ ID NO 95)
RVKFSRSADAPAYQQGQNQLYNELNLGRREEYDVLDKRRGRDPEMGGKP
RRKNPQEGLYNELQKDKMAEAYSEIGMKGERRRGKGHDGLYQGLSTATK
DTYDALHMQALPPR.
```

The CAR constructs described herein were cloned into a lentiviral vector (LVV) that included a murine stem cell virus (mSCV) promoter to drive constitutive expression of the CARs.

The CARs used in the following examples included a CD8a signal sequence, having the architecture anti-CD19 scFv, CD28 hinge, CD28 transmembrane domain, CD28 costim domain and a signaling domain as described above.

Example 2

CAR-T Product cells were manufactured from apheresis material from a healthy human donor. The collected apheresis material was washed, incubated with anti-CD8 antibody-linked magnetic beads and processed using a CliniMACS® cell separation system (Miltenyi Biotech) per the manufacturer's instructions using anti-CD8 antibody-linked magnetic beads to enrich for CD8+ T cells, which were then cryopreserved. The resulting negative fraction was washed and processed as described above using anti-CD4 antibody-linked magnetic beads to enrich for CD4+ T cells, which were then cryopreserved. Isolated CD4+ and CD8+ primary human T cells were thawed in OpTmizer CTS™ T-cell expansion basal media supplemented with 2.6% OpTmizer CTS™ T-cell expansion supplement, 2.5% CTS immune cell serum replacement, 1% penicillin/streptomycin/L-glutamine, and 305 international units/mL human interleukin (IL)-2, henceforth referred to as complete OpTmizer™ media. T cells were resuspended in complete OpTmizer™ media containing 1.66 μg/mL of anti-CD28 antibody (clone 28.2) at a density of $1.5\times10^6$ cells/mL and then seeded into a T-75 flask pre-coated with 1.23 μg/mL anti-CD3 antibody (clone OKT3) to induce T-cell activation (Day 0). On Day 1 post-activation, cells were either transduced with an LVV encoding the parental anti-CD19 CAR or the daughter constructs Epsilon, Delta, Gamma, and Dap12 at a multiplicity of infection (MOI) of 20. Additional experimental groups consisting of the Zeta CO and Epsilon CO constructs were transduced at a MOI of 5 and a Non-transduced (NTD) sample served as a negative control. T cells were washed with complete OpTmizer™ media on Day 3, normalized and were expanded for an additional 4 days (Days 3 to 7). At the harvest time point (Day 7), cells were cryopreserved for future use. At multiple time points during expansion (Days 3 to 7), cell counts were taken using a Vi-CELL® and the cell density was normalized down to 0.5 to $1\times10^6$ cells/mL by addition of complete OpTmizer™ media. At these time points, average cell viability, diameter, and cell density were recorded on the Vi-CELL®.

Cell counts, cell viability, and cell diameter were tracked from Day 0 to Day 7 for each of the different experimental groups and are summarized in Table 6.

TABLE 6

Seven-Day Expansion Data of Transduced Constructs

| Experimental Groups | Cell counts (10^6) Day 0 | Day 3 | Day 5 | Day 7 | Viability (%) Day 0 | Day 3 | Day 5 | Day 7 | Diameter (uM) Day 0 | Day 3 | Day 5 | Day 7 |
|---|---|---|---|---|---|---|---|---|---|---|---|---|
| NTD | 7.9 | 8.3 | 65.6 | 370.5 | 96.7 | 88.6 | 90.3 | 93.7 | 8.6 | 12.0 | 12.1 | 10.8 |
| Zeta | 7.9 | 9.9 | 78.9 | 336.9 | 96.7 | 87.6 | 91.9 | 92.5 | 8.6 | 11.4 | 12.1 | 11.0 |
| Epsilon | 7.9 | 7.4 | 60.0 | 213.6 | 96.7 | 85.9 | 88.0 | 89.2 | 8.6 | 11.7 | 12.1 | 10.9 |
| Delta | 7.9 | 7.6 | 63.0 | 301.3 | 96.7 | 87.3 | 90.1 | 92.1 | 8.6 | 11.8 | 12.1 | 11.1 |
| Gamma | 7.9 | 8.8 | 69.0 | 331.8 | 96.7 | 87.4 | 90.3 | 92.1 | 8.6 | 11.7 | 12.2 | 10.9 |
| Dap12 | 7.9 | 7.51 | 58.3 | 325.5 | 96.7 | 85.6 | 89.4 | 92.8 | 8.6 | 12.0 | 12.1 | 11.0 |
| Zeta-CO | 7.9 | 8.9 | 59.3 | 312.4 | 96.7 | 89.2 | 89.6 | 91.0 | 8.6 | 11.8 | 12.3 | 11.1 |
| Epsilon-CO | 7.9 | 8.0 | 53.2 | 229.8 | 96.7 | 86.4 | 85.9 | 80.8 | 8.6 | 11.4 | 12.5 | 11.2 |
| Zeta 1xx | 7.9 | 8.6 | 72.4 | 348.9 | 96.7 | 89.6 | 92.5 | 93.1 | 8.62 | 11.7 | 12.1 | 10.9 |

A total of $7.9\times10^6$ cells per experimental group were stimulated at Day 0. At the end of the seven-day manufacturing process the Epsilon, Epsilon CO, and CD19-RVV constructs expanded the least at just above $200\times10^6$ total cells. The diameter of the product cells is used as an indirect measure of T-cell activation and showed no significant differences between any of groups during manufacturing.

Example 3

CAR expression was measured by flow cytometry on days 6 and 7 to determine the transduction efficiency of CAR-T product cells. T cells were stained with a panel of fluorophore-conjugated antibodies against CD3, CD4, CD8 and Whitlow linker (CAR), and characterized by flow cytometry to determine transduction efficiency, and CD4+/CD8+ T cell ratios. Assessment of CAR expression (anti-CD19 CAR) was enabled by fluorophore-conjugated antibody directed to the Whitlow linker present in the anti-CD19 scFvs. A fixable cell viability dye was also used to allow specific analysis of viable cells. Cells were stained by incubating with the appropriate antibody mix for 20 minutes at 4° C. followed by 2 washes with stain buffer, and subsequently fixed by incubating in 0.6% paraformaldehyde in phosphate-buffered saline or Hank's balanced salt solution for 10 minutes at room temperature. All flow cytometry data was collected on a FACSCanto™ instrument and data was analyzed using FlowJo software.

CAR expression was measured on both Day 6 and Day 7 of manufacturing using the Whitlow linker staining and subsequent flow cytometry analysis (Table 7). The experimental groups showed comparable CAR expression on Day 6 ranging from 81.5% to 91.9% and remained relatively stable on Day 7. The only exception was the Epsilon construct which had the lowest CAR expression on Day 6 at 74.2% and also significantly dropped down to 58.4% on Day 7.

TABLE 7

Expression Data of Transduced Constructs During Manufacturing

| Experimental Groups | % Transduction Day 0 | Day 3 | Day 6 | Day 7 |
|---|---|---|---|---|
| NTD | N/A | N/A | N/A | N/A |
| Zeta | N/A | N/A | 81.5 | 83.9 |
| Epsilon | N/A | N/A | 74.2 | 58.4 |
| Delta | N/A | N/A | 91.8 | 90.4 |
| Gamma | N/A | N/A | 91.9 | 89.9 |
| Dap12 | N/A | N/A | 91.7 | 91.3 |
| Zeta-CO | N/A | N/A | 89.1 | 94.3 |
| Epsilon-CO | N/A | N/A | 90.3 | 95.1 |
| Zeta 1xx | N/A | N/A | 88.2 | 87.9 |

Example 4

T-cell mediated cytotoxicity was measured as a function of the reduction in target luciferase signal in co-culture wells compared to the signal emitted by target cells plated alone. T-cell products manufactured from T cells derived from healthy donor apheresis were cryopreserved on the harvest day (Day 7 of manufacture). At day 0 of coculture, T-cell products were thawed and rested overnight in complete OpTmizer™ media before initiation of co-culture with target cells. Immediately before co-culture initiation, an aliquot of each T-cell sample was incubated with a panel of antibody-fluorophores against CD3, CD4, CD8 and Whitlow linker (CAR), and analyzed by flow cytometry to evaluate transduction efficiency. Total transduction efficiency was assessed using a custom-made antibody that binds the Whitlow linker between the heavy and light chains of the single-chain variable fragment (scFv). T cells were then labeled with CellTrace™ Violet (CTV) reagent and subsequently washed with R-10% media [RPMI-1640 media supplemented with 10% fetal bovine serum, penicillin streptomycin L-Glutamine, and HEPES]. A portion of the CTV-labeled samples was fixed and stored at 4° C. until day 4, when samples were analyzed in parallel with day 4 co-culture samples by flow cytometry to assess initial levels of CTV signal (CTV Max). T-cell products and luciferase-expressing target cells were plated together at different effector to target (E:T) ratios, ranging from 3:1 to 1:243, in R-10% media (Day 0 of co-culture). T-cell products were serially diluted 3-fold while the number of target cells per well was held constant at 20,000 cells. Positive target cells included Nalm6 (CD19+) and ST486 (CD19+). As a control, T-cell products were cultured in the absence of any target cells (i.e., T cells alone) to assess basal levels of T-cell function in the absence of antigen stimulation. Co-cultures were incubated at 37° C. for either 1 or 4 days and functional assessments were performed as described below.

After thaw and overnight rest, a sample of each experimental group was stained for CD3, CD4, CD8 and Whitlow linker (CAR) to assess their percent recovery and CAR expression. Groups were then normalized down to the lowest transduction percentage (43.7%) by the addition of NTD cells. This was done to ensure that all samples had the same number of CAR+ samples in the downstream assays. The product cells were successfully normalized and ranged from 41.0 to 46.8 percent (Table 8). The Epsilon construct was observed to downregulate CAR on the cell surface and dropped down to 27.7% CAR+ by the time of co-culture initiation with target cells.

TABLE 8

CAR Expression of CAR-T Product Cells on Day 0 of the Co-culture Setup

| Experimental Groups | % Transduction: Pre Normalization/ Overnight Rest | % Transduction: Post Normalization |
|---|---|---|
| NTD | N/A | N/A |
| Zeta | 83.4 | 41.9 |
| Epsilon | 43.7 | 27.7 |
| Delta | 86.4 | 42.1 |
| Gamma | 85.7 | 41.0 |
| Dap12 | 88.1 | 43.1 |
| Zeta-CO | 93.7 | 42.5 |
| Epsilon-CO | 94.1 | 43.6 |
| Zeta 1xx | 87.1 | 43.8 |

T-cell mediated cytotoxicity was measured as a function of the reduction in target luciferase signal in co-culture wells compared to the signal emitted by target cells plated alone. On Days 1 and 4 after co-culture initiation, D-luciferin substrate was added to the co-culture wells at a final concentration of 0.14 mg/mL and plates were incubated at 37° C. in the dark for 10 minutes. Luminescent signal was read immediately after in a VarioSkan™ LUX or VarioSkan® Flash multimode microplate reader. T cell-mediated cytotoxicity was calculated as follows:

% Cytotoxicity=[1−luciferase signal of (sample of interest/target alone control)]*100

Day 1 (Table 9) and Day 4 (Table 10) readouts showed equivalent dose-dependent cytotoxicity across all both antigen-expressing cells lines (Nalm6 and ST486), with no significant differences between constructs.

TABLE 9

Day 1 Functional Characterization Data: Percent Cytotoxicity of Nalm6 Cell Line in Triplicates

| Experimental Groups | E:T ratio 3:1 | 1:1 | 1:3 | 1:9 | 1:27 | 1:81 | 1:243 |
|---|---|---|---|---|---|---|---|
| NTD | 17.1 | 5.2 | −0.1 | 7.8 | −0.1 | 0.1 | −5.3 |
| | 18.5 | 0.4 | −0.3 | 12.5 | −1.8 | 1.3 | −1.5 |
| | 11.5 | 8.9 | 4.0 | 5.0 | 6.3 | 3.6 | −3.1 |
| Zeta | 92.4 | 64.3 | 27.1 | 19.1 | −0.6 | −6.6 | −7.6 |
| | 92.8 | 64.8 | 29.6 | 22.5 | −4.4 | 0.0 | −0.1 |
| | 91.5 | 59.2 | 33.4 | 15.8 | 20.1 | 2.1 | 0.1 |
| Epsilon | 90.5 | 59.6 | 27.6 | 18.5 | 1.2 | −0.5 | −3.6 |
| | 91.7 | 59.4 | 21.0 | 17.0 | 1.9 | −2.1 | −6.0 |
| | 90.7 | 62.5 | 37.0 | 14.9 | 20.2 | 15.9 | 14.8 |
| Delta | 78.4 | 45.1 | 25.1 | 17.4 | 0.0 | 2.5 | 0.9 |
| | 79.1 | 42.4 | 21.2 | 16.7 | 1.0 | 0.2 | −3.4 |
| | 75.5 | 47.6 | 24.8 | 10 | 20 | 16.3 | 13.4 |
| Gamma | 73.4 | 44.3 | 23.2 | 14.9 | 2.1 | 1.6 | −3.8 |
| | 74.7 | 40.5 | 16.3 | 17.9 | 0.8 | 0.7 | 0.0 |
| | 70.1 | 40.0 | 24.0 | 12.6 | 6.7 | 3.0 | 4.2 |
| Dap12 | 83.2 | 51.6 | 29.2 | 21.5 | 5.8 | −1.0 | −3.9 |
| | 82.3 | 46.2 | 22.2 | 20.1 | 3.0 | 1.2 | 0.7 |
| | 81.2 | 48.3 | 22.6 | 12.0 | 13.8 | 3.3 | 2.6 |
| Zeta-CO | 94.5 | 74.2 | 41.8 | 25.7 | 3.9 | 3.7 | −1.8 |
| | 96.4 | 68.3 | 34.6 | 23.5 | 5.9 | 3.4 | −1.1 |
| | 93.4 | 70.0 | 34.4 | 21.0 | 3.1 | 0.4 | 1.5 |
| Epsilon-CO | 89.3 | 54.5 | 24.3 | 21.9 | 4.6 | 6.1 | −0.6 |
| | 86.1 | 50.3 | 23.5 | 20.4 | 3.7 | 0.1 | 2.6 |
| | 88.8 | 46.3 | 26.8 | 13.8 | 5.5 | 5.3 | 0.0 |
| Zeta 1xx | 88.9 | 59.2 | 27.0 | 18.4 | −0.8 | −1.1 | −1.8 |
| | 87.6 | 56.0 | 21.3 | 17.9 | −2.4 | −2.7 | −0.2 |
| | 85.2 | 55.7 | 37.7 | 15.0 | 14.4 | 20.3 | 19.0 |

TABLE 10

Day 4 Functional Characterization Data: Percent Cytotoxicity of Nalm6 Cell Line in Triplicates

| Experimental Groups | E:T ratio 3:1 | 1:1 | 1:3 | 1:9 | 1:27 | 1:81 | 1:243 |
|---|---|---|---|---|---|---|---|
| NTD | 60.3 | 20.4 | 7.1 | −1.8 | −1.3 | −6.8 | 0.6 |
| | 57.8 | 20.9 | 4.9 | −2.5 | −4.2 | −4.1 | −0.9 |
| | 64.9 | 16.6 | −2.7 | −3.2 | −2.3 | −5.6 | −0.2 |
| Zeta | 100.1 | 100.1 | 97.2 | 77.9 | 43.6 | 21.3 | 6.9 |
| | 100.1 | 99.9 | 95.7 | 73.3 | 37.3 | 18.1 | 8.8 |
| | 100.1 | 100.1 | 98.2 | 79.8 | 37.2 | 16.1 | 6.2 |
| Epsilon | 100.1 | 100.1 | 98.2 | 59.3 | 11.4 | −1.6 | −6.3 |
| | 100.1 | 100.1 | 96.5 | 46.1 | 13.9 | −0.9 | 1.6 |
| | 100.1 | 100.1 | 98.2 | 58.1 | 13.4 | −1.7 | −3.3 |
| Delta | 100.1 | 100.1 | 98.0 | 64.0 | 30.6 | 4.0 | −2.3 |
| | 100.1 | 100.1 | 96.4 | 62.5 | 25.1 | 7.3 | 5.5 |
| | 100.1 | 100.1 | 97.5 | 64.9 | 27.8 | 6.9 | 2.4 |
| Gamma | 100.1 | 100.1 | 96.2 | 61.4 | 25.9 | 4.6 | −1.0 |
| | 100.1 | 100.0 | 94.0 | 60.4 | 20.6 | 6.1 | 0.1 |
| | 100.1 | 100.1 | 96.4 | 62.7 | 23.0 | 3.3 | −1.4 |
| Dap12 | 100.1 | 100.1 | 98.1 | 73.8 | 33.7 | 4.2 | −1.0 |
| | 100.1 | 100.1 | 96.7 | 68.6 | 26.8 | 4.0 | 3.5 |
| | 100.1 | 100.1 | 98.9 | 73.1 | 28.6 | −1.8 | −0.3 |
| Zeta-CO | 100.1 | 100.1 | 99.9 | 85.0 | 42.5 | 9.5 | 1.8 |
| | 100.1 | 100.1 | 99.4 | 81.3 | 40.6 | 14.7 | 2.6 |
| | 100.1 | 100.1 | 99.5 | 84.9 | 46.3 | 11.8 | −0.1 |
| Epsilon-CO | 100.1 | 100.0 | 97.5 | 61.2 | 27.0 | 5.1 | −1.8 |
| | 100.1 | 99.9 | 96.4 | 58.2 | 26.9 | 6.4 | −2.6 |
| | 100.0 | 100.0 | 96.9 | 62.4 | 27.0 | 0.3 | 0.1 |
| Zeta 1xx | 100.1 | 100.1 | 97.5 | 68.6 | 36.8 | 6.8 | 5.2 |
| | 100.1 | 100.1 | 94.3 | 63.7 | 23.3 | 13.3 | 5.3 |
| | 100.1 | 100.1 | 97.8 | 67.2 | 34.5 | 10.0 | 5.2 |

Example 5

On Day 1 after co-culture initiation as described in the preceding example, supernatants were collected and analyzed for cytokine levels using the Meso Scale Discovery V-PLEX® Pro inflammatory Panel 1 human kit according to the manufacturer's instructions. Specifically, supernatants from the co-cultures of T-cell products plated at the 1:1 E:T ratio with antigen-expressing Nalm6 and ST486 were analyzed for levels of interferon gamma (IFN-γ), IL-2, and tumor necrosis factor alpha (TNF-α) secretion mediated by antigen engagement. Supernatants from T cells cultured in the absence of target cells (T cells alone) were analyzed in parallel to assess basal levels of cytokine production in the absence of antigen. All samples were diluted to be within the range of detection.

Supernatant was collected from the 1:1 E:T ratio and analyzed via MSD for IFN-γ, IL-2, and TNF-α secretion. Analysis showed that all constructs secreted cytokines when co-cultured with the antigen-expressing cell lines Nalm6 and ST486 (Table 11). Zeta 1xx, Epsilon-CO, and to a certain extent Delta all secreted comparable high levels of the pro-inflammatory cytokines compared to the Zeta and Zeta-CO benchmark controls. Epsilon, Gamma, and Dap12 produced lower levels of cytokines compared to the Zeta and Zeta-CO benchmark controls. Co-culture with the Nalm6 cell line elicited higher levels of cytokines when compared to the levels secreted with the ST486 cell line, however, the overall hierarchical pattern of the constructs was consistent across both cell lines. On the other hand, the NTD control group did not secrete any measurable or significant levels of cytokine when cultured alone or with antigen-expressing cell lines.

TABLE 11

Day 1 Functional Characterization Data: Cytokine Analysis of IFN-γ, TNF-α, IL-2 in Nalm6 and ST486 Cell Lines via MSD

| Experimental Groups | Cytokine | Nalm6 | % CV | ST486 | % CV | T cells Alone | % CV |
|---|---|---|---|---|---|---|---|
| NTD | IFN-γ | 720.2 | 28.8 | 1289.0 | 24.1 | 16.9 | 0.0 |
| | TNF-α | 0.0 | 0.0 | 0.0 | 0.0 | 0.0 | 0.0 |
| | IL-2 | 0.0 | 0.0 | 0.0 | 0.0 | 0.0 | 0.0 |
| Zeta | IFN-γ | 96335.4 | 20.9 | 27645.8 | 15.0 | 200.9 | 0.0 |
| | TNF-α | 1394.4 | 12.0 | 424.3 | 15.6 | 0.0 | 0.0 |
| | IL-2 | 1857.6 | 10.8 | 275.0 | 27.0 | 0.0 | 0.0 |
| Epsilon | IFN-γ | 40251.9 | 28.0 | 14887.6 | 11.6 | 126.8 | 0.0 |
| | TNF-α | 495.8 | 14.0 | 226.2 | 10.8 | 0.0 | 0.0 |
| | IL-2 | 217.6 | 1.5 | 62.4 | 23.8 | 0.0 | 0.0 |
| Delta | IFN-γ | 58829.3 | 20.0 | 16827.2 | 5.3 | 60.8 | 0.0 |
| | TNF-α | 1071.2 | 7.7 | 338.2 | 9.9 | 0.0 | 0.0 |
| | IL-2 | 1189.5 | 5.2 | 148.0 | 15.3 | 0.0 | 0.0 |
| Gamma | IFN-γ | 37352.4 | 19.5 | 8944.0 | 3.9 | 47.3 | 0.0 |
| | TNF-α | 582.5 | 3.6 | 136.9 | 7.0 | 0.0 | 0.0 |
| | IL-2 | 418.6 | 7.9 | 29.1 | 26.2 | 0.0 | 0.0 |
| Dap12 | IFN-γ | 44462.9 | 20.6 | 12763.5 | 7.9 | 67.3 | 0.0 |
| | TNF-α | 625.8 | 3.5 | 171.9 | 10.7 | 0.0 | 0.0 |
| | IL-2 | 467.8 | 9.0 | 47.7 | 48.1 | 0.0 | 0.0 |
| Zeta-CO | IFN-γ | 101222.2 | 20.4 | 31320.8 | 4.0 | 67.3 | 0.0 |
| | TNF-α | 1310.0 | 5.7 | 442.6 | 2.1 | 0.0 | 0.0 |
| | IL-2 | 1559.1 | 3.7 | 247.9 | 18.0 | 0.0 | 0.0 |
| Epsilon-CO | IFN-γ | 81122.0 | 20.3 | 27685.4 | 3.3 | 148.8 | 0.0 |
| | TNF-α | 857.5 | 9.8 | 374.9 | 3.6 | 0.0 | 0.0 |
| | IL-2 | 1180.8 | 11.1 | 257.8 | 7.2 | 0.0 | 0.0 |
| Zeta 1xx | IFN-γ | 80623.9 | 26.4 | 22041.0 | 5.4 | 175.2 | 0.0 |
| | TNF-α | 1126.6 | 11.4 | 352.4 | 3.6 | 0.0 | 0.0 |
| | IL-2 | 1493.0 | 15.3 | 227.7 | 12.3 | 0.0 | 0.0 |

Example 6

On Day 4 after co-culture initiation, T-cell products plated at the 1:1 E:T ratio with target cells were harvested, stained with a panel of antibody-fluorophores to identify T cells, and analyzed by flow cytometry. The proliferative capacity of the T-cell products was determined by flow cytometric analysis of the cell division-driven dilution of CTV dye in response to antigen-expressing target cells compared with that of T-cell products that had been cultured alone (T cells alone), which was used to assess basal levels of homeostatic proliferation in the absence of stimuli. CTV-labeled T cells which were fixed on the day of co-culture setup (CTV Max) were analyzed by flow cytometry in parallel to assess the intensity of the initial CTV signal prior to cell proliferation.

Dilution of the Cell Trace Violet (CTV) label was used to assess proliferation. As the product CAR-T cells divide, the dye is diluted with each division and thus, a lower CTV MFI when compared to the Day 0 cells, is indicative of proliferation. Minimal homeostatic or antigen-independent proliferation is seen in the NTD control group when cultured alone or with antigen-expressing cell lines. All other constructs showed comparable MFI levels when cultured against the ST486 cell line. When cultured with the Nalm6 cell line, Zeta-CO and Epsilon both had the lowest CTV MFI indicating greater proliferation. All the other constructs had comparable levels of proliferation against this same target line. A full summary is found in Table 12.

TABLE 12

Day 4 Functional Characterization Data: Proliferation Analysis Nalm6 and ST486 Cell Lines via Cell Trace Violet (CTV) Staining. Values reported are the Median of the CTV distribution curves.

| Experimental Groups | Nalm6 | ST486 | T cells Alone |
|---|---|---|---|
| NTD | 19120 | 15672 | 19256 |
| Zeta | 5762 | 4997 | 17367 |
| Epsilon | 4193 | 5257 | 11481 |
| Delta | 5874 | 6186 | 16613 |
| Gamma | 6418 | 7869 | 20137 |
| Dap12 | 5725 | 7365 | 17696 |
| Zeta-CO | 3441 | 4211 | 15277 |
| Epsilon-CO | 5812 | 5103 | 21260 |
| Zeta 1xx | 5427 | 5359 | 18286 |

Example 7

For in vivo studies, one day prior to injection Anti-CD19 product CAR T cells were prepared as described above were removed from cryostorage, thawed in a 37° C. water bath, and resuspended in prewarmed, complete OpTmizer™ media. An aliquot of the cell suspension was diluted in trypan blue and cells were manually counted. The cell suspensions were centrifuged at 400×g for 5 minutes at room temperature and the supernatant was aspirated. The cells were then resuspended at 2.0 to $5.0\times10^6$ cells/mL in complete OpTmizer™ media and cultured overnight in a 37° C./5% $CO_2$ incubator. On the day of injection, NTD T cells were pooled with CAR+ T cells at the ratios specified to normalize test groups by total cell number. An aliquot of the homogenous cell suspension was diluted in a trypan blue solution and cells were manually counted using a hemocytometer to determine the pre-injection viability of the cells. The cell suspensions were then centrifuged at 200×g for 10 minutes at 4° C. The supernatants of each vial were aspirated, and the cell pellets were resuspended in DPBS at room temperature. Two CAR T cell doses were tested: $5.0\times10^5$ and $2.0\times10^6$ CAR+ cells per group. After implantation, an aliquot of the remaining cells from each suspension were diluted with a trypan blue solution and counted to determine the post implantation cell viabilities.

The same total number of T cells (2.4×10$^{6}$ cells) were administered to mice in each of the treatment groups. The doses to be administered to each treatment group were normalized to deliver the same total number of T cells for each group based on the anti-CD19 CAR transduction efficiency.

In vivo BLI was performed using an IVIS 5 optical imaging system. Animals were imaged under approximately 1% to 2% isoflurane gas anesthesia. Each mouse was injected IP with 0.2 mL/20 g D-luciferin and imaged in the prone, then supine, positions 10 minutes after the injection. Large binning of the charge-coupled device (CCD) chip was used and the exposure time was adjusted to obtain at least several hundred counts from the metastatic tumors that were observable in each mouse in the image and to avoid saturation of the CCD chip. BLI images were collected on Days 6, 13, 20, 27, 34, 41, and 48. Images were analyzed using the Living Image software version 4.7.1. Whole body fixed-volume regions of interest (ROI) were placed on prone and supine images for each individual animal and were labeled based on animal identification. Total flux (photons/second) was calculated and exported for all ROIs, where a custom-written script tabulated the various signals found for each mouse, to facilitate analyses between groups. The prone and supine regions of interest were summed together to estimate whole body tumor burden.

The BLI for each experimental group is summarized in Table 13. Groups that received either the Vehicle control or NTD cells showed no tumor control and both groups were euthanized by Day 20 due to high tumor burden. All high dose constructs showed significant and comparable efficacy on Day 13. Loss of tumor control in the high dose groups began as early as Day 20. Epsilon-CO, Dap12, and Zeta 1XX of the high dose groups maintained tumor control until termination of the study on Day 48.

Tumor control in the low dose groups was more variable from the onset on the study. Zeta 1xx had the best tumor control early on and maintained its efficacy throughout the entirety of the study. Epsilon-CO exhibited minimal tumor control through the first three readouts but then showed abrupt and complete tumor control on Day 27 across all mice and maintained this tumor control throughout the remainder of the study. Epsilon showed similar late-stage tumor control on Day 34 in three out of the five mice that continued to the end of the study. The remaining two were eventually euthanized due to high tumor burden. Although more varied, Dap12 showed similar tumor control efficacy in the low dose as it did in the high dose study. One mouse specifically seemed to lose tumor control starting on day 27 but then regained it by Day 48.

TABLE 13

| Bioluminescence imaging (BLI) of Mice (photons/sec) | | | | | | | |
|---|---|---|---|---|---|---|---|
| | Day 6 | Day 13 | Day 20 | Day 27 | Day 34 | Day 41 | Day 48 |
| Vehicle | 5.70E+07 | 2.14E+10 | 1.56E+11 | | | | |
| | 4.96E+07 | 2.07E+10 | 1.28E+11 | | | | |
| | 5.62E+07 | 2.26E+10 | 1.02E+11 | | | | |
| | 4.25E+07 | 2.03E+10 | 1.34E+11 | | | | |
| | 2.61E+07 | 1.62E+10 | 9.01E+10 | | | | |
| NTD | 5.62E+07 | 2.19E+10 | 1.50E+11 | | | | |
| | 2.62E+07 | 1.19E+10 | 9.40E+10 | | | | |
| | 4.92E+07 | 1.97E+10 | 1.11E+11 | | | | |
| | 4.18E+07 | 1.78E+10 | 9.67E+10 | | | | |
| | 5.74E+07 | 1.60E+10 | 1.27E+11 | | | | |
| Epsilon | 3.17E+07 | 9.08E+06 | 1.86E+07 | 1.22E+06 | 6.94E+05 | 8.57E+05 | 8.93E+05 |
| (5E5) | 5.46E+07 | 1.55E+07 | 2.81E+08 | 2.45E+09 | 8.25E+05 | 8.94E+05 | 1.02E+06 |
| | 5.94E+07 | 2.57E+07 | 8.71E+07 | 2.56E+09 | 1.24E+11 | | |
| | 3.93E+07 | 5.34E+07 | 1.30E+09 | 9.95E+08 | 1.06E+07 | 2.70E+07 | 4.23E+06 |
| | 4.42E+07 | 4.66E+07 | 5.03E+08 | 3.32E+09 | 3.98E+10 | 9.85E+10 | |
| Delta | 5.97E+07 | 7.89E+05 | 8.52E+05 | 7.74E+05 | 7.64E+05 | 9.26E+05 | 2.22E+06 |
| (2E6) | 5.43E+07 | 8.14E+05 | 8.03E+05 | 7.48E+05 | 7.16E+05 | 5.97E+05 | 9.86E+05 |
| | 3.73E+07 | 8.93E+05 | 7.57E+05 | 7.99E+05 | 7.37E+06 | 1.88E+08 | 7.91E+09 |
| | 3.49E+07 | 8.59E+05 | 9.92E+05 | 8.21E+05 | 1.01E+06 | 1.15E+06 | 1.14E+06 |
| | 4.44E+07 | 8.84E+05 | 1.46E+06 | 1.30E+06 | 5.17E+06 | 2.13E+07 | 1.51E+08 |
| Delta | 6.25E+07 | 1.58E+06 | 1.53E+06 | 1.55E+06 | 9.61E+05 | 7.58E+05 | 7.34E+05 |
| (5E5) | 5.37E+07 | 3.33E+07 | 3.85E+06 | 5.04E+06 | 1.58E+08 | 4.31E+09 | 2.37E+10 |
| | 4.84E+07 | 1.63E+07 | 1.19E+08 | 5.33E+06 | 1.60E+06 | 1.43E+07 | 5.58E+08 |
| | 2.96E+07 | 2.02E+06 | 9.34E+07 | 1.85E+09 | 7.08E+09 | 1.12E+10 | 4.70E+10 |
| | 3.85E+07 | 5.34E+06 | 3.09E+06 | 2.65E+07 | 6.85E+09 | 8.03E+08 | 1.20E+07 |
| Gamma | 3.85E+07 | 9.60E+05 | 7.93E+05 | 7.37E+05 | 8.41E+06 | 1.77E+08 | 1.11E+10 |
| (2E6) | 6.26E+07 | 1.04E+06 | 9.63E+05 | 7.41E+05 | 9.52E+05 | 2.64E+06 | 7.53E+07 |
| | 4.55E+07 | 8.43E+05 | 7.65E+05 | 5.96E+05 | 1.65E+06 | 8.39E+05 | 7.27E+05 |
| | 2.97E+07 | 9.05E+05 | 7.96E+05 | 7.40E+05 | 3.62E+06 | 1.32E+08 | 9.97E+09 |
| | 5.31E+07 | 6.22E+05 | 1.06E+06 | 7.53E+05 | 1.14E+06 | 1.24E+08 | 6.14E+09 |
| Gamma | 3.09E+07 | 5.77E+06 | 1.71E+07 | 6.61E+08 | 1.44E+10 | 2.43E+10 | 5.18E+09 |
| (5E5) | 5.28E+07 | 3.46E+07 | 1.24E+07 | 1.55E+08 | 1.39E+09 | 2.44E+06 | 1.38E+06 |
| | 6.27E+07 | 3.04E+07 | 2.11E+07 | 8.96E+07 | 9.76E+07 | 3.92E+08 | 2.85E+09 |
| | 3.76E+07 | 2.60E+07 | 2.10E+08 | 1.46E+08 | 8.88E+09 | 5.52E+10 | |
| | 4.60E+07 | 3.49E+06 | 4.15E+06 | 3.32E+07 | 8.46E+07 | 3.57E+09 | 1.62E+10 |
| Dap12 | 4.67E+07 | 1.01E+06 | 9.08E+05 | 7.37E+05 | 1.03E+06 | 1.92E+06 | 1.05E+06 |
| (2E6) | 3.10E+07 | 8.80E+05 | 7.88E+05 | 7.33E+05 | 9.11E+05 | 1.55E+06 | 7.12E+05 |
| | 6.33E+07 | 9.11E+05 | 1.23E+06 | 7.46E+05 | 7.70E+05 | 1.67E+06 | 8.30E+05 |
| | 3.70E+07 | 9.45E+05 | 8.30E+05 | 8.39E+05 | 8.82E+05 | 1.72E+06 | 9.20E+05 |
| | 5.24E+07 | 8.75E+05 | 1.06E+06 | 8.59E+05 | 1.13E+06 | 2.13E+06 | 8.41E+05 |
| Dap12 | 3.69E+07 | 9.94E+05 | 9.22E+05 | 7.98E+05 | 7.52E+05 | 1.70E+06 | 9.51E+05 |
| (5E5) | 6.37E+07 | 3.56E+06 | 3.15E+06 | 1.42E+07 | 1.12E+06 | 1.68E+06 | 9.18E+05 |
| | 3.12E+07 | 5.41E+06 | 3.69E+06 | 2.80E+08 | 2.84E+09 | 1.29E+08 | 9.88E+05 |
| | 5.20E+07 | 1.23E+06 | 8.99E+05 | 7.79E+05 | 1.09E+07 | 1.47E+06 | 5.84E+05 |
| | 4.67E+07 | 1.14E+06 | 8.74E+05 | 6.81E+05 | 7.76E+05 | 1.54E+06 | 8.81E+05 |

TABLE 13-continued

| Bioluminescence imaging (BLI) of Mice (photons/sec) | | | | | | | |
|---|---|---|---|---|---|---|---|
| | Day 6 | Day 13 | Day 20 | Day 27 | Day 34 | Day 41 | Day 48 |
| Zeta- | 3.62E+07 | 1.14E+06 | 1.84E+06 | 9.89E+06 | 7.24E+07 | 5.05E+08 | 1.01E+06 |
| CO | 2.72E+07 | 9.86E+05 | 2.26E+06 | 5.22E+07 | 1.10E+10 | 4.26E+08 | 3.53E+07 |
| (2E6) | 7.18E+07 | 2.18E+06 | 7.91E+05 | 8.01E+05 | 1.70E+06 | 8.12E+07 | 2.05E+09 |
| | 5.10E+07 | 1.05E+06 | 1.08E+06 | 1.21E+06 | 9.76E+05 | 1.09E+06 | 7.52E+05 |
| | 4.83E+07 | 1.43E+06 | 2.80E+06 | 5.00E+07 | 2.36E+08 | 2.07E+06 | 1.15E+06 |
| Zeta- | 7.24E+07 | 2.10E+07 | 1.19E+07 | 5.65E+08 | 2.75E+10 | 1.19E+08 | 6.57E+07 |
| CO | 2.67E+07 | 1.21E+06 | 8.73E+06 | 4.56E+08 | 4.22E+08 | 1.60E+06 | 9.52E+05 |
| (5E5) | 3.61E+07 | 9.48E+06 | 2.05E+07 | 8.72E+08 | 4.24E+09 | 2.46E+07 | 5.10E+06 |
| | 5.06E+07 | 5.67E+06 | 1.38E+07 | 3.41E+08 | 2.27E+09 | 1.15E+09 | 6.31E+08 |
| | 4.11E+07 | 2.95E+07 | 2.91E+07 | 1.60E+09 | 2.27E+10 | 9.11E+10 | 2.80E+10 |
| Epsilon- | 4.25E+07 | 1.20E+06 | 6.99E+05 | 8.92E+05 | 9.26E+05 | 1.09E+06 | 1.08E+06 |
| CO | 3.57E+07 | 9.05E+05 | 7.41E+05 | 7.97E+05 | 8.20E+05 | 1.02E+06 | 9.12E+05 |
| (2E6) | 5.01E+07 | 1.11E+06 | 7.32E+05 | 8.47E+05 | 8.07E+05 | 9.47E+05 | 1.12E+06 |
| | 7.34E+07 | 8.06E+05 | 7.28E+05 | 8.15E+05 | 8.70E+05 | 8.80E+05 | 8.66E+05 |
| | 2.90E+07 | 1.01E+06 | 7.35E+05 | 8.70E+05 | 9.52E+05 | 1.07E+06 | 1.02E+06 |
| Epsilon- | 3.50E+07 | 7.97E+08 | 1.47E+09 | 1.06E+06 | 1.18E+06 | 1.25E+06 | 1.26E+06 |
| CO | 4.25E+07 | 3.23E+08 | 1.47E+09 | 8.90E+05 | 9.61E+05 | 1.10E+06 | 6.87E+05 |
| (5E5) | 4.92E+07 | 3.94E+08 | 4.44E+08 | 9.13E+05 | 8.40E+05 | 1.16E+06 | 9.43E+05 |
| | 2.81E+07 | 7.75E+07 | 6.65E+08 | 8.45E+05 | 9.78E+05 | 1.11E+06 | 1.03E+06 |
| | 7.74E+07 | 1.36E+08 | 3.30E+08 | 9.72E+05 | 9.65E+05 | 1.27E+06 | 1.08E+06 |
| Zeta | 5.53E+07 | 8.26E+05 | 7.03E+05 | 6.64E+05 | 7.29E+05 | 8.34E+05 | 8.46E+05 |
| 1xx | 5.85E+07 | 7.04E+05 | 7.94E+05 | 6.84E+05 | 7.38E+05 | 8.70E+05 | 8.28E+05 |
| (2E6) | 4.05E+07 | 8.02E+05 | 8.53E+05 | 6.34E+05 | 7.94E+05 | 7.76E+05 | 7.06E+05 |
| | 4.83E+07 | 7.98E+05 | 7.91E+05 | 7.33E+05 | 8.15E+05 | 8.45E+05 | 9.63E+05 |
| | 2.74E+07 | 8.59E+05 | 8.38E+05 | 1.13E+06 | 8.34E+05 | 8.70E+05 | 9.61E+05 |
| Zeta | 5.90E+07 | 1.57E+06 | 1.20E+06 | 2.26E+07 | 9.42E+05 | 9.44E+05 | 9.98E+05 |
| 1xx | 3.50E+07 | 2.29E+06 | 9.56E+05 | 7.49E+05 | 8.15E+05 | 1.08E+06 | 9.61E+05 |
| (5E5) | 4.41E+07 | 9.23E+06 | 2.07E+07 | 1.77E+07 | 9.04E+05 | 9.48E+05 | 1.03E+06 |
| | 3.94E+07 | 3.50E+06 | 3.27E+06 | 1.33E+06 | 8.11E+05 | 9.81E+05 | 7.68E+05 |
| | 5.51E+07 | 5.59E+06 | 1.45E+06 | 2.05E+06 | 7.72E+05 | 9.54E+05 | 9.32E+05 |

Example 8

For ex Vivo ddPCR analysis a weekly blood volume of 100 µl was collected via the retro-orbital sinus and stored on ice. Animals were sampled starting 24 hours after T-cell injection and continued weekly throughout the duration of the study on Days 8, 15, 22, 29, 36, and 43. DNA purification was performed using KingFisher™ Flex (small volume) per the manufacturer's instructions, ddPCR was then performed on the purified DNA via internal Kite protocols and Bio-Rad instrumentation.

To assess CAR T-cell expansion and persistence in vivo, peripheral blood was analyzed via ddPCR for CAR copies per ug of DNA (Table 14). Analysis was restricted to the constructs that showed improved tumor control (Zeta 1xx, Dap12 and Epsilon-CO). Zeta exhibited little to no expansion in the peripheral blood of mice as expected for our standard anti-CD19 CAR in the Nalm6 tumor model. However, Epsilon-CO and to a lesser extent Zeta 1xx and Dap12, had increased CAR T-cell peak expansion and persistence in the peripheral blood of mice in both treatment doses.

TABLE 14

| CAR copies (per ug of DNA) | | | | | | |
|---|---|---|---|---|---|---|
| | Day 1 | Day 7 | Day 14 | Day 21 | Day 28 | Day 35 |
| Vehicle | 0.00E+00 | 3.88E−03 | 0.00E+00 | | | |
| | 7.91E−03 | 0.00E+00 | 0.00E+00 | | | |
| | 0.00E+00 | 0.00E+00 | 0.00E+00 | | | |
| | 4.56E−03 | 1.85E−03 | 0.00E+00 | | | |
| | 6.94E−03 | 2.61E−03 | 0.00E+00 | | | |
| NTD | 0.00E+00 | 0.00E+00 | 0.00E+00 | | | |
| | 0.00E+00 | 5.36E−03 | 3.10E−03 | | | |
| | 4.22E−03 | 0.00E+00 | 0.00E+00 | | | |
| | 0.00E+00 | 0.00E+00 | 0.00E+00 | | | |
| | 0.00E+00 | 0.00E+00 | 0.00E+00 | | | |
| | 7.27E−02 | 3.03E−01 | 1.13E−01 | 9.41E−02 | 8.81E−01 | 2.62E+00 |
| | | 1.06E−01 | 4.53E−03 | 1.36E−01 | 9.35E−01 | 1.50E+00 |
| Zeta | 1.20E−01 | 5.31E−01 | 5.82E−03 | 2.56E−02 | 2.70E−02 | 1.25E+00 |
| (2E6) | 3.53E−01 | 1.44E−01 | 8.30E−03 | 1.91E−02 | 2.65E−02 | 1.79E−01 |
| | 3.36E−01 | 8.36E−01 | 6.26E−02 | 8.51E−03 | 3.00E−02 | 2.68E−01 |
| | 5.79E−01 | 5.09E−02 | 7.91E−03 | 8.67E−02 | 3.89E−01 | 4.29E−02 |
| | 1.25E−01 | 3.33E−01 | 1.80E−02 | 5.71E−02 | 2.06E−02 | 7.68E−01 |
| Zeta | 2.22E−02 | 2.02E−01 | 5.50E−03 | 1.34E−02 | 2.67E+00 | 2.18E+00 |
| (5E5) | 1.67E−01 | 1.66E−01 | 1.11E−01 | 5.04E−02 | 3.10E−01 | 6.50E−01 |
| | 1.64E−01 | 5.94E−02 | 0.00E+00 | 1.34E−01 | 1.51E−01 | 1.07E−01 |
| | 7.27E−02 | 3.03E−01 | 1.13E−01 | 9.41E−02 | 8.81E−01 | 2.62E+00 |
| | | 1.06E−01 | 4.53E−03 | 1.36E−01 | 9.35E−01 | 1.50E+00 |

TABLE 14-continued

| | CAR copies (per ug of DNA) | | | | | |
|---|---|---|---|---|---|---|
| | Day 1 | Day 7 | Day 14 | Day 21 | Day 28 | Day 35 |
| Dap12 | 2.52E−01 | 2.52E+00 | 2.33E−01 | 1.65E−01 | 2.35E−02 | 1.87E−01 |
| (2E6) | 8.40E−02 | 2.31E+00 | 3.45E−01 | 5.22E−01 | 7.69E−01 | 1.73E+00 |
| | 1.48E−01 | 2.76E+00 | 1.45E−01 | 2.82E−01 | 1.99E−01 | 1.75E−01 |
| | 7.20E−02 | 1.04E+00 | 5.66E−01 | 1.81E+00 | 1.55E+00 | 2.09E+00 |
| | 2.52E−01 | 1.23E+00 | 2.76E−01 | 9.82E−03 | 9.13E−02 | 3.39E+00 |
| Dap12 | 6.40E−02 | 4.32E−01 | 1.24E+00 | 3.98E−01 | 2.23E+00 | 2.08E+00 |
| (5E5) | 4.36E−01 | 3.65E−01 | 1.08E−01 | 3.20E−01 | 1.39E+01 | 2.60E+00 |
| | 9.60E−02 | 1.32E−01 | 9.15E−02 | 4.36E−01 | 6.12E+00 | 5.05E+01 |
| | 1.92E−01 | 4.69E−01 | 1.36E+00 | 3.23E−01 | 7.11E+00 | 0.00E+00 |
| | 7.60E−02 | 6.14E−01 | 5.73E−01 | 3.79E+01 | 8.67E+00 | 7.62E+00 |
| Epsilon- | 3.76E−01 | 8.87E+00 | 2.57E+01 | 1.44E+02 | 6.06E+01 | 2.12E+02 |
| CO | 8.40E−02 | 2.46E+00 | 2.63E+00 | 1.53E+02 | 2.42E+02 | 1.40E+02 |
| (2E6) | 3.08E−01 | 1.96E+00 | 3.01E+00 | 1.56E+02 | 1.34E+02 | 5.83E+01 |
| | 1.56E−01 | 3.59E+00 | 8.98E−01 | 8.78E+01 | 4.13E+02 | 2.44E+02 |
| | 2.12E−01 | 1.85E+00 | 5.95E+00 | 2.27E+02 | 4.65E+02 | 3.61E+02 |
| Epsilon- | 6.80E−02 | 1.72E−01 | 2.57E+00 | 2.20E+01 | 1.26E+02 | 4.90E+02 |
| CO | 2.84E−01 | 2.36E−01 | 4.77E−01 | 5.42E+01 | 1.42E+02 | 3.61E+02 |
| (5E5) | 1.84E−01 | | 1.71E+01 | 3.13E+02 | 1.22E+02 | 1.69E+02 |
| | 3.20E−01 | | 1.73E+00 | 9.09E+01 | 5.20E+01 | 6.21E+01 |
| | 8.00E−02 | 2.32E−01 | 1.92E+00 | 1.29E+02 | 4.08E+01 | 8.49E+01 |
| Zeta | 1.96E−01 | 9.51E+00 | 5.64E−01 | 9.47E+00 | 2.08E+01 | 5.62E+01 |
| 1xx | 1.24E−01 | 6.42E+00 | 8.06E−01 | 2.28E+00 | 6.61E+00 | 1.87E+01 |
| (2E6) | 8.00E−02 | 5.61E+00 | 7.52E−01 | 1.95E+00 | 5.59E−01 | 1.35E+00 |
| | 1.60E−01 | 3.79E−01 | 2.17E−01 | 7.47E−01 | 1.46E+00 | 2.39E+00 |
| | 5.08E−01 | 4.49E+00 | 5.98E−01 | 1.50E−01 | 1.11E+00 | 4.21E−01 |
| Zeta | 4.80E−02 | 1.08E+00 | 8.70E−01 | 4.41E+00 | 1.65E+01 | 6.01E+01 |
| 1xx | 1.48E−01 | 2.90E−01 | 1.13E+00 | 1.31E+01 | 3.47E+01 | 3.23E+01 |
| (5E5) | 1.08E−01 | 2.01E−01 | 5.33E−03 | 1.18E+01 | 2.45E+00 | 2.74E+00 |
| | 3.32E−01 | 1.17E−01 | 1.44E+00 | 1.58E+01 | 3.59E+00 | 1.77E+00 |
| | 1.04E−01 | 1.58E−01 | 2.39E−01 | 4.21E+00 | 1.19E+01 | 6.39E+00 |

Example 9

The following example describes three new second-generation CD19/CD20 bicistronic CAR constructs that utilize one of three novel CD19_CD3 Epsilon-CO mutant domains, as replacement for CD3 Zeta in a benchmark anti-CD19 control CAR. The three CD3 Epsilon mutants exhibited improved CD19 CAR expression to the membrane relative to wild type CD3 Epsilon-CO, in bicistronic constructs with CD20 CAR. All were successfully transduced and expressed in primary human T cells. These new CAR constructs were characterized through in vitro assays.

Construct Design. An anti CD19 CD3zeta second generation chimeric antigen receptor (CAR), henceforth referred to as CD19z was used to generate an anti-CD19 CD3 Epsilon-CO construct with sequence ATGGCACTTCCAGTCACCGCACTCTTGCTTC-CACTGGCCTTGTTGCTGCATGCTGCG CGGCCAGA-TATACAGATGACC-CAAACGACGTCTAGCCTCAGTGCGTCACTCGGGGA TCGGGTGACAATTAGCTGCAGGGCTAGCCAGGAT-ATTTCAAAATATCTTAACTGGT ATCAACAAAAGCCAGATGGAACCGTAAAACTGCT-CATATACCACACCAGTCGCCTG CAT-TCAGGGGTTCCGAGCCGCTTTTCTGG-GAGCGGTAGCGGAACtGATATAGCTTGA CAATAAGCAACCTCGAGCAGGAAGACAT-TGCGACGTACTTCTGTCAGCAAGGGAAC ACGCTGCCGTATACCTTCGGTGGCGGCACTAAACTG-GAAATCACGGGATCTACGTC TGGATCCG-GAAAACCTGGATCTGGTGAAGGATC-CACTAAAGGCGAAGTCAAGTTGC AAGAGTCTGGACCTGGTCTCGTGGCACCTT-CACAGTCACTCTCCGTTACCTGTACCG TATCTG-GAGTTTCACTTCCCGACTATGGCGTGTCATGGA-TACGCCAACCACCGCGAA AAGGTCTTGAATGGCTGGGCGTTATCTGGG-GATCCGAAACCACATACTACAACTCT GCGCT-CAAGTCACGGCTGACTATTATAAAGGACAATT-CAAAGAGCCAAGTGTTCCT GAAAATGAACAGCCTGCAGACT-GATGACACTGCAATATATTACTGCGCCAAGCATT ACTATTACGGCGGATCTTACGCGATGGATTAT-TGGGGCCAGGGCACCTCTGTAACA GTCAGCTCCGCGGCCGCATTGGACAAT-GAAAAATCCAATGGCACAATAATTCATGT AAAGGGCAAACACTTGTGTCCTAGCC-CACTCTTTCCTGGTCCGTCTAAACCGTTTTG GGTGCTCGTTGTGGTTGGAGGCGTCCTGGCTTGT-TACTCTCTGTTGGTGACTGTAGC CTTTATAATAT-TCTGGGTTAGAAGCAAACGAAGTAGGCTTTTACAT-TCAGACTATAT GAACATGACACCAAGACGCCCCGGCCC-CACAAGAAAACACTATCAGCCCTATGCTC CGCCTCGGGACTTCGCTGCT-TACCGAAGCAAGAACCGCAAAGCAAAGGCAAA-ACCC GTCACACGAG-GAGCGGGCGCAGGGGGACGACAACGCGGTCAGA-ATAAGGAACGCC CGCCTCCAGTACCAAATCCA-GATTATGAACCAATTCGGAAGGGACAACGC-GATCTC TACTCCGGTCTCAATCAGAGGCGAATT (SEQ ID NO: 90), which in turn was used as the parental template to engineer three daughter constructs containing mutations within the Epsilon-CO signaling domain referred to as Epsilon-CO (Δ181-185), Epsilon-CO (R183K) and Epsilon-CO (S178N.R183K). To generate the daughter constructs from the original CD3 Zeta signaling protein, nucleic acids 3316 to 3651 of the parental template were replaced with the following sequences:

```
Epsilon-CO:
                                                (SEQ ID NO: 54)
AAGAACCGCAAAGCAAAGGCAAAACCCGTCACACGAGGAGCGGGCGCAG

GGGGACGACAACGCGGTCAGAATAAGGAACGCCCGCCTCCAGTACCAAA

TCCAGATTATGAACCAATTCGGAAGGGACAACGCGATCTCTACTCCGGT

CTCAATCAGAGGCGAATT

Epsilon-CO (Δ181-185):
                                                (SEQ ID NO: 79)
AAGAACCGCAAAGCAAAGGCAAAACCCGTCACACGAGGAGCGGGCGCAG

GGGGACGACAACGCGGTCAGAATAAGGAACGCCCGCCTCCAGTACCAAA

TCCAGATTATGAACCAATTCGGAAGGGACAACGCGATCTCTACTCCGGT

CTC

Epsilon-CO (R183K):
                                                (SEQ ID NO: 80)
AAGAACCGCAAAGCAAAGGCAAAACCCGTCACACGAGGAGCGGGCGCAG

GGGGACGACAACGCGGTCAGAATAAGGAACGCCCGCCTCCAGTACCAAA

TCCAGATTATGAACCAATTCGGAAGGGACAACGCGATCTCTACTCCGGT

CTCAATCAGAAGCGAATT

Epsilon-CO (S178N.R183K)
                                                (SEQ ID NO: 81)
AAGAACCGCAAAGCAAAGGCAAAACCCGTCACACGAGGAGCGGGCGCAG

GGGGACGACAACGCGGTCAGAATAAGGAACGCCCGCCTCCAGTACCAAA

TCCAGATTATGAACCAATTCGGAAGGGACAACGCGATCTCTACAACGGT

CTCAATCAGAAGCGAATT
```

The CD19 zeta CAR construct and those containing CD3 Epsilon-CO and mutations in the CD3 Epsilon signaling domain were then assembled in a bicistronic format through the incorporation of a T2A furin cleavable region with a second generation CD20 CD3 zeta (CD20z) CAR to yield co-expression of two distinct CARs, henceforth referred to as CD19z/CD20z, CD19 Epsilon (Δ181-185)/CD20z, CD19 Epsilon (R183K)/CD20z and CD19 Epsilon (S178N.R183K)/CD20z as shown in FIG. 1.

Manufacturing of CAR T-Cell Products. Apheresis material from a healthy human donor was washed, incubated with anti-CD8 antibody-linked magnetic beads, and processed using a CliniMACS® cell separation system (Miltenyi Biotech) per the manufacturer's instructions to enrich for CD8+ T cells, which were then cryopreserved. The resulting negative fraction was washed and processed as described above using anti-CD4 antibody-linked magnetic beads to enrich for CD4+ T cells, which were then cryopreserved. Isolated CD4+ and CD8+ primary human T cells were thawed in OpTmizer CTS™ T-cell expansion basal media supplemented with 2.6% OpTmizer CTS™ T-cell expansion supplement, 2.5% CTS immune cell serum replacement, 1% penicillin/streptomycin/L-glutamine, and 305 international units/mL human interleukin (IL)-2, henceforth referred to as complete OpTmizer™ media. T cells were resuspended in complete OpTmizer™ media containing 1.66 μg/mL of anti-CD28 antibody (clone 28.2) at a density of $1.5\times10^6$ cells/mL and then seeded into PL07 bags pre-coated with 1.23 μg/mL anti-CD3 antibody (clone OKT3) to induce T-cell activation (Day 0). On Day 1 post-activation, cells were either transduced with an LVV encoding the parental bicistronic CD19z/CD20z CAR and a construct containing CD19-Epsilon-CO/CD20z CAR at a MOI of 10. A non-transduced (NTD) sample served as a negative control. T cells were washed with complete OpTmizer™ media on Day 3, normalized and were expanded for an additional 9 days (Days 3 to 9). At the harvest time point (Day 9), cells were cryopreserved for future expression assessment. At multiple time points during expansion (Days 3 to 9), cell counts were taken using a Vi-CELL® and the cell density was normalized down to $0.5\times10^6$ cells/mL by addition of complete OpTmizer™ media. At these time points, average cell viability, diameter, and cell density were recorded on the Vi-CELL®.

Expression determination of CD3 Epsilon-CO/CD20z CAR. Manufactured D9 CD19z/CD20z, CD19-Epsilon-CO/CD20z and NTD cells were thawed and rested overnight in OpTmizer™ media to assess CAR expression. Expression was assessed by using a huCD19-His recombinant peptide and an anti-Idiotype antibody (24C12) to assess individual expression of the CD19 and CD20 CARs respectively. Parallel membrane and intracellular expression for each CAR was assessed.

Manufacturing of CAR T-Cell Products. Apheresis material from a healthy human donor was washed, incubated with anti-CD8 antibody-linked magnetic beads, and processed using a CliniMACS® cell separation system (Miltenyi Biotech) per the manufacturer's instructions to enrich for CD8+ T cells, which were then cryopreserved. The resulting negative fraction was washed and processed as described above using anti-CD4 antibody-linked magnetic beads to enrich for CD4+ T cells, which were then cryopreserved. Isolated CD4+ and CD8+ primary human T cells were thawed in OpTmizer CTS™ T-cell expansion basal media supplemented with 2.6% OpTmizer CTS™ T-cell expansion supplement, 2.5% CTS immune cell serum replacement, 1% penicillin/streptomycin/L-glutamine, and 305 international units/mL human interleukin (IL)-2, henceforth referred to as complete OpTmizer™ media. T cells were resuspended in complete OpTmizer™ media containing 1.66 μg/mL of anti-CD28 antibody (clone 28.2) at a density of $1.5\times10^6$ cells/mL and then seeded into PL07 bags pre-coated with 1.23 μg/mL anti-CD3 antibody (clone OKT3) to induce T-cell activation (Day 0). On Day 1 post-activation, cells were either transduced with an LVV encoding the parental bicistronic CD19z/CD20z CAR or constructs containing CD19-Epsilon-CO (Δ181-185)/CD20z, CD19-Epsilon-CO (R183K)/CD20z, or CD19-Epsilon-CO (S178N.R183K)/CD20z at a MOI of 10. A non-transduced (NTD) sample served as a negative control. T cells were washed with complete OpTmizer™ media on Day 3, normalized and were expanded for an additional 6 days (Days 3 to 9). At the harvest time point (Day 9), cells were cryopreserved for future use. At multiple time points during expansion (Days 3 to 9), cell counts were taken using a Vi-CELL® and the cell density was normalized down to $0.5\times10^6$ cells/mL by addition of complete OpTmizer™ media. At these time points, average cell viability, diameter, and cell density were recorded on the Vi-CELL®.

CAR expression was measured by flow cytometry on days 7 and 9. T cells were stained with a panel of fluorophore-conjugated antibodies and characterized by flow cytometry to determine transduction efficiency, and CD4+/CD8+ T cell ratios. Expression assessment of each CAR arm was enabled by fluorophore-conjugated anti FMC63 (Idiotype for anti CD19 CAR, also known as CDL) and 24C12 (Idiotype for anti CD20 CAR) antibodies. Total CAR transduction efficiency was assessed using KIP-1, a custom-made antibody that binds the Whitlow linker between the heavy and light chains of the single-chain variable fragment (scFv) of the CD19 and CD20 CARs. A fixable cell viability dye allowed specific analysis of viable cells. Cells were stained by incubating with the appropriate antibody mix for 30 minutes at 4° C. followed by 2 washes with stain buffer, and subsequently fixed by incubating in paraformaldehyde in phosphate-buffered saline for 10 minutes at room temperature. All flow cytometry data was collected on a Attune NxT instrument and data was analyzed using FlowJo software.

Day 0 Co-culture Setup. T-cell products manufactured from T cells derived from healthy donor apheresis were cryopreserved on the harvest day (Day 9 of manufacture). T-cell products were subsequently thawed and rested overnight in complete R-10% media [RPMI-1640 media supplemented with 10% fetal bovine serum, penicillin streptomycin L-Glutamine, and HEPES] before initiation of co-culture with target cells. Immediately before co-culture initiation, an aliquot of each T-cell sample was incubated with a panel of antibody-fluorophores and analyzed by flow cytometry to evaluate transduction efficiency. Expression assessment of each CAR arm was enabled by fluorophore-conjugated anti FMC63 (Idiotype for anti CD19 CAR, also known as CDL) and 24C12 (Idiotype for anti CD20 CAR) antibodies. Total CAR transduction efficiency was assessed using KIP-1, a custom-made antibody that binds the Whitlow linker between the heavy and light chains of the single-chain variable fragment (scFv) of the CD19 and CD20 CARs. T cells were then labeled with CellTrace™ Violet (CTV) reagent and subsequently washed with R-10% media. A portion of the CTV-labeled samples was fixed and stored at 4° C. until day 4, when samples were analyzed in parallel with day 4 co-culture samples by flow cytometry to assess initial levels of CTV signal (CTV Max). T-cell products and luciferase-expressing target cells were plated together at different effector to target (E:T) ratios, ranging from 3:1 to 1:243, in R-10% media (Day 0 of co-culture). T-cell products were serially diluted 3-fold while the number of target cells per well was held constant at 25,000 cells. Positive target cells included Raji (CD19+/CD20+) Nalm6 MHC I/II KO (CD19+.CD20+) and ST486 (CD19+/CD20+), while Raji CD19 KO (CD19−/CD20+), Raji CD20 KO (CD19+/CD20−) and K-562 (CD19−/CD20−) served as antigen negative controls. T-cell products were cultured in the absence of any target cells (i.e., T cells alone) to assess basal levels of T-cell function in the absence of antigen stimulation. Co-cultures were incubated at 37° C. for either 1 or 4 days and functional assessments were performed as described below.

Day 1 & Day 4 Cytotoxicity. T-cell mediated cytotoxicity was measured as a function of the reduction in target luciferase signal in co-culture wells compared to the signal emitted by target cells plated alone. On Days 1 and 4 after co-culture initiation, D-luciferin substrate was added to the co-culture wells at a final concentration of 0.14 mg/mL and plates were incubated at 37° C. in the dark for 10 minutes. Luminescent signal was read immediately after in a PerkinElmer EnVision® multimode microplate reader. T cell-mediated cytotoxicity was calculated as follows:

$$\%\ \text{Cytotoxicity}=[1-\text{luciferase signal of (sample of interest/target alone control)}]*100.$$

Day 1 Cytokine Production. On Day 1 after co-culture initiation, supernatants were collected and analyzed for cytokine levels using the Meso Scale Discovery V-PLEX Pro inflammatory Panel 1 human kit according to the manufacturer's instructions. Specifically, supernatants from the co-cultures of T-cell products plated at the 1:1 E:T ratio with antigen-expressing Raji (CD19+CD20+), Raji CD19 Knockout (KO) (CD19−CD20+), Raji CD20 Knockout (KO) (CD19+CD20−), Nalm6 MHC I/II Knockout (KO) (CD19+CD20minimal), ST486 (CD19+CD20+) and K-562 (CD19-CD20−) were analyzed for levels of interferon gamma (IFN-γ), IL-2, and tumor necrosis factor alpha (TNF-α) secretion mediated by antigen engagement. Supernatants from antigen negative co-cultures (K-562) were analyzed in parallel to assess basal levels of cytokine production in the absence of antigen. All samples were diluted to be within the range of detection.

Day 4 Proliferation. On Day 4 after co-culture initiation, T-cell products plated at the 3:1 E:T ratio with target cells were harvested, stained with a panel of antibody-fluorophores to identify T cells, and analyzed by flow cytometry. The proliferative capacity of the T-cell products was determined by flow cytometric analysis of the cell division-driven dilution of CTV dye in response to antigen-expressing target cells compared with that of T-cell products that had been cultured alone (T cells alone), which was used to assess basal levels of homeostatic proliferation in the absence of stimuli. CTV-labeled T cells which were fixed on the day of co-culture setup (CTV Max) were analyzed by flow cytometry in parallel to assess the intensity of the initial CTV signal prior to cell proliferation.

Manufacturing of CAR-T Product Cells. Cell counts, cell viability, and cell diameter were tracked from Day 0 to Day 9 for each of the different experimental groups and are summarized in Table 15.

TABLE 15

Nine-Day Expansion Data of Transduced Constructs

| | Cell counts (10^6) | | | | | Viability (%) | | | | | Diameter (um) | | | | | |
|---|---|---|---|---|---|---|---|---|---|---|---|---|---|---|---|---|
| Experimental Groups | Day 1 | Day 3 | Day 6 | Day 8 | Day 9 | Day 0 | Day 3 | Day 6 | Day 8 | Day 9 | Day 0 | Day 1 | Day 3 | Day 6 | Day 8 | Day 9 |
| NTD | 8.4 | 6.65 | 55.9 | 90.5 | 110.4 | 92.4 | 85.7 | 87.8 | 92.1 | 92.8 | 7.91 | 8.73 | 10.9 | 10.0 | 9.38 | 9.29 |
| CD19z/CD20z | 8.4 | 10.1 | 85.3 | 148 | 235 | 92.4 | 81.0 | 85.0 | 93.4 | 94.8 | 7.91 | 8.73 | 11.2 | 10.0 | 9.54 | 9.49 |
| CD19 Epsilon-CO/CD20z | 8.4 | 6.0 | 50.4 | 104 | 118 | 92.4 | 83.4 | 82.8 | 89.4 | 96.7 | 7.91 | 8.73 | 11.2 | 10.5 | 9.82 | 9.93 |

Transduction Efficiency of CAR-T Product Cells at Day 9. CAR expression was measured on thawed and recovered overnight Day 9 cells via membrane and intracellular staining conditions using an huCD19-His recombinant peptide and an anti CD20 CAR idiotype (24C12) antibody to detect each CAR individually. Expression of the CD19 CAR in the CD19 Epsilon-CO/CD20z construct is increased from 14% to 53.5% under membrane permeabilization conditions. The expression of the CD20 CAR in either staining condition or construct remained similar with an increase of around 11-12% under membrane permeable conditions. Transduction percentages are summarized in Table 16.

TABLE 16

| Expression Data of Transduced Constructs | | | | |
|---|---|---|---|---|
| Experimental | % Transduction (huCD19-His+) CD19 CAR | | % Transduction (24C12+) CD20 CAR | |
| Groups | Membrane | Intracellular | Membrane | Intracellular |
| NTD | N/A | N/A | N/A | N/A |
| CD19z/CD20z | 49.23 | 44.9 | 40.1 | 52.6 |
| CD19 Epsilon-CO/CD20z | 14.4 | 53.5 | 63.4 | 74 |

Manufacturing of CAR-T Product Cells. Cell counts, cell viability, and cell diameter were tracked from Day 0 to Day 9 for each of the different experimental groups and are summarized in Table 17.

TABLE 17

| Nine-Day Expansion Data of Transduced Constructs | | | | | | | | | | | | |
|---|---|---|---|---|---|---|---|---|---|---|---|---|
| | Cell counts (10^6) | | | | Viability (%) | | | | Diameter (um) | | | |
| Experimental Groups | Day 1 | Day 3 | Day 6 | Day 9 | Day 0 | Day 3 | Day 6 | Day 9 | Day 0 | Day 3 | Day 6 | Day 9 |
| NTD | 3.9 | 4.5 | 21 | 147 | 92.2 | 77.0 | 90.8 | 94.6 | 8.9 | 10.5 | 9.6 | 10.0 |
| CD19z/CD20z | 3.9 | 5.6 | 32 | 159 | 92.2 | 70.1 | 89.3 | 95.3 | 8.9 | 10.9 | 9.9 | 10.0 |
| CD19 Epsilon-CO (Δ181-185)/CD20z | 3.9 | 4.8 | 26 | 98 | 92.2 | 71.8 | 84.1 | 88.3 | 8.9 | 10.8 | 10.6 | 10.5 |
| CD19 Epsilon-CO (R183K)/CD20z | 3.9 | 2.4 | 16 | 68 | 92.2 | 69.3 | 77.7 | 90.3 | 8.9 | 10.8 | 10.6 | 10.5 |
| CD19 Epsilon-CO (S178N. R183K)/CD20z | 3.9 | 4.6 | 24 | 119 | 92.2 | 74.2 | 84.4 | 93.6 | 8.9 | 10.6 | 10.4 | 10.3 |

Transduction Efficiency of CAR-T Product Cells. CAR expression was measured on either Day 7 and/or Day 9 of manufacturing via KIP-1 (total), CDL (CD19 CAR) and 24C12 (CD20 CAR) staining and subsequent flow cytometry analysis (Table 18). The experimental groups showed comparable total and individual CAR expression on Day 7 ranging from 85% to 98% for CD3 Epsilon-CO mutant expressing constructs and 42 to 49% for CD19z/CD20z. CAR expression remained relatively stable on Day 9 for all constructs.

TABLE 18

| Expression Data of Transduced Constructs During Manufacturing | | | | | | | | | | | | |
|---|---|---|---|---|---|---|---|---|---|---|---|---|
| | % Transduction (Kip1+) total CAR | | | | % Transduction (CDL+) CD19 CAR | | | | % Transduction (24C12+) CD20 CAR | | | |
| Experimental Groups | Day 0 | Day 3 | Day 7 | Day 9 | Day 0 | Day 3 | Day 7 | Day 9 | Day 0 | Day 3 | Day 7 | Day 9 |
| NTD | N/A | N/A | N/A | N/A | N/A | N/A | N/A | N/A | N/A | N/A | N/A | N/A |
| CD19z/CD20z | N/A | N/A | N/A | 42.2 | N/A | N/A | 44.1 | 39.0 | N/A | N/A | 47.6 | 49.0 |
| CD19 Epsilon-CO (Δ181-185)/CD20z | N/A | N/A | N/A | 90.2 | N/A | N/A | 91.7 | 85.8 | N/A | N/A | 97.6 | 94.9 |
| CD19 Epsilon-CO (R183K)/CD20z | N/A | N/A | N/A | 91.1 | N/A | N/A | 92.3 | 86.3 | N/A | N/A | 98.5 | 97.4 |
| CD19 Epsilon-CO (S178N. R183K)/CD20z | N/A | N/A | N/A | 86.3 | N/A | N/A | 88.8 | 79.5 | N/A | N/A | 97.6 | 95.9 |

Transduction Efficiency of CAR-T Product Cells on Day 0 of the Co-culture Setup. After thaw and overnight rest, a sample of each experimental group was stained to assess their percent recovery and CAR expression. Groups were then normalized down to the lowest transduction percentage per 24C12 expression (31%) by the addition of NTD cells. This was done to ensure that all samples had the same number of CAR+ samples in the downstream assays. The product cells were normalized and ranged from 22% to 32% by CD20 CAR expression (Table 19).

TABLE 19

CAR Expression of CAR-T Product Cells on Day 0 of the Co-culture Setup

| Experimental Groups | % Transduction (Kip1+) total CAR | | % Transduction (CDL+) CD19 CAR | | % Transduction (24C12+) CD20 CAR | |
|---|---|---|---|---|---|---|
| | Pre Normal-ization/ Overnight Rest | Post Normal-ization | Pre Normal-ization/ Overnight Rest | Post Normal-ization | Pre Normal-ization/ Overnight Rest | Post Normal-ization |
| NTD | N/A | N/A | N/A | N/A | N/A | N/A |
| CD19z/CD20z | 34.5 | 32.8 | 34.6 | 30.4 | 33.8 | 32.0 |
| CD19 Epsilon-CO (Δ181-185)/CD20z | 80.6 | 22.2 | 76.7 | 19.5 | 83.8 | 24.5 |
| CD19 Epsilon-CO (R183K)/CD20z | 81.4 | 19.4 | 75.2 | 15.7 | 85.6 | 22.4 |
| CD19 Epsilon-CO (S178N.R183K)/ CD20z | 72.7 | 24.3 | 67.4 | 20.0 | 76.3 | 27.3 |

Cytotoxicity. Day 1 (Table 20) and Day 4 (Table 21) readouts showed dose-dependent cytotoxicity across antigen-expressing cell line Raji, with no significant differences between constructs.

TABLE 20

Day 1 Functional Characterization Data: Percent Cytotoxicity of Raji Cell Line in Triplicate

| Experimental | E:T ratio | | | | | | |
|---|---|---|---|---|---|---|---|
| Groups | 3:1 | 1:1 | 1:3 | 1:9 | 1:27 | 1:81 | 1:243 |
| NTD | −1.8 | −2.2 | −6.4 | −0.7 | −5.9 | −0.8 | 5.1 |
| | −2 | −3.2 | 0.9 | −2.8 | −9.3 | −0.6 | −1.5 |
| | −3.8 | −8.2 | −6.3 | −5.8 | −14.8 | −4.9 | −7.1 |
| CD19z/CD20z | 26.1 | 11.2 | 1.8 | −0.5 | −7.1 | −7.5 | −5.2 |
| | 24.8 | 6.6 | 4.1 | 1.3 | −6.6 | −6.7 | 0.3 |
| | 21.2 | 2.4 | 0.5 | −3 | −10.4 | −9.1 | −7.6 |
| CD19 Epsilon-CO | 22.4 | 4.8 | 0.2 | 2.8 | −8.3 | −3 | −2.4 |
| (Δ181-185)/CD20z | 26.4 | 4.7 | 2.5 | −1.5 | −9.9 | 0.5 | −4.4 |
| | 20.8 | 7.8 | −5.5 | −2.4 | −14.3 | −11 | −10 |
| CD19 Epsilon-CO | 26.2 | 10.5 | 5.8 | −1.3 | −4.9 | −7.4 | −10.3 |
| (R183K)/CD20z | 22.4 | 7.3 | 1.1 | 1.8 | −3.9 | −5.3 | −1.8 |
| | 18.8 | 3.1 | 2.3 | −7.7 | −12 | −12.9 | −11.4 |
| CD19 Epsilon-CO | 30 | 10.7 | 4.9 | 0.4 | −7.8 | −5 | −4.4 |
| (S178N.R183K)/CD20z | 23 | 11.1 | 3.3 | 2.1 | −7.1 | −0.1 | −2 |
| | 24.7 | 3.2 | −0.4 | −5.2 | −9.3 | −4.8 | −4.3 |

TABLE 21

Day 4 Functional Characterization Data: Percent Cytotoxicity of Raji Cell Line in Triplicate

| Experimental | E:T ratio | | | | | | |
|---|---|---|---|---|---|---|---|
| Groups | 3:1 | 1:1 1 | 1:3 | 1:9 | 1:27 | 1:81 | 1:243 |
| NTD | 38.8 | 14.1 | 4.1 | −1.3 | −7.8 | −11 | −4.5 |
| | 46.3 | 16.4 | 6.4 | −5.8 | −10.9 | −8.6 | −7.9 |
| | 36.8 | 15.4 | 3.6 | −10.2 | −9.4 | −12.8 | −7 |

TABLE 21-continued

Day 4 Functional Characterization Data: Percent Cytotoxicity of Raji Cell Line in Triplicate

| Experimental | E:T ratio | | | | | | |
|---|---|---|---|---|---|---|---|
| Groups | 3:1 | 1:1 1 | 1:3 | 1:9 | 1:27 | 1:81 | 1:243 |
| CD19z/CD20z | 83.7 | 35.6 | 20 | 5.3 | −1.7 | −7.8 | −4.8 |
| | 85.2 | 29.8 | 17.1 | −1.1 | −10.8 | −9.6 | −2 |
| | 90.9 | 30.8 | 13.9 | 3 | −11.1 | −10.9 | −10.8 |
| CD19 Epsilon-CO | 81.8 | 41.1 | 23.5 | −0.8 | −7.3 | −11 | −7.9 |
| (Δ181-185)/CD20z | 84.3 | 39.7 | 16.3 | −0.4 | −13.1 | −10 | −8 |
| | 84.9 | 37.3 | 22.1 | −0.4 | −9.4 | −6.4 | −9.3 |
| CD19 Epsilon-CO | 76.8 | 40.1 | 19.5 | 1.8 | −8.4 | −10.3 | −7.3 |
| (R183K)/CD20z | 75.8 | 32.8 | 18.8 | 1.6 | −12.9 | −10.1 | −6.6 |
| | 82 | 40.6 | 19.4 | 3.7 | −16.4 | −13.7 | −6.4 |
| CD19 Epsilon-CO | 82 | 38.6 | 22.6 | 10.7 | −7.3 | −8 | −6.9 |
| (S178N.R183K)/ | 84.1 | 35.3 | 19 | 0.1 | −12.2 | −8.6 | −5.5 |
| CD20z | 87.5 | 38.5 | 20.1 | −0.1 | −8.5 | −6.3 | −1.6 |

Day 1 (Table 22) and Day 4 (Table 23) readouts showed dose-dependent cytotoxicity across antigen-expressing cell line Raji CD19 KO, with no significant differences between constructs.

TABLE 22

Day 1 Functional Characterization Data: Percent Cytotoxicity of Raji CD19 KO Cell Line in Triplicate

| Experimental | E:T ratio | | | | | | |
|---|---|---|---|---|---|---|---|
| Groups | 3:1 | 1:1 | 1:3 | 1:9 | 1:27 | 1:81 | 1:243 |
| NTD | −6.3 | −10.3 | −7.2 | −7.6 | −12.1 | −8.9 | −9.4 |
| | 4.3 | 1.2 | −1.3 | −0.7 | −6.9 | −5.1 | −3 |
| | −0.2 | −5.2 | −2.4 | −4.3 | −9.5 | −5.3 | −3 |
| CD19z/CD20z | 22.1 | 6.4 | 0 | −4.4 | −9.4 | −9.5 | −9 |
| | 26.7 | 9.5 | 4.3 | −1.1 | −8.9 | −6.5 | −7.6 |
| | 24.9 | 6.5 | 1.4 | −4.8 | −11.8 | −10.1 | −5.6 |

TABLE 22-continued

| Day 1 Functional Characterization Data: Percent Cytotoxicity of Raji CD19 KO Cell Line in Triplicate | | | | | | | |
|---|---|---|---|---|---|---|---|
| Experimental | E:T ratio | | | | | | |
| Groups | 3:1 | 1:1 | 1:3 | 1:9 | 1:27 | 1:81 | 1:243 |
| CD19 Epsilon-CO | 23.4 | 5.2 | −3.1 | −7.3 | −16.2 | −11.8 | −6 |
| (Δ181-185)/CD20z | 27.9 | 8.6 | 1 | −4.7 | −10.1 | −9.3 | −4.2 |
| | 23.7 | 7.8 | 1.6 | −12.9 | −20.1 | −10.5 | −6 |
| CD19 Epsilon-CO | 22.8 | 6.6 | −3.5 | −5.4 | −12.4 | −7.9 | −6.4 |
| (R183K)/CD20z | 27.4 | 6.9 | 2 | −7.3 | −15.8 | −8.6 | −8.9 |
| | 22.9 | 7.1 | −1 | −6.7 | −15.8 | −12.8 | −6.9 |
| CD19 Epsilon-CO | 27.3 | 9 | 1.4 | −3.8 | −12 | −10.2 | −9.5 |
| (S178N.R183K)/ | 30.1 | 12.5 | 1.6 | −3.3 | −13.8 | −9.5 | −5.2 |
| CD20z | 27.3 | 9.4 | 0.2 | −4.2 | −18.7 | −10.1 | −8.3 |

TABLE 23

| Day 4 Functional Characterization Data: Percent Cytotoxicity of Raji CD19 KO Cell Line in Triplicate | | | | | | | |
|---|---|---|---|---|---|---|---|
| | E:T ratio | | | | | | |
| Experimental Groups | 3:1 | 1:1 | 1:3 | 1:9 | 1:27 | 1:81 | 1:243 |
| NTD | 34 | 12 | −0.3 | −5.5 | −9.5 | −9.6 | −5.9 |
| | 36 | 11.5 | 0.2 | −5.3 | −10.8 | −8.7 | N/A |
| | 34.2 | 12.4 | 0.8 | −3.5 | −10.6 | −7.3 | −6.2 |
| CD19z/CD20z | 79.9 | 42.9 | 17.3 | −3.9 | −8.2 | −12.8 | −7.3 |
| | 81.7 | 44.2 | 16.5 | −2.1 | −9.1 | −11.1 | −8.1 |
| | 80.7 | 44.6 | 17.4 | −0.9 | −11.9 | −12.1 | −10.3 |
| CD19 Epsilon-CO | 80.7 | 47.6 | 21.1 | −1.4 | −10.9 | −12.3 | −7 |
| (Δ181-185)/CD20z | 79 | 47.7 | 19.7 | 2.3 | −12.7 | −13.9 | −5.5 |
| | 82.2 | 47.6 | 18.4 | −1.3 | −12.1 | −14.1 | −7.1 |
| CD19 Epsilon-CO | 78.9 | 42.3 | 17.8 | −2.4 | −14.7 | −12.2 | −5.7 |
| (R183K)/CD20z | 77.9 | 42.9 | 16.6 | −0.8 | −11.6 | −12.4 | −8.1 |
| | 79.3 | 44.9 | 15.7 | −2.9 | −15.4 | −9.5 | N/A |
| CD19 Epsilon-CO | 85.2 | 52 | 20.3 | 0.5 | −13.8 | −13.1 | −9.2 |
| (S178N.R183K)/CD20z | 84.4 | 50.2 | 21.2 | −0.2 | −11.6 | −12.2 | −8.6 |
| | 85 | 49.2 | 18.7 | −1.2 | −12.2 | −9.1 | −8.1 |

Day 1 (Table 24) and Day 4 (Table 25) readouts showed dose-dependent cytotoxicity across antigen-expressing cell line Raji CD20 KO, with no significant differences between constructs.

TABLE 24

| Day 1 Functional Characterization Data: Percent Cytotoxicity of Raji CD20KO Cell Line in Triplicate | | | | | | | |
|---|---|---|---|---|---|---|---|
| | E:T ratio | | | | | | |
| Experimental Groups | 3:1 | 1:1 | 1:3 | 1:9 | 1:27 | 1:81 | 1:243 |
| NTD | 4.2 | −6.8 | −5 | −0.7 | −5 | −4.2 | −4.8 |
| | 9.9 | −1.3 | −3.7 | −1.6 | −5.2 | −4.5 | 4.3 |
| | 6.3 | −3.3 | 0.4 | −2.8 | −5.6 | −3.1 | −1.7 |
| CD19z/CD20z | 64.7 | 34.4 | 13.1 | 2.2 | −5.7 | −8 | −2.4 |
| | 66.5 | 35.9 | 20.7 | 6.3 | −3.1 | −2.3 | 0.1 |
| | 64.4 | 32.7 | 16 | 3.8 | −7.6 | −3.1 | −1.6 |
| CD19 Epsilon-CO | 61.1 | 28.6 | 8.9 | −1.3 | −9.2 | −3.3 | 0.7 |
| (Δ181-185)/CD20z | 60.5 | 28.9 | 11 | 3.6 | −3.5 | −1.8 | 2.9 |
| | 57.9 | 31.3 | 14.4 | −4.5 | −17.8 | −5.2 | −1 |
| CD19 Epsilon-CO | 59.7 | 31.4 | 14.3 | 1.9 | −8.4 | −9.2 | −3.1 |
| (R183K)/CD20z | 61 | 31.2 | 14.3 | 3.4 | −5.9 | −1.9 | 1.9 |
| | 58.8 | 29.4 | 8.7 | −1.9 | −8.3 | −9.5 | −4.9 |
| CD19 Epsilon-CO | 58.1 | 30.5 | 14.2 | 3.5 | −7.8 | −7.1 | −1.3 |
| (S178N.R183K)/CD20z | 59.4 | 33.7 | 11.5 | 7.7 | −7 | −1.7 | −4.6 |
| | 55.6 | 33.6 | 7.4 | −0.8 | −7.3 | −6.3 | −5.8 |

TABLE 25

| Day 4 Functional Characterization Data: Percent Cytotoxicity of Raji CD20 KO Cell Line in Triplicate | | | | | | | |
|---|---|---|---|---|---|---|---|
| | E:T ratio | | | | | | |
| Experimental Groups | 3:1 | 1:1 | 1:3 | 1:9 | 1:27 | 1:81 | 1:243 |
| NTD | 47.2 | 14.5 | −2.5 | −11.5 | −15.9 | −11.1 | −5.3 |
| | 48 | 10.8 | 0.9 | −7.5 | −9.3 | −6.1 | −3.1 |
| | 45.1 | 12.3 | −2.4 | −9.2 | −9.3 | −12 | 5.2 |
| CD19z/CD20z | 98.8 | 89.6 | 51.9 | 16.8 | −5.9 | −4.3 | −4.4 |
| | 99.5 | 90 | 58.1 | 26.4 | 0.1 | 3.9 | −2.9 |
| | 99.4 | 92.3 | 67.4 | 18.9 | −7.5 | −4.7 | 6.4 |
| CD19 Epsilon-CO | 94.9 | 82.2 | 46.7 | 14.9 | −3.4 | −8 | 0.3 |
| (Δ181-185)/CD20z | 95.3 | 83.2 | 49 | 20.8 | 3 | 0.5 | 0.5 |
| | 95.4 | 89.9 | 63.3 | 21.7 | −2.8 | −5.3 | −3.4 |
| CD19 Epsilon-CO | 94.6 | 80 | 42.9 | 7.3 | −1 | −1.8 | 1.9 |
| (R183K)/CD20z | 95.5 | 83.1 | 44.1 | 13.5 | −0.9 | −3.1 | 4.9 |
| | 96.4 | 88.4 | 63 | 25.1 | 5.2 | −11.8 | −8.6 |
| CD19 Epsilon-CO | 92.3 | 81.8 | 49.6 | 14.5 | −6.9 | −0.8 | 5 |
| (S178N.R183K)/CD20z | 91.8 | 81.4 | 49.3 | 20.5 | 0.2 | −1.9 | 5.5 |
| | 93.9 | 88.9 | 68.7 | 14.2 | −2.3 | −11.7 | 10.1 |

Day 1 (Table 26) and Day 4 (Table 27) readouts showed dose-dependent cytotoxicity across antigen-expressing cell line Nalm6 MHC I/II KO, with no significant differences between constructs.

TABLE 26

| Day 1 Functional Characterization Data: Percent Cytotoxicity of Nalm6 MHC I/II KO Cell Line in Triplicate | | | | | | | |
|---|---|---|---|---|---|---|---|
| | E:T ratio | | | | | | |
| Experimental Groups | 3:1 | 1:1 | 1:3 | 1:9 | 1:27 | 1:81 | 1:243 |
| NTD | −1.2 | −5.2 | −8 | −6.1 | −11.1 | −8.3 | −9.5 |
| | 4.5 | −1.7 | −0.4 | −4.8 | −8.3 | −6 | −4.4 |
| | 3 | −2 | −1.9 | −2.2 | −6 | −6.1 | −4 |
| CD19z/CD20z | 97.3 | 82.4 | 45.3 | 16.6 | −0.8 | −4.4 | −4.6 |
| | 97.9 | 81.2 | 43.6 | 13.9 | −2.9 | −5.6 | −1.4 |
| | 96.2 | 79.7 | 43.8 | 18.8 | −2.4 | −5.9 | −4.6 |
| CD19 Epsilon-CO | 94.2 | 63.1 | 30.4 | 8.7 | −7.3 | −7.8 | −7.2 |
| (Δ181−185)/CD20z | 93.9 | 65.6 | 29.1 | 5.6 | −7.5 | −11.4 | −6.9 |
| | 91.9 | 61.9 | 28.5 | 4.7 | −8.2 | −5.2 | −3.7 |
| CD19 Epsilon-CO | 93.2 | 61.4 | 24.7 | 4.4 | −7.7 | −8.9 | −6.2 |
| (R183K)/CD20z | 93.1 | 61.2 | 24.9 | 5.1 | −10.6 | −7 | −8 |
| | 92.4 | 63 | 27.6 | 1.9 | −9.5 | −9.1 | −5.3 |
| CD19 Epsilon-CO | 95.4 | 66.7 | 29.6 | 8.2 | −7 | −8.7 | −6.9 |
| (S178N.R183K)/CD20z | 94.7 | 67.9 | 30 | 8.9 | −9.7 | −5.7 | −6 |
| | 94.8 | 66.7 | 31.4 | 4.2 | −6 | −6.4 | −6.7 |

TABLE 27

| Day 4 Functional Characterization Data: Percent Cytotoxicity of Nalm6 MHC I/II KO Cell Line in Triplicate | | | | | | | |
|---|---|---|---|---|---|---|---|
| | E:T ratio | | | | | | |
| Experimental Groups | 3:1 | 1:1 | 1:3 | 1:9 | 1:27 | 1:81 | 1:243 |
| NTD | 6 | −3.3 | N/A | −15 | 0 | −18.5 | N/A |
| | 4.8 | −5.3 | N/A | −16.1 | −4.6 | −15 | N/A |
| | 4.8 | −2.3 | N/A | −15.4 | 0.9 | −19.4 | N/A |
| CD19z/CD20z | 100 | 100 | 98.4 | 83.9 | 47.9 | 13.8 | N/A |
| | 100 | 100 | 98.6 | 84.6 | 52.3 | 14.9 | N/A |
| | 100 | 100 | 98.8 | 87.9 | 52.1 | 20.6 | N/A |
| CD19 Epsilon-CO | 100 | 99.3 | 80.5 | 20.5 | −6.3 | −19.1 | N/A |
| (Δ181-185)/CD20z | 100 | 99.6 | 77 | 20.7 | −12 | −20.1 | N/A |
| | 100 | 99.8 | 81.8 | 16 | −3.2 | −20.6 | N/A |
| CD19 Epsilon-CO | 100 | 99.3 | 75.4 | 12 | −10.6 | −16 | N/A |
| (R183K)/CD20z | 100 | 98.9 | 75.8 | 10.4 | −11.5 | −17 | N/A |
| | 100 | 99.8 | 80.5 | 9.8 | −9.6 | −18.7 | N/A |

TABLE 27-continued

| Day 4 Functional Characterization Data: Percent Cytotoxicity of Nalm6 MHC I/II KO Cell Line in Triplicate | | | | | | | |
|---|---|---|---|---|---|---|---|
| | E:T ratio | | | | | | |
| Experimental Groups | 3:1 | 1:1 | 1:3 | 1:9 | 1:27 | 1:81 | 1:243 |
| CD19 Epsilon-CO | 100 | 100 | 86.1 | 24 | −4.6 | −17.5 | N/A |
| (S178N.R183K)/CD20z | 100 | 99.9 | 82.8 | 22.9 | −6.2 | −17.1 | N/A |
| | 100 | 100 | 90.8 | 24.8 | −10.2 | −18.7 | N/A |

Day 1 (Table 26) and Day 4 (Table 27) readouts showed dose-dependent cytotoxicity across antigen-expressing cell line ST486, with no significant differences between constructs.

TABLE 26

| Day 1 Functional Characterization Data: Percent Cytotoxicity of ST486 Cell Line in Triplicate | | | | | | | |
|---|---|---|---|---|---|---|---|
| | E:T ratio | | | | | | |
| Experimental Groups | 3:1 | 1:1 | 1:3 | 1:9 | 1:27 | 1:81 | 1:243 |
| NTD | 3.6 | −5.7 | −7.9 | −10.3 | −12.8 | −10.3 | 7.3 |
| | 10.3 | 0.4 | −1.2 | −3.2 | −7.2 | −4.8 | −4.7 |
| | 0.4 | −3.1 | −1.5 | −0.6 | −3.1 | −2.7 | 0.4 |
| CD19z/CD20z | 98.3 | 86.2 | 45.6 | 15.4 | −7.7 | −9.2 | −8.2 |
| | 98.2 | 86.3 | 53.7 | 18.9 | 0.8 | −5 | −4.4 |
| | 97.3 | 85.2 | 51 | 21.7 | 3.4 | −1.4 | 0.1 |
| CD19 Epsilon-CO | 98.1 | 87.2 | 51.6 | 12.6 | −7.4 | −9.7 | −7.7 |
| (Δ181-185)/CD20z | 98.5 | 87.5 | 53.2 | 18.1 | −7.8 | −7.5 | −4.2 |
| | 98 | 87.8 | 49.2 | 16.7 | −0.8 | 0.5 | −1.9 |
| CD19 Epsilon-CO | 98.1 | 86.6 | 48 | 11.1 | −8.4 | −7.8 | −5.3 |
| (R183K)/CD20z | 98.1 | 86.2 | 50.3 | 15.5 | −8.1 | −5.7 | −8 |
| | 97.5 | 83.8 | 46.8 | 17.4 | −1.4 | −3.7 | −1.7 |
| CD19 Epsilon-CO | 98.5 | 89.2 | 55.4 | 15.6 | −4.3 | −8.2 | −7.6 |
| (S178N.R183K)/CD20z | 98.8 | 90 | 55.3 | 19.8 | −4.7 | −4.4 | −4.7 |
| | 98.4 | 89.7 | 54.7 | 21.5 | −0.6 | 2.5 | −2.5 |

TABLE 27

| Day 4 Functional Characterization Data: Percent Cytotoxicity of ST486 Cell Line in Triplicate | | | | | | | |
|---|---|---|---|---|---|---|---|
| | E:T ratio | | | | | | |
| Experimental Groups | 3:1 | 1:1 | 1:3 | 1:9 | 1:27 | 1:81 | 1:243 |
| NTD | 59.2 | 8.5 | −8.1 | −12.5 | 0.3 | −12.3 | 30.4 |
| | 44.5 | 4.5 | −6.2 | −9.5 | 1.8 | −9.7 | 25.5 |
| | 46.5 | −3.7 | −13.4 | −17.9 | 9.6 | −23.9 | 16.2 |
| CD19z/CD20z | 100 | 99.9 | 99.2 | 88.1 | 53 | 24.4 | 22.9 |
| | 99.9 | 100 | 98.1 | 83.6 | 49.6 | 20.7 | 17.8 |
| | 99.9 | 99.9 | 99.6 | 84.3 | 46.2 | 7.8 | 10.7 |
| CD19 Epsilon-CO | 99.9 | 100 | 98.5 | 80.5 | 39 | 0.9 | 8.4 |
| (Δ181-185)/CD20z | 99.9 | 99.9 | 99.6 | 82.5 | 34.9 | 7.4 | 14.7 |
| | 99.8 | 99.9 | 99.8 | 80.4 | 27.6 | 1.1 | 1.9 |
| CD19 Epsilon-CO | 100 | 100 | 98 | 76.9 | 29.4 | 2.3 | 8.9 |
| (R183K)/CD20z | 99.9 | 99.9 | 98.4 | 77.2 | 35.5 | 4.6 | 17 |
| | 99.8 | 99.9 | 99.3 | 71.1 | 27.6 | −0.4 | 1.1 |
| CD19 Epsilon-CO | 99.9 | 100 | 99.4 | 86.3 | 45 | 13 | 4.6 |
| (S178N.R183K)/CD20z | 99.9 | 99.9 | 99.2 | 85.5 | 50.3 | 8.4 | 14.2 |
| | 99.8 | 99.9 | 99.9 | 89.4 | 39.5 | 3.9 | 22.3 |

Day 1 (Table 28) and Day 4 (Table 29) readouts showed dose-dependent cytotoxicity across antigen-expressing cell line K-562, with no significant differences between constructs.

TABLE 28

| Day 1 Functional Characterization Data: Percent Cytotoxicity of K-562 Cell Line in Triplicate | | | | | | | |
|---|---|---|---|---|---|---|---|
| | E:T ratio | | | | | | |
| Experimental Groups | 3:1 | 1:1 | 1:3 | 1:9 | 1:27 | 1:81 | 1:243 |
| NTD | −3.9 | −9.2 | −6.8 | −4.5 | −8.2 | −11.4 | −5.7 |
| | 5.1 | −8.3 | 1.5 | −0.3 | 0 | 0.3 | 0.8 |
| | −1.2 | −4.8 | −1 | −2.3 | −6.8 | −6.8 | −1.6 |
| CD19z/CD20z | −8.1 | −6.9 | −3.7 | −3.5 | −12.2 | −9.7 | −3.7 |
| | −3.4 | −7.7 | 2.5 | −3.3 | −7 | −2.4 | 2.2 |
| | −1.8 | −8.3 | −4.9 | −4.3 | −8.5 | −2.3 | −2.6 |
| CD19 Epsilon-CO | −0.1 | −8.2 | −2.1 | −10.8 | −15.2 | −9.5 | −2.1 |
| (Δ181-185)/CD20z | 3.5 | −10.5 | −5.6 | −7.8 | −14.1 | −12.3 | −2.6 |
| | 6.5 | −7.7 | −8.9 | −12.9 | −18.9 | −10.2 | 1.2 |
| CD19 Epsilon-CO | 4.8 | −4.9 | −1 | −11.6 | −13.4 | −9.2 | −3 |
| (R183K)/CD20z | 5.4 | −4.7 | −1 | −4.2 | −15.3 | −7.6 | 2.2 |
| | 7.5 | −6.6 | −11.2 | −7.2 | −15.9 | −11.2 | 2.6 |
| CD19 Epsilon-CO | −1.9 | −8.3 | −5.5 | −10.3 | −13 | −8.5 | −4 |
| (S178N.R183K)/CD20z | 5.3 | −6.1 | −2 | −8.8 | −10.6 | −9.8 | 2.4 |
| | 6.6 | −3.5 | −5.9 | −13.2 | −18.2 | −5.9 | 2.1 |

TABLE 29

| Day 4 Functional Characterization Data: Percent Cytotoxicity of K-562 Cell Line in Triplicate | | | | | | | |
|---|---|---|---|---|---|---|---|
| | E:T ratio | | | | | | |
| Experimental Groups | 3:1 | 1:1 | 1:3 | 1:9 | 1:27 | 1:81 | 1:243 |
| NTD | 6.3 | −9.7 | −14.1 | −24.7 | −25.6 | −25.6 | 17.5 |
| | 2.2 | −0.1 | −17.4 | −19.4 | −20.4 | −21.4 | N/A |
| | 6.4 | −3.8 | −14.5 | −15.6 | −23.2 | −18.8 | −9.5 |
| CD19z/CD20z | −8.1 | −6.9 | −3.7 | −3.5 | −12.2 | −9.7 | −3.7 |
| | −3.4 | −7.7 | 2.5 | −3.3 | −7 | −2.4 | 2.2 |
| | −1.8 | −8.3 | −4.9 | −4.3 | −8.5 | −2.3 | −2.6 |
| CD19 Epsilon-CO | −0.1 | −8.2 | −2.1 | −10.8 | −15.2 | −9.5 | −2.1 |
| (Δ181-185)/CD20z | 3.5 | −10.5 | −5.6 | −7.8 | −14.1 | −12.3 | −2.6 |
| | 6.5 | −7.7 | −8.9 | −12.9 | −18.9 | −10.2 | 1.2 |
| CD19 Epsilon-CO | 4.8 | −4.9 | −1 | −11.6 | −13.4 | −9.2 | −3 |
| (R183K)/CD20z | 5.4 | −4.7 | −1 | −4.2 | −15.3 | −7.6 | 2.2 |
| | 7.5 | −6.6 | −11.2 | −7.2 | −15.9 | −11.2 | 2.6 |
| CD19 Epsilon-CO | −1.9 | −8.3 | −5.5 | −10.3 | −13 | −8.5 | −4 |
| (S178N.R183K)/CD20z | 5.3 | −6.1 | −2 | −8.8 | −10.6 | −9.8 | 2.4 |
| | 6.6 | −3.5 | −5.9 | −13.2 | −18.2 | −5.9 | 2.1 |

Day 1 Cytokine Production. Supernatant was collected from the 1:1 E:T ratio and analyzed via MSD for IFN-γ, IL-2, and TNF-α secretion. Analysis showed that all constructs (Tables 30 and 31) secreted cytokines when co-cultured with the antigen-expressing cell lines Raji, Raji CD19 KO, Raji CD20 KO, Nalm6 MHC I/II KO and ST486. CD3 Epsilon-CO mutant constructs all secreted similar levels of cytokines across all cell lines. Co-culture with the Raji and Nalm6 cell lines elicited higher levels of cytokines when compared to the levels secreted with the ST486 cell line, however, the overall hierarchical pattern of the constructs was consistent across all cell lines. On the other hand, the NTD control group did not secrete any measurable or significant levels of cytokine when cultured alone or with antigen-expressing cell lines. Cytokine measurements for INFγ<1.76 μg/mL, IL-2<0.890 μg/mL and TNFα<0.690 μg/mL were below the limit of quantitation for the assay (<LOQ).

TABLE 30

Day 1 Functional Characterization: Cytokine Analysis of IFN-γ, TNF-α, IL-2 in Raji, Raji CD19 KO and Raji CD20 KO Cell Lines via MSD

| Experimental Groups | Cytokine | Raji Avg pg/mL | % CV | Raji CD19 KO Avg pg/mL | % CV | Raji CD20 KO Avg pg/mL | % CV |
|---|---|---|---|---|---|---|---|
| NTD | IFN-γ | 152 | 10 | 113.7 | 14 | 136.3 | 3 |
| | IL-2 | 180.3 | 17 | 17.2 | 18 | 17.16 | 27 |
| | TNF-α | 6.4 | 41 | <LOQ | <LOQ | <LOQ | <LOQ |
| CD19z/CD20z | IFN-γ | 82649.3 | 10 | 43944.5 | 4 | 37889.3 | 11 |
| | IL-2 | 4497 | 9 | 1162.23 | 7 | 1867.5 | 3 |
| | TNF-α | 845.8 | 10 | 324.8 | 2 | 347.4 | 8 |
| CD19 Epsilon-CO | IFN-γ | 66484.9 | 15 | 42188.2 | 7 | 28774.2 | 24 |
| (Δ181-185)/CD20z | IL-2 | 3146.7 | 6 | 1282.2 | 6 | 1397.4 | 16 |
| | TNF-α | 32.6 | 5 | 56.8 | 18 | 9.8 | 4 |
| CD19 Epsilon-CO | IFN-γ | 61523.6 | 2 | 42984.9 | 3 | 28355.8 | 3 |
| (R183K)/CD20z | IL-2 | 3139 | 8 | 1503.8 | 8 | 1249.9 | 3 |
| | TNF-α | 18.9 | 3 | 16.0 | 5.0 | 19.2 | 8 |
| CD19 Epsilon-CO | IFN-γ | 55819.4 | 1 | 43493.9 | 6 | 32833.1 | 20 |
| (S178N.R183K)/CD20z | IL-2 | 2184.5 | 2 | 1226.3 | 6 | 971.3 | 5 |
| | TNF-α | 487.6 | 6 | 294.2 | 1 | 247.7 | 1 |

TABLE 31

Day 1 Functional Characterization: Cytokine Analysis of IFN-γ, TNF-α, IL-2 in Nalm6 MHC I/II KO, ST486 and K-562 Cell Lines via MSD

| Experimental Groups | Cytokine | Nalm6 MHC I/II KO Avg pg/mL | % CV | ST486 Avg pg/mL | % CV | K562 Avg pg/mL | % CV |
|---|---|---|---|---|---|---|---|
| NTD | IFN-γ | 17.7 | 64 | 176.7 | 16 | 146.7 | 27 |
| | IL-2 | <LOQ | <LOQ | 29.58 | 41 | <LOQ | <LOQ |
| | TNF-α | 3.8 | 14 | <LOQ | <LOQ | <LOQ | <LOQ |
| CD19z/CD20z | IFN-γ | 62212.8 | 4 | 62767.7 | 4 | 12.8 | 12 |
| | IL-2 | 2962 | 6 | 2939.7 | 6 | <LOQ | <LOQ |
| | TNF-α | 679.4 | 8 | 627.2 | 2 | <LOQ | <LOQ |
| CD19 Epsilon-CO | IFN-γ | 48370.7 | 6 | 48368.5 | 6 | 177.6 | 67 |
| (Δ181-185)/CD20z | IL-2 | 1737.9 | 5 | 1485.9 | 10 | <LOQ | <LOQ |
| | TNF-α | 56.8 | 14 | 12.6 | 4 | <LOQ | <LOQ |
| CD19 Epsilon-CO | IFN-γ | 48617.6 | 17 | 47661.9 | 6 | 177.6 | 67 |
| (R183K)/CD20z | IL-2 | 1387.2 | 6 | 1435.6 | 11 | <LOQ | <LOQ |
| | TNF-α | 48.1 | 16 | 32.2 | 10 | <LOQ | <LOQ |
| CD19 Epsilon-CO | IFN-γ | 42380.4 | 12 | 45879.7 | 3 | 159.8 | 64 |
| (S178N.R183K)/CD20z | IL-2 | 1360 | 16 | 1175.9 | 5 | <LOQ | <LOQ |
| | TNF-α | 353.5 | 7 | 329.5 | 4 | <LOQ | <LOQ |

Day 4 Proliferation. Dilution of the Cell Trace™ Violet (CTV) label was used to assess proliferation. As the product CAR-T cells divide, the dye is diluted with each division and thus, a lower CTV MFI when compared to the Day 0 cells, is indicative of proliferation. Minimal homeostatic or antigen-independent proliferation is seen in the NTD control group when cultured alone or with antigen-expressing cell lines. All constructs showed comparable MFI levels when cultured against the, Raji, Raji CD19 KO, Raji CD20 KO, Nalm6 MHC I/II KO, ST486 and K-562 cell line. A full summary is found in Table 32.

TABLE 32

Day 4 Functional Characterization Data: Proliferation Analysis Nalm6 MHC I/II KO, Raji, Raji CD19 KO, Raji CD20 KO, ST486 and K562 Cell Lines via Cell Trace™ Violet (CTV) Staining.

| Experimental Groups | Raji | Raji CD19 KO | Raji CD20 KO | Nalm6 MHC I/II KO | ST486 | K562 | T cells alone |
|---|---|---|---|---|---|---|---|
| NTD | 16924 | 17079 | 18037 | 18326 | 17914 | 17752 | 27568 |
| CD19z/CD20z | 12518 | 12155 | 11410 | 11670 | 10262 | 20396 | 31696 |
| CD19 Epsilon-CO (Δ181-185)/CD20z | 11910 | 11384 | 10193 | 11005 | 12433 | 19049 | 26396 |
| CD19 Epsilon-CO (R183K)/CD20z | 11723 | 10735 | 10332 | 11410 | 12489 | 17996 | 23440 |

TABLE 32-continued

| Day 4 Functional Characterization Data: Proliferation Analysis Nalm6 MHC I/II KO, Raji, Raji CD19 KO, Raji CD20 KO, ST486 and K562 Cell Lines via Cell Trace™ Violet (CTV) Staining. | | | | | | | |
|---|---|---|---|---|---|---|---|
| Experimental Groups | Raji | Raji CD19 KO | Raji CD20 KO | Nalm6 MHC I/II KO | ST486 | K562 | T cells alone |
| CD19 Epsilon-CO (S178N.R183K)/CD20z | 10425 | 9722 | 8689 | 8289 | 10472 | 18578 | 25045 |

Values reported are the Median of the CTV distribution curves.

Example 10

The following example describes anti-CD19 CARs utilizing Epsilon-CO (Δ181-185), Epsilon-CO (R183K) and Epsilon-CO (S178N.R183K) signaling domains which demonstrate significantly improved tumor control in vivo compared to a benchmark anti-CD19 control CAR with a CD3 Zeta signaling domain. These new second-generation CAR constructs with mutations within the CD3 Epsilon signaling domain were also compared to an original CD3 Epsilon-CO construct. All were successfully transduced and expressed in primary human T cells. In vivo studies demonstrated superior tumor control, CAR expansion and persistence by the Epsilon-CO and Epsilon-CO mutant constructs when compared to the CD3 Zeta benchmark controls, demonstrating that anti-CD19 CARs utilizing the CD3 Epsilon signaling domain have enhanced efficacy in vivo.

Figure 2:
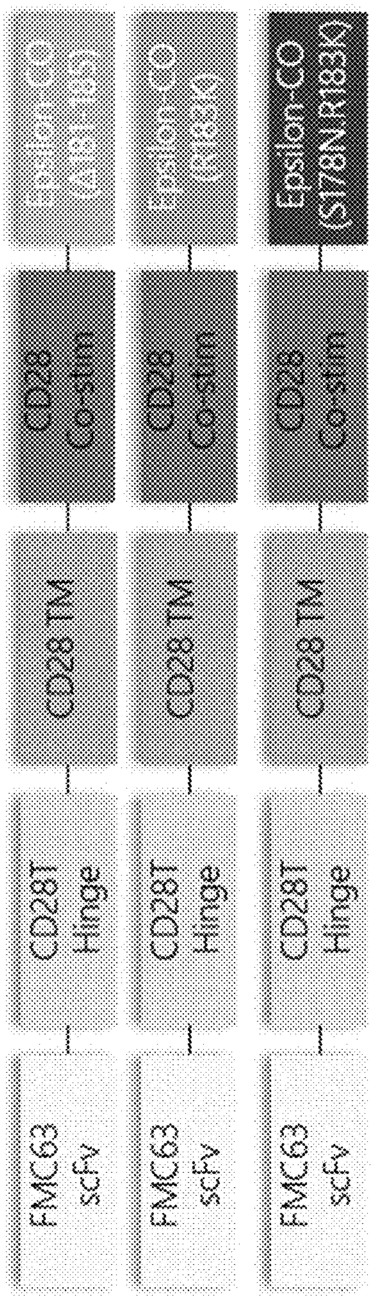
FIG. 2 illustrates embodiments of an anti-CD19 CAR with a signaling domain selected from the group consisting of codon optimized Epsilon (Δ181-185), codon optimized Epsilon (R183K), and codon optimized Epsilon (S178N.R183K).

Construct Design. An anti-CD19 second generation chimeric antigen receptor (CAR), henceforth referred to as Zeta, with sequence
ATGGCTCTGCCTGTGACCGCTCTGCTGTTGCCCC-
TTGCTTTACTCCTGCACGCCGCAA GACCCGACATC-
CAAATGACCCAAACCACCTCCTCCCT-
GAGCGCCTCCCTTGGAGAC CGAGTTAC-
CATCTCCTGCCGAGCTTCTCAAGACATCTCCAAG-
TACTTGAATTGGTAT CAACAAAAGCCCGACG-
GAACCGTGAAGCTGCTGATCTACCACA-
CATCCCGGCTGCA CTCTGGCGTTCCCTCAAGAT-
TCTCCGGCTCTGGAAGCGGAACCGACTACTCCCT-
GAC CATCTCCAACCTGGAGCAAGAGGACATCGC-
TACCTACTTCTGCCAACAAGGCAACA CCCTGCCT-
TACACCTTCGGAGGAGGAACCAAGCTGGAGAT-
CACCGGAAGCACAAGC
GGATCTGGCAAGCCTGGAAGCGGAGAGG-
GAAGCACCAAGGGAGAGGTGAAGCTGC
AAGAGAGCGGACCTGGATTGGTGGCCCCCT-
CACAATCCCTGAGCGTTACATGCACT
GTGAGCGGCGTGTCCCTTCCTGAC-
TACGGCGTTTCCTGGATCCGCCAACCTCCAAGA
AAGGGACTGGAGTGGCTGGGAGTGATCTGGG-
GAAGCGAGACCACCTACTACAACTC CGCCCT-
GAAGAGCCGACTGACCATCATCAAGGACAACTC-
CAAGAGCCAAGTGTTCC
TGAAGATGAACTCTCTCCAAACCGACGACACCGC-
TATCTACTACTGCGCTAAGCACT ACTACTACGGAG-
GAAGCTACGCTATGGAC-
TACTGGGGACAAGGCACCTCTGTGACC
GTCTCCTCTGCCGCCGCTCTGGACAACGAGAAG-
AGCAACGGAACCATCATCCACGT GAAGG-
GAAAGCACCTGTGCCCCTCTCCTCTGTTCCCTGG-
ACCCTCCAAGCCTTTCTG
GGTGCTCGTGGTGGTGGGAGGAGTGCTGGCTTGC-
TACTCCCTGCTTGTGACCGTGGC TTTCAT-
CATCTTCTGGGTTAGAAGCAAGAGAAGCA-
GACTGCTGCACAGCGACTACA TGAA-
CATGACCCCTAGAAGGCCCGGACC-
TACCAGAAAGCACTACCAGCCTTACGCT
CCTCCTAGAGACTTCGCTGCTTACAGAAGCAGGGT-
GAAGTTCTCAAGAAGCGCTGA CGCTCCTGCTTAC-
CAACAAGGCCAAAACCAACTGTACAACGAGCT-
GAACCTGGGAA
GAAGAGAG-
GAATACGACGTCCTGGACAAGAGAAGAGGAAGA-
GACCCTGAGATGGG AGGAAAGC-
CAAGAAGAAAGAACCCTCAAGAGGGCCTGTACA-
ACGAGCTGCAAAAG GACAAGATGGCTGAGGCT-
TACTCCGAGATCGGAATGAAGG-
GAGAGAGAAGAAGAG
GAAAGGGACACGACGGACTGTACCAAGGCCT-
GAGCACCGCTACCAAGGACACCTA
CGACGCTCTGCACATGCAAGCCCTGCCTCCTAGG
(SEQ ID NO: 91) was used as the parental template to engineer and synthesize daughter constructs. Constructs containing mutations within the Epsilon-CO signaling domain were also made and are referred to as Epsilon-CO (Δ181-185), Epsilon-CO (R183K) and Epsilon-CO (S178N.R183K). To generate the daughter constructs, the CD3 Zeta signaling protein starting at nucleic acids 3316 to 3651 of the parental template were replaced with the following sequences (see FIG. 2):

```
Epsilon-CO (Δ181-185):
                                          (SEQ ID NO: 79)
AAGAACCGCAAAGCAAAGGCAAAACCCGTCACACGAGGAGCGGGCGCAG

GGGGACGACAACGCGGTCAGAATAAGGAACGCCCGCCTCCAGTACCAAA

TCCAGATTATGAACCAATTCGGAAGGGACAACGCGATCTCTACTCCGGT

CTC

Epsilon-CO (R183K):
                                          (SEQ ID NO: 80)
AAGAACCGCAAAGCAAAGGCAAAACCCGTCACACGAGGAGCGGGCGCAG

GGGGACGACAACGCGGTCAGAATAAGGAACGCCCGCCTCCAGTACCAAA

TCCAGATTATGAACCAATTCGGAAGGGACAACGCGATCTCTACTCCGGT

CTCAATCAGAAGCGAATT

Epsilon-CO (S178N.R183K)
                                          (SEQ ID NO: 81)
AAGAACCGCAAAGCAAAGGCAAAACCCGTCACACGAGGAGCGGGCGCAG

GGGGACGACAACGCGGTCAGAATAAGGAACGCCCGCCTCCAGTACCAAA

TCCAGATTATGAACCAATTCGGAAGGGACAACGCGATCTCTACAACGGT

CTCAATCAGAAGCGAATT
```

Manufacturing of CAR T-Cell Products. Apheresis material from a healthy human donor was washed, incubated with anti-CD8 antibody-linked magnetic beads and processed using a CliniMACS® cell separation system (Miltenyi Biotech) per the manufacturer's instructions to enrich for CD8+ T cells, which were then cryopreserved. The resulting negative fraction was washed and processed as described above using anti-CD4 antibody-linked magnetic beads to enrich for CD4+ T cells, which were then cryopreserved. Isolated CD4+ and CD8+ primary human T cells were thawed in OpTmizer CTS™ T-cell expansion basal media supplemented with 2.6% OpTmizer™ CTS T-cell expansion supplement, 2.5% CTS immune cell serum replacement, 1% penicillin/streptomycin/L-glutamine, and 305 international units/mL human interleukin (IL)-2, henceforth referred to as complete OpTmizer™ media. T cells were resuspended in complete OpTmizer™ media containing 1.66 μg/mL of anti-CD28 antibody (clone 28.2) at a density of $1.0\times10^6$ cells/mL and then seeded into T-25 flasks pre-coated with 1.23 μg/mL anti-CD3 antibody (clone OKT3) to induce T-cell activation (Day 0). On Day 1 post-activation, cells were either transduced with an LVV encoding the parental anti-CD19 CAR or the daughter constructs Epsilon-CO, Epsilon-CO (Δ181-185), Epsilon-CO (R183K), or Epsilon-CO (S178N.R183K) at a MOI of 5 or 10. A non-transduced (NTD) sample served as a negative control. T cells were washed with complete OpTmizer™ media on Day 3, normalized and were expanded for an additional 6 days (Days 3 to 9). At the harvest time point (Day 9), cells were cryopreserved for future use. At multiple time points during expansion (Days 3 to 9), cell counts were taken using a Vi-CELL® and the cell density was normalized down to $0.5\times10^6$ cells/mL by addition of complete OpTmizer™ media. At these time points, average cell viability, diameter, and cell density were recorded on the Vi-CELL®.

CAR expression was measured by flow cytometry on days 6 and 9. T cells were stained with a panel of fluorophore-conjugated antibodies and characterized by flow cytometry to determine transduction efficiency, and CD4+/CD8+ T cell ratios. Assessment of CAR expression (anti-CD19 CAR) was enabled by fluorophore-conjugated KIP-1. A fixable cell viability dye allowed specific analysis of viable cells. Cells were stained by incubating with the appropriate antibody mix for 30 minutes at 4° C. followed by 2 washes with stain buffer, and subsequently fixed by incubating in paraformaldehyde in phosphate-buffered saline for 10 minutes at room temperature. All flow cytometry data was collected on a Fortessa-X20 instrument and data was analyzed using FlowJo software.

Day 0 Co-culture Setup. T-cell products manufactured from T cells derived from healthy donor apheresis were cryopreserved on the harvest day (Day 9 of manufacture). T-cell products were subsequently thawed and rested overnight in complete R-10% media [RPMI-1640 media supplemented with 10% fetal bovine serum, penicillin streptomycin L-Glutamine, and HEPES] before initiation of co-culture with target cells. Immediately before co-culture initiation, an aliquot of each T-cell sample was incubated with a panel of antibody-fluorophores and analyzed by flow cytometry to evaluate transduction efficiency. Total transduction efficiency was assessed using KIP-1, a custom-made antibody that binds the Whitlow linker between the heavy and light chains of the single-chain variable fragment (scFv). T cells were then labeled with CellTrace™ Violet (CTV) reagent and subsequently washed with R-10% media. A portion of the CTV-labeled samples was fixed and stored at 4° C. until day 4, when samples were analyzed in parallel with day 4 co-culture samples by flow cytometry to assess initial levels of CTV signal (CTV Max). T-cell products and luciferase-expressing target cells were plated together at different effector to target (E:T) ratios, ranging from 3:1 to 1:243, in R-10% media (Day 0 of co-culture). T-cell products were serially diluted 3-fold while the number of target cells per well was held constant at 25,000 cells. Positive target cells included Raji (CD19+), Nalm6 (CD19+), ST486 (CD19+), and Raji CD19 KO (CD19−) or K562 (CD19−). As a control, T-cell products were cultured in the absence of any target cells (i.e., T cells alone) to assess basal levels of T-cell function in the absence of antigen stimulation. Co-cultures were incubated at 37° C. for either 1 or 4 days and functional assessments were performed as described below.

Day 1 & Day 4 Cytotoxicity. T-cell mediated cytotoxicity was measured as a function of the reduction in target luciferase signal in co-culture wells compared to the signal emitted by target cells plated alone. On Days 1 and 4 after co-culture initiation, D-luciferin substrate was added to the co-culture wells at a final concentration of 0.14 mg/mL and plates were incubated at 37° C. in the dark for 10 minutes. Luminescent signal was read immediately after in a PerkinElmer EnVision® multimode microplate reader. T cell-mediated cytotoxicity was calculated as follows:

% Cytotoxicity=[1−luciferase signal of (sample of interest/target alone control)]*100.

Day 1 Cytokine Production. On Day 1 after co-culture initiation, supernatants were collected and analyzed for cytokine levels using the Meso Scale Discovery V-PLEX Pro inflammatory Panel 1 human kit according to the manufacturer's instructions. Specifically, supernatants from the co-cultures of T-cell products plated at the 1:1 E:T ratio with antigen-expressing Raji, Nalm6 and ST486 were analyzed for levels of interferon gamma (IFN-γ), IL-2, and tumor necrosis factor alpha (TNF-α) secretion mediated by antigen engagement. Supernatants from T cells cultured in the absence of target cells (T cells alone) or in antigen negative co-cultures (Raji CD19 KO or K562) were analyzed in parallel to assess basal levels of cytokine production in the absence of antigen. All samples were diluted to be within the range of detection.

Day 4 Proliferation. On Day 4 after co-culture initiation, T-cell products plated at the 1:1 E:T ratio with target cells were harvested, stained with a panel of antibody-fluorophores to identify T cells, and analyzed by flow cytometry. The proliferative capacity of the T-cell products was determined by flow cytometric analysis of the cell division-driven dilution of CTV dye in response to antigen-expressing target cells compared with that of T-cell products that had been cultured alone (T cells alone), which was used to assess basal levels of homeostatic proliferation in the absence of stimuli. CTV-labeled T cells which were fixed on the day of co-culture setup (CTV Max) were analyzed by flow cytometry in parallel to assess the intensity of the initial CTV signal prior to cell proliferation.

Serial Killing. Product CAR-T cells were normalized for CAR expression on Day 0 similar to the co-culture setup described above. T cells were co-cultured with the antigen-expressing Nalm6 target line at a 1:1 E:T ratio in R-10% media. Every 3-4 days, the cultures were challenged with an additional 25,000 Nalm6 (CD19+) target cells in new R-10% media. Cytotoxicity (assessed similar to cytotoxicity described above) and CD3+ T cell counts (analyzed on the Attune cytometer) were measured every round that more target cells were added. For rounds 9-13, total well volume was split by 1/3 before Nalm6 target cells were added.

Manufacturing of CAR-T Product Cells. Cell counts, cell viability, and cell diameter were tracked from Day 0 to Day 9 for each of the different experimental groups and are summarized in Tables 33 and 34.

TABLE 33

Nine-Day Expansion Data of Transduced Constructs - Donor 1

| Experimental | Cell counts (10 ^ 6) | | | | Viability (%) | | | | Diameter (uM) | | | |
|---|---|---|---|---|---|---|---|---|---|---|---|---|
| Groups | Day 0 | Day 3 | Day 7 | Day 9 | Day 0 | Day 3 | Day 7 | Day 9 | Day 0 | Day 3 | Day 7 | Day 9 |
| NTD | 4.0 | 5.1 | 47.1 | 106.0 | 88.1 | 83 | 75.8 | 83.6 | 8.0 | 11.4 | 9.9 | 10.1 |
| Zeta-CO | 4.0 | 4.9 | 44.2 | 118.0 | 88.1 | 76.6 | 73.5 | 81.6 | 8.0 | 11.9 | 10.0 | 10.1 |
| Epsilon-CO | 4.0 | 5.1 | 38.0 | 92.2 | 88.1 | 83.5 | 73.4 | 81.4 | 8.0 | 11.8 | 10.2 | 10.2 |
| Epsilon-CO (Δ181-185) | 4.0 | 4.7 | 39.9 | 117.0 | 88.1 | 72.4 | 76.0 | 76.2 | 8.0 | 11.9 | 10.2 | 10.1 |
| Epsilon-CO (R183K) | 4.0 | 4.6 | 37.8 | 92.5 | 88.1 | 82.6 | 71.9 | 82.7 | 8.0 | 12.4 | 10.1 | 10.1 |
| Epsilon-CO (S178N.R183K) | 4.0 | 5.0 | 47.1 | 120.2 | 88.1 | 73.8 | 76.7 | 85.2 | 8.0 | 11.7 | 10.2 | 10.1 |
| Zeta 1xx | 4.0 | 5.1 | 52.0 | 191.4 | 88.1 | 79.3 | 77.0 | 87.0 | 8.0 | 12.4 | 10.0 | 9.9 |

TABLE 34

Nine-Day Expansion Data of Transduced Constructs - Donor 2

| Experimental | Cell counts (10 ^ 6) | | | | Viability (%) | | | | Diameter (uM) | | | |
|---|---|---|---|---|---|---|---|---|---|---|---|---|
| Groups | Day 0 | Day 3 | Day 7 | Day 9 | Day 0 | Day 3 | Day 7 | Day 9 | Day 0 | Day 3 | Day 7 | Day 9 |
| NTD | 6.6 | 13.7 | 130.2 | 540.4 | 78.6 | 79.5 | 91.2 | 96.6 | 9.3 | 11.0 | 9.7 | 10.1 |
| Epsilon-CO | 3.3 | 5.8 | 37.1 | 136.0 | 78.6 | 77.5 | 82.5 | 91.9 | 9.3 | 11.0 | 9.9 | 10.1 |
| Epsilon-CO (Δ181-185) | 3.3 | 4.6 | 41.6 | 132.0 | 78.6 | 75.5 | 88.1 | 93.5 | 9.3 | 11.6 | 9.7 | 10.0 |
| Epsilon-CO (R183K) | 3.3 | 5.3 | 35.4 | 122.0 | 78.6 | 76.8 | 83.5 | 92.1 | 9.3 | 11.1 | 9.9 | 9.8 |
| Epsilon-CO (S178N.R183K) | 3.3 | 5.6 | 44.0 | 158.2 | 78.6 | 75.8 | 89.4 | 93.6 | 9.3 | 10.6 | 9.8 | 10.1 |
| Zeta 1xx | 3.3 | 5.4 | 45.7 | 180.7 | 78.6 | 82.2 | 89.0 | 93.0 | 9.3 | 11.7 | 9.5 | 9.9 |

Transduction Efficiency of CAR-T Product Cells. CAR expression was measured on either Day 6 or Day 7 and Day 9 of manufacturing via KIP-1 staining and subsequent flow cytometry analysis (Table 35). The experimental groups showed comparable CAR expression on Day 7 ranging from 83% to 95% for Donor 1 and on Day 6 ranging from 82% to 96% for Donor 2. CAR expression remained relatively stable on Day 9 for both donors.

TABLE 35

Expression Data of Transduced Constructs During Manufacturing

| Experimental | % Transduction (Kip1+) - Donor 1 | | | | % Transduction (Kip1+) - Donor 2 | | | |
|---|---|---|---|---|---|---|---|---|
| Groups | Day 0 | Day 3 | Day 7 | Day 9 | Day 0 | Day 3 | Day 6 | Day 9 |
| NTD | N/A | N/A | N/A | N/A | N/A | N/A | N/A | N/A |
| Zeta-CO | N/A | N/A | 96.5 | 93.1 | N/A | N/A | N/A | N/A |
| Epsilon-CO | N/A | N/A | 98.0 | 94.9 | N/A | N/A | 94.9 | 88.1 |
| Epsilon-CO (Δ181-185) | N/A | N/A | 96.3 | 89.6 | N/A | N/A | 93.2 | 82.2 |
| Epsilon-CO (R183K) | N/A | N/A | 98.3 | 95.2 | N/A | N/A | 95.1 | 88.0 |
| Epsilon-CO (S178N.R183K) | N/A | N/A | 97.1 | 89.7 | N/A | N/A | 95.5 | 84.6 |
| Zeta 1xx | N/A | N/A | 91.4 | 83.2 | N/A | N/A | 82.8 | 84.1 |

Transduction Efficiency of CAR-T Product Cells on Day 0 of the Co-culture Setup. After thaw and overnight rest, a sample of each experimental group was stained to assess their percent recovery and CAR expression. Groups were then normalized down to the lowest transduction percentage (75% for Donor 1 and 74% for Donor 2) by the addition of NTD cells. This was done to ensure that all samples had the same number of CAR+ samples in the downstream assays. The product cells were successfully normalized and ranged from 68% to 73% for Donor 1 and 73% to 78% for Donor 2 (Table 36).

TABLE 36

CAR Expression of CAR-T Product Cells on Day 0 of the Co-culture Setup

| | % Transduction (Kip1+) - Donor 1 | | % Transduction (Kip1+) - Donor 2 | |
|---|---|---|---|---|
| Experimental Groups | Pre-Normalization/ Overnight Rest | Post-Normalization | Pre-Normalization/ Overnight Rest | Post-Normalization |
| NTD | N/A | N/A | N/A | N/A |
| Zeta-CO | 90 | 72 | N/A | N/A |
| Epsilon-CO | 92 | 68 | 85 | 77 |
| Epsilon-CO (Δ181-185) | 83 | 72 | 72 | 78 |
| Epsilon-CO (R183K) | 92 | 70 | 84 | 78 |
| Epsilon-CO (S178N.R183K) | 83 | 73 | 79 | 78 |
| Zeta 1xx | 75 | 69 | 79 | 73 |

Cytotoxicity. Day 1 (Table 37) and Day 4 (Table 38) readouts from Donor 1 showed dose-dependent cytotoxicity across antigen-expressing cell line Nalm6, with no significant differences between constructs.

TABLE 37

Day 1 Functional Characterization Data from Donor 1: Percent Cytotoxicity of Nalm6 Cell Line in Triplicate

| | E:T ratio | | | | | | |
|---|---|---|---|---|---|---|---|
| Experimental Groups | 3:1 | 1:1 | 1:3 | 1:9 | 1:27 | 1:81 | 1:243 |
| NTD | 16.1 | 12.3 | 11.9 | 14.1 | 4.3 | 5.9 | 7.1 |
| | 4.8 | 5.6 | 0.9 | −10.6 | −17.3 | −12.2 | −3.5 |
| | 3.9 | −0.1 | 1.6 | −7.3 | −13.1 | −9.5 | 0.2 |
| Zeta-CO | 99.9 | 98.8 | 82.8 | 56.2 | 25.3 | 17.1 | 8.9 |
| | 100 | 98.4 | 80.6 | 50.4 | 14.6 | −4.8 | 0.8 |
| | 99.8 | 96.7 | 74.2 | 44.5 | 10.8 | −3 | 2.3 |
| Epsilon-CO | 99.9 | 97.9 | 80.9 | 51.8 | 21.7 | 17.5 | 10.8 |
| | 99.9 | 97.8 | 79.2 | 42.8 | 9.6 | −10 | 0.9 |
| | 99.9 | 96 | 72.7 | 36.3 | 3.1 | −5.9 | 4.7 |
| Epsilon-CO (Δ181-185) | 99.9 | 98.1 | 80.9 | 48.3 | 17.3 | 13.5 | 2.3 |
| | 99.9 | 96.9 | 77.4 | 36.3 | 4.4 | −11.7 | −4.6 |
| | 99.9 | 95.2 | 71.7 | 28.6 | −3.2 | −12 | 0.1 |
| Epsilon-CO (R183K) | 99.9 | 97.6 | 80.2 | 45.7 | 19.4 | 11.9 | 1.3 |
| | 99.9 | 97 | 79.1 | 43.1 | 8.9 | −7.7 | −4.5 |
| | 99.6 | 95.2 | 72.3 | 35.3 | −3.1 | −8 | −3.2 |
| Epsilon-CO (S178N.R183K) | 99.9 | 99.3 | 87.2 | 55.4 | 16.8 | 4.2 | −0.6 |
| | 99.9 | 99.1 | 84.1 | 48.8 | 12.5 | −3.3 | −5.5 |
| | 99.8 | 97.9 | 80.2 | 42.8 | 9.9 | −5.8 | 0.1 |
| Zeta 1xx | 99.9 | 99.4 | 89 | 61.9 | 26.1 | 13.8 | 7.7 |
| | 100 | 99.2 | 86.4 | 55.6 | 16.9 | −4.4 | 5.9 |
| | 99.8 | 97.5 | 81.6 | 44.5 | 12.5 | −9.6 | 2.1 |

TABLE 38

Day 4 Functional Characterization Data from Donor 1: Percent Cytotoxicity of Nalm6 Cell Line in

| | E:T ratio | | | | | | |
|---|---|---|---|---|---|---|---|
| Experimental Groups | 3:1 | 1:1 | 1:3 | 1:9 | 1:27 | 1:81 | 1:243 |
| NTD | 15.2 | 0.8 | −9.6 | −10.7 | −9.6 | −11.1 | 0.6 |
| | 12.9 | −2.6 | −12.8 | −13.2 | −18.3 | −14 | −6.2 |
| | 11 | 0.3 | −9.7 | −12.6 | −12.5 | −11.7 | −2.5 |
| Zeta-CO | 100 | 100 | 98.4 | 83.9 | 47.9 | 13.8 | 7.1 |
| | 100 | 100 | 98.6 | 84.6 | 52.3 | 14.9 | 9.4 |
| | 100 | 100 | 98.8 | 87.9 | 52.1 | 20.6 | 10.2 |
| Epsilon-CO | 100 | 100 | 97.8 | 83.4 | 41.8 | 12.5 | 9.3 |
| | 100 | 100 | 98.3 | 81.2 | 44.8 | 7.8 | 5.3 |
| | 100 | 100 | 98.6 | 86.7 | 47 | 6.7 | 10.2 |
| Epsilon-CO (Δ181-185) | 100 | 100 | 98.9 | 83.6 | 41.7 | 9.2 | 8.8 |
| | 100 | 100 | 98.6 | 85 | 41.2 | 11.6 | 1.2 |
| | 100 | 100 | 99.5 | 90 | 48.4 | 15 | 4.8 |
| Epsilon-CO (R183K) | 100 | 100 | 98 | 81 | 45.6 | 18.1 | 4.4 |
| | 100 | 100 | 97.8 | 82.9 | 44.6 | 12.7 | 2.9 |
| | 100 | 100 | 98.9 | 84.6 | 45.5 | 14.7 | 2.9 |
| Epsilon-CO (S178N.R183K) | 100 | 100 | 99.3 | 88 | 55.9 | 16.8 | 8.7 |
| | 100 | 100 | 99.6 | 89.9 | 56 | 15 | 4.7 |
| | 100 | 100 | 99.8 | 92.8 | 65.4 | 17.9 | 6.6 |
| Zeta 1xx | 100 | 100 | 99.4 | 90.5 | 56.4 | 18.5 | 6.7 |
| | 100 | 100 | 99.4 | 90.3 | 61.5 | 20.5 | 15 |
| | 100 | 100 | 99.5 | 91.8 | 65.8 | 26.7 | 15.4 |

Day 1 (Table 39) and Day 4 (Table 40) readouts from Donor 1 showed dose-dependent cytotoxicity across antigen-expressing cell line Raji, with no significant differences between constructs.

TABLE 39

Day 1 Functional Characterization Data from Donor 1: Percent Cytotoxicity of Raji Cell Line in Triplicate

| Experimental Groups | E:T ratio 3:1 | 1:1 | 1:3 | 1:9 | 1:27 | 1:81 | 1:243 |
|---|---|---|---|---|---|---|---|
| NTD | 8.9 | −2.3 | −10.2 | −10 | −13.6 | −23.6 | −19.7 |
| | 15.9 | 7.2 | −1 | −15.6 | −8.8 | −32.8 | −1.3 |
| | 8.1 | 2.1 | −0.1 | −26.4 | −32.8 | −34.7 | 2.2 |
| Zeta-CO | 85.6 | 58.5 | 19.7 | −10.7 | −16.1 | −29.6 | 1.2 |
| | 86.2 | 59.2 | 29.7 | −11.8 | −19.9 | −28.7 | 8.2 |
| | 83.5 | 51.6 | 18 | −20.2 | −27.9 | −39.7 | −5.8 |
| Epsilon-CO | 80 | 50.4 | 17.3 | −16.7 | −20.5 | −21.6 | 6.3 |
| | 78.8 | 50.4 | 20.6 | −22.1 | −23 | −30.8 | 3.5 |
| | 76.8 | 44.6 | 19.7 | −18.5 | −36.4 | −36.8 | −7.7 |
| Epsilon-CO | 80 | 48.6 | 21.4 | −4.9 | −19.6 | −30.9 | −20.1 |
| (Δ181-185) | 81.2 | 48.9 | 22.5 | −23.1 | −19.3 | −33.1 | 1.2 |
| | 80 | 41.2 | 17.7 | −30.4 | −31.9 | −36.7 | −6.6 |
| Epsilon-CO | 78.3 | 45.9 | 21.1 | −13.2 | −21.6 | −25.8 | −10.1 |
| (R183K) | 78 | 45.3 | 27.4 | −11.3 | −21.1 | −24.6 | 7.3 |
| | 80 | 40.2 | 13.4 | −28.5 | −39 | −37.8 | 1 |
| Epsilon-CO | 87.4 | 57.6 | 27.1 | −5.9 | −19.8 | −18.1 | −4.1 |
| (S178N.R183K) | 87.2 | 57.6 | 26.6 | −13.4 | −25.7 | −25.4 | 3.6 |
| | 87.1 | 50.7 | 25.9 | −32 | −19.9 | −25.3 | 1.3 |
| Zeta 1xx | 92.1 | 65.3 | 19.3 | −4.6 | −17.4 | −19.1 | −7.2 |
| | 93 | 67.5 | 37.6 | −9.5 | −13.5 | −20.8 | −5.7 |
| | 91.9 | 59.1 | 32 | −19.6 | −32.3 | −34.1 | 3.9 |

TABLE 40

Day 4 Functional Characterization Data from Donor 1: Percent Cytotoxicity of Raji Cell Line in Triplicate

| Experimental Groups | E:T ratio 3:1 | 1:1 | 1:3 | 1:9 | 1:27 | 1:81 | 1:243 |
|---|---|---|---|---|---|---|---|
| NTD | 42.6 | 21.1 | 7.8 | 2.9 | −3.2 | −4.3 | −5.1 |
| | 35.6 | 16.5 | 8.3 | 3 | −3.9 | −3.9 | −2.9 |
| | 36.6 | 16.5 | 4 | −2.9 | −7.9 | −7.1 | −2.5 |
| Zeta-CO | 99.8 | 92.3 | 19.4 | 0.6 | 0.4 | −3.7 | −2.9 |
| | 99.8 | 93.9 | 14.1 | −3.6 | −4.7 | −8.2 | −1.5 |
| | 99.5 | 92.3 | 18.9 | −0.3 | −3.4 | −9.3 | −6.7 |
| Epsilon-CO | 99.7 | 74 | 6.5 | 2.2 | −4.5 | −3.7 | −5.3 |
| | 99.6 | 73.7 | 9.7 | −6.7 | −7.2 | −4.5 | −5.5 |
| | 99.7 | 76 | 12.4 | 0.1 | −4.7 | −6.8 | −1 |
| Epsilon-CO | 99.3 | 70.3 | 4.4 | 1.6 | −4.2 | −1.6 | −3.8 |
| (Δ181-185) | 99.2 | 62.9 | 3.6 | −1.8 | −4.1 | −4.7 | −9.3 |
| | 99.3 | 65.3 | 5.4 | 3 | −3.9 | −7.2 | −2 |
| Epsilon-CO (R183K) | 99.8 | 76.5 | 11.6 | 3.1 | −3.6 | −8.1 | −3.6 |
| | 99.8 | 73.1 | 5.1 | 0.6 | 2.9 | 3.1 | −3 |
| | 99.8 | 81 | 7.8 | 0.7 | −3.2 | −9 | 0 |
| Epsilon-CO | 99.7 | 91.1 | 12 | 0 | −3.5 | −9.9 | 4.7 |
| (S178N.R183K) | 99.8 | 90.4 | 8.5 | 1.4 | −2.1 | −1 | −6.8 |
| | 99.7 | 88.6 | 13.8 | 2.1 | −1.2 | −6.8 | −6.9 |
| Zeta 1xx | 99.7 | 95.9 | 24.7 | −3.6 | 0 | −7.2 | −3.1 |
| | 99.7 | 94.6 | 20.3 | −1.4 | −2.7 | −8.4 | −6.8 |
| | 99.7 | 95.6 | 24.4 | −2.1 | −5.6 | −8.2 | −9 |

Day 1 (Table 41) and Day 4 (Table 42) readouts from Donor 1 showed dose-dependent cytotoxicity across antigen-expressing cell line ST486, with no significant differences between constructs.

TABLE 41

Day 1 Functional Characterization Data from Donor 1: Percent Cytotoxicity of ST486 Cell Line in Triplicate

| Experimental Groups | E:T ratio 3:1 | 1:1 | 1:3 | 1:9 | 1:27 | 1:81 | 1:243 |
|---|---|---|---|---|---|---|---|
| NTD | 12.4 | 0.8 | −11.6 | −16.5 | −19.9 | −19.6 | −10.7 |
| | 18 | 4 | −6.6 | −14 | −22.3 | −19.1 | −5.1 |
| | 8.5 | 1.8 | −2.7 | −11.1 | −11.7 | −6.8 | −5.8 |
| Zeta-CO | 99.6 | 98.7 | 85.2 | 47.8 | 6.7 | −14.8 | −3.1 |
| | 99.7 | 98.5 | 84.2 | 47.7 | 6.9 | −15.5 | −2 |
| | 99.6 | 98.8 | 88.4 | 49.8 | 17 | −3.2 | −2.4 |
| Epsilon-CO | 99.7 | 96.3 | 82 | 31.9 | −0.3 | −14.8 | −5.1 |
| | 99.7 | 98.1 | 83.4 | 36.3 | 3 | −15 | −1.9 |
| | 99.6 | 95 | 83.2 | 48.4 | 10.8 | −1.9 | −4.1 |
| Epsilon-CO | 99.4 | 98.1 | 80 | 32.5 | −0.4 | −15 | −6.1 |
| (Δ181-185) | 99.3 | 95.5 | 78.1 | 39.8 | 0.1 | −14.2 | −6.7 |
| | 99.4 | 98.1 | 85.7 | 42.3 | 8.1 | −8.7 | −2.6 |
| Epsilon-CO (R183K) | 99.4 | 95.2 | 79.5 | 37 | −2.9 | −13 | −6.1 |
| | 99.4 | 96.9 | 80.4 | 31.1 | −2.5 | −13.5 | −2.9 |
| | 99.6 | 95.9 | 83.4 | 47 | 11 | −2.9 | −3.4 |
| Epsilon-CO | 99.6 | 98.9 | 87.7 | 49.9 | 8.2 | −9.3 | −5 |
| (S178N.R183K) | 99.6 | 97 | 86.8 | 48.1 | 8 | −5.6 | −1 |
| | 99.6 | 99.1 | 90.3 | 54.8 | 19.7 | 2.2 | 1.2 |
| Zeta 1xx | 99.7 | 99.2 | 90.1 | 53.7 | 12.1 | −12.3 | −7.5 |
| | 99.7 | 98.9 | 91.6 | 55.9 | 6.1 | −6 | −2.6 |
| | 99.6 | 98.1 | 91.4 | 61.5 | 17.8 | −3.5 | −2.9 |

TABLE 42

Day 4 Functional Characterization Data from Donor 1: Percent Cytotoxicity of ST486 Cell Line in Triplicate

| Experimental Groups | E:T ratio 3:1 | 1:1 | 1:3 | 1:9 | 1:27 | 1:81 | 1:243 |
|---|---|---|---|---|---|---|---|
| NTD | 66.1 | −1.8 | −21.9 | −25.9 | −31.6 | −28.9 | −6.5 |
| | 68.6 | 0.5 | −12.3 | −18.1 | −23.8 | −18.3 | −5.8 |
| | 63.5 | 0.3 | −13.1 | −22.5 | −29.3 | −17.3 | −7.3 |
| Zeta-CO | 100 | 99.9 | 99.9 | 94.8 | 64.2 | 30 | 22.4 |
| | 100 | 99.8 | 99.9 | 93.4 | 65.3 | 39.5 | 19.7 |
| | 99.9 | 99.9 | 99.9 | 93.7 | 68.8 | 31 | 21 |
| Epsilon-CO | 99.9 | 100 | 100 | 92.6 | 55.3 | 16.4 | 14.9 |
| | 100 | 100 | 99.9 | 88 | 61.1 | 28 | 15.1 |
| | 99.9 | 100 | 99.9 | 92.6 | 58.8 | 23.1 | 17.4 |
| Epsilon-CO | 100 | 99.9 | 100 | 93.8 | 63.3 | 29.2 | 6.4 |
| (Δ181-185) | 99.9 | 100 | 99.9 | 91.1 | 62.5 | 34.2 | 4.3 |
| | 99.9 | 100 | 100 | 94.4 | 62.7 | 23.3 | 1 |
| Epsilon-CO | 100 | 99.9 | 100 | 92.8 | 56.3 | 18.9 | 1.4 |
| (R183K) | 100 | 99.8 | 99.7 | 89.1 | 58.1 | 29.5 | 12.4 |
| | 99.9 | 99.9 | 100 | 90.9 | 60.5 | 23.7 | 11.8 |
| Epsilon-CO | 100 | 100 | 99.9 | 97.2 | 71.2 | 29.4 | 14.6 |
| (S178N.R183K) | 99.9 | 99.9 | 99.9 | 96.1 | 67.9 | 41.2 | 23.5 |
| | 99.9 | 99.9 | 99.9 | 97.6 | 75.2 | 40.2 | 7.4 |
| Zeta 1xx | 100 | 100 | 99.9 | 98.5 | 69.3 | 30.8 | 9.8 |
| | 99.9 | 99.9 | 99.9 | 98.1 | 74.8 | 31.8 | 12.6 |
| | 99.9 | 99.9 | 100 | 95.9 | 67.7 | 37.8 | 12.2 |

Day 1 (Table 43) and Day 4 (Table 44) readouts from Donor 2 showed dose-dependent cytotoxicity across antigen-expressing cell line Nalm6, with no significant differences between constructs.

TABLE 43

Day 1 Functional Characterization Data from Donor 2: Percent Cytotoxicity of Nalm6 Cell Line in Triplicate

| Experimental | E:T ratio | | | | | | |
|---|---|---|---|---|---|---|---|
| Groups | 3:1 | 1:1 | 1:3 | 1:9 | 1:27 | 1:81 | 1:243 |
| NTD | −4.3 | 3.4 | −6 | −4.7 | −6.1 | −6.2 | −5.5 |
| | 2.2 | 4.5 | −2.2 | −3.4 | −3.8 | −4 | −5.8 |
| | 1.8 | 7.5 | 2.4 | −2.5 | −3.5 | −5.6 | −6.6 |
| Epsilon-CO | 97.1 | 86 | 55 | 20.4 | 4.1 | −3.6 | −3.4 |
| | 98.4 | 87.2 | 54.6 | 18.1 | 3.6 | −3.8 | −3.2 |
| | 99.2 | 91.7 | 55.3 | 20.5 | 2.8 | −4 | −4.1 |
| Epsilon-CO | 94.5 | 82.5 | 50.9 | 17 | 0.8 | −2.1 | −3.9 |
| (Δ181-185) | 98.1 | 83.2 | 50.9 | 20.1 | 0.6 | −2.4 | −2.5 |
| | 99.4 | 88.7 | 48.8 | 16.6 | −0.6 | −4.8 | −4 |
| Epsilon-CO | 97.8 | 86 | 55.3 | 22.8 | 5.8 | 1.5 | −6.3 |
| (R183K) | 98.2 | 87.2 | 55.4 | 20.1 | 7.4 | −1.5 | −7 |
| | 99.6 | 90.5 | 56.4 | 19.2 | 4.3 | −1.3 | −4.2 |
| Epsilon-CO | 96.5 | 86.7 | 54.3 | 22 | 4.4 | −1.1 | −2.4 |
| (S178N.R183K) | 98.2 | 87.9 | 53.2 | 21 | 1.5 | −1.1 | −5.3 |
| | 99.7 | 92.4 | 56 | 17 | 3.3 | −3.7 | −5.5 |
| Zeta 1xx | 96.2 | 85 | 58.4 | 23.5 | 3.6 | −0.5 | −3.1 |
| | 96.9 | 84.9 | 55.7 | 24.7 | 5.5 | −0.7 | −5.3 |
| | 99.4 | 91.3 | 61.1 | 21.4 | 5.1 | −3 | −2.6 |

TABLE 44

Day 4 Functional Characterization Data from Donor 2: Percent Cytotoxicity of Nalm6 Cell Line in Triplicate

| Experimental | E:T ratio | | | | | | |
|---|---|---|---|---|---|---|---|
| Groups | 3:1 | 1:1 | 1:3 | 1:9 | 1:27 | 1:81 | 1:243 |
| NTD | 23.4 | −3 | −6.1 | −5.2 | −4.4 | −4 | 14.2 |
| | 26.2 | 0.9 | −17.6 | −13 | −9.6 | −11 | 13 |
| | 25 | 6 | −14 | −14.2 | −7 | −6.1 | 12.9 |
| Epsilon-CO | 100 | 99.5 | 93.5 | 69.2 | 29.5 | 3.7 | 14 |
| | 100 | 99.8 | 96.7 | 67.2 | 28 | −1.6 | 12 |
| | 100 | 100 | 99.1 | 78.5 | 18.4 | −2.6 | 14.9 |
| Epsilon-CO | 100 | 100 | 95.8 | 67 | 24.5 | 0 | 13.2 |
| (Δ181-185) | 100 | 99.9 | 96.1 | 73.9 | 25 | −6 | 12.5 |
| | 100 | 100 | 99.4 | 77.4 | 22 | −3.8 | 17.3 |
| Epsilon-CO | 100 | 99.7 | 94.4 | 73.7 | 31.8 | 2.1 | 12.4 |
| (R183K) | 100 | 100 | 94.5 | 69.2 | 27.3 | 1.2 | 16.6 |
| | 100 | 100 | 99 | 78.4 | 24.4 | −7.4 | 16 |
| Epsilon-CO | 100 | 100 | 94.5 | 72.1 | 29.7 | 4 | 11 |
| (S178N.R183K) | 100 | 100 | 96.2 | 75.3 | 24.5 | −2 | 11.2 |
| | 100 | 100 | 99.5 | 82.5 | 30.7 | −2.4 | 13.5 |
| Zeta 1xx | 100 | 99.8 | 95.1 | 71.3 | 30.6 | 6.4 | 11.7 |
| | 100 | 99.8 | 95.7 | 71.5 | 31.3 | 1 | 15.5 |
| | 100 | 100 | 99.1 | 81.3 | 29.7 | 8.1 | 18 |

Day 1 (Table 45) and Day 4 (Table 46) readouts from Donor 2 showed dose-dependent cytotoxicity across antigen-expressing cell line Raji, with no significant differences between constructs.

TABLE 45

Day 1 Functional Characterization Data from Donor 2: Percent Cytotoxicity of Raji Cell Line in Triplicate

| Experimental | E:T ratio | | | | | | |
|---|---|---|---|---|---|---|---|
| Groups | 3:1 | 1:1 | 1:3 | 1:9 | 1:27 | 1:81 | 1:243 |
| NTD | −7 | 2 | −6.7 | −1.5 | −6.2 | −9.2 | −10.9 |
| | −2.7 | 2 | 0.6 | −4.7 | −5.3 | −5.6 | −2.7 |
| | −3.8 | 0.6 | −2.1 | −3.4 | −4.7 | −4 | −3.1 |
| Epsilon-CO | 62.7 | 37.6 | 13.6 | 1.8 | −2.2 | −4.1 | −3.4 |
| | 64.2 | 33.8 | 13 | 2.6 | −3.2 | −5.5 | −3.1 |
| | 67.6 | 35.3 | 12.1 | −1.3 | −5.2 | −4.6 | −2.3 |

TABLE 45-continued

Day 1 Functional Characterization Data from Donor 2: Percent Cytotoxicity of Raji Cell Line in Triplicate

| Experimental | E:T ratio | | | | | | |
|---|---|---|---|---|---|---|---|
| Groups | 3:1 | 1:1 | 1:3 | 1:9 | 1:27 | 1:81 | 1:243 |
| Epsilon-CO | 54.7 | 32.1 | 11.4 | −0.1 | −3.1 | −4.7 | −5.2 |
| (Δ181-185) | 57.2 | 28.8 | 11.9 | −0.2 | −3.8 | −6.3 | −2.6 |
| | 60.3 | 31 | 9.4 | 1.3 | −5.4 | −2.9 | −2.8 |
| Epsilon-CO | 64 | 38 | 9.6 | 1.9 | −6.2 | −5.7 | −4.1 |
| (R183K) | 64.4 | 35.8 | 15.5 | 1.3 | −3.5 | −6.2 | −2.5 |
| | 68.8 | 39 | 11.1 | 2.3 | −4.6 | −4.6 | −4.2 |
| Epsilon-CO | 60.2 | 32.9 | 10.1 | 4.3 | −3.2 | −5.3 | −2.8 |
| (S178N.R183K) | 62.1 | 33.1 | 14.7 | 2.1 | −2.1 | −6.2 | −1.5 |
| | 63.8 | 36.4 | 13.6 | 2.2 | −4 | −3.8 | −2.8 |
| Zeta 1xx | 62.2 | 37.6 | 8.9 | 0.8 | −4.7 | −6.8 | −6.6 |
| | 64.8 | 36.1 | 8.3 | −0.8 | −6 | −6.1 | −4.8 |
| | 67.6 | 35.9 | 9.7 | −1 | −6.6 | −6.6 | −4.2 |

TABLE 46

Day 4 Functional Characterization Data from Donor 2: Percent Cytotoxicity of Raji Cell Line in Triplicate

| Experimental | E:T ratio | | | | | | |
|---|---|---|---|---|---|---|---|
| Groups | 3:1 | 1:1 | 1:3 | 1:9 | 1:27 | 1:81 | 1:243 |
| NTD | 16.6 | 14.7 | −5.4 | −3.1 | −5.5 | −6.6 | 13.1 |
| | 10.2 | 6.6 | −15.2 | −11.5 | −14 | −13.1 | 9.8 |
| | 3.9 | 6.2 | −22.6 | −21.8 | −16.5 | −20 | 8.8 |
| Epsilon-CO | 100 | 98.4 | 51.8 | 16.7 | 5.7 | 1.6 | 20.7 |
| | 100 | 98.9 | 64.7 | 25.1 | 0.6 | −4 | 16.9 |
| | 100 | 98.5 | 67.8 | 23.9 | 1.3 | −10.9 | 16.2 |
| Epsilon-CO | 99.8 | 93 | 41.9 | 12.4 | 2.3 | 1.9 | 16.9 |
| (Δ181-185) | 99.7 | 94.2 | 46.5 | 12.2 | −2.4 | −6 | 14.1 |
| | 99.5 | 94 | 53.9 | 11.9 | −8.7 | −11.4 | 14.5 |
| Epsilon-CO | 100 | 98.1 | 52 | 19.3 | 4 | −0.6 | 22 |
| (R183K) | 100 | 98.6 | 58.4 | 16.5 | 3.8 | −4.5 | 18.7 |
| | 100 | 98.1 | 65.6 | 20.3 | −1.3 | −9.1 | 18.7 |
| Epsilon-CO | 99.9 | 96.3 | 51 | 19.6 | 5.8 | 0.9 | 20.1 |
| (S178N.R183K) | 99.9 | 97.5 | 63.9 | 20.9 | 1 | −4 | 15.9 |
| | 99.9 | 96.6 | 63.5 | 20.9 | −0.2 | −12.1 | 14.7 |
| Zeta 1xx | 100 | 95.2 | 43.6 | 18.1 | 4.4 | 3.2 | 18.9 |
| | 99.9 | 96.8 | 55.6 | 16.6 | −1.7 | −6.3 | 16.3 |
| | 99.9 | 97.6 | 62.2 | 11.6 | −0.6 | −9.1 | 12.9 |

Day 1 (Table 47) and Day 4 (Table 48) readouts from Donor 2 showed dose-dependent cytotoxicity across antigen-expressing cell line ST486, with no significant differences between constructs.

TABLE 47

Day 1 Functional Characterization Data from Donor 2: Percent Cytotoxicity of ST486 Cell Line in Triplicate

| Experimental | E:T ratio | | | | | | |
|---|---|---|---|---|---|---|---|
| Groups | 3:1 | 1:1 | 1:3 | 1:9 | 1:27 | 1:81 | 1:243 |
| NTD | 9.1 | 5.5 | −3.4 | −2.9 | −3.9 | −5.1 | −1.8 |
| | 8 | 7.8 | −2.3 | −1.9 | −1.6 | −1.3 | −1.8 |
| | 3.9 | 6 | 0.3 | −1.8 | −5 | −4 | −6.9 |
| Epsilon-CO | 95.8 | 83.2 | 52.4 | 17.8 | 4.1 | −6.1 | 0.2 |
| | 96.1 | 83.5 | 48.3 | 17.9 | 1.9 | −0.6 | −1.8 |
| | 96.4 | 83 | 48.6 | 15.8 | −4.3 | −7.2 | −1.2 |
| Epsilon-CO | 94.6 | 81.1 | 43.9 | 16 | 3.3 | 2.1 | −3.9 |
| (Δ181-185) | 95.6 | 80.6 | 41.6 | 12.6 | 0.9 | −3.8 | −2.2 |
| | 95.8 | 81.4 | 43.1 | 11.3 | −1.9 | −3.1 | −4.7 |
| Epsilon-CO | 94.2 | 81.7 | 49.7 | 18.7 | 4.3 | 2.2 | −3.9 |
| (R183K) | 96.1 | 84.4 | 48.3 | 19.3 | 4.8 | −1.4 | −2.5 |
| | 95.5 | 81.2 | 49.2 | 17.3 | −1.9 | −3.3 | −0.9 |

TABLE 47-continued

Day 1 Functional Characterization Data from Donor 2: Percent Cytotoxicity of ST486 Cell Line in Triplicate

| Experimental Groups | E:T ratio 3:1 | 1:1 | 1:3 | 1:9 | 1:27 | 1:81 | 1:243 |
|---|---|---|---|---|---|---|---|
| Epsilon-CO | 95.1 | 81.6 | 47 | 20.6 | 1.8 | −4.8 | −2.4 |
| (S178N.R183K) | 95.7 | 81.6 | 49.1 | 16.7 | 4.7 | 1 | 1.9 |
| | 96.1 | 80.2 | 45.7 | 14.9 | 0.7 | −3.3 | 0.7 |
| Zeta 1xx | 94.7 | 79.3 | 51.8 | 20.9 | 2.1 | −4.9 | −5 |
| | 95.6 | 82.8 | 50.7 | 20 | 4.1 | −2.3 | −0.8 |
| | 95.5 | 83 | 49.2 | 16.4 | 0.6 | −4.2 | −6.4 |

TABLE 48

Day 4 Functional Characterization Data from Donor 2: Percent Cytotoxicity of ST486 Cell Line in Triplicate

| Experimental Groups | E:T ratio 3:1 | 1:1 | 1:3 | 1:9 | 1:27 | 1:81 | 1:243 |
|---|---|---|---|---|---|---|---|
| NTD | 60 | 10.6 | −10.7 | −15.7 | −13.8 | −12.4 | 0.3 |
| | 81.7 | 5.9 | −21.7 | −23.8 | −27.8 | −25.5 | −13.6 |
| | 98.5 | 3.5 | −13.6 | −22.6 | −28 | −22.1 | −15.7 |
| Epsilon-CO | 100 | 99.9 | 97.7 | 81.4 | 44.9 | 6 | 5.2 |
| | 100 | 99.9 | 98.4 | 78.2 | 38.5 | −0.3 | −4.9 |
| | 100 | 99.9 | 99.2 | 82.5 | 28.7 | −3.9 | −2.1 |
| Epsilon-CO | 100 | 100 | 98.6 | 81.2 | 27.5 | 1.4 | 9.9 |
| (Δ181-185) | 100 | 99.9 | 98.4 | 70.8 | 18.3 | −7.3 | 0 |
| | 100 | 99.9 | 99.3 | 79.5 | 14.8 | −9.9 | 0.9 |
| Epsilon-CO | 99.9 | 99.9 | 98.6 | 80.9 | 37.9 | 3.2 | 6.6 |
| (R183K) | 100 | 99.9 | 98 | 73.2 | 18 | 0.4 | 3.4 |
| | 100 | 100 | 99.4 | 78.4 | 19.1 | −7.9 | 4.4 |

TABLE 48-continued

Day 4 Functional Characterization Data from Donor 2: Percent Cytotoxicity of ST486 Cell Line in Triplicate

| Experimental Groups | E:T ratio 3:1 | 1:1 | 1:3 | 1:9 | 1:27 | 1:81 | 1:243 |
|---|---|---|---|---|---|---|---|
| Epsilon-CO | 99.9 | 99.9 | 98.2 | 80.6 | 35.2 | 5 | 8.7 |
| (S178N.R183K) | 99.9 | 99.8 | 98.5 | 79.4 | 36.4 | 0.4 | 4 |
| | 100 | 99.9 | 99.3 | 85.3 | 20.8 | −3.8 | 0.9 |
| Zeta 1xx | 99.9 | 99.9 | 97.2 | 77 | 36.2 | 11.2 | 7.5 |
| | 100 | 99.9 | 97.7 | 73.3 | 33.7 | 8.5 | −7.2 |
| | 100 | 99.9 | 98.9 | 79.9 | 30 | −10.7 | −1.8 |

Day 1 Cytokine Production. Supernatant was collected from the 1:1 E:T ratio and analyzed via MSD for IFN-γ, IL-2, and TNF-α secretion. Analysis showed that all constructs from Donor 1 (Table 49) and Donor 2 (Table 50) secreted cytokines when co-cultured with the antigen-expressing cell lines Raji, Nalm6 and ST486. Epsilon-CO constructs all secreted similar levels of cytokines across all cell lines. Co-culture with the Raji and Nalm6 cell lines elicited higher levels of cytokines when compared to the levels secreted with the ST486 cell line, however, the overall hierarchical pattern of the constructs was consistent across all cell lines. On the other hand, the NTD control group did not secrete any measurable or significant levels of cytokine when cultured alone or with antigen-expressing cell lines. Cytokine measurements for INFγ<1.76 pg/mL, IL-2<0.890 µg/mL and TNFα<0.690 µg/mL were below the limit of quantitation for the assay (<LOQ).

TABLE 49

Day 1 Functional Characterization Data from Donor 1: Cytokine Analysis of IFN-γ, TNF-α, IL-2 in Nalm6, Raji and ST486 Cell Lines via MSD

| Experimental Groups | Cytokine | Nalm6 Avg pg/mL | % CV | Raji Avg pg/mL | % CV | ST486 Avg pg/mL | % CV | T cells Alone Avg pg/mL | % CV |
|---|---|---|---|---|---|---|---|---|---|
| NTD | IFN-γ | 80.34 | 47.31 | 107.1 | 34.0 | 48.8 | 74.4 | 9.5 | 0 |
| | TNF-α | 7.455 | 89.23 | 4.6 | 17.0 | <LOQ | <LOQ | <LOQ | <LOQ |
| | IL-2 | <LOQ | <LOQ | 25.8 | 10.7 | 7.6 | 0.0 | <LOQ | <LOQ |
| Zeta-CO | IFN-γ | 59492 | 9.795 | 87703.0 | 6.4 | 21184.0 | 4.4 | 40.8 | 28.2 |
| | TNF-α | 787.7 | 2.009 | 886.7 | 4.6 | 159.4 | 6.6 | <LOQ | <LOQ |
| | IL-2 | 2537 | 2.639 | 3946.0 | 5.8 | 355.9 | 2.9 | <LOQ | <LOQ |
| Epsilon-CO | IFN-γ | 46010 | 15.13 | 77696.0 | 14.0 | 14368.0 | 11.2 | <LOQ | <LOQ |
| | TNF-α | 491 | 3.374 | 609.1 | 5.7 | 102.0 | 6.8 | <LOQ | <LOQ |
| | IL-2 | 1369 | 4.467 | 2492.0 | 5.4 | 176.7 | 14.1 | <LOQ | <LOQ |
| Epsilon-CO | IFN-γ | 39789 | 19.61 | 42344.0 | 1.6 | 9089.0 | 4.2 | <LOQ | <LOQ |
| (Δ181-185) | TNF-α | 457.5 | 0.9958 | 439.8 | 6.0 | 67.5 | 5.0 | <LOQ | <LOQ |
| | IL-2 | 1233 | 3.23 | 1576.0 | 1.2 | 142.1 | 2.7 | <LOQ | <LOQ |
| Epsilon-CO | IFN-γ | 47032 | 10.03 | 65030.0 | 12.5 | 13994.0 | 7.2 | <LOQ | <LOQ |
| (R183K) | TNF-α | 514.3 | 6.333 | 608.6 | 3.5 | 94.4 | 7.0 | <LOQ | <LOQ |
| | IL-2 | 1458 | 1.115 | 2253.0 | 5.5 | 130.4 | 10.1 | <LOQ | <LOQ |
| Epsilon-CO | IFN-γ | 40935 | 1.924 | 61333.0 | 6.1 | 627.1 | 14.2 | <LOQ | <LOQ |
| (S178N.R183K) | TNF-α | 384 | 2.205 | 461.5 | 6.3 | 63.2 | 6.3 | <LOQ | <LOQ |
| | IL-2 | 864.7 | 1.906 | 1729.0 | 4.8 | 101.1 | 9.6 | <LOQ | <LOQ |
| Zeta 1xx | IFN-γ | 47208 | 8.041 | 87703.0 | 12.9 | 6814.0 | 11.8 | <LOQ | <LOQ |
| | TNF-α | 671 | 2.794 | 886.7 | 4.5 | 70.8 | 4.7 | <LOQ | <LOQ |
| | IL-2 | 974.2 | 6.685 | 3946.0 | 5.5 | 44.2 | 8.1 | <LOQ | <LOQ |

TABLE 50

Day 1 Functional Characterization Data from Donor 2: Cytokine Analysis of IFN-γ, TNF-α, IL-2 in Nalm6, Raji and ST486 Cell Lines via MSD

| Experimental Groups | Cytokine | Nalm6 Avg pg/mL | % CV | Raji Avg pg/mL | % CV | ST486 Avg pg/mL | % CV | T cells Alone Avg pg/mL | % CV |
|---|---|---|---|---|---|---|---|---|---|
| NTD | IFN-γ | <LOQ | <LOQ | <LOQ | <LOQ | <LOQ | <LOQ | <LOQ | <LOQ |
| | TNF-α | <LOQ | <LOQ | <LOQ | <LOQ | <LOQ | <LOQ | <LOQ | <LOQ |
| | IL-2 | <LOQ | <LOQ | <LOQ | <LOQ | <LOQ | <LOQ | <LOQ | <LOQ |
| Epsilon-CO | IFN-γ | 22590 | 6.817 | 25597 | 13.68 | 7747 | 8.423 | <LOQ | <LOQ |
| | TNF-α | 337 | 8.108 | 364.9 | 4.323 | 149 | 4.631 | <LOQ | <LOQ |
| | IL-2 | 561.2 | 3.67 | 890.4 | 7.355 | 162.8 | 6.672 | <LOQ | <LOQ |
| Epsilon-CO | IFN-γ | 21800 | 25.5 | 20054 | 17.09 | 7024 | 24.7 | <LOQ | <LOQ |
| (Δ181-185) | TNF-α | 334.4 | 8.974 | 304.8 | 2.257 | 114.8 | 7.499 | <LOQ | <LOQ |
| | IL-2 | 738.4 | 3.888 | 863 | 8.073 | 177.6 | 13.02 | <LOQ | <LOQ |
| Epsilon-CO | IFN-γ | 20059 | 15.68 | 25805 | 9.312 | 7617 | 2.417 | <LOQ | <LOQ |
| (R183K) | TNF-α | 271.2 | 6.115 | 310.6 | 4.641 | 109.2 | 3.469 | <LOQ | <LOQ |
| | IL-2 | 406.1 | 6.488 | 703.8 | 9.69 | 107.8 | 6.429 | <LOQ | <LOQ |
| Epsilon-CO | IFN-γ | 21088 | 7.545 | 23819 | 3.331 | 6920 | 4.379 | <LOQ | <LOQ |
| (S178N.R183K) | TNF-α | 288.3 | 5.261 | 319.1 | 1.502 | 110.2 | 2.425 | <LOQ | <LOQ |
| | IL-2 | 644.9 | 4.876 | 932.1 | 4.962 | 202.9 | 6.91 | <LOQ | <LOQ |
| Zeta 1xx | IFN-γ | 38985 | 8.731 | 54426 | 21.61 | 13036 | 17.44 | <LOQ | <LOQ |
| | TNF-α | 649.6 | 6.788 | 649.1 | 6.535 | 195.2 | 6.075 | <LOQ | <LOQ |
| | IL-2 | 1054 | 6.141 | 1589 | 6.852 | 225.1 | 4.065 | <LOQ | <LOQ |

Day 4 Proliferation. Dilution of the Cell Trace Violet (CTV) label was used to assess proliferation. As the product CAR-T cells divide, the dye is diluted with each division and thus, a lower CTV MFI when compared to the Day 0 cells, is indicative of proliferation. Minimal homeostatic or antigen-independent proliferation is seen in the NTD control group when cultured alone or with antigen-expressing cell lines. All constructs showed comparable MFI levels when cultured against the Raji, Nalm6 and ST486 cell line. A full summary is found in Table 51 for Donor 1 and Table 52 for Donor 2.

TABLE 51

Day 4 Functional Characterization Data: Proliferation Analysis Raji, Nalm6 and ST486 Cell Lines via Cell Trace Violet (CTV) Staining. Values reported are the Median of the CTV distribution curves.

| Experimental Groups | Raji | Nalm6 | ST486 | T cells Alone |
|---|---|---|---|---|
| NTD | 12156 | 14618 | 14754 | 19120 |
| Zeta CO | 3926 | 3305 | 2373 | 19256 |
| Epsilon-CO | 4924 | 4594 | 2629 | 18502 |
| Epsilon-CO (Δ181-185) | 4462 | 4193 | 2849 | 18502 |
| Epsilon-CO (R183K) | 4841 | 4444 | 2788 | 19165 |
| Epsilon-CO (S178N.R183K) | 4308 | 3561 | 3126 | 18589 |
| Zeta 1xx | 4272 | 4614 | 4041 | 19576 |

TABLE 52

Day 4 Functional Characterization Data: Proliferation Analysis Raji, Nalm6 and ST486 Cell Lines via Cell Trace Violet (CTV) Staining. Values reported are the Median of the CTV distribution curves.

| Experimental Groups | Raji | Nalm6 | ST486 | T cells Alone |
|---|---|---|---|---|
| NTD | 18282 | 18552 | 17666 | 20460 |
| Epsilon-CO | 2778 | 2797 | 2250 | 19868 |
| Epsilon-CO (Δ181-185) | 2766 | 2875 | 2235 | 20968 |
| Epsilon-CO (R183K) | 2902 | 2935 | 2370 | 20814 |
| Epsilon-CO (S178N.R183K) | 2548 | 2577 | 2176 | 21226 |
| Zeta 1xx | 3101 | 4415 | 2595 | 25142 |

TABLE 52-continued

Day 4 Functional Characterization Data: Proliferation Analysis Raji, Nalm6 and ST486 Cell Lines via Cell Trace Violet (CTV) Staining. Values reported are the Median of the CTV distribution curves.

| Experimental Groups | Raji | Nalm6 | ST486 | T cells Alone |
|---|---|---|---|---|

Serial Killing. Product CAR-T cells were normalized for CAR expression and co-cultured with the antigen-expressing Nalm6 target line at a 1:1 E:T ratio. Every 3-4 days, the cultures were challenged with more Nalm6 target cells. Cytotoxicity (Table 53) and CD3+ T cell counts (Table 54) were measured every round that more target cells were added. After 14 rounds, there were no significant differences between constructs.

TABLE 53

Serial Killing Data: Percent Cytotoxicity of Nalm6 Cell Line in Sextuplet

| Experimental Groups | Round 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| NTD | 13.9 | 0 | 25.6 | 0 | 14.1 | 0 | 19.8 | 0 | 3.3 | 0 | 0 | 0 | 0 | 0 |
| | 12 | 0 | 20.3 | 0 | 4.3 | 0 | 15.4 | 0 | 0 | 0 | 0 | 0 | 0 | 0 |
| | 7.1 | 0 | 23.4 | 0 | 1.4 | 0 | 12.8 | 0 | 0 | 0 | 0 | 0 | 0.2 | 0 |
| | 8.5 | 0 | 20 | 0 | 0.5 | 0 | 11.4 | 0 | 5 | 0 | 13.2 | 0 | 3.6 | 0 |
| | 5.8 | 0 | 17.8 | 0 | 5.3 | 0 | 10.6 | 0 | n/a | n/a | n/a | n/a | n/a | n/a |
| | 9.2 | 0 | 18.5 | 0 | 7.2 | 0 | 14.4 | 0 | 2.2 | 0 | 26.4 | 0 | 6.3 | 0 |
| Zeta-CO | 100 | 100 | 100 | 100 | 100 | 100 | 100.1 | 100.1 | 99.6 | 97.2 | 14.2 | 0 | 3.6 | 0 |
| | 100 | 100 | 100 | 100 | 100 | 100 | 100.1 | 100.1 | 100 | 99.9 | 77.5 | 0 | 0 | 0 |
| | 100 | 100 | 100 | 100 | 100 | 100 | 100.1 | 100.1 | 100 | 98.1 | 44.1 | 0 | 0 | 0 |
| | 100 | 100 | 100 | 100 | 100 | 100 | 100.1 | 100.1 | 99.8 | 98.7 | 17.4 | 0 | 3 | 0 |
| | 100 | 100 | 100 | 100 | 100 | 100 | 100.1 | 100.1 | 100.1 | 92.5 | 0 | 0 | 10.3 | 0 |
| | 100 | 100 | 100 | 100 | 100 | 100 | 100.1 | 100.1 | 100 | 99.9 | 99.5 | 45.1 | 0 | 0 |
| Epsilon-CO | 100 | 100 | 100 | 100 | 100 | 100 | 100.1 | 100.1 | 99.2 | 92.9 | 0 | 0 | 2.1 | 0 |
| | 100 | 100 | 100 | 100 | 100 | 100 | 100.1 | 100.1 | 99.6 | 91 | 0 | 0 | 0 | 0 |
| | 100 | 100 | 100 | 100 | 100 | 100 | 100.1 | 100.1 | 99.9 | 92 | 0 | 0 | 1.1 | 0 |
| | 100 | 100 | 100 | 100 | 100 | 100 | 100.1 | 100.1 | 100 | 91.9 | 0 | 0 | 11.2 | 0 |
| | 100 | 100 | 100 | 100 | 100 | 100 | 100.1 | 100.1 | 100 | 93.8 | 0 | 0 | 15.1 | 0 |
| | 100 | 100 | 100 | 99.8 | 100 | 99.9 | 100.1 | 100.1 | 97.1 | 75.2 | 0 | 0 | 11.9 | 0 |
| Epsilon-CO | 100 | 100 | 100 | 100 | 100 | 100 | 100.1 | 100.1 | 98.6 | 94.9 | 0 | 0 | 3.6 | 0 |
| (Δ181-185) | 100 | 100 | 100 | 100 | 100 | 100 | 100.1 | 100.1 | 99.9 | 99.8 | 97.8 | 19.5 | 0 | 0 |
| | 100 | 100 | 100 | 100 | 100 | 100 | 100.1 | 100.1 | 99.5 | 93.7 | 0 | 0 | 0 | 0 |
| | 100 | 99.9 | 100 | 100 | 100 | 100 | 100.1 | 100.1 | 99.9 | 98.1 | 0 | 0 | 1.7 | 0 |
| | 100 | 100 | 100 | 99.7 | 100 | 100 | 100.1 | 100.1 | 99.1 | 95 | 0 | 0 | 3.3 | 0 |
| | 100 | 100 | 100 | 99.9 | 100 | 100 | 100.1 | 100.1 | 99.8 | 95.7 | 0 | 0 | 6.1 | 0 |
| Epsilon-CO | 100 | 99.9 | 100 | 99.9 | 99.9 | 99.9 | 100 | 100.1 | 99 | 86.1 | 0 | 0 | 0 | 0 |
| (R183K) | 100 | 100 | 100 | 100 | 100 | 100 | 100.1 | 100.1 | 95.4 | 82.3 | 0 | 0 | 6.1 | 0 |
| | 99.9 | 100 | 100 | 100 | 100 | 100 | 100.1 | 100.1 | 98.9 | 86.7 | 0 | 0 | 0 | 0 |
| | 100 | 100 | 100 | 99.9 | 100 | 100 | 100.1 | 100.1 | 100.2 | 100 | 96.4 | 43.9 | 0 | 0 |
| | 99.9 | 100 | 100 | 99.9 | 100 | 100 | 100.1 | 100 | 97.7 | 71.4 | 0 | 0 | 5.2 | 0 |
| | 100 | 99.9 | 100 | 99.9 | 100 | 100 | 99.3 | 100 | 89.1 | 53.9 | 0 | 0 | 14.7 | 0 |
| Epsilon-CO | 100 | 100 | 100 | 100 | 100 | 100 | 100 | 100 | 97.9 | 89.6 | 0 | 0 | 0.3 | 0 |
| (S178N.R183K) | 100 | 100 | 100 | 100 | 100 | 100 | 100.1 | 100 | 98.8 | 89.9 | 0 | 0 | 0 | 0 |
| | 100 | 100 | 100 | 100 | 100 | 100 | 100.1 | 100 | 98.2 | 95.7 | 0 | 0 | 2.6 | 0 |
| | 100 | 100 | 100 | 100 | 100 | 100 | 100.1 | 100.1 | 98.8 | 86.7 | 0 | 0 | 11.2 | 0 |
| | 100 | 100 | 100 | 100 | 100 | 100 | 100.1 | 100 | 100.1 | 99.9 | 95.4 | 31.1 | 0 | 0 |
| | 100 | 100 | 100 | 99.9 | 100 | 99.9 | 100.1 | 100 | 97.2 | 81 | 0 | 0 | 13.9 | 0 |
| Zeta 1xx | 100 | 99.9 | 100 | 99.9 | 100 | 99.9 | 100.1 | 100.1 | 100.2 | 100 | 99.8 | 89.7 | 0 | 0 |
| | 100 | 99.9 | 100 | 100 | 100 | 100 | 100.1 | 100.1 | 100.1 | 99.6 | 47.4 | 0 | 0 | 0 |
| | 100 | 99.9 | 100 | 99.9 | 100 | 100 | 100 | 100.1 | 100.2 | 100 | 79 | 0 | 0 | 0 |
| | 100 | 99.9 | 100 | 99.9 | 100 | 100 | 100.1 | 100.1 | 100.1 | 99.7 | 89.6 | 66.8 | 0 | 0 |
| | 100 | 99.9 | 100 | 100 | 100 | 100 | 100.1 | 100.1 | 100.2 | 99.2 | 11.1 | 0 | 2.1 | 0 |
| | 100 | 99.9 | 100 | 99.9 | 100 | 99.9 | 100.1 | 100.1 | 100.2 | 100 | 98.1 | 83.6 | 0 | 0 |

TABLE 54

Serial Killing Data: CD3+ T Cell Counts in Co-culture with Nalm6 Cell Line in Sextuplet

| Experimental Groups | Round 1 | 2 | 3 | 4 | 5 | 6 | 7 | 8 | 9 | 10 | 11 | 12 | 13 |
|---|---|---|---|---|---|---|---|---|---|---|---|---|---|
| NTD | 88 | 25 | 53 | 98 | 22 | 25 | 105 | 9 | 28 | 68 | 304 | 759 | 608 |
| | 103 | 6 | 35 | 43 | 30 | 6 | 58 | 41 | 42 | 51 | 456 | 456 | 4556 |
| | 90 | 30 | 22 | 65 | 38 | 16 | 60 | 23 | 28 | 101 | 506 | 152 | 3189 |
| | 148 | 13 | 19 | 73 | 63 | 13 | 65 | 33 | 70 | 101 | 759 | 608 | 4101 |
| | 113 | 28 | 25 | 63 | 30 | 22 | 95 | 28 | 180 | 68 | 911 | 0 | 456 |
| | 110 | 25 | 50 | 53 | 58 | 19 | 38 | 28 | 28 | 17 | 101 | 304 | 2278 |
| Zeta-CO | 3200 | 10475 | 52000 | 39500 | 29500 | 25750 | 24925 | 14588 | 2531 | 4219 | 11846 | 2278 | 911 |
| | 5075 | 22950 | 57250 | 40000 | 29500 | 30000 | 41500 | 22163 | 9878 | 40500 | 3443 | 5164 | 7746 |
| | 7625 | 31750 | 59250 | 42250 | 33000 | 22725 | 35750 | 28088 | 3645 | 9720 | 8201 | 7290 | 8657 |
| | 8675 | 37000 | 48250 | 48000 | 34750 | 35750 | 43750 | 27938 | 2318 | 6278 | 4759 | 2278 | 4556 |
| | 5325 | 24275 | 47000 | 36250 | 34000 | 22175 | 30000 | 29025 | 3803 | 4556 | 962 | 1367 | 1823 |
| | 5925 | 24800 | 45500 | 44750 | 32750 | 23825 | 51750 | 26288 | 10598 | 82350 | 31590 | 9720 | 10024 |
| Epsilon-CO | 3825 | 7775 | 24250 | 26000 | 23275 | 24700 | 19350 | 18825 | 1789 | 1148 | 1215 | 608 | 3645 |
| | 6300 | 10700 | 40000 | 43250 | 36250 | 25750 | 41500 | 28950 | 1676 | 439 | 2734 | 3645 | 2278 |
| | 7675 | 14325 | 58750 | 52000 | 46000 | 29250 | 41500 | 23850 | 2104 | 405 | 2025 | 2582 | 2734 |
| | 7850 | 12150 | 62500 | 34000 | 35250 | 24825 | 23975 | 28613 | 1373 | 4556 | 1215 | 608 | 1367 |
| | 6850 | 9175 | 19925 | 47500 | 35500 | 32250 | 24150 | 28688 | 2689 | 2599 | 6075 | 2886 | 2278 |
| | 5700 | 7275 | 19400 | 35000 | 18025 | 29000 | 28000 | 13538 | 349 | 439 | 1721 | 1367 | 911 |
| Epsilon-CO | 6925 | 26250 | 26500 | 22850 | 21425 | 19400 | 19725 | 12263 | 2070 | 2261 | 3038 | 1671 | 4556 |
| (Δ181-185) | 9200 | 34000 | 26250 | 22350 | 34250 | 19200 | 22100 | 15600 | 8595 | 76275 | 4455 | 2582 | 3189 |

TABLE 54-continued

| Serial Killing Data: CD3+ T Cell Counts in Co-culture with Nalm6 Cell Line in Sextuplet | | | | | | | | | | | | | |
|---|---|---|---|---|---|---|---|---|---|---|---|---|---|
| Experimental | Round | | | | | | | | | | | | |
| Groups | 1 | 2 | 3 | 4 | 5 | 6 | 7 | 8 | 9 | 10 | 11 | 12 | 13 |
| | 11150 | 32750 | 35250 | 15100 | 26750 | 32750 | 19775 | 13050 | 923 | 1890 | 2025 | 1367 | 2278 |
| | 12400 | 38750 | 33500 | 13025 | 35500 | 25500 | 19225 | 16088 | 2711 | 7324 | 1418 | 759 | 2278 |
| | 11375 | 34000 | 17625 | 16175 | 32750 | 32000 | 23025 | 14325 | 1598 | 979 | 5063 | 1215 | 3645 |
| | 7900 | 26750 | 20800 | 17675 | 32750 | 24875 | 21500 | 13913 | 585 | 608 | 456 | 456 | 911 |
| Epsilon-CO | 3175 | 3250 | 7700 | 4225 | 38250 | 7000 | 12050 | 14250 | 878 | 945 | 1114 | 1519 | 2734 |
| (R183K) | 4975 | 4850 | 18375 | 26750 | 32500 | 17200 | 15075 | 9900 | 765 | 675 | 810 | 911 | 911 |
| | 5225 | 9725 | 33000 | 26250 | 33000 | 18300 | 17200 | 14325 | 641 | 945 | 2025 | 1367 | 3645 |
| | 8975 | 9400 | 39750 | 37750 | 21125 | 19025 | 22475 | 27300 | 15638 | 74925 | 13365 | 10328 | 8201 |
| | 5275 | 4625 | 28500 | 20475 | 27250 | 21125 | 34500 | 14363 | 259 | 574 | 1114 | 1671 | 4556 |
| | 4525 | 7325 | 27500 | 26250 | 31750 | 31000 | 198 | 4875 | 169 | 709 | 557 | 759 | 3189 |
| Epsilon-CO | 9000 | 23525 | 28250 | 18250 | 27250 | 27500 | 26000 | 9788 | 1069 | 1485 | 2430 | 1215 | 2734 |
| (S178N.R183K) | 13075 | 36500 | 20100 | 16800 | 35750 | 19950 | 21125 | 14850 | 1766 | 1384 | 1823 | 1823 | 2734 |
| | 16875 | 44250 | 16250 | 18500 | 33500 | 32500 | 38000 | 11363 | 2723 | 19305 | 11036 | 3645 | 3645 |
| | 18575 | 42750 | 22500 | 10225 | 35250 | 45500 | 33500 | 21225 | 698 | 878 | 2025 | 3341 | 1367 |
| | 13400 | 38750 | 23550 | 17750 | 41000 | 21175 | 26000 | 33225 | 28013 | 92138 | 35438 | 20959 | 4101 |
| | 9725 | 36000 | 27500 | 21500 | 29250 | 34750 | 34000 | 15375 | 405 | 270 | 810 | 456 | 456 |
| Zeta 1xx | 4850 | 4475 | 20450 | 28000 | 40750 | 30000 | 34000 | 38625 | 33413 | 102600 | 112388 | 61965 | 6379 |
| | 7225 | 9700 | 34500 | 29000 | 24950 | 25500 | 73500 | 36413 | 9698 | 14546 | 6176 | 20351 | 4101 |
| | 8375 | 14725 | 46250 | 32500 | 31250 | 41000 | 38000 | 41250 | 15075 | 30848 | 5974 | 14884 | 7746 |
| | 7850 | 20700 | 42750 | 33000 | 30000 | 42500 | 64000 | 32025 | 11183 | 39150 | 34223 | 60750 | 30071 |
| | 6525 | 8425 | 40750 | 35250 | 45500 | 25500 | 48000 | 26438 | 7740 | 6008 | 7088 | 1974 | 456 |
| | 6625 | 8250 | 26750 | 44000 | 26750 | 23850 | 74250 | 62250 | 60525 | 96188 | 22984 | 12758 | 30983 |

Example 11

As herein described, other ITAM-containing proteins were assessed that could replace CD3 Zeta as the signaling domain in an anti-CD19 second generation chimeric antigen receptor (CAR) and enhance the therapeutic potential of a CAR T-cell product. 5 new second-generation CAR constructs were designed that utilize one of five novel signaling domains, including CD3 Epsilon, CD3 Delta, CD3 Gamma and Dap12, as replacements for CD3 Zeta in a benchmark anti-CD19 control CAR. All were successfully transduced and expressed in primary human T cells. These new CAR constructs were characterized through in vitro assays and showed comparable CAR T-cell functionality. In vivo studies demonstrated superior tumor control, CAR expansion and persistence by the Epsilon-CO constructs when compared to the CD3 Zeta benchmark controls, demonstrating that anti-CD19 CARs utilizing the CD3 Epsilon signaling domain have enhanced efficacy in vivo. Here is shown that anti-CD19 CARs utilizing the CD3 Epsilon, Dap12, CD3 Delta or CD3 Gamma signaling domains demonstrated significantly improved tumor control in vivo compared to a benchmark anti-CD19 control CAR with the CD3 Zeta signaling domain.

Figure 3:
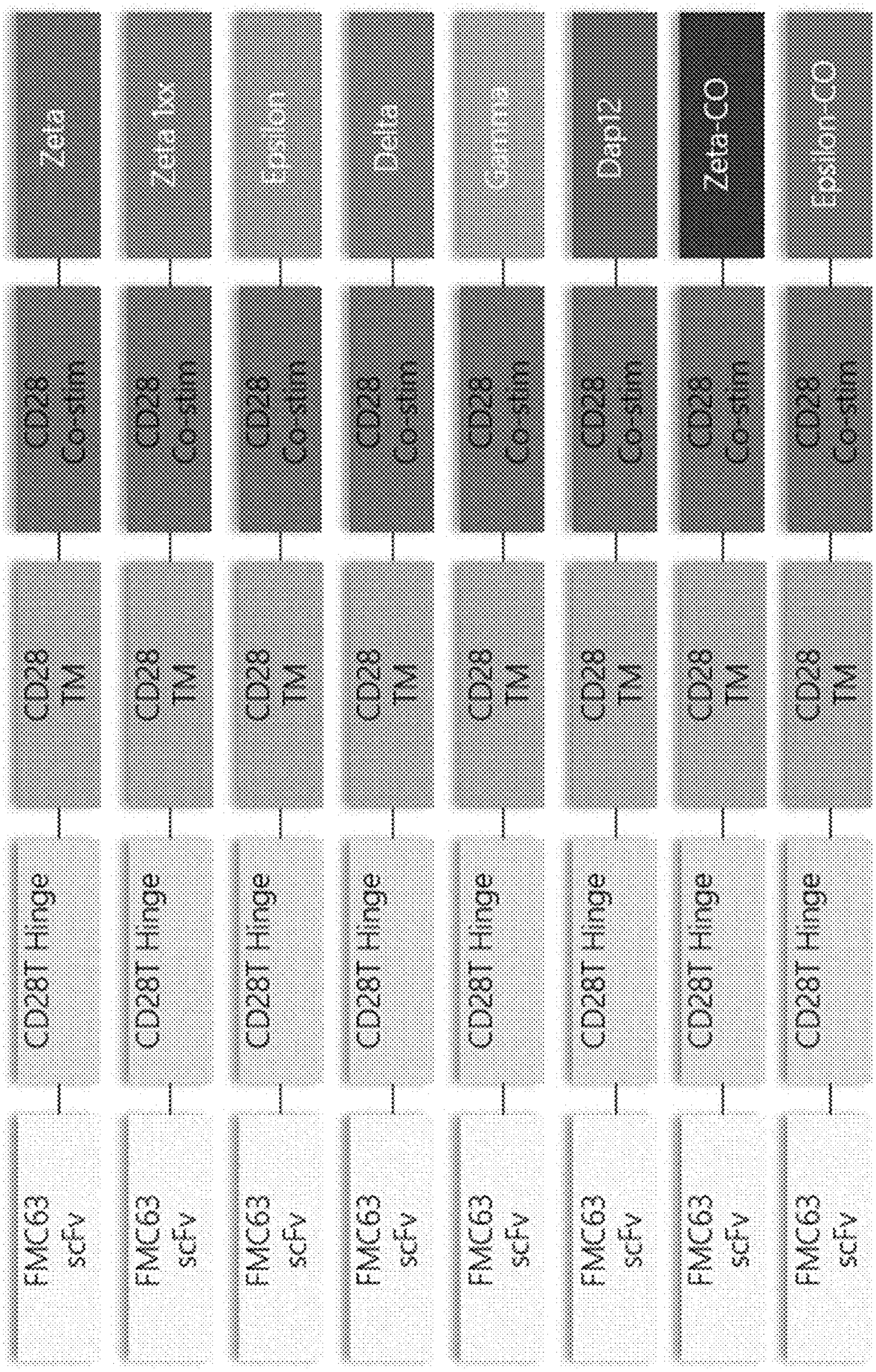
FIG. 3 illustrates embodiments of an anti-CD19 CAR with a signaling domain selected from the group consisting of Zeta, Zeta 1xx, Epsilon, Delta, Gamma, Dap12, codon optimized Zeta, and codon optimized Epsilon.

Construct Design. An anti-CD19 second generation chimeric antigen receptor (CAR), henceforth referred to as with sequence Zeta, ATGGCTCTGCCTGTGACCGCTCTGCTGTTGCCCCTTGCTTTACTCCTGCACGCCGCAA GACCCGACATCCAAATGACCCAAACCACCTCCTCCCTGAGCGCCTCCCTTGGAGAC CGAGTTACCATCTCCTGCCGAGCTTCTCAAGACATCTCCAAGTACTTGAATTGGTAT CAACAAAAGCCCGACGGAACCGTGAAGCTGCTGATCTACCACACATCCCGGCTGCA CTCTGGCGTTCCCTCAAGATTCTCCGGCTCTGGAAGCGGAACCGACTACTCCCTGAC CATCTCCAACCTGGAGCAAGAGGACATCGCTACCTACTTCTGCCAACAAGGCAACA CCCTGCCTTACACCTTCGGAGGAGGAACCAAGCTGGAGATCACCGGAAGCACAAGC GGATCTGGCAAGCCTGGAAGCGGAGAGGGAAGCACCAAGGGAGAGGTGAAGCTGC AAGAGAGCGGACCTGGATTGGTGGCCCCCTCACAATCCCTGAGCGTTACATGCACT GTGAGCGGCGTGTCCCTTCCTGACTACGGCGTTTCCTGGATCCGCCAACCTCCAAGA AAGGGACTGGAGTGGCTGGGAGTGATCTGGGGAAGCGAGACCACCTACTACAACTC CGCCCTGAAGAGCCGACTGACCATCATCAAGGACAACTCCAAGAGCCAAGTGTTCC TGAAGATGAACTCTCTCCAAACCGACGACACCGCTATCTACTACTGCGCTAAGCACT ACTACTACGGAGGAAGCTACGCTATGGACTACTGGGGACAAGGCACCTCTGTGACC GTCTCCTCTGCCGCCGCTCTGGACAACGAGAAGAGCAACGGAACCATCATCCACGT GAAGGGAAAGCACCTGTGCCCCTCTCCTCTGTTCCCTGGACCCTCCAAGCCTTTCTG GGTGCTCGTGGTGGTGGGAGGAGTGCTGGCTTGCTACTCCCTGCTTGTGACCGTGGC TTTCATCATCTTCTGGGTTAGAAGCAAGAGAAGCAGACTGCTGCACAGCGACTACA TGAACATGACCCCTAGAAGGCCCGGACCTACCAGAAAGCACTACCAGCCTTACGCT CCTCCTAGAGACTTCGCTGCTTACAGAAGCAGGGTGAAGTTCTCAAGAAGCGCTGA CGCTCCTGCTTACCAACAAGGCCAAAACCAACTGTACAACGAGCTGAACCTGGGAA GAAGAGAGGAATACGACGTCCTGGACAAGAGAAGAGGAAGAGACCCTGAGATGGG AGGAAAGCCAAGAAGAAAGAACCCTCAAGAGGGCCTGTACAACGAGCTGCAAAAG GACAAGATGGCTGAGGCTTACTCCGAGATCGGAATGAAGGGAGAGAGAAGAAGAG GAAAGGGACACGACGGACTGTACCAAGGCCTGAGCACCGCTACCAAGGACACCTA CGACGCTCTGCACATGCAAGCCCTGCCTCCTAGG (SEQ ID NO: 91) was used as the parental template to engineer and synthesize seven daughter constructs. These constructs are henceforth referred to as Zeta 1xx, Epsilon, Delta, Gamma, Dap12, Zeta-CO, and Epsilon-CO. To generate the daughter constructs, the CD3 Zeta signaling protein at nucleic acids 3316 to 3651 of the parental template were replaced with the following sequences (see FIG. 3);

```
Zeta 1 xx:
                                        (SEQ ID NO: 82)
CGGGTGAAGTTCTCAAGAAGCGCTGACGCTCCTGCTTACCAACAAGGCC

AAAACCAACTGTACAACGAGCTGAACCTGGGAAGAAGAGAGGAATACGA

CGTCCTGGACAAGAGAAGAGGAAGAGACCCTGAGATGGGAGGAAAGCCA

AGAAGAAAGAACCCTCAAGAGGGCCTGTTTAACGAGCTGCAAAAGGACA

AGATGGCTGAGGCTTTCTCCGAGATCGGAATGAAGGGAGAGAGAAGAAG

AGGAAAGGGACACGACGGACTGTTCCAAGGCCTGAGCACCGCTACCAAG

GACACCTTCGACGCTCTGCACATGCAAGCCCTGCCTCCTAGG

Epsilon:
                                        (SEQ ID NO: 53)
AAGAACCGGAAGGCCAAGGCCAAGCCTGTGACAAGAGGTGCTGGTGCTG

GCGGCAGACAGAGAGGCCAGAACAAAGAAAGACCTCCTCCTGTGCCTAA

TCCTGACTACGAGCCCATCCGGAAGGGCCAGAGAGATCTGTACAGCGGC

CTGAACCAGCGGCGGATT

Delta:
                                        (SEQ ID NO: 83)
GGACACGAAACAGGCAGACTTTCTGGCGCCGCTGATACACAGGCCCTGC

TGAGAAACGACCAGGTGTACCAGCCTCTGAGAGACAGAGATGACGCCCA

GTACTCTCACCTCGGCGGCAATTGGGCCAGAAACAAG

Gamma:
                                        (SEQ ID NO: 84)
GGACAGGATGGCGTCAGACAGAGCAGAGCCAGCGACAAGCAAACCCTGC

TGCCTAACGACCAGCTGTACCAGCCTCTGAAGGACAGAGAGGACGACCA

GTACAGCCATCTGCAGGGCAACCAGCTGCGGAGAAAC

Dap12:
                                        (SEQ ID NO: 85)
TACTTCCTGGGCAGACTGGTGCCTAGAGGAAGAGGAGCTGCTGAGGCTG

CTACCAGAAAGCAGAGAATCACCGAGACCGAGAGCCCTTACCAGGAGCT

GCAGGGACAGAGAAGCGACGTGTACAGCGACCTGAACACCCAGAGACCT

TACTACAAG

Zeta-CO:
                                        (SEQ ID NO: 86)
AGAGTTAAGTTCAGCAGGAGCGCCGACGCACCTGCCTACCAaCAAGGGC

AGAATCAACTGTACAACGAGCTGAACCTGGGCAGACGGGAGGAATACGA

TGTGCTGGACAAGAGGAGAGGCAGAGACCCCGAGATGGGCGGCAAACCT

AGAAGAAAGAACCCCCAGGAGGGCCTGTATAATGAGCTCCAGAAGGATA

AGATGGCCGAGGCCTACAGCGAGATCGGCATGAAGGGCGAAAGAAGAAG

AGGCAAGGGCCACGACGGCCTCTACCAGGGCTTAAGCACAGCTACTAAG

GACACCTACGACGCCCTGCACATGCAAGCTCTGCCCCCTAGA

Epsilon-CO:
                                        (SEQ ID NO: 54)
AAGAACCGCAAAGCAAAGGCAAAACCCGTCACACGAGGAGCGGGCGCAG

GGGGACGACAACGCGGTCAGAATAAGGAACGCCCGCCTCCAGTACCAAA
```

-continued

```
TCCAGATTATGAACCAATTCGGAAGGGACAACGCGATCTCTACTCCGGT

CTCAATCAGAGGCGAATT
```

Manufacturing of CAR T-Cell Products. Apheresis material from a healthy human donor was washed, incubated with anti-CD8 antibody-linked magnetic beads and processed using a CliniMACS® cell separation system (Miltenyi Biotech) per the manufacturer's instructions to enrich for CD8+ T cells, which were then cryopreserved. The resulting negative fraction was washed and processed as described above using anti-CD4 antibody-linked magnetic beads to enrich for CD4+ T cells, which were then cryopreserved. Isolated CD4+ and CD8+ primary human T cells were thawed in OpTmizer™ CTS T-cell expansion basal media supplemented with 2.6% OpTmizer™ CTS T-cell expansion supplement, 2.5% CTS immune cell serum replacement, 1% penicillin/streptomycin/L-glutamine, and 305 international units/mL human interleukin (IL)-2, henceforth referred to as complete OpTmizer™ media. T cells were resuspended in complete OpTmizer™ media containing 1.66 μg/mL of anti-CD28 antibody (clone 28.2) at a density of $1.5\times10^{6}$ cells/mL and then seeded into a T-75 flask pre-coated with 1.23 μg/mL anti-CD3 antibody (clone OKT3) to induce T-cell activation (Day 0). On Day 1 post-activation, cells were either transduced with an LVV encoding the parental anti-CD19 CAR or the daughter constructs Epsilon, Delta, Gamma, and Dap12 at an MOI of 20. Additional experimental groups consisting of the Zeta CO and Epsilon CO constructs were transduced at an MOI of 5 and a Non-transduced (NTD) sample served as a negative control. T cells were washed with complete OpTmizer™ media on Day 3, normalized and were expanded for an additional 4 days (Days 3 to 7). At the harvest time point (Day 7), cells were cryopreserved for future use. At multiple time points during expansion (Days 3 to 7), cell counts were taken using a Vi-CELL® and the cell density was normalized down to 0.5 to $1\times10^{6}$ cells/mL by addition of complete OpTmizer™ media. At these time points, average cell viability, diameter, and cell density were recorded on the Vi-CELL®.

CAR expression was measured by flow cytometry on days 6 and 7. T cells were stained with a panel of fluorophore-conjugated antibodies and characterized by flow cytometry to determine transduction efficiency, and CD4+/CD8+ T cell ratios. Assessment of CAR expression (anti-CD19 CAR) was enabled by fluorophore-conjugated KIP-1. A fixable cell viability dye allowed specific analysis of viable cells. Cells were stained by incubating with the appropriate antibody mix for 20 minutes at 4° C. followed by 2 washes with stain buffer, and subsequently fixed by incubating in 0.6% paraformaldehyde in phosphate-buffered saline or Hank's balanced salt solution for 10 minutes at room temperature. All flow cytometry data was collected on a FACS Canto instrument and data was analyzed using FlowJo software.

Day 0 Co-culture Setup. T-cell products manufactured from T cells derived from healthy donor apheresis were cryopreserved on the harvest day (Day 7 of manufacture). T-cell products were subsequently thawed and rested overnight in complete OpTmizer™ media before initiation of co-culture with target cells. Immediately before co-culture initiation, an aliquot of each T-cell sample was incubated with a panel of antibody-fluorophores and analyzed by flow cytometry to evaluate transduction efficiency. Total transduction efficiency was assessed using KIP-1, a custom-made antibody that binds the Whitlow linker between the heavy and light chains of the single-chain variable fragment (scFv). T cells were then labeled with CellTrace™ Violet (CTV) reagent and subsequently washed with R-10% media [RPMI-1640 media supplemented with 10% fetal bovine serum, penicillin streptomycin L-Glutamine, and HEPES]. A portion of the CTV-labeled samples was fixed and stored at 4° C. until day 4, when samples were analyzed in parallel with day 4 co-culture samples by flow cytometry to assess initial levels of CTV signal (CTV Max). T-cell products and luciferase-expressing target cells were plated together at different effector to target (E:T) ratios, ranging from 3:1 to 1:243, in R-10% media (Day 0 of co-culture). T-cell products were serially diluted 3-fold while the number of target cells per well was held constant at 20,000 cells. Positive target cells included Nalm6 (CD19+) and ST486 (CD19+). As a control, T-cell products were cultured in the absence of any target cells (i.e., T cells alone) to assess basal levels of T-cell function in the absence of antigen stimulation. Co-cultures were incubated at 37° C. for either 1 or 4 days and functional assessments were performed as described below.

Day 1 Cytotoxicity. T-cell mediated cytotoxicity was measured as a function of the reduction in target luciferase signal in co-culture wells compared to the signal emitted by target cells plated alone. On Days 1 and 4 after co-culture initiation, D-luciferin substrate was added to the co-culture wells at a final concentration of 0.14 mg/mL and plates were incubated at 37° C. in the dark for 10 minutes. Luminescent signal was read immediately after in a VarioSkan™ LUX or VarioSkan® Flash multimode microplate reader. T cell-mediated cytotoxicity was calculated as follows:

% Cytotoxicity=[1−luciferase signal of (sample of interest/target alone control)]*100.

Day 1 Cytokine Production. On Day 1 after co-culture initiation, supernatants were collected and analyzed for cytokine levels using the Meso Scale Discovery V-PLEX Pro inflammatory Panel 1 human kit according to the manufacturer's instructions. Specifically, supernatants from the co-cultures of T-cell products plated at the 1:1 E:T ratio with antigen-expressing Nalm6 and ST486 were analyzed for levels of interferon gamma (IFN-γ), IL-2, and tumor necrosis factor alpha (TNF-α) secretion mediated by antigen engagement. Supernatants from T cells cultured in the absence of target cells (T cells alone) were analyzed in parallel to assess basal levels of cytokine production in the absence of antigen. All samples were diluted to be within the range of detection.

Day 4 Proliferation. On Day 4 after co-culture initiation, T-cell products plated at the 1:1 E:T ratio with target cells were harvested, stained with a panel of antibody-fluorophores to identify T cells, and analyzed by flow cytometry. The proliferative capacity of the T-cell products was determined by flow cytometric analysis of the cell division-driven dilution of CTV dye in response to antigen-expressing target cells compared with that of T-cell products that had been cultured alone (T cells alone), which was used to assess basal levels of homeostatic proliferation in the absence of stimuli. CTV-labeled T cells which were fixed on the day of co-culture setup (CTV Max) were analyzed by flow cytometry in parallel to assess the intensity of the initial CTV signal prior to cell proliferation.

In vivo Study (Dosage 1-Dosage 2-Dosage 3). Anti-CD19 product CAR T cells and NTD cells were prepared and frozen cells in cryovials were shipped on dry ice. Upon receipt, the cryovials were stored in liquid nitrogen. The day before injection, the vials were removed from cryostorage, thawed in a 37° C. water bath, and cells were resuspended in prewarmed, complete OpTmizer™ media containing 305 international units (IU)/mL interleukin (IL)-2. The cell suspensions were centrifuged at 400×g for 5 minutes at room temperature and the supernatant was aspirated and discarded. The cell pellets were then resuspended in complete OpTmizer™ media and 305 IU/mL IL-2 and an aliquot of the cell suspension was analyzed for cell counting and viability using a Vi-CELL® BLU automated cell counter by trypan blue dye exclusion method. The cells were then resuspended at 2.0-5.0×$10^6$ cells/mL in complete OpTmizer™ media and 305 IU/mL IL-2, transferred in culture flasks and cultured overnight in a 37° C./5% $CO_2$ incubator. On the day of injection, after resuspending the cells, an aliquot of each condition was counted using a Vi-CELL® BLU automated cell counter to determine the cell concentration and the pre-injection viability of the cells. The cell suspensions were then centrifuged at 400×g for 5 minutes at 4° C. The supernatants were aspirated and discarded, and the cell pellets were resuspended in cold PBS. Following the studies, different CAR T cell doses were tested:

For Dosage 1:1 dose of 1.0×$10^7$ CAR+ cells per group,
For Dosage 2:1 dose of 2.0×$10^6$ CAR+ cells per group,
For Dosage 3:3 doses of CAR+ cells per group: 1.0×$10^6$, 2.0×$10^5$ or 4.0×$10^4$.

Treatment Groups and Dose Normalization. For each study, the same total number of T cells were administered to mice in each of the treatment groups. The doses administered to each treatment group were normalized to deliver the same total number of T cells for each group based on the anti-CD19 CAR transduction efficiency.

In Vivo Bioluminescence Imaging. In vivo BLI was performed using an IVIS Lumina S5 optical imaging system (Xenogen, Alameda, CA). Five animals were imaged at a time under approximately 1% to 2% isoflurane gas anesthesia. Each mouse was injected intraperitoneally (IP) with 150 mg/kg D-luciferin and imaged in the prone position 15 minutes after the injection. Medium binning of the charge-coupled device (CCD) chip was used, and the exposure time was adjusted (2 seconds to 2 minutes) to obtain at least several hundred counts from the disseminated tumors that were observable in each mouse in the image and to avoid saturation of the CCD chip. BLI images were collected twice a week. Images were analyzed using the Living Image software version 4.7.3 (Xenogen, Alameda, CA). Whole body fixed-volume regions of interest (ROI) were placed on prone images for each individual animal and labeled based on animal identification. Total flux (photons/second) was calculated and exported for all ROIs.

Ex Vivo ddPCR and Flow Cytometry Analysis. A weekly blood volume of 100 μL was collected via the retro-orbital sinus in EDTA-coated tubes and was either directly frozen for subsequent ddPCR analysis or processed to be analyzed by flow cytometry. Animals were sampled starting 24 hours after T-cell injection and continued weekly throughout the duration of the study. For ddPCR, genomic DNA purification from whole blood was performed using KingFisher™ Flex (small volume) per the manufacturer's instructions, ddPCR was then performed on the purified DNA via internal Kite protocols and Bio-Rad instrumentation. For flow cytometry analysis, whole blood was stained using fluorochrome-conjugated antibodies following internal Kite protocols and then analyzed on a flow cytometer. Absolute cell counts in blood were obtained using CountBright™ Absolute Counting Beads for flow cytometry.

In vivo Study (Dosage 1). This study evaluated the potential antigen-independent T-cell expansion in vivo and functionality of persisting CAR T cells. Change in body weight at various time points from the initial value at start of treatment is summarized in Table 62. All mice from all groups gained body weight over time until Day 49 consistent with the absence of toxicity. At Day 49, 4 mice from each group (except the Epsilon-CO group) were euthanized for ex vivo analysis and on Day 50, the other 4 mice from each group were implanted with Nalm6-luc MHC I/II double knock out (DKO) tumor cells ($5.0\times10^5$ in 100 µL intravenously (IV)) and body weight change for all remaining mice was recorded until the end of the study on Day 85. From Day 50 to Day 85, mice from the Epsilon-CO group showed body weight gain until the end of the study but mice from Vehicle, NTD and Zeta-CO groups had a decreased body weight change related to tumor burden as mice reached the study end point by Day 70.

Tumor burden was evaluated through BLI measurements at various time points (Table 63). Bioluminescence imaging (BLI) for each experimental group is summarized in Table 63. The Vehicle control group or groups that received either NTD cells or Zeta-CO CAR T cells on Day 0 showed no tumor control and were euthanized due to high tumor burden by Day 70 post-T cell infusion (Day 20 post-tumor cell implantation). Only the Epsilon-CO group showed no tumor growth until termination of the study on Day 85 (35 days post-tumor cell implantation), demonstrating that the Epsilon-CO CAR T cells persisted and maintained their functionality and anti-tumor potency in the absence of antigen for 50 days and were able to efficiently clear tumor burden thereafter, significantly improving tumor control compared to Zeta CO benchmark control.

TABLE 62

| DAYS POST T CELL INFUSION | VEHICLE | | | | | | | | NTD | | | | | | | |
|---|---|---|---|---|---|---|---|---|---|---|---|---|---|---|---|---|
| 5 | −3.2 | −5.5 | 4 | 0.5 | 2.1 | 3.5 | −8.1 | 2.1 | 2.7 | 2.7 | 0.5 | 0.5 | 4.2 | 2.5 | 2 | 3.3 |
| 8 | 4.9 | 2.5 | 2 | 1.4 | 4.7 | 0.5 | −4.5 | 3.2 | 3.2 | 3.2 | 0.5 | −1 | 4.2 | 2 | −1 | 1.6 |
| 11 | 12.4 | 0.5 | 6.5 | 3.8 | 6.8 | 2.5 | −2 | 8.5 | 5.9 | 6.5 | 3.6 | 6.2 | 7.3 | 5 | 5.4 | 4.3 |
| 13 | 13 | 5.5 | 6 | 4.3 | 9.5 | 1 | −2 | 9.6 | 5 | 7.5 | 3.6 | 5.2 | 9.4 | 5 | 6.4 | 4.9 |
| 15 | 11.9 | 9 | 9.5 | 4.3 | 9.5 | 7.1 | 16.2 | 13.8 | 6.4 | 10.8 | 5.9 | 8.8 | 9.9 | 7 | 7.8 | 9.2 |
| 22 | 11.4 | 12.6 | 10.1 | 13.5 | 15.3 | 15.2 | 3 | 18.6 | 7.8 | 12.9 | 10.4 | 13.5 | 9.9 | 13.6 | 12.7 | 21.7 |
| 27 | 11.9 | 10.1 | 10.1 | 11.5 | 17.9 | −1 | 9.6 | 13.8 | 8.2 | 13.4 | 9 | 10.9 | 14.7 | 11.1 | 11.3 | 21.7 |
| 29 | 16.8 | 11.6 | 12.6 | 15.9 | 21.6 | 14.1 | 5.6 | 19.1 | 12.3 | 16.1 | 14 | 16.6 | 13.1 | 13.1 | 11.3 | 25 |
| 33 | 13.5 | 12.6 | 12.1 | 14.9 | 22.6 | 10.1 | 6.1 | 18.6 | 13.7 | 15.6 | 11.7 | 17.6 | 13.1 | 13.1 | 11.3 | 16.8 |
| 36 | 14.1 | 13.1 | 10.6 | 13.9 | 22.6 | 11.1 | 7.1 | 19.7 | 13.2 | 15.1 | 12.2 | 16.6 | 12 | 13.1 | 9.8 | 16.8 |
| 42 | 11.4 | 15.6 | 16.1 | 13.5 | 23.7 | 13.6 | 10.1 | 21.3 | 16.9 | 18.3 | 15.3 | 18.7 | 18.3 | 15.6 | 13.2 | 14.1 |
| 48 | 20 | 15.6 | 15.1 | 20.2 | 25.3 | 14.1 | 6.1 | 19.1 | 14.2 | 18.8 | 11.3 | 20.7 | 17.8 | 13.6 | 13.2 | 14.1 |
| 56 | | | | | 28.4 | 21.2 | 5.6 | 22.3 | | | | | 15.7 | 15.6 | 17.6 | 16.8 |
| 64 | | | | | 26.8 | 22.7 | 5.6 | 19.7 | | | | | 15.2 | 15.6 | 12.7 | 19.6 |
| 70 | | | | | 23.7 | 16.2 | 3 | 17 | | | | | 13.6 | 12.6 | 15.2 | 16.8 |
| 80 | | | | | | | | | | | | | | | | |
| 85 | | | | | | | | | | | | | | | | |
| **DAYS POST T CELL INFUSION** | **ZETA-CO** | | | | | | | | **EPSILON-CO** | | | | | | | |
| 5 | −5.7 | −2.5 | 1.6 | −4 | 0 | 2 | −1 | 0 | −6.1 | −3.1 | −2 | 0 | −4.3 | 1.9 | 2 | 6.9 |
| 8 | 3.1 | −0.5 | 8.6 | 0.5 | 2.5 | −11.6 | −10 | −12.6 | 0.4 | −1 | −1.9 | −1 | 1.2 | 0.5 | −4 | 6.5 |
| 11 | −4.1 | −0.5 | 10.2 | 2.5 | 3.5 | −10.6 | −0.5 | −1.5 | 4 | 2.5 | 2.4 | 1 | 7.1 | 6.4 | 5.5 | 12.9 |
| 13 | −1.6 | 0.5 | 10.8 | 2 | 9.1 | −7 | −3 | 2.5 | 6.2 | 2.5 | 2.9 | 2 | 10 | 5.4 | 4 | 13.9 |
| 15 | 4.7 | 0.5 | 10.2 | 6 | 14.1 | 4 | 3 | 7.6 | 7.5 | 3 | 2.9 | 6.1 | 11.2 | 8.4 | 6.5 | 17.4 |
| 22 | 11.4 | 1 | 19.9 | 11.6 | 16.2 | 9 | 5 | 12.1 | 14.1 | 7.6 | 7.7 | 7.6 | 17.1 | 12.3 | 11.9 | 20.9 |
| 27 | 7.3 | −2 | 18.8 | 4.5 | 15.7 | 14.6 | 9.5 | 8.1 | 12.3 | 10.1 | 8.7 | 12.6 | 15.3 | 11.8 | 12.4 | 24.4 |
| 29 | 11.9 | 3.5 | 22 | 8 | 17.2 | 14.1 | 8.5 | 16.7 | 13.7 | 11.6 | 9.2 | 14.6 | 22.4 | 13.8 | 13.9 | 11.9 |
| 33 | 6.7 | 3.5 | 17.2 | 9 | 14.6 | 13.6 | 6.5 | 17.7 | 13.2 | 13.1 | 10.1 | 12.1 | 22.9 | 14.3 | 13.4 | 11.9 |
| 36 | 4.7 | 4 | 15.6 | 8 | 15.7 | 14.1 | 5 | 18.7 | 12.3 | 14.1 | 8.2 | 13.1 | 27.1 | 16.3 | 12.9 | 14.4 |
| 42 | 10.9 | 6 | 16.1 | 12.1 | 18.2 | 14.6 | 6.5 | 22.7 | 14.5 | 16.2 | 9.2 | 9.1 | 25.3 | 15.8 | 13.9 | 20.9 |
| 48 | 8.3 | 5.5 | 17.2 | 11.1 | 20.2 | 8.5 | 8.5 | 22.7 | 18.5 | 12.6 | 13 | 11.6 | 26.5 | 16.3 | 15.4 | 6.5 |
| 56 | | | | | 12.1 | 13.6 | 11 | 21.2 | 21.1 | 16.2 | 15.5 | 21.7 | 27.6 | 25.1 | 21.9 | 11.9 |
| 64 | | | | | 7.1 | 10.6 | 7 | 12.6 | 19.8 | 12.1 | 15.5 | 16.7 | 31.2 | 18.7 | 9.5 | 15.4 |
| 70 | | | | | 7.6 | 11.1 | 6.5 | 14.6 | 18.9 | 11.1 | 16.4 | 16.2 | 32.4 | 21.2 | 9.5 | 14.4 |
| 80 | | | | | | | | | 18.5 | 13.6 | 15.0 | 18.2 | 34.7 | 25.6 | 11.9 | 20.9 |
| 85 | | | | | | | | | 19.8 | 12.6 | 14.0 | 16.2 | 35.9 | 26.6 | 12.9 | 22.4 |

TABLE 63

| DAYS POST T CELL INFUSION | VEHICLE | | | | NTD | | | |
|---|---|---|---|---|---|---|---|---|
| 56 | 1.64E+06 | 1.64E+06 | 1.39E+06 | 1.92E+06 | 1.67E+06 | 1.53E+06 | 1.29E+06 | 1.02E+06 |
| 60 | 3.08E+07 | 4.13E+07 | 2.87E+07 | 1.85E+07 | 3.86E+07 | 2.04E+07 | 2.29E+07 | 3.55E+07 |
| 67 | 7.01E+09 | 6.49E+09 | 5.63E+09 | 9.02E+09 | 4.68E+09 | 6.05E+09 | 6.97E+09 | 6.53E+09 |
| 70 | 1.56E+10 | 2.06E+10 | 9.75E+09 | 1.65E+10 | 1.80E+10 | 1.41E+10 | 1.15E+10 | 1.32E+10 |
| 81 | | | | | | | | |
| 85 | | | | | | | | |
| **DAYS POST T CELL INFUSION** | **ZETA-CO** | | | | **EPSILON-CO** | | | |
| 56 | 1.57E+06 | 1.72E+06 | 1.19E+06 | 1.22E+06 | 7.20E+05 | 7.64E+05 | 9.01E+05 | 7.34E+05 |
| 60 | 2.12E+07 | 8.97E+06 | 2.17E+07 | 2.80E+07 | 8.50E+05 | 8.22E+05 | 7.74E+05 | 9.29E+05 |
| 67 | 3.36E+09 | 4.02E+09 | 5.87E+09 | 3.91E+09 | 7.29E+05 | 7.71E+05 | 6.80E+05 | 6.34E+05 |
| 70 | 1.25E+10 | 1.09E+10 | 1.29E+10 | 1.13E+10 | 7.38E+05 | 8.04E+05 | 8.00E+05 | 5.38E+05 |
| 81 | | | | | 6.50E+05 | 7.19E+05 | 6.75E+05 | 5.52E+05 |
| 85 | | | | | 6.84E+05 | 6.51E+05 | 6.59E+05 | 7.65E+05 |

Ex Vivo Flow Cytometry Analysis. To assess CAR T-cell expansion and persistence in vivo, peripheral blood was analyzed via flow cytometry for number of $CD3^{+}CAR^{+}$ cells/μL of blood over time (Table 64). Zeta-CO group exhibited no CAR T-cell expansion in the peripheral blood of mice as $CD3^{+}CAR^{+}$ cells decreased steadily to reach <1 cell/μL after Day 20. However, Epsilon-CO group demonstrated sustained CAR T-cell persistence until Day 62-76 after which 3 mice out of 4 started to show declined numbers of CAR T cells in the blood (Table 64).

TABLE 64

| DAYS POST T CELL INFUSION | G1. VEHICLE | | | | | | | |
|---|---|---|---|---|---|---|---|---|
| 7 | 0.000 | 0.000 | 0.000 | 0.000 | 0.000 | 0.000 | | |
| 13 | 0.000 | 0.000 | 0.000 | 0.000 | 0.000 | 0.000 | 0.000 | 0.000 |
| 20 | 0.000 | 0.000 | 0.000 | 0.000 | 0.000 | 0.000 | 0.000 | 0.000 |
| 27 | 0.000 | 0.000 | 0.000 | 0.000 | 0.000 | 0.000 | 0.000 | 0.000 |
| 34 | 0.000 | | 0.000 | 0.000 | | 0.000 | | 0.000 |
| 48 | | | | | | 0.000 | 0.000 | 0.000 |
| 62 | | | | | | | | |
| 76 | | | | | | | | |
| 90 | | | | | | | | |
| **DAYS POST T CELL INFUSION** | **G2. NTD** | | | | | | | |
| 7 | 0.347 | 0.175 | 0.825 | 0.000 | 0.114 | 0.000 | 0.120 | 0.369 |
| 13 | 0.170 | 0.109 | 0.373 | 0.000 | 0.420 | 0.086 | 0.144 | 0.354 |
| 20 | 0.000 | 0.000 | 0.385 | 0.000 | 0.274 | 0.204 | 0.000 | 0.126 |
| 27 | 0.000 | 0.000 | 0.000 | 0.000 | 0.131 | 0.000 | 0.000 | 0.184 |
| 34 | 0.000 | 0.000 | | 0.467 | | 0.261 | | 0.403 |
| 48 | 0.094 | 0.000 | | | 0.000 | | | 0.000 |
| 62 | | | | | | | | |
| 76 | | | | | | | | |
| 90 | | | | | | | | |
| **DAYS POST T CELL INFUSION** | **G3. ZETA-CO** | | | | | | | |
| 7 | 35.534 | 17.402 | 28.549 | 20.086 | 22.085 | 27.287 | 22.490 | 19.594 |
| 13 | 23.963 | 4.346 | 2.759 | 6.972 | 3.752 | 10.656 | 9.974 | 11.073 |
| 20 | 5.220 | 1.600 | 0.806 | 1.922 | 0.503 | 2.251 | 3.056 | 2.893 |
| 27 | 0.450 | 0.716 | 0.613 | 0.405 | 1.342 | 0.164 | 0.131 | 0.191 |
| 34 | 0.124 | 0.225 | | | 0.140 | | | |
| 48 | | | | 0.000 | | | | 0.000 |
| 62 | | | | | | | | |
| 76 | | | | | | | | |
| 90 | | | | | | | | |
| **DAYS POST T CELL INFUSION** | **G4. EPSILON-CO** | | | | | | | |
| 7 | 23.241 | 42.539 | 36.782 | 30.664 | 50.756 | 46.322 | 29.184 | |
| 13 | 18.441 | 39.762 | 27.582 | 13.122 | 13.798 | 21.930 | 24.618 | |
| 20 | 15.903 | 12.763 | 7.976 | | 9.984 | 28.934 | 7.763 | |

TABLE 64-continued

| | | | | | | | |
|---|---|---|---|---|---|---|---|
| 27 | 21.538 | 14.389 | 37.939 | 47.398 | 59.796 | 40.141 | 45.476 |
| 34 | 14.514 | 21.238 | 12.328 | 16.891 | 152.486 | 20.150 | 50.277 |
| 48 | 20.212 | 52.309 | 24.140 | 11.335 | 19.689 | 10.574 | 22.921 |
| 62 | 17.946 | 44.988 | 21.224 | 6.286 | | | |
| 76 | 17.039 | 13.121 | 32.051 | 6.270 | | | |
| 90 | 6.683 | 1.744 | 16.380 | 22.514 | | | |

In vivo Study (Dosage 2). This study evaluated the persistence and anti-tumor efficacy of Epsilon-CO CAR T cells after multiple tumor rechallenges with Nalm6 MHC I/II DKO cells. Change in body weight at various time points from the initial value at start of treatment is summarized in Table 65. All CAR T cells were well tolerated with animals maintaining consistent body weight for the duration of the study. The BLI for each experimental group is summarized in Table 66. The Vehicle and NTD groups showed no tumor control and were euthanized due to high tumor burden by Day 21. Zeta-CO groups either after 1 initial tumor implantation at Day 0 or after 4 subsequent tumor rechallenges with Nalm6 MHC I/II DKO at Day 21, 28, 35 and 42, showed comparable efficacy: tumor control up to Day 20 followed by tumor relapse until euthanasia by Day 47 due to high tumor burden. In contrast, Epsilon-CO groups either after 1 initial tumor implantation at Day 0 or after 5 subsequent tumor rechallenges with Nalm6 MHC I/II DKO at Day 21, 28, 35, 42 and 63, maintained complete tumor clearance until termination of the study on Day 84, demonstrating that these cells significantly improved tumor control compared to Zeta CO benchmark control.

TABLE 65

| DAYS POST TUMOR INOCULATION | VEHICLE | | | | | NTD | | | | | ZETA-CO | | | | | EPSILON-CO | | | | |
|---|---|---|---|---|---|---|---|---|---|---|---|---|---|---|---|---|---|---|---|---|
| 7 | 1.9 | 1.9 | 2 | 3.5 | 1 | 1.7 | 1.4 | 1.3 | 4.8 | −0.5 | 1.5 | −0.9 | 0.5 | 0 | 1 | −7.8 | 5.2 | 4.4 | 2.4 | 0.4 |
| 11 | 3.7 | 4.8 | 7.6 | 8.9 | −1.9 | 8.7 | 11.8 | 2.2 | 8.7 | 3.9 | 2 | −6.5 | 7 | 4.9 | 2.5 | −1.3 | 10.3 | 9.2 | 8.2 | 4 |
| 14 | 8.4 | 5.2 | 10.6 | 9.4 | 0 | 5.7 | 9.1 | 0 | 8.7 | 4.3 | 0.5 | −4.1 | 8 | 7.4 | 15.2 | 0.4 | 13.4 | 9.7 | 9.7 | 4.8 |
| 18 | 7 | 8.1 | 12.6 | 11.4 | −3.4 | −3.9 | 4.5 | −0.4 | 8.2 | 4.8 | 4.4 | −2.3 | 10.4 | 10.3 | 15.7 | 5.2 | 19.6 | 12.6 | 8.2 | 4 |
| 21 | | | | | | | | | | | 2.9 | 1.8 | 9.5 | 8.4 | 7.6 | −1.3 | 17.5 | 11.7 | 9.2 | 2.6 |
| 24 | | | | | | | | | | | 7.3 | 0.5 | 14.9 | 13.3 | 18.2 | −1.3 | 19.6 | 15.5 | 15 | 5.7 |
| 28 | | | | | | | | | | | 7.3 | 0.5 | 14.9 | 13.3 | 18.2 | −1.3 | 19.6 | 15.5 | 15 | 5.7 |
| 32 | | | | | | | | | | | 6.8 | 0 | 13.4 | 13.3 | 15.2 | −1.3 | 17 | 18 | 14 | 4 |
| 35 | | | | | | | | | | | 6.3 | −0.9 | 14.4 | 13.3 | 13.6 | −2.2 | 15.5 | 17 | 14.5 | 4.8 |
| 41 | | | | | | | | | | | 6.3 | 4.1 | 10.9 | 9.9 | 19.7 | −4.3 | 17 | 17.5 | 13 | 4.4 |
| 47 | | | | | | | | | | | 7.3 | 2.3 | 7 | 13.8 | 5.1 | 5.7 | 14.9 | 16 | 9.7 | 1.3 |
| 55 | | | | | | | | | | | | | | | | 1.3 | 20.6 | 18 | 18.4 | 2.6 |
| 67 | | | | | | | | | | | | | | | | −5.7 | 13.4 | 11.7 | 10.6 | 1.3 |
| 77 | | | | | | | | | | | | | | | | −5.7 | 14.9 | 16 | 9.7 | 1.3 |
| 84 | | | | | | | | | | | | | | | | −4.3 | 16 | 18 | 11.1 | 1.8 |

| DAYS POST TUMOR INOCULATION | ZETA-CO TUMOR RECHALLENGE | | | | | | | | | EPSILON-CO TUMOR RECHALLENGE | | | | | | | | |
|---|---|---|---|---|---|---|---|---|---|---|---|---|---|---|---|---|---|---|
| 7 | 2 | −2.9 | −5.9 | −10.2 | −1.9 | 4.3 | 1 | −5.6 | 2 | 0.9 | −5.5 | −0.9 | 8.3 | 0.5 | −1 | 1 | −6.8 | 0.4 |
| 11 | 20.7 | 1 | 0.5 | −7.1 | 6.1 | 2.9 | 12.6 | 4.2 | 1 | 3.3 | −3.7 | −1.8 | 11.5 | −3.9 | 3.8 | 4.9 | 5.1 | 1.7 |
| 14 | 21.7 | 2.9 | 7.9 | −5.3 | 8.5 | 7.2 | 17.8 | 0 | 7.9 | 9.4 | −5.1 | −4.1 | 16.1 | −1.5 | 6.7 | 8.3 | 6.8 | 0.9 |
| 18 | 19.7 | 6.3 | 4.4 | −5.3 | 10.8 | 12.6 | 20.9 | 0.5 | 10.4 | 11.7 | −4.1 | −2.3 | 13.8 | 0 | 3.8 | 9.7 | 10.7 | 1.3 |
| 21 | 22.2 | 4.8 | 4.9 | −3.1 | 9.9 | 6.8 | 19.4 | −3.7 | 11.4 | 9.9 | −3.7 | −6 | 11.5 | 1 | 4.3 | 7.8 | 11.1 | 0 |
| 24 | 27.3 | 10.1 | 9.4 | −1.3 | 14.6 | 9.7 | 23.6 | 2.8 | 16.3 | 13.1 | −0.9 | −1.4 | 12.4 | 26.6 | 1.9 | 9.2 | −2.1 | 7.7 |
| 28 | 27.3 | 10.1 | 9.4 | −1.3 | 14.6 | 9.7 | 23.6 | 2.8 | 16.3 | 13.1 | −0.9 | −1.4 | 12.4 | 26.6 | 1.9 | 9.2 | −2.1 | 7.7 |
| 32 | 22.2 | 8.2 | 5.9 | −0.9 | 11.8 | 6.3 | 20.4 | −2.8 | 11.9 | 12.2 | −4.1 | −4.1 | 11.5 | 21.7 | −1.9 | 8.3 | −5.1 | 4.7 |
| 35 | 22.7 | 8.7 | 6.4 | −0.4 | 11.3 | 6.3 | 21.5 | −2.8 | 12.9 | 12.7 | −3.2 | −3.7 | 12.4 | 20.2 | −1.9 | 9.2 | −3 | 3.8 |
| 41 | 21.7 | 10.1 | 5.4 | 1.8 | 9.9 | 5.8 | 22.5 | −6.9 | 13.9 | 13.1 | −1.4 | −0.5 | 12.8 | 23.6 | 0.5 | 9.7 | −6 | 9.4 |
| 47 | 12 | 3.9 | −0.9 | 6.1 | 4.3 | 22.5 | −8.8 | 12.4 | 12.2 | 0.5 | 0.9 | 13.8 | 23.6 | 5.8 | 8.3 | −7.7 | 8.9 | |
| 55 | | | | | | | | | | 13.6 | 4.1 | 3.7 | 23.9 | 28.1 | 6.3 | 10.7 | −2.6 | 14.9 |
| 67 | | | | | | | | | | 10.3 | 1.4 | 1.4 | 14.7 | 22.7 | 6.7 | 8.3 | −6 | 9.8 |
| 77 | | | | | | | | | | 12.2 | 0.5 | 0.9 | 13.8 | 23.6 | 5.8 | 8.3 | −7.7 | 8.9 |
| 84 | | | | | | | | | | 12.2 | 1.4 | 1.4 | 13.8 | 23.2 | 7.2 | 7.8 | −7.3 | 9.4 |

TABLE 66

| DAYS POST TUMOR INOCULATION | VEHICLE | | | | | NTD | | | | |
|---|---|---|---|---|---|---|---|---|---|---|
| 7 | 2.32E+06 | 1.97E+06 | 3.44E+06 | 2.18E+06 | 3.01E+06 | 2.68E+06 | 1.95E+06 | 2.18E+06 | 2.50E+06 | 1.61E+06 |
| 11 | 2.78E+08 | 1.58E+08 | 1.20E+08 | 2.25E+08 | 2.66E+08 | 3.42E+08 | 4.07E+08 | 2.05E+08 | 2.56E+08 | 1.46E+08 |
| 14 | 2.67E+09 | 1.09E+09 | 2.96E+09 | 2.57E+09 | 2.55E+09 | 1.68E+09 | 2.27E+09 | 7.29E+09 | 1.94E+09 | 1.52E+09 |

TABLE 66-continued

| | | | | | | | | | | |
|---|---|---|---|---|---|---|---|---|---|---|
| 18 | 1.28E+10 | 9.95E+09 | 1.20E+10 | 1.27E+10 | 1.02E+10 | 1.04E+10 | 1.09E+10 | 1.08E+10 | 1.15E+10 | 1.01E+10 |
| 21 | 2.04E+10 | 1.61E+10 | 2.74E+10 | 1.79E+10 | 1.68E+10 | 1.08E+10 | 2.08E+10 | 2.17E+10 | 2.14E+10 | 1.38E+10 |
| 24 | | | | | | | | | | |
| 28 | | | | | | | | | | |
| 32 | | | | | | | | | | |
| 5 | | | | | | | | | | |
| 42 | | | | | | | | | | |
| 47 | | | | | | | | | | |
| 53 | | | | | | | | | | |
| 59 | | | | | | | | | | |
| 63 | | | | | | | | | | |
| 67 | | | | | | | | | | |
| 79 | | | | | | | | | | |
| 84 | | | | | | | | | | |

| DAYS POST TUMOR INOCULATION | ZETA-CO | | | | | EPSILON-CO | | | | |
|---|---|---|---|---|---|---|---|---|---|---|
| 7 | 1.96E+06 | 2.01E+06 | 2.22E+06 | 2.05E+06 | 2.14E+06 | 1.51E+06 | 1.19E+06 | 1.47E+06 | 1.65E+06 | 1.70E+06 |
| 11 | 6.47E+05 | 7.03E+05 | 6.01E+05 | 6.09E+05 | 6.69E+05 | 6.75E+05 | 8.17E+05 | 7.74E+05 | 8.26E+05 | 6.95E+05 |
| 14 | 7.75E+05 | 9.77E+05 | 7.36E+05 | 9.10E+05 | 7.98E+05 | 7.23E+05 | 7.31E+05 | 8.45E+05 | 7.31E+05 | 7.21E+05 |
| 18 | 8.23E+05 | 8.35E+05 | 8.70E+05 | 8.36E+05 | 2.47E+06 | 8.58E+05 | 6.55E+05 | 7.95E+05 | 8.33E+05 | 8.11E+05 |
| 21 | 8.07E+05 | 7.83E+05 | 9.87E+05 | 8.89E+05 | 3.86E+06 | 8.29E+05 | 9.84E+05 | 8.56E+05 | 8.59E+05 | 7.72E+05 |
| 24 | 7.90E+05 | 8.21E+05 | 8.11E+05 | 1.28E+06 | 1.46E+07 | 7.12E+05 | 5.54E+05 | 6.01E+05 | 8.23E+05 | 6.39E+05 |
| 28 | 1.25E+06 | 1.49E+06 | 1.24E+06 | 3.40E+06 | 5.80E+06 | 1.01E+06 | 1.12E+06 | 1.01E+06 | 1.13E+06 | 9.30E+05 |
| 32 | 1.02E+06 | 1.12E+06 | 1.09E+06 | 2.49E+07 | 1.18E+06 | 7.05E+05 | 7.67E+05 | 7.52E+05 | 7.99E+05 | 7.23E+05 |
| 35 | 1.67E+06 | 2.01E+06 | 4.60E+06 | 2.52E+08 | 4.62E+06 | 1.20E+06 | 1.19E+06 | 1.21E+06 | 1.34E+06 | 1.37E+06 |
| 42 | 1.11E+08 | 6.48E+07 | 6.33E+09 | 1.25E+08 | 9.50E+07 | 6.40E+05 | 6.38E+05 | 7.19E+05 | 6.33E+05 | 5.45E+05 |
| 47 | 6.82E+08 | 2.24E+08 | 1.17E+10 | 2.85E+08 | 9.46E+08 | 8.46E+05 | 7.80E+05 | 7.05E+05 | 8.30E+05 | 6.76E+05 |
| 53 | | | | | | 6.79E+05 | 7.08E+05 | 6.65E+05 | 7.23E+05 | 7.11E+05 |
| 59 | | | | | | 7.49E+05 | 8.27E+05 | 6.95E+05 | 7.23E+05 | 6.88E+05 |
| 63 | | | | | | 8.26E+05 | 6.99E+05 | 6.21E+05 | 7.14E+05 | 8.91E+05 |
| 67 | | | | | | 6.91E+05 | 7.00E+05 | 6.03E+05 | 6.93E+05 | 7.09E+05 |
| 79 | | | | | | 5.39E+05 | 6.46E+05 | 6.12E+05 | 6.20E+05 | 7.07E+05 |
| 84 | | | | | | 6.83E+05 | 7.87E+05 | 8.06E+05 | 6.31E+05 | 8.41E+05 |

| DAYS POST TUMOR INOCULATION | ZETA-CO TUMOR RECHALLENGE | | | | | | | | |
|---|---|---|---|---|---|---|---|---|---|
| 7 | 1.38E+06 | 1.09E+06 | 1.10E+06 | 1.86E+06 | 1.26E+06 | 1.49E+06 | 1.50E+06 | 1.36E+06 | 1.63E+06 |
| 11 | 6.08E+05 | 7.81E+05 | 6.04E+05 | 6.69E+05 | 7.97E+05 | 9.92E+05 | 7.97E+05 | 7.15E+05 | 7.86E+05 |
| 14 | 7.18E+05 | 8.09E+05 | 6.37E+05 | 7.69E+05 | 7.53E+05 | 7.68E+05 | 8.39E+05 | 8.81E+05 | 7.98E+05 |
| 18 | 8.09E+05 | 7.84E+05 | 9.42E+05 | 7.47E+05 | 8.69E+05 | 9.00E+05 | 8.83E+05 | 9.36E+05 | 8.92E+05 |
| 21 | 6.91E+05 | 7.46E+05 | 8.45E+05 | 7.71E+05 | 8.40E+05 | 7.61E+05 | 7.63E+05 | 7.45E+05 | 8.03E+05 |
| 24 | 1.00E+06 | 1.04E+06 | 9.41E+05 | 1.44E+06 | 9.49E+05 | 1.79E+06 | 2.01E+06 | 2.04E+06 | 1.11E+06 |
| 28 | 6.32E+06 | 2.89E+06 | 7.90E+06 | 2.52E+06 | 2.96E+06 | 8.77E+06 | 1.27E+07 | 1.27E+07 | 4.34E+06 |
| 32 | 1.23E+08 | 1.36E+07 | 5.57E+07 | 2.44E+06 | 5.30E+06 | 3.20E+07 | 1.22E+08 | 2.34E+08 | 1.01E+08 |
| 35 | 1.12E+09 | 9.57E+07 | 7.82E+06 | 2.39E+08 | 3.82E+07 | 6.63E+07 | 4.75E+08 | 1.32E+09 | 5.65E+08 |
| 42 | 4.30E+09 | 1.57E+09 | 8.46E+07 | 1.31E+09 | 6.78E+08 | 6.00E+08 | 1.09E+09 | 1.10E+10 | 5.67E+09 |
| 47 | 6.23E+09 | 1.06E+10 | 5.04E+08 | 3.73E+09 | 3.04E+09 | 1.47E+09 | 1.54E+10 | 1.79E+09 | 9.18E+09 |
| 53 | | | | | | | | | |
| 59 | | | | | | | | | |
| 63 | | | | | | | | | |
| 67 | | | | | | | | | |
| 79 | | | | | | | | | |
| 84 | | | | | | | | | |

| DAYS POST TUMOR INOCULATION | EPSILON-CO TUMOR RECHALLENGE | | | | | | | | |
|---|---|---|---|---|---|---|---|---|---|
| 7 | 1.95E+06 | 1.56E+06 | 2.00E+06 | 1.54E+06 | 2.87E+06 | 2.06E+06 | 1.63E+06 | 1.93E+06 | 1.34E+06 |
| 11 | 8.37E+05 | 7.06E+05 | 7.10E+05 | 7.33E+05 | 6.03E+05 | 7.35E+05 | 5.81E+05 | 7.59E+05 | 5.87E+05 |
| 14 | 7.20E+05 | 6.55E+05 | 7.16E+05 | 7.59E+05 | 8.19E+05 | 7.93E+05 | 9.69E+05 | 9.20E+05 | 6.51E+05 |
| 18 | 7.19E+05 | 7.11E+05 | 8.77E+05 | 7.51E+05 | 7.80E+05 | 7.33E+05 | 7.57E+05 | 7.52E+05 | 5.94E+05 |
| 21 | 7.95E+05 | 7.29E+05 | 7.10E+05 | 8.54E+05 | 9.77E+05 | 7.81E+05 | 6.91E+05 | 8.38E+05 | 1.04E+06 |
| 24 | 7.33E+05 | 6.59E+05 | 7.18E+05 | 8.05E+05 | 6.44E+05 | 7.35E+05 | 7.52E+05 | 6.92E+05 | 6.69E+05 |
| 28 | 8.29E+05 | 8.01E+05 | 9.04E+05 | 1.06E+06 | 8.40E+05 | 8.47E+05 | 8.06E+05 | 8.78E+05 | 8.69E+05 |
| 32 | 8.99E+05 | 8.54E+05 | 8.60E+05 | 9.16E+05 | 9.00E+05 | 8.57E+05 | 9.42E+05 | 9.29E+05 | 8.47E+05 |
| 35 | 1.03E+06 | 1.03E+06 | 1.12E+06 | 1.04E+06 | 8.66E+05 | 8.71E+05 | 8.39E+05 | 8.81E+05 | 7.98E+05 |
| 42 | 7.58E+05 | 8.69E+05 | 6.97E+05 | 7.31E+05 | 8.19E+05 | 1.00E+06 | 8.09E+05 | 9.39E+05 | 8.29E+05 |
| 47 | 8.02E+05 | 7.53E+05 | 7.02E+05 | 6.44E+05 | 7.85E+05 | 8.25E+05 | 9.45E+05 | 8.31E+05 | 7.63E+05 |
| 53 | 7.79E+05 | 7.69E+05 | 7.73E+05 | 8.35E+05 | 8.13E+05 | 7.55E+05 | 7.35E+05 | 8.00E+05 | 7.33E+05 |
| 59 | 9.14E+05 | 9.78E+05 | 9.71E+05 | 1.09E+06 | 9.81E+05 | 1.01E+06 | 9.33E+05 | 8.67E+05 | 1.07E+06 |
| 63 | 9.81E+05 | 8.62E+05 | 1.20E+05 | 9.61E+05 | 1.16E+06 | 9.13E+05 | 1.05E+06 | 9.41E+05 | 1.19E+06 |
| 67 | 6.54E+05 | 7.18E+05 | 6.99E+05 | 7.62E+05 | 6.65E+05 | 8.11E+05 | 7.16E+05 | 7.55E+05 | 7.39E+05 |
| 79 | 8.73E+05 | 7.11E+05 | 7.51E+05 | 7.58E+05 | 7.78E+05 | 9.71E+05 | 8.71E+05 | 1.02E+05 | 7.87E+05 |
| 84 | 8.67E+05 | 8.75E+05 | 8.97E+05 | 8.82E+05 | 8.41E+05 | 9.01E+05 | 7.47E+05 | 7.57E+05 | 7.45E+05 |

In vivo Study (Dosage 3). This study evaluated the anti-tumor efficacy and PK of Epsilon-CO CAR T cells vs Zeta 1xx CAR T cells. Change in body weight at various time points from the initial value at start of treatment is summarized in Table 67. Increasing tumor burden over time in the following groups: Vehicle, NTD, Epsilon-CO and Zeta 1xx at 4e4 and 2e5 doses, led to a mean body weight loss and/or adverse clinical signs, after which all animals were removed from the study. In contrast, all mice from Epsilon-CO and Zeta 1xx at 1e6 dose maintained consistent body weight for the duration of the study due to the significant control of tumor burden.

The BLI for each experimental group is summarized in Table 68. The Vehicle and NTD groups showed no tumor control and were euthanized due to high tumor burden by Day 26. In the 4e4 dose groups, 1 to 2 mice out of 5 in Epsilon-CO groups and 3 mice out of 5 in Zeta 1xx group showed no tumor control and were euthanized due to high tumor burden. At a dose of 2e5, only Zeta 1xx group showed no tumor control in 2 mice out of 5. In contrast, Epsilon-CO mice at the dose of 2e5 all controlled tumor until the endpoint for this dose at Day 57 at the exception of 1 mouse in group 7 that was found dead at Day 26. All high dose constructs, Epsilon-CO and Zeta 1xx at 1e6, maintained tumor control until Day 57, after which the groups were rechallenged with Nalm6 MHC I/II DKO tumor implantation. Until Day 105 when the study was terminated, all rechallenged groups, Epsilon-CO and Zeta 1xx at 1e6, maintained complete tumor clearance, similarly.

TABLE 67

| DAYS POST TUMOR INOCULATION | G1. VEHICLE | | | | | G2. NTD | | | | |
|---|---|---|---|---|---|---|---|---|---|---|
| 5 | 3.7 | 5.8 | 1 | 8.2 | 0.5 | 0.4 | 1.2 | 0.5 | 5.3 | 4.7 |
| 7 | 4.6 | 0.5 | 2 | 7.7 | −0.5 | 0 | 6.1 | −3.2 | 6.2 | 6.5 |
| 11 | 4.1 | 0.5 | −0.5 | 6.8 | 0.5 | 3.1 | 5.3 | 4.6 | 7.2 | 5.6 |
| 15 | 3.7 | −1.4 | 0 | 7.2 | 0 | −0.9 | 3.2 | −5.9 | 7.7 | 3.4 |
| 19 | 8.3 | 0.5 | −0.5 | 7.7 | 1.9 | 0 | 5.7 | 2.3 | 7.2 | 0.4 |
| 22 | 5.5 | −2.4 | 0.5 | 6.3 | 0.5 | −2.2 | 2.4 | 0.5 | 4.8 | −0.9 |
| 26 | −7.8 | −13.5 | −7.4 | 1.4 | −3.8 | −10.3 | −2.8 | −7.8 | −1.9 | −11.2 |
| 29 | | | | | | | | | | |
| 33 | | | | | | | | | | |
| 36 | | | | | | | | | | |
| 43 | | | | | | | | | | |
| 47 | | | | | | | | | | |
| 50 | | | | | | | | | | |
| 54 | | | | | | | | | | |
| 57 | | | | | | | | | | |
| 67 | | | | | | | | | | |
| 81 | | | | | | | | | | |
| 84 | | | | | | | | | | |
| 88 | | | | | | | | | | |
| 95 | | | | | | | | | | |
| 99 | | | | | | | | | | |
| 104 | | | | | | | | | | |
| DAYS POST TUMOR INOCULATION | G3. EPSILON-CO (1e6) | | | | | G4. EPSILON-CO (2e5) | | | | |
| 5 | −4.7 | −1.6 | −2.5 | 0.4 | −2 | 4.8 | −1.2 | −1.3 | −0.9 | 3 |
| 7 | −3 | −2 | 0.8 | 2 | 1.2 | 7 | −0.4 | 0.4 | 0.4 | 3.4 |
| 11 | −3 | −0.4 | 0.4 | 0.4 | 1.2 | 8.1 | −2.4 | 0.4 | 0.4 | 3.8 |
| 15 | −4.3 | −1.6 | 0.4 | 0 | 1.2 | 8.6 | −2 | 1.3 | 1.3 | 6.4 |
| 19 | −2.6 | 1.2 | 4.7 | 0 | 1.6 | 8.1 | 1.2 | −0.4 | 2.6 | 2.1 |
| 22 | −1.7 | 2 | 5.9 | 0.4 | −0.4 | 8.6 | 0 | 0 | 4.8 | 2.1 |
| 26 | −0.4 | 3.6 | 6.4 | −0.4 | −1.6 | 12.4 | 0.4 | 2.2 | 9.3 | 7.7 |
| 29 | 2.1 | 11.3 | 8.9 | 0.4 | 2.8 | 15.1 | −0.4 | 4 | 7 | 7.2 |
| 33 | 6.8 | 15.4 | 14.4 | 2.8 | 5.7 | 17.7 | 2.9 | 11 | 8.4 | 9.8 |
| 36 | 8.5 | 13.8 | 13.6 | 7.2 | 6.1 | 28 | 6.9 | 11 | 11 | 13.6 |
| 43 | 7.3 | 10.1 | 13.6 | 5.6 | 4.9 | 29.6 | 2.4 | 7 | 9.3 | 3.8 |
| 47 | 3 | 11.7 | 16.5 | 9.6 | 7.7 | 26.9 | 2.9 | 1.8 | 4.4 | 6.4 |
| 50 | 3.8 | 9.3 | 15.3 | 12.8 | 4.5 | 25.8 | 2.4 | 4.4 | 4.4 | 6.4 |
| 54 | 11.5 | 15 | 22.9 | 20.4 | 8.1 | 28 | 7.8 | 10.6 | 9.7 | 10.2 |
| 57 | 8.1 | 14.2 | 20.3 | 22.8 | 8.5 | 32.3 | 10.6 | 7.5 | 11.5 | 11.9 |
| 67 | 9 | 17.4 | 19.1 | 14.8 | 3.3 | | | | | |
| 81 | 5.6 | 22.7 | 14.4 | 16 | 6.5 | | | | | |
| 84 | 9.4 | 11.3 | 17.8 | 21.6 | 10.6 | | | | | |
| 88 | 14.5 | 19 | 13.6 | 18.8 | 14.2 | | | | | |
| 95 | 6.4 | 16.2 | 12.7 | 20.4 | 5.7 | | | | | |
| 99 | 7.7 | 13 | 11 | 24.4 | 4.9 | | | | | |
| 104 | 11.1 | 25.5 | 20.8 | 25.6 | 9.3 | | | | | |
| DAYS POST TUMOR INOCULATION | G5. EPSILON-CO (4e4) | | | | | G6. EPSILON CO (Δ181-185) (1e6) | | | | |
| 5 | 2.7 | 0.4 | 0.5 | −1.6 | 0 | 2.5 | −1.2 | 0.8 | 0.5 | 0.4 |
| 7 | 2.3 | 0.4 | −1.4 | 0 | 1.2 | −3 | −2.8 | 1.2 | 1.4 | −3.1 |
| 11 | 2.7 | 0.8 | −0.5 | 0.8 | 2.4 | 5.5 | −3.2 | 5.1 | 1.8 | −3.1 |
| 15 | 0.5 | −2.1 | −0.5 | 1.6 | 0 | 4.7 | −2.4 | 2.7 | 3.6 | −2 |
| 19 | 1.8 | 4.6 | 0 | 2 | −1.2 | 4.7 | 4 | 3.5 | 5 | 1.6 |
| 22 | 3.2 | 7.1 | 1.9 | 4.4 | 0 | 5.5 | −3.6 | 2.7 | 6.3 | 2 |

TABLE 67-continued

| | | | | | | | | | | |
|---|---|---|---|---|---|---|---|---|---|---|
| 26 | 6.4 | 6.7 | 3.3 | 2 | 0 | 8.5 | 0.8 | 7.8 | 7.2 | 5.9 |
| 29 | 12.8 | 0.4 | 6.2 | −0.8 | 3.6 | 8.5 | 0.8 | 8.2 | 8.1 | 4.7 |
| 33 | 20.1 | −7.9 | 10.4 | −4.4 | 8 | 12.3 | 5.2 | 7.8 | 7.7 | 4.7 |
| 36 | 14.6 | −24.3 | 12.3 | −23.7 | 14 | 20.3 | 8.4 | 14.4 | 12.6 | 7.8 |
| 43 | 18.3 | | 11.8 | | 8.4 | 9.7 | 10.8 | 17.1 | 15.8 | 9.4 |
| 47 | 15.5 | | 19 | | 10.8 | 9.7 | 2.4 | 12.8 | 10.4 | 3.5 |
| 50 | 11 | | 16.6 | | 11.2 | 10.6 | 5.6 | 15.6 | 13.1 | 3.5 |
| 54 | 13.2 | | 16.6 | | 9.6 | 20.3 | 6 | 25.7 | 17.1 | 7.5 |
| 57 | 21 | | 19.9 | | 13.6 | 18.2 | 8 | 24.1 | 19.4 | 11.4 |
| 67 | | | | | | 12.3 | 5.6 | 30.7 | 23 | 11.4 |
| 81 | | | | | | 14.4 | 10.4 | 23.3 | 17.1 | 7.5 |
| 84 | | | | | | 15.7 | 12.4 | 26.1 | 21.2 | 6.7 |
| 88 | | | | | | 24.2 | 15.3 | 25.3 | 27 | 12.9 |
| 95 | | | | | | 15.3 | 9.2 | 24.5 | 19.4 | 9 |
| 99 | | | | | | 14 | 7.6 | 27.2 | 19.4 | 12.5 |
| 104 | | | | | | 20.3 | 16.5 | 24.1 | 14.4 | 12.9 |

| DAYS POST TUMOR INOCULATION | G7. EPSILON CO (Δ 181-185) (2e5) | | | | | G8. EPSILON CO (Δ 181-185) (4e4) | | | | |
|---|---|---|---|---|---|---|---|---|---|---|
| 5 | −3.3 | 0.5 | 4.6 | 0.5 | 5.7 | −2.5 | −1.3 | −0.4 | −2.2 | −1.9 |
| 7 | −4.1 | 0 | 5.1 | −1.9 | 4.7 | −3 | −0.4 | 0.4 | −2.7 | −1 |
| 11 | −10.3 | −1.1 | 3.2 | −2.4 | 2.1 | −6.4 | −1.3 | 1.1 | −2.7 | 2.4 |
| 15 | −9.5 | 0 | 3.7 | 0 | 4.2 | −9.7 | −3.1 | −7.2 | −4.4 | 1.4 |
| 19 | −7 | 5.8 | 1.9 | 1.9 | 4.7 | −5.9 | 2.2 | 2.6 | 4 | 5.3 |
| 22 | 6.2 | 6.3 | 1.9 | 3.3 | 5.7 | −5.5 | 1.3 | 1.5 | 4.9 | 5.7 |
| 26 | −0.4 | 8.4 | 11.1 | | 10.9 | −1.7 | 5.3 | 2.6 | 4.4 | 9.1 |
| 29 | 2.9 | 9.5 | 5.6 | | 9.9 | 1.7 | 6.2 | 4.5 | 6.7 | 11.5 |
| 33 | 0 | 11.1 | 6.5 | | 13.5 | 6.8 | 10.1 | 9.4 | 4.9 | 4.3 |
| 36 | 6.6 | | 22.1 | 9.7 | 20.3 | 9.7 | 17.6 | 8.3 | 14.2 | −6.7 |
| 43 | −1.2 | | 22.1 | 7.9 | 21.9 | 5.5 | 18.9 | 9.4 | 4.4 | −24.4 |
| 47 | 3.3 | | 24.7 | 10.2 | 26.6 | 4.2 | 14.1 | 6.8 | 8.4 | |
| 50 | 2.9 | | 22.1 | 10.2 | 30.7 | 5.9 | 14.1 | 3.8 | 11.6 | |
| 54 | −0.8 | | 22.6 | 14.4 | 29.2 | 6.4 | 24.7 | −6.4 | 18.7 | |
| 57 | 3.7 | | 25.3 | 15.7 | 37.5 | 8.9 | 19.4 | 8.3 | 14.2 | |
| 67 | | | | | | | | | | |
| 81 | | | | | | | | | | |
| 84 | | | | | | | | | | |
| 88 | | | | | | | | | | |
| 95 | | | | | | | | | | |
| 99 | | | | | | | | | | |
| 104 | | | | | | | | | | |

| DAYS POST TUMOR INOCULATION | G9. EPSILON CO (R183K) (1e6) | | | | | G10. EPSILON CO (R183K) (2e5) | | | | |
|---|---|---|---|---|---|---|---|---|---|---|
| 5 | −1.8 | −0.9 | 2.7 | −0.5 | 0.4 | −0.9 | 7.6 | 0 | −1 | 1.2 |
| 7 | −7.1 | −0.5 | 3.6 | −0.5 | 0.4 | 0.9 | 7.2 | 1.8 | 1 | 0 |
| 11 | 5.4 | −1.9 | 3.6 | −1 | −1.7 | −0.4 | 0.4 | −0.4 | 2.9 | 4.3 |
| 15 | −5.4 | 2.3 | 3.2 | 1 | −0.9 | 0.4 | 1.3 | 0 | 4.4 | 5.5 |
| 19 | −8.9 | 2.3 | 0 | −0.5 | −0.4 | −0.9 | 4.5 | 3.6 | 2.9 | 4.9 |
| 22 | 7.6 | 3.7 | 1.4 | 1 | 1.3 | −1.3 | 4.9 | 2.2 | 4.4 | 6.1 |
| 26 | −5.4 | 6.5 | 5 | 9.6 | 5.1 | 1.7 | 1.3 | 9.4 | 9.3 | 8.6 |
| 29 | −4 | 10.2 | 5.4 | 14.1 | 6.4 | 5.1 | 4.9 | 13.8 | 7.8 | 13.5 |
| 33 | −1.8 | 16.3 | 9.5 | 22.7 | 14.5 | 8.1 | 9.9 | 17.4 | 10.8 | 13.5 |
| 36 | 1.3 | 22.3 | 11.3 | 16.2 | 19.1 | 9.4 | 12.6 | 22.3 | 11.3 | 1.9 |
| 43 | 8.9 | 22.3 | 21.6 | 18.7 | 19.1 | 6.4 | 11.2 | 17.4 | 6.4 | 25.2 |
| 47 | 11.2 | 14 | 14.9 | 23.7 | 14 | 10.3 | 12.1 | 20.5 | 7.4 | 28.8 |
| 50 | −0.9 | 19.5 | 14.9 | 22.7 | 12.3 | 10.7 | 9.4 | 19.6 | 7.8 | 25.8 |
| 54 | 2.2 | 25.6 | 16.2 | 22.7 | 21.3 | 11.5 | 10.3 | 21.4 | 8.8 | 27 |
| 57 | 7.6 | 26.5 | 19.8 | 21.7 | 21.3 | 10.7 | 11.2 | 20.5 | 13.2 | 30.1 |
| 67 | 0.9 | 20.9 | 17.1 | 29.3 | 18.3 | | | | | |
| 81 | 3.1 | 25.1 | 23 | 19.7 | 18.3 | | | | | |
| 84 | 6.3 | 23.7 | 28.4 | 23.7 | 15.3 | | | | | |
| 88 | 8.5 | 25.1 | 19.8 | 24.7 | 18.7 | | | | | |
| 95 | 4.9 | 27 | 18 | 25.8 | 24.7 | | | | | |
| 99 | 0.9 | 24.2 | 18.5 | 24.2 | 20.9 | | | | | |
| 104 | 11.6 | 30.7 | 17.1 | 31.8 | 20.9 | | | | | |

| DAYS POST TUMOR INOCULATION | G11. EPSILON CO (R183K) (4e4) | | | | | G12. ZETA 1xx (1e6) | | | | |
|---|---|---|---|---|---|---|---|---|---|---|
| 5 | −3.3 | −1 | 0.9 | 2.1 | 0 | 0 | 1.4 | 0.9 | 1 | −0.5 |
| 7 | −4.1 | −1.6 | 0.4 | 2.6 | 1 | 1.4 | 1.9 | 0.9 | 0.5 | −1.4 |
| 11 | −2.1 | 4.1 | 3.5 | 3.4 | 1 | 1.9 | 1.4 | 4.8 | 0.5 | 3.3 |
| 15 | −2.9 | 5.2 | 4.4 | 3.8 | 4.2 | 2.8 | 1.9 | 3.9 | 3.1 | 4.7 |
| 19 | −1.2 | 4.1 | 1.3 | 2.6 | 5.7 | 4.2 | 1.4 | 4.4 | 6.2 | 1.9 |
| 22 | −1.2 | 4.7 | 1.8 | 1.7 | 6.3 | 4.2 | 2.3 | 0.4 | 8.2 | 3.3 |
| 26 | 2.5 | 6.7 | 4.4 | 4.3 | 9.4 | 4.2 | 3.7 | 4.4 | 9.3 | 8.5 |
| 29 | 0.8 | 3.6 | 7.1 | 1.7 | | 6.1 | 1.9 | 8.3 | 13.4 | 7.5 |

TABLE 67-continued

| | | | | | | | | | | |
|---|---|---|---|---|---|---|---|---|---|---|
| 33 | −2.9 | 7.8 | 11.9 | 6 | | 8.5 | 4.2 | 9.6 | 13.9 | 11.7 |
| 36 | −25.5 | 19.2 | 11.5 | 13.2 | | 13.7 | 15.9 | 17 | 22.7 | 18.3 |
| 43 | | 20.7 | 15 | 8.1 | | 17.9 | 20.6 | 17.9 | 16.5 | 21.1 |
| 47 | | 23.3 | 11.1 | 9.8 | | 20.3 | 15.9 | 18.8 | 14.9 | 23.5 |
| 50 | | 25.4 | 12.8 | 9 | | 17.9 | 16.8 | 16.6 | 15.5 | 23 |
| 54 | | 17.1 | 12.4 | 2.6 | | 17 | 17.3 | 19.2 | 19.1 | 25.8 |
| 57 | | 20.2 | 14.6 | 6.4 | | 22.2 | 17.8 | 21 | 23.2 | 22.1 |
| 67 | | | | | | 19.8 | 20.6 | 24.5 | 19.6 | 22.1 |
| 81 | | | | | | 20.8 | 25.2 | 24.5 | 19.1 | 24.4 |
| 84 | | | | | | 21.7 | 31.8 | 23.6 | 22.7 | 23.5 |
| 88 | | | | | | 24.1 | 33.6 | 30.6 | 28.4 | 21.6 |
| 95 | | | | | | 25 | 24.3 | 34.9 | 23.2 | 21.1 |
| 99 | | | | | | 24.1 | 24.3 | 33.2 | 24.2 | 23 |
| 104 | | | | | | 28.3 | 25.2 | 38.9 | 27.3 | 27.7 |

| DAYS POST TUMOR INOCULATION | G13. ZETA 1xx (2e5) | | | | | G14. ZETA 1xx (4e4) | | | | |
|---|---|---|---|---|---|---|---|---|---|---|
| 5 | −0.9 | −1.6 | 8.4 | 2.4 | 0.5 | 6.1 | 2.4 | −3.7 | 5.9 | 1.3 |
| 7 | −2.8 | −3.6 | 8.9 | 1.9 | 0 | 6.5 | 3.3 | −2.8 | 5.4 | 1.3 |
| 11 | −0.5 | −3.6 | 8.4 | 5.2 | 3.2 | 7.9 | 1.4 | −0.5 | 2.5 | 3.1 |
| 15 | 0.9 | −2.1 | 8.9 | 6.7 | 4.5 | 8.9 | 1.9 | 0.9 | 3 | 4.5 |
| 19 | 2.3 | 0.5 | 12.3 | 6.7 | 5.9 | 12.6 | 4.7 | 3.7 | 3 | 4.5 |
| 22 | 1.9 | 0 | 11.8 | 6.2 | 7.3 | 15 | 5.2 | 5.1 | 3.4 | 7.1 |
| 26 | 7.9 | 9.3 | 11.3 | 10.5 | 2.7 | 17.3 | 5.7 | 1.9 | 4.4 | 7.1 |
| 29 | 6.9 | 9.8 | 13.3 | 12.9 | 3.6 | 19.2 | −3.3 | −0.9 | 3.9 | 3.6 |
| 33 | 6.9 | 11.4 | 10.3 | 16.2 | 1.8 | 20.6 | −14.2 | −19.2 | 10.3 | 3.6 |
| 36 | 10.2 | 8.3 | 15.3 | 9 | 2.7 | 25.2 | | | 18.2 | |
| 43 | 4.6 | −9.8 | 11.3 | −17.1 | 1.8 | 16.8 | | | 17.2 | |
| 47 | 6.5 | −25.9 | 9.9 | | 6.4 | 19.6 | | | 16.7 | |
| 50 | 4.6 | | 12.8 | | 7.3 | 16.8 | | | 14.3 | |
| 54 | 12.5 | | 17.2 | | 4.5 | 21.5 | | | 17.2 | |
| 57 | 17.6 | | 12.8 | | 5 | 22 | | | 16.3 | |
| 67 | | | | | | | | | | |
| 81 | | | | | | | | | | |
| 84 | | | | | | | | | | |
| 88 | | | | | | | | | | |
| 95 | | | | | | | | | | |
| 99 | | | | | | | | | | |
| 104 | | | | | | | | | | |

| DAYS POST TUMOR INOCULATION | G15.VEHICLE FOR TUMOR RECHALLENGE | | | |
|---|---|---|---|---|
| 5 | | | | |
| 7 | | | | |
| 11 | | | | |
| 15 | | | | |
| 19 | | | | |
| 22 | | | | |
| 26 | | | | |
| 29 | | | | |
| 33 | | | | |
| 36 | | | | |
| 43 | | | | |
| 47 | | | | |
| 50 | | | | |
| 54 | | | | |
| 57 | | | | |
| 67 | 27.6 | 19.9 | 23.7 | 6.8 |
| 81 | 30 | 24.4 | 28.4 | 8.9 |
| 84 | 25.2 | 27.9 | 22.3 | 11 |
| 88 | 10.5 | 10.9 | 11.6 | −5.1 |
| 95 | | | | |
| 99 | | | | |
| 104 | | | | |

TABLE 68

| DAYS POST TUMOR INOCULATION | G1. VEHICLE | | | | | G2. NTD | | | | |
|---|---|---|---|---|---|---|---|---|---|---|
| 5 | 5.06E+06 | 3.42E+06 | 3.29E+06 | 2.42E+06 | 3.84E+06 | 2.65E+06 | 1.66E+06 | 2.54E+06 | 1.95E+06 | 2.02E+06 |
| 7 | 2.15E+07 | 1.82E+07 | 1.17E+07 | 1.46E+07 | 1.25E+07 | 2.31E+07 | 9.88E+07 | 1.73E+07 | 1.55E+07 | 1.40E+07 |
| 11 | 8.43E+08 | 9.38E+08 | 8.31E+08 | 8.70E+08 | 1.05E+09 | 1.10E+09 | 5.48E+08 | 8.93E+08 | 6.36E+08 | 8.21E+08 |
| 15 | 4.45E+09 | 4.93E+09 | 7.04E+09 | 8.68E+09 | 6.46E+09 | 4.01E+09 | 5.02E+09 | 6.74E+09 | 5.85E+09 | 3.96E+09 |
| 19 | 1.85E+10 | 1.96E+10 | 1.07E+10 | 1.60E+10 | 1.79E+10 | 1.36E+10 | 1.46E+10 | 1.50E+10 | 1.28E+10 | 1.53E+10 |

TABLE 68-continued

| | | | | | | | | | | |
|---|---|---|---|---|---|---|---|---|---|---|
| 22 | 2.53E+10 | 3.08E+10 | 2.97E+10 | 3.43E+10 | 3.83E+10 | 3.11E+10 | 3.07E+10 | 3.16E+10 | 3.11E+10 | 3.72E+10 |
| 26 | | 3.69E+10 | 5.30E+10 | 4.98E+10 | 4.92E+10 | 4.31E+10 | 4.71E+10 | 4.74E+10 | 3.82E+10 | |
| 29 | | | | | | | | | | |
| 33 | | | | | | | | | | |
| 36 | | | | | | | | | | |
| 40 | | | | | | | | | | |
| 43 | | | | | | | | | | |
| 47 | | | | | | | | | | |
| 50 | | | | | | | | | | |
| 54 | | | | | | | | | | |
| 57 | | | | | | | | | | |
| 67 | | | | | | | | | | |
| 76 | | | | | | | | | | |
| 81 | | | | | | | | | | |
| 84 | | | | | | | | | | |
| 88 | | | | | | | | | | |
| 92 | | | | | | | | | | |
| 96 | | | | | | | | | | |
| 99 | | | | | | | | | | |
| 105 | | | | | | | | | | |
| DAYS POST TUMOR INOCULATION | G3. EPSILON-CO (1e6) | | | | | G4. EPSILON-CO (2e5) | | | | |
| 5 | 1.63E+06 | 1.79E+06 | 1.81E+06 | 1.81E+06 | 2.56E+06 | 2.67E+06 | 1.72E+06 | 2.50E+06 | 3.15E+06 | 1.94E+06 |
| 7 | 1.23E+06 | 1.43E+06 | 1.04E+06 | 1.21E+06 | 1.46E+06 | 6.35E+06 | 7.49E+06 | 6.52E+06 | 1.39E+07 | 5.45E+06 |
| 11 | 1.07E+06 | 1.81E+06 | 1.10E+06 | 1.27E+06 | 1.38E+06 | 2.87E+06 | 4.05E+06 | 5.89E+06 | 1.68E+07 | 7.22E+06 |
| 15 | 1.41E+06 | 1.51E+06 | 1.24E+06 | 1.33E+06 | 1.23E+06 | 1.83E+06 | 3.99E+06 | 5.97E+06 | 1.46E+07 | 4.02E+06 |
| 19 | 9.60E+05 | 8.80E+05 | 9.09E+05 | 1.17E+05 | 1.04E+06 | 1.02E+06 | 1.49E+06 | 1.09E+06 | 1.13E+06 | 1.07E+06 |
| 22 | 8.93E+05 | 9.23E+05 | 7.23E+05 | 7.74E+05 | 1.70E+05 | 9.40E+05 | 1.21E+06 | 1.09E+06 | 1.14E+06 | 1.32E+06 |
| 26 | 8.80E+05 | 9.37E+05 | 9.53E+05 | 9.57E+05 | 9.83E+05 | 1.25E+06 | 1.31E+06 | 8.89E+05 | 1.10E+06 | 1.18E+06 |
| 29 | 1.19E+06 | 1.20E+06 | 1.07E+06 | 1.40E+06 | 1.19E+06 | 1.24E+06 | 1.35E+06 | 9.17E+05 | 1.13E+06 | 1.15E+06 |
| 33 | 8.76E+05 | 9.83E+05 | 8.77E+05 | 8.80E+05 | 8.29E+05 | 1.28E+06 | 1.30E+06 | 1.33E+06 | 1.04E+06 | 1.33E+06 |
| 36 | 8.07E+05 | 8.70E+05 | 6.07E+05 | 7.18E+05 | 7.65E+05 | 1.13E+06 | 1.21E+06 | 9.41E+05 | 1.14E+06 | 1.21E+06 |
| 40 | 7.86E+05 | 8.55E+05 | 1.10E+05 | 8.35E+05 | 9.46E+05 | 1.17E+06 | 1.15E+06 | 1.02E+06 | 1.05E+06 | 1.24E+06 |
| 43 | 1.55E+06 | 1.34E+06 | 1.25E+06 | 1.45E+06 | 1.14E+06 | 1.24E+06 | 1.31E+06 | 1.09E+06 | 1.28E+06 | 1.30E+06 |
| 47 | 1.18E+06 | 1.42E+06 | 1.17E+06 | 1.13E+06 | 1.03E+06 | 1.11E+06 | 1.17E+06 | 1.27E+06 | 9.18E+05 | 9.65E+05 |
| 50 | 8.62E+05 | 1.18E+06 | 8.75E+05 | 1.10E+06 | 1.01E+06 | 1.30E+06 | 1.29E+06 | 8.71E+05 | 1.04E+06 | 8.90E+05 |
| 54 | 8.61E+05 | 1.02E+06 | 1.02E+05 | 9.86E+05 | 9.36E+05 | 1.22E+06 | 1.04E+06 | 8.71E+05 | 8.82E+05 | 8.27E+05 |
| 57 | 8.79E+05 | 9.78E+05 | 8.27E+05 | 1.16E+06 | 9.38E+05 | 1.08E+06 | 1.36E+06 | 1.02E+06 | 1.12E+06 | 1.05E+06 |
| 67 | 5.02E+05 | 5.27E+05 | 6.89E+05 | 5.51E+05 | 5.35E+05 | | | | | |
| 76 | 8.62E+05 | 8.14E+05 | 9.70E+05 | 8.40E+05 | 6.35E+05 | | | | | |
| 81 | 9.43E+05 | 1.24E+06 | 1.03E+05 | 9.15E+05 | 8.18E+05 | | | | | |
| 84 | 5.07E+05 | 6.80E+05 | 5.79E+05 | 5.62E+05 | 5.67E+05 | | | | | |
| 88 | 6.75E+05 | 7.56E+05 | 6.41E+05 | 7.63E+05 | 7.12E+05 | | | | | |
| 92 | 8.91E+05 | 8.19E+05 | 8.84E+05 | 8.21E+05 | 8.16E+05 | | | | | |
| 96 | 7.47E+05 | 9.10E+05 | 8.79E+05 | 8.10E+05 | 7.31E+05 | | | | | |
| 99 | 7.01E+05 | 6.47E+05 | 7.91E+05 | 6.81E+05 | 6.00E+05 | | | | | |
| 105 | 5.74E+05 | 5.92E+05 | 5.66E+05 | 6.06E+05 | 6.63E+05 | | | | | |
| DAYS POST TUMOR INOCULATION | G5. EPSILON-CO (4e4) | | | | | G6. EPSILON CO (Δ 181-185) (1e6) | | | | |
| 5 | 1.84E+06 | 1.50E+06 | 7.13E+05 | 1.65E+06 | 1.70E+06 | 1.96E+06 | 2.06E+06 | 2.09E+06 | 3.88E+06 | 2.23E+06 |
| 7 | 8.92E+06 | 7.41E+06 | 1.51E+07 | 9.48E+06 | 7.71E+06 | 1.94E+06 | 1.36E+06 | 1.73E+06 | 1.96E+06 | 2.10E+06 |
| 11 | 8.68E+07 | 7.78E+07 | 2.46E+08 | 1.31E+08 | 6.56E+07 | 1.16E+06 | 1.13E+06 | 1.37E+06 | 1.46E+06 | 1.15E+06 |
| 15 | 5.40E+08 | 8.16E+08 | 7.58E+08 | 8.96E+08 | 2.38E+08 | 1.47E+06 | 1.46E+06 | 1.38E+06 | 1.57E+06 | 1.44E+06 |
| 19 | 3.23E+07 | 2.74E+09 | 3.70E+08 | 1.00E+09 | 1.50E+09 | 9.24E+05 | 1.08E+06 | 1.01E+06 | 9.73E+05 | 1.44E+05 |
| 22 | 2.41E+08 | 3.50E+09 | 5.98E+07 | 4.53E+09 | 5.50E+07 | 1.06E+06 | 1.13E+06 | 1.04E+06 | 1.05E+06 | 1.04E+06 |
| 26 | 1.10E+08 | 9.13E+09 | 1.94E+08 | 1.13E+10 | 1.28E+08 | 1.04E+06 | 1.05E+06 | 1.03E+06 | 1.19E+06 | 1.05E+06 |
| 29 | 1.61E+08 | 1.39E+10 | 3.12E+08 | 1.55E+10 | 3.02E+08 | 1.06E+06 | 1.10E+06 | 1.09E+06 | 1.05E+06 | 8.45E+05 |
| 33 | 5.95E+08 | 3.80E+10 | 1.09E+09 | 5.72E+10 | 9.93E+08 | 1.01E+06 | 9.77E+05 | 8.65E+05 | 9.75E+06 | 1.37E+06 |
| 36 | 1.26E+09 | 9.87E+10 | 2.90E+09 | 7.34E+10 | 2.12E+09 | 1.03E+06 | 9.62E+05 | 1.21E+06 | 1.03E+06 | 1.47E+06 |
| 40 | 1.14E+06 | | 9.54E+05 | | 1.15E+06 | 1.43E+06 | 1.06E+06 | 9.10E+05 | 1.06E+06 | 1.24E+06 |
| 43 | 1.27E+06 | | 1.11E+06 | | 1.21E+06 | 9.30E+05 | 1.17E+06 | 1.29E+06 | 9.96E+05 | 1.07E+06 |
| 47 | 1.18E+06 | | 9.67E+05 | | 9.68E+06 | 9.68E+05 | 9.41E+05 | 8.96E+05 | 9.98E+05 | 9.07E+05 |
| 50 | 1.01E+06 | | 8.99E+05 | | 1.24E+06 | 9.40E+05 | 9.64E+05 | 1.03E+06 | 1.10E+06 | 1.07E+06 |
| 54 | 9.60E+05 | | 9.51E+05 | | 8.81E+05 | 9.62E+05 | 9.29E+05 | 9.39E+05 | 9.78E+05 | 1.07E+06 |
| 57 | 9.48E+05 | | 9.43E+05 | | 1.22E+06 | 1.01E+06 | 9.75E+06 | 1.06E+06 | 1.11E+06 | 8.54E+05 |
| 67 | | | | | | 5.58E+05 | 5.41E+05 | 5.48E+05 | 7.06E+05 | 6.81E+05 |
| 76 | | | | | | 8.97E+05 | 1.02E+06 | 1.05E+06 | 1.02E+06 | 1.10E+06 |
| 81 | | | | | | 7.28E+05 | 8.35E+05 | 7.25E+05 | 8.55E+05 | 7.02E+05 |
| 84 | | | | | | 8.56E+05 | 9.60E+05 | 8.88E+05 | 9.88E+05 | 7.85E+05 |
| 88 | | | | | | 7.90E+05 | 7.94E+05 | 7.37E+05 | 1.02E+06 | 8.50E+05 |
| 92 | | | | | | 1.01E+06 | 9.93E+05 | 8.36E+05 | 1.09E+06 | 1.02E+06 |
| 96 | | | | | | 9.18E+05 | 9.64E+05 | 8.16E+05 | 8.42E+05 | 7.88E+05 |
| 99 | | | | | | 9.58E+05 | 1.13E+06 | 1.01E+06 | 1.20E+06 | 1.05E+06 |
| 105 | | | | | | 1.08E+06 | 1.10E+06 | 9.71E+05 | 1.12E+06 | 9.68E+06 |
| DAYS POST TUMOR | | | | | | | | | | |

TABLE 68-continued

| INOCULATION | G7. EPSILON CO (Δ 181-185) (2e5) | | | | | G8. EPSILON CO (Δ 181-185) (4e4) | | | | |
|---|---|---|---|---|---|---|---|---|---|---|
| 5 | 2.49E+06 | 3.89E+06 | 3.21E+06 | 2.92E+06 | 3.97E+06 | 2.43E+06 | 2.14E+06 | 2.31E+06 | 1.92E+06 | 2.28E+06 |
| 7 | 8.41E+06 | 1.57E+07 | 1.27E+07 | 1.16E+07 | 1.45E+07 | 1.48E+07 | 2.05E+07 | 1.52E+07 | 1.51E+07 | 1.64E+07 |
| 11 | 4.44E+06 | 3.81E+06 | 3.25E+06 | 3.90E+06 | 8.11E+06 | 3.48E+08 | 1.35E+08 | 1.26E+08 | 1.93E+08 | 9.64E+07 |
| 15 | 5.34E+06 | 5.24E+06 | 6.20E+06 | 6.32E+06 | 9.64E+06 | 8.50E+08 | 5.15E+08 | 3.35E+08 | 4.61E+08 | 2.90E+08 |
| 19 | 1.10E+06 | 1.09E+06 | 9.63E+06 | 1.29E+06 | 8.28E+05 | 2.54E+09 | 1.44E+09 | 1.29E+09 | 3.39E+09 | 1.28E+09 |
| 22 | 1.09E+06 | 1.19E+06 | 1.20E+06 | 1.29E+06 | 1.29E+06 | 2.19E+09 | 1.16E+09 | 3.40E+08 | 1.50E+09 | 2.48E+09 |
| 26 | 1.01E+06 | | 9.24E+05 | 1.06E+06 | 1.09E+06 | 3.92E+07 | 4.38E+09 | 4.82E+07 | 7.16E+08 | 1.94E+07 |
| 29 | 8.91E+05 | | 1.10E+06 | 1.05E+06 | 9.98E+05 | | 5.07E+07 | 1.35E+07 | 1.23E+08 | 1.37E+10 |
| 33 | 1.04E+06 | | 9.58E+05 | 1.10E+06 | 1.07E+06 | 2.13E+07 | 4.72E+07 | 2.24E+07 | 4.20E+08 | 3.45E+10 |
| 36 | 9.27E+05 | | 9.50E+05 | 1.06E+06 | 8.82E+05 | 1.59E+05 | 3.01E+07 | 2.30E+07 | 3.93E+08 | 3.10E+10 |
| 40 | 8.92E+05 | | 8.15E+05 | 1.07E+06 | 9.90E+05 | 1.87E+07 | 1.51E+07 | 2.29E+07 | 2.77E+08 | 3.44E+10 |
| 43 | 1.17E+06 | | 1.15E+06 | 1.19E+06 | 1.10E+06 | 4.36E+07 | 2.92E+07 | 3.73E+07 | 5.04E+08 | 7.55E+10 |
| 47 | 8.59E+05 | | 8.56E+05 | 9.95E+05 | 9.73E+05 | 9.75E+05 | 2.83E+06 | 1.06E+06 | 9.37E+05 | |
| 50 | 8.59E+05 | | 8.56E+05 | 9.95E+05 | 9.73E+05 | 9.79E+05 | 1.56E+06 | 9.66E+05 | 9.22E+05 | |
| 54 | 1.06E+06 | | 1.09E+06 | 1.02E+06 | 1.12E+06 | 1.15E+06 | 4.66E+06 | 9.79E+05 | 1.09E+06 | |
| 57 | 9.24E+06 | | 9.54E+05 | 9.85E+05 | 1.08E+06 | 1.01E+06 | 1.27E+07 | 1.29E+06 | 9.40E+05 | |
| 67 | | | | | | | | | | |
| 76 | | | | | | | | | | |
| 81 | | | | | | | | | | |
| 84 | | | | | | | | | | |
| 88 | | | | | | | | | | |
| 92 | | | | | | | | | | |
| 96 | | | | | | | | | | |
| 99 | | | | | | | | | | |
| 105 | | | | | | | | | | |

| DAYS POST TUMOR INOCULATION | G9. EPSILON CO (R183K) (1e6) | | | | | G10. EPSILON CO (R183K) (2e5) | | | | |
|---|---|---|---|---|---|---|---|---|---|---|
| 5 | 3.05E+06 | 4.45E+06 | 2.32E+06 | 2.89E+06 | 3.33E+06 | 2.11E+06 | 2.23E+06 | 2.96E+06 | 2.84E+06 | 3.50E+06 |
| 7 | 1.73E+06 | 2.00E+06 | 2.09E+06 | 1.11E+06 | 1.80E+06 | 1.00E+07 | 1.59E+07 | 1.70E+07 | 1.55E+07 | 1.91E+07 |
| 11 | 1.13E+06 | 1.44E+06 | 1.02E+06 | 1.44E+06 | 1.18E+06 | 2.92E+06 | 7.70E+06 | 1.35E+07 | 9.31E+06 | 1.28E+07 |
| 15 | 1.48E+06 | 1.28E+06 | 1.18E+06 | 1.45E+06 | 1.61E+06 | 2.70E+06 | 9.03E+06 | 2.23E+07 | 1.80E+07 | 2.60E+07 |
| 19 | 1.25E+06 | 1.21E+06 | 9.96E+05 | 9.49E+05 | 1.20E+06 | 1.11E+06 | 1.56E+06 | 3.26E+07 | 3.51E+06 | 2.15E+06 |
| 22 | 1.13E+06 | 1.14E+06 | 1.00E+06 | 1.09E+06 | 1.05E+06 | 9.22E+05 | 1.02E+06 | 2.52E+06 | 1.04E+06 | 1.11E+06 |
| 26 | 1.11E+06 | 1.05E+06 | 1.03E+06 | 9.12E+05 | 1.05E+06 | 9.09E+05 | 1.10E+06 | 1.18E+06 | 1.04E+06 | 1.03E+06 |
| 29 | 1.08E+06 | 9.12E+05 | 9.06E+05 | 9.64E+05 | 9.38E+05 | 1.18E+06 | 1.15E+06 | 1.01E+06 | 1.04E+06 | 1.12E+06 |
| 33 | 1.31E+06 | 1.36E+06 | 1.12E+06 | 1.15E+06 | 1.40E+06 | 1.21E+06 | 1.24E+06 | 1.12E+06 | 1.28E+06 | 1.11E+06 |
| 36 | 1.27E+06 | 1.10E+06 | 1.05E+06 | 1.11E+06 | 1.09E+06 | 7.80E+05 | 1.05E+06 | 1.15E+06 | 9.95E+05 | 1.27E+06 |
| 40 | 6.04E+06 | 5.69E+05 | 6.25E+05 | 6.51E+05 | 6.21E+05 | 7.45E+05 | 6.58E+05 | 6.15E+05 | 7.80E+05 | 8.52E+05 |
| 43 | 1.04E+06 | 1.06E+06 | 1.02E+06 | 1.20E+06 | 1.29E+06 | 1.20E+06 | 1.31E+06 | 1.11E+06 | 1.00E+06 | 9.90E+06 |
| 47 | 1.08E+06 | 1.06E+06 | 1.08E+06 | 1.12E+06 | 9.11E+05 | 1.02E+06 | 1.26E+06 | 9.20E+05 | 1.03E+06 | 1.07E+06 |
| 50 | 1.00E+06 | 9.91E+05 | 1.00E+06 | 1.02E+06 | 1.04E+06 | 9.10E+05 | 1.11E+06 | 8.31E+05 | 1.11E+06 | 1.02E+06 |
| 54 | 8.98E+05 | 1.12E+06 | 1.10E+06 | 1.15E+06 | 1.04E+06 | 9.41E+05 | 1.07E+06 | 7.66E+05 | 9.14E+05 | 8.88E+05 |
| 57 | 1.03E+06 | 1.01E+06 | 1.27E+06 | 9.90E+05 | 1.05E+06 | 1.10E+06 | 1.33E+06 | 9.35E+05 | 1.16E+06 | 1.02E+06 |
| 67 | 4.98E+05 | 4.73E+05 | 4.89E+05 | 4.73E+05 | 5.26E+05 | | | | | |
| 76 | 8.61E+05 | 1.24E+06 | 7.65E+05 | 9.46E+05 | 1.04E+06 | | | | | |
| 81 | 8.54E+05 | 1.11E+06 | 9.42E+05 | 7.41E+05 | 1.03E+06 | | | | | |
| 84 | 1.10E+06 | 9.41E+05 | 8.73E+05 | 9.10E+05 | 9.83E+05 | | | | | |
| 88 | 8.32E+05 | 6.89E+05 | 8.78E+05 | 8.62E+05 | 8.13E+05 | | | | | |
| 92 | 9.05E+05 | 1.10E+06 | 6.72E+05 | 1.05E+06 | 9.59E+05 | | | | | |
| 96 | 6.20E+05 | 8.26E+05 | 5.50E+05 | 8.37E+05 | 1.06E+06 | | | | | |
| 99 | 1.15E+06 | 7.29E+05 | 8.90E+05 | 1.02E+06 | 9.10E+05 | | | | | |
| 105 | 9.11E+05 | 7.75E+05 | 9.10E+05 | 9.21E+05 | 9.06E+05 | | | | | |

| DAYS POST TUMOR INOCULATION | G11. EPSILON CO (R183K) (4e4) | | | | | G12. ZETA 1xx (1e6) | | | | |
|---|---|---|---|---|---|---|---|---|---|---|
| 5 | 3.42E+06 | 3.48E+06 | 2.87E+06 | 2.64E+06 | 4.54E+06 | 4.92E+06 | 5.44E+06 | 2.29E+06 | 5.23E+06 | 5.31E+06 |
| 7 | 3.15E+07 | 3.23E+07 | 2.39E+07 | 2.99E+07 | 5.13E+07 | 2.86E+06 | 3.50E+06 | 2.35E+06 | 2.97E+06 | 3.80E+06 |
| 11 | 2.90E+08 | 2.77E+08 | 3.31E+08 | 3.05E+08 | 6.05E+08 | 1.23E+06 | 1.30E+06 | 1.54E+06 | 1.21E+06 | 1.35E+06 |
| 15 | 9.78E+08 | 1.09E+09 | 1.03E+09 | 9.80E+08 | 1.93E+09 | 1.32E+06 | 1.39E+06 | 1.23E+06 | 1.32E+06 | 1.10E+06 |
| 19 | 6.40E+09 | 6.18E+09 | 7.47E+09 | 6.27E+09 | 8.15E+09 | 1.61E+06 | 1.26E+06 | 1.19E+06 | 1.34E+06 | 8.34E+06 |
| 22 | 6.53E+09 | 3.96E+09 | 3.49E+09 | 2.12E+09 | 1.16E+10 | 1.01E+06 | 8.33E+05 | 8.40E+05 | 9.04E+05 | 3.67E+06 |
| 26 | 1.72E+10 | 4.60E+08 | 1.73E+08 | 2.71E+08 | 2.61E+10 | 1.13E+06 | 1.10E+06 | 1.02E+06 | 1.06E+06 | 1.09E+06 |
| 29 | 2.34E+10 | 2.09E+08 | 1.99E+07 | 9.50E+06 | | 1.04E+06 | 1.09E+06 | 9.97E+05 | 1.03E+06 | 9.89E+05 |
| 33 | 5.72E+10 | 8.33E+08 | 4.98E+07 | 2.40E+07 | | 1.26E+06 | 1.24E+06 | 1.12E+06 | 1.20E+06 | 1.18E+06 |
| 36 | | 9.93E+06 | 1.08E+06 | 1.01E+06 | | 5.99E+05 | 8.60E+05 | 7.70E+05 | 8.21E+05 | 7.86E+05 |
| 40 | | 3.09E+07 | 1.32E+06 | 1.02E+06 | | 1.15E+06 | 9.51E+05 | 1.05E+06 | 1.21E+06 | 8.73E+05 |
| 43 | | 2.83E+07 | 1.33E+06 | 1.10E+06 | | 9.68E+05 | 9.71E+05 | 9.28E+05 | 9.00E+05 | 9.03E+05 |
| 47 | | 2.35E+07 | 7.79E+05 | 6.62E+05 | | 1.02E+06 | 1.05E+06 | 1.26E+06 | 1.09E+06 | 1.18E+06 |
| 50 | | 4.55E+07 | 1.31E+06 | 9.20E+05 | | 1.13E+06 | 1.04E+06 | 1.02E+06 | 1.06E+06 | 1.05E+06 |
| 54 | | 9.92E+07 | 1.10E+06 | 7.86E+05 | | 1.09E+06 | 1.10E+06 | 9.14E+05 | 1.08E+06 | 9.18E+05 |
| 57 | | 1.13E+07 | 1.01E+06 | 1.02E+06 | | 1.02E+06 | 1.04E+06 | 1.16E+06 | 1.01E+06 | 1.12E+06 |
| 67 | | | | | | 6.97E+05 | 6.22E+05 | 6.66E+05 | 6.19E+05 | 7.17E+05 |
| 76 | | | | | | 1.17E+06 | 9.10E+05 | 7.50E+05 | 9.02E+05 | 9.51E+05 |
| 81 | | | | | | 1.20E+06 | 9.35E+05 | 9.50E+05 | 1.23E+06 | 9.41E+05 |
| 84 | | | | | | 7.15E+05 | 8.87E+05 | 1.13E+06 | 9.09E+05 | 9.14E+05 |

TABLE 68-continued

| | | | | | | | | | | |
|---|---|---|---|---|---|---|---|---|---|---|
| 88 | | | | | | 8.33E+05 | 9.84E+05 | 9.05E+05 | 8.47E+05 | 8.34E+05 |
| 92 | | | | | | 1.14E+06 | 1.04E+06 | 8.26E+05 | 9.30E+05 | 9.43E+05 |
| 96 | | | | | | 1.14E+06 | 1.10E+06 | 1.11E+06 | 8.49E+05 | 1.09E+06 |
| 99 | | | | | | 9.49E+05 | 8.83E+05 | 8.07E+05 | 7.12E+05 | 7.81E+05 |
| 105 | | | | | | 8.54E+05 | 7.50E+05 | 7.92E+05 | 1.03E+06 | |

| DAYS POST TUMOR INOCULATION | G13. ZETA 1xx (2e5) | | | | | G14. ZETA 1xx (4e4) | | | | |
|---|---|---|---|---|---|---|---|---|---|---|
| 5 | 5.16E+06 | 4.12E+06 | 4.29E+06 | 3.82E+06 | 6.70E+06 | 3.50E+06 | 4.83E+06 | 7.91E+06 | 3.89E+06 | 5.66E+06 |
| 7 | 7.07E+07 | 3.38E+07 | 2.49E+07 | 3.05E+07 | 4.36E+07 | 2.70E+07 | 2.62E+07 | 4.92E+07 | 3.02E+07 | 2.56E+07 |
| 11 | 5.18E+07 | 1.02E+07 | 1.67E+07 | 1.31E+07 | 1.61E+07 | 2.69E+08 | 2.95E+08 | 7.03E+08 | 2.66E+08 | 4.95E+08 |
| 15 | 3.43E+07 | 1.07E+07 | 2.41E+07 | 1.19E+07 | 1.64E+07 | 1.12E+09 | 6.51E+08 | 2.09E+09 | 5.76E+08 | 1.32E+09 |
| 19 | 1.47E+08 | 5.87E+07 | 7.69E+07 | 3.99E+07 | 2.47E+07 | 1.18E+09 | 1.46E+09 | 4.70E+09 | 1.37E+09 | 3.08E+09 |
| 22 | 3.12E+08 | 1.65E+08 | 2.87E+08 | 7.41E+07 | 2.73E+07 | 8.22E+08 | 2.93E+09 | 7.11E+09 | 3.40E+08 | 2.94E+09 |
| 26 | 2.27E+09 | 1.65E+09 | 1.41E+09 | 5.62E+08 | 1.85E+07 | 1.70E+09 | 8.90E+09 | 1.37E+10 | 2.14E+08 | 6.80E+09 |
| 29 | 1.01E+08 | 4.24E+09 | 8.58E+09 | 2.81E+09 | 9.40E+09 | 2.32E+09 | 2.32E+10 | 2.03E+10 | 4.45E+08 | 1.19E+10 |
| 33 | 1.62E+10 | 9.97E+09 | 2.14E+10 | 8.42E+09 | 3.01E+08 | 2.09E+09 | 2.01E+10 | 3.62E+10 | 1.49E+09 | 4.40E+10 |
| 36 | 1.08E+09 | 3.22E+10 | 7.31E+08 | 2.47E+10 | 7.26E+08 | 9.23E+06 | | | 1.31E+08 | |
| 40 | 4.69E+08 | 3.13E+10 | 9.25E+08 | 4.70E+10 | 1.13E+09 | 3.05E+06 | | | 4.50E+07 | |
| 43 | 1.47E+09 | 7.26E+10 | 1.98E+09 | 4.87E+10 | 1.40E+09 | 1.66E+06 | | | 2.59E+07 | |
| 47 | 1.03E+09 | 6.28E+10 | 1.20E+09 | | 5.39E+07 | 6.69E+05 | | | 3.41E+06 | |
| 50 | 3.12E+06 | | 3.79E+06 | | 3.22E+06 | 1.08E+06 | | | 3.66E+06 | |
| 54 | 5.93E+06 | | 1.32E+07 | | 1.77E+08 | 1.09E+06 | | | 4.72E+06 | |
| 57 | 5.86E+06 | | 3.73E+07 | | 9.73E+08 | 1.04E+06 | | | 8.88E+06 | |
| 67 | | | | | | | | | | |
| 76 | | | | | | | | | | |
| 81 | | | | | | | | | | |
| 84 | | | | | | | | | | |
| 88 | | | | | | | | | | |
| 92 | | | | | | | | | | |
| 96 | | | | | | | | | | |
| 99 | | | | | | | | | | |
| 105 | | | | | | | | | | |

| DAYS POST TUMOR INOCULATION | G15. VEHICLE FOR TUMOR RECHALLENGE | | | |
|---|---|---|---|---|
| 5 | | | | |
| 7 | | | | |
| 11 | | | | |
| 15 | | | | |
| 19 | | | | |
| 22 | | | | |
| 26 | | | | |
| 29 | | | | |
| 33 | | | | |
| 36 | | | | |
| 40 | | | | |
| 43 | | | | |
| 47 | | | | |
| 50 | | | | |
| 54 | | | | |
| 57 | | | | |
| 67 | 1.21E+06 | 1.22E+06 | 1.15E+06 | 1.24E+06 |
| 76 | 1.69E+06 | 2.21E+06 | 1.74E+06 | 1.92E+06 |
| 81 | 6.91E+07 | 1.23E+08 | 4.24E+07 | 8.53E+07 |
| 84 | 3.01E+09 | 3.20E+09 | 2.37E+09 | 2.22E+09 |
| 88 | 4.81E+09 | 5.50E+09 | 4.69E+09 | 4.94E+09 |
| 92 | | | | |
| 96 | | | | |
| 99 | | | | |
| 105 | | | | |

Ex vivo ddPCR Analysis. To assess CAR T-cell expansion and persistence in vivo, peripheral blood was analyzed via ddPCR for CAR copies per μg of genomic DNA (gDNA) (Table 69). Zeta 1xx CAR T cells were detected in the peripheral blood of mice but showed limited expansion compared to Epsilon-CO. All Epsilon-CO groups similarly demonstrated a robust CAR T-cell expansion and persistence in the peripheral blood of mice especially in the 2e5 and 4e4 treatment groups.

TABLE 69

| DAYS POST TUMOR INOCULATION | G1. VEHICLE | | | | | G2. NTD | | | | | G3. EPSILON-CO (1e6) | | | | | G4. EPSILON-CO (2e5) | | | | |
|---|---|---|---|---|---|---|---|---|---|---|---|---|---|---|---|---|---|---|---|---|
| 7 | 0 | 0 | 0 | 0 | 0 | 0 | 0 | 0 | 0 | 0 | 329.67 | 242.62 | 743.49 | 581.48 | 465.02 | 73 | 36.41 | 184.25 | 84.31 | 95.97 |
| 14 | 0 | 0 | 0 | 0 | 0 | 0 | 0 | 0 | 0 | 0 | 2148.61 | 736.43 | 3049.64 | 1111.11 | 733.62 | 101.67 | 297.34 | 97.52 | 48.29 | 192.99 |
| 21 | 0 | 0 | 0 | 0 | 0 | 0 | 0 | 0 | 0 | 0 | 6139.29 | 6331.33 | 4301.27 | 7192.81 | 3089.58 | 9365.08 | 3182.9 | 12211.67 | 3785.66 | 5860.66 |
| 28 | | | | | | | | | | | 2579.25 | 1767.5 | 1622.14 | 1958.58 | 837.7 | 16474.46 | 4720.97 | 7252.28 | 3340.53 | 3412.55 |
| 35 | | | | | | | | | | | | 5008.08 | 3562.14 | 3990.33 | 2107.82 | 1700.77 | 10178.57 | 3930.85 | 11362.67 | 11500.95 |
| 42 | | | | | | | | | | | 2457.83 | 2160.15 | 1234.44 | 2256.06 | 1431.61 | 22877.85 | 8703.7 | 2144.69 | 6166.19 | 12860.52 |

| DAYS POST TUMOR INOCULATION | G5. EPSILON-CO (4e4) | | | | | G6. EPSILON CO (Δ 181-185) (1e6) | | | | | G7. EPSILON CO (Δ 181-185) (2e5) | | | | |
|---|---|---|---|---|---|---|---|---|---|---|---|---|---|---|---|
| 7 | 34.06 | 13.7 | 20.8 | 35.75 | 16.99 | 300.66 | 795.45 | 479.78 | 278.88 | 327.87 | 81.7 | 61.68 | 40.99 | 83.75 | 78.13 |
| 14 | 505.72 | 57.64 | 122.35 | 45.18 | 97.15 | 472.97 | 394.62 | 981.82 | 234 | 176.42 | 30.67 | 71.17 | 14.81 | 35.63 | 61.19 |
| 21 | 401.29 | 61.76 | 454.55 | 88.24 | 340.78 | 5370.22 | 2657.34 | 5684.36 | 2874.16 | 3215.74 | 5654.45 | 1536.44 | 10466.96 | 3611.35 | 3330.63 |
| 28 | 1103.8 | 339.09 | 4287.62 | 615.31 | 5737.18 | 1300.37 | 1804.74 | 2051.76 | 1742.52 | 1395.66 | 1362.23 | 12794.9 | 14279.97 | 0 | 5024.33 |
| 35 | 15541.85 | 1938.11 | 9038.63 | 2081.73 | 17734.86 | 557.62 | 1428.73 | 2884.78 | 2976.3 | 357.14 | 537.58 | 0 | 14614.3 | 7491.18 | 0 |
| 42 | 3477.81 | 0 | 6799.7 | 0 | 19946.81 | 1460.99 | 150.79 | 1142.48 | 1096.24 | 692.52 | 606.52 | 0 | 3477.12 | 8501.2 | 2880.75 |

| DAYS POST TUMOR INOCULATION | G8. EPSILON CO (Δ 181-185) (4e4) | | | | | G9. EPSILON CO (R183K) (1e6) | | | | | G10. EPSILON CO (R183K) (2e5) | | | | |
|---|---|---|---|---|---|---|---|---|---|---|---|---|---|---|---|
| 7 | 1.8 | 1.43 | 4.66 | 1.81 | 0 | 261.81 | 643.01 | 591.49 | 409.32 | 345.47 | 120.9 | 113.74 | 0 | 97.33 | 226.69 |
| 14 | 285.04 | 424.96 | 224.09 | 73.42 | 43.52 | 733.27 | 702.27 | | 0 | 473.8 | 116.14 | 234.99 | 131.04 | 65.94 | 86.73 |
| 21 | 1092.8 | 823.42 | 728.76 | 1044.1 | 236.58 | 2493.42 | 2069.89 | 2244.9 | 3132.53 | 1287.73 | 8213.58 | 3532.34 | 992.7 | 1203.93 | 2547.33 |
| 28 | 1746.31 | 3692.52 | 197.69 | 1671.36 | 1826.92 | 833.9 | 1157.63 | 1465.59 | 1106.35 | 1096.41 | 2378.69 | 4095.74 | 1510.42 | 1446.77 | 8071.43 |
| 35 | 2623.38 | 1837.27 | 1676.07 | 822.7 | 957.03 | 1216.49 | 1942.43 | 1989.27 | 1128.3 | 6210.77 | 5681.21 | 9858.1 | 2149.95 | 8534.67 | 7705.19 |
| 42 | 3398.13 | 3627.85 | 1900.65 | 1966.69 | 1043.93 | 3768.39 | 0 | 3502 | 874.7 | 735.53 | 7585.11 | 5750.69 | 1527.86 | 4683.12 | 5032.8 |

| DAYS POST TUMOR INOCULATION | G11. EPSILON CO (R183K) (4e4) | | | | | G12. ZETA 1xx (1e6) | | | | | G13. ZETA 1xx (2e5) | | | | |
|---|---|---|---|---|---|---|---|---|---|---|---|---|---|---|---|
| 7 | 16.82 | 40.63 | 29.49 | 16.87 | 13.21 | 301.58 | 408.23 | 381.72 | 320.2 | 284.05 | 36.21 | 52.69 | 76.22 | 16.01 | 47.26 |
| 14 | 37.59 | 70.92 | 84.37 | 29.98 | 95.92 | 151.4 | 0 | 13.16 | 0 | 62.12 | 259.29 | 63.42 | 237.09 | 117.32 | 94.25 |
| 21 | 171.06 | 298.3 | 102.12 | 173.89 | 31.45 | 142.76 | 190.48 | 148.15 | 250.63 | 173.51 | 0 | 37.02 | 27.88 | 0 | 46 |
| 28 | 732.54 | 2266.24 | 1123.09 | 1055.16 | 1785.71 | 401.22 | 270.58 | 205.25 | 339.9 | 794.61 | 155.47 | 40.5 | 9.17 | 16.06 | 54.42 |
| 35 | 3992.95 | 400 | 1279.83 | 272.02 | 2291.99 | 446.99 | 513.91 | | 2386.39 | 296.57 | 120.03 | 316.07 | 242.94 | 370.37 | 0 |
| 42 | | 171.37 | 1902.79 | 90.23 | | 565.37 | 82.15 | 267.98 | 407.24 | 781.41 | 296.97 | 817.83 | 129.31 | 381.25 | 185.05 |

| DAYS POST TUMOR INOCULATION | G14. ZETA 1xx (4e4) | | | | |
|---|---|---|---|---|---|
| 7 | 0 | 49.88 | 16 | 26.9 | 19.43 |
| 14 | 43.52 | 77.51 | 31.6 | 46.95 | 623.7 |
| 21 | 88.63 | 109.17 | | 106.8 | 21.71 |
| 28 | 25.92 | 911.16 | 410.13 | 92.23 | |
| 35 | 1041.12 | 0 | 0 | 380.23 | |
| 42 | 58.19 | 0 | 0 | 502.16 | |

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A chimeric antigen receptor (CAR) comprising a CD3ε signaling domain consisting of amino acid sequence SEQ ID NO: 89.

2. The CAR of claim 1, wherein the CAR comprises a binding domain specific to an antigen selected from the group consisting of 707-AP (707 alanine proline), AFP (alpha (α)-fetoprotein), ART-4 (adenocarcinoma antigen recognized by T4 cells), BAGE (B antigen; b-catenin/m, b-catenin/mutated), BCMA (B cell maturation antigen), Bcr-abl (breakpoint cluster region-Abelson), CAIX (carbonic anhydrase IX), CD19 (cluster of differentiation 19), CD20 (cluster of differentiation 20), CD22 (cluster of differentiation 22), CD30 (cluster of differentiation 30), CD33 (cluster of differentiation 33), CD44v7/8 (cluster of differentiation 44, exons 7/8), CAMEL (CTL-recognized antigen on melanoma), CAP-1 (carcinoembryonic antigen peptide-1), CASP-8 (caspase-8), CDC27m (cell-division cycle 27 mutated), CDK4/m (cycline-dependent kinase 4 mutated), CEA (carcinoembryonic antigen), C-type lectin-like-1 (CLL-1), CT (cancer/testis (antigen)), Cyp-B (cyclophilin B), DAM (differentiation antigen melanoma), EGFR (epidermal growth factor receptor), EGFRvlll (epidermal growth factor receptor, variant III), EGP-2 (epithelial glycoprotein 2), EGP-40 (epithelial glycoprotein 40), Erbb2, 3, 4 (erythroblastic leukemia viral oncogene homolog-2, -3, 4), ELF2M (elongation factor 2 mutated), ETV6-AML1 (Ets variant gene 6/acute myeloid leukemia 1 gene ETS), FBP (folate binding protein), fAchR (Fetal acetylcholine receptor), G250 (glycoprotein 250), GAGE (G antigen), GD2 (disialoganglioside 2), GD3 (disialoganglioside 3), glypican 3 (GPC3), GnT-V (N-acetylglucosaminyltransferase V), Gp100 (glycoprotein 100 kD), HAGE (helicose antigen), HER-2/neu (human epidermal receptor-2/neurological; also known as EGFR2), HLA-A (human leukocyte antigen-A) HPV (human papilloma virus), HSP70-2M (heat shock protein 70-2 mutated), HST-2 (human signet ring tumor-2), hTERT or hTRT (human telomerase reverse transcriptase), iCE (intestinal carboxyl esterase), IL-13R-a2 (Interleukin-13 receptor subunit alpha-2), KIAA0205, KDR (kinase insert domain receptor), κ-light chain, LAGE (L antigen), LDLR/FUT (low density lipid receptor/GDP-L-fucose: b-D-galactosidase 2-a-Lfucosyltransferase), LeY (Lewis-Y antibody), L1 CAM (L1 cell adhesion molecule), MAGE (melanoma antigen), MAGE-A1 (Melanoma-associated antigen 1), mesothelin, Murine CMV infected cells, MART-1/Melan-A (melanoma antigen recognized by T cells-I/Melanoma antigen A), MC1 R (melanocortin 1 receptor), Myosin/m (myosin mutated), MUC1 (mucin 1), MUM-1, -2, -3 (melanoma ubiquitous mutated 1, 2, 3), NA88-A (NA cDNA clone of patient M88), NKG2D (Natural killer group 2, member D) ligands, NY-BR-1 (New York breast differentiation antigen 1), NY-ESO-1 (New York esophageal squamous cell carcinoma-1), oncofetal antigen (h5T4), P15 (protein 15), p190 minor bcr-abl (protein of $190K_D$ bcr-abl), Pml/RARa (promyelocytic leukaemia/retinoic acid receptor a), PRAME (preferentially expressed antigen of melanoma), PSA (prostate-specific antigen), PSCA (Prostate stem cell antigen), PSMA (prostate-specific membrane antigen), RAGE (renal antigen), RU1 or RU2 (renal ubiquitous 1 or 2), SAGE (sarcoma antigen), SART-1 or SART-3 (squamous antigen rejecting tumor 1 or 3), SSX1, -2, -3, 4 (synovial sarcoma X1, -2, -3, -4), TAA (tumor-associated antigen), TAG-72 (Tumor-associated glycoprotein 72), TEL/AML1 (translocation Ets-family leukemia/acute myeloid leukemia 1), TPI/m (triosephosphate isomerase mutated), TRP-1 (tyrosinase related protein 1, or gp75), TRP-2 (tyrosinase related protein 2), TRP-2/INT2 (TRP-2/intron 2), VEGF-R2 (vascular endothelial growth factor receptor 2), and WT1 (Wilms' tumor gene).

3. The CAR of claim 1, wherein the CAR is encoded by a bicistronic nucleic acid construct.

4. The CAR of claim 1, wherein the CAR comprises a binding domain specific to CD19.

5. The CAR of claim 1, wherein the CD3ε signaling domain is encoded by a nucleic acid having at least 90% sequence identity to sequence SEQ ID NO: 81.

6. The CAR of claim 1, wherein, when the CAR is expressed in a cell, the CAR exhibits a greater degree of trafficking to the cell membrane than a corresponding CAR with a wild-type CD3ε signaling domain in place of the CD3ε signaling domain of claim 1.

7. A polynucleotide encoding the CAR of claim 1.

8. A vector comprising the polynucleotide of claim 7.

9. A host cell comprising the vector of claim 8.

10. The host cell of claim 9, wherein the cell is selected from the group consisting of a T cell, an iNKT cell, or a NK cell.

11. A pharmaceutical composition comprising the host cell of claim 9.

12. A method of treating a disease or condition in a patient in need thereof, comprising administering the host cell of claim 9.

13. A method of making a CAR T cell, comprising providing for the expression of the CAR of claim 1 in a T-cell.

* * * * *